United States Patent
Austin et al.

(10) Patent No.: US 8,916,553 B2
(45) Date of Patent: Dec. 23, 2014

(54) SULFONAMIDE COMPOUNDS USEFUL AS CYP17 INHIBITORS

(75) Inventors: Joel Francis Austin, Secaucus, NJ (US); Lisa S. Sharma, Lawrenceville, NJ (US); James Aaron Balog, Princeton, NJ (US); Audris Huang, Princeton, NJ (US); Upender Velaparthi, Wallingford, CT (US); Chetan Padmakar Darne, Wallingford, CT (US); Mark George Saulnier, Wallingford, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 13/812,056

(22) PCT Filed: Jul. 25, 2011

(86) PCT No.: PCT/US2011/045153
§ 371 (c)(1),
(2), (4) Date: May 31, 2013

(87) PCT Pub. No.: WO2012/015723
PCT Pub. Date: Feb. 2, 2012

(65) Prior Publication Data
US 2014/0148453 A1 May 29, 2014

Related U.S. Application Data

(60) Provisional application No. 61/367,612, filed on Jul. 26, 2010.

(51) Int. Cl.
*C07D 213/42* (2006.01)
*C07D 213/55* (2006.01)
(Continued)

(52) U.S. Cl.
CPC ............ *C07D 213/42* (2013.01); *C07D 213/61* (2013.01); *C07D 213/68* (2013.01); *C07D 213/70* (2013.01); *C07D 213/71* (2013.01); *C07D 213/81* (2013.01); *C07D 217/14* (2013.01); *C07D 239/26* (2013.01); *C07D 239/34* (2013.01); *C07D 239/42* (2013.01); *C07D 401/12* (2013.01); *C07D 405/12* (2013.01); *C07D 409/12* (2013.01); *C07D 413/12* (2013.01); *C07D 471/04* (2013.01); *C07D 487/04* (2013.01); *C07D 213/55* (2013.01); *C07D 213/56* (2013.01); *C07D 213/57* (2013.01); *C07D 401/06* (2013.01)
USPC ........ 514/235.8; 514/357; 514/347; 514/344; 514/314; 514/340; 514/336; 514/335; 514/256; 514/235.5; 546/338; 546/293; 546/335; 546/286; 546/337; 546/172; 546/272; 546/280.4; 546/261; 544/335; 544/333; 544/131; 544/122

(58) Field of Classification Search
CPC .. C07D 213/42; C07D 213/55; C07D 213/56; C07D 213/57; C07D 213/61; C07D 213/68; C07D 213/70; C07D 213/71; C07D 213/81; C07D 217/14; C07D 239/26; C07D 239/34; C07D 239/42; C07D 401/06
USPC .............. 514/235.8, 357, 347, 344, 314, 340, 514/336, 335, 256, 235.5; 546/338, 293, 546/335, 286, 337, 172, 272.1, 280.4, 261; 544/335, 333, 131, 122
See application file for complete search history.

(56) References Cited

U.S. PATENT DOCUMENTS 7,235,667 B2 6/2007 Naganawa et al.
2004/0048891 A1 3/2004 Kato et al.
(Continued)

FOREIGN PATENT DOCUMENTS

WO    WO 98/05315    2/1998
WO    WO 01/82916    11/2001
(Continued)

OTHER PUBLICATIONS

DataBase Chemcats Chem Abstracts No. 0040248107, Jan. 3, 2011.
Yap T.A., et al., "Targeting CYP17: established and novel approaches in prostate cancer," Current Opinion in Pharmacology, vol. 8, pp. 449-457(2008).
International Preliminary Report on Patentability issued Jan. 29, 2013.
Search Report for Chinese Patent Application No. 201180046307.X, Jul. 25, 2011

*Primary Examiner* — San-Ming Hui
*Assistant Examiner* — Kathrien Cruz
(74) *Attorney, Agent, or Firm* — Gary D. Greenblatt

(57) ABSTRACT

Disclosed are sulfonamide compounds of Formula (I): or stereoisomers, N-oxides, prodrugs, or pharmaceutically acceptable salts thereof, wherein ring A, $R^1$, $R^2$, $R^3$, $R^4$ and $R^5$ are defined herein. Also disclosed are methods of using such compounds in the treatment of conditions related to CYP17 enzyme, such as cancer, and pharmaceutical compositions comprising such compounds.

(I)

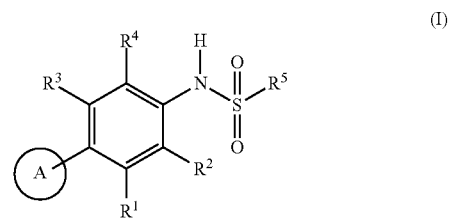

14 Claims, 1 Drawing Sheet

(51) Int. Cl.

| | |
|---|---|
| C07D 213/57 | (2006.01) |
| C07D 213/56 | (2006.01) |
| C07D 487/04 | (2006.01) |
| C07D 413/12 | (2006.01) |
| C07D 409/12 | (2006.01) |
| C07D 239/26 | (2006.01) |
| C07D 401/06 | (2006.01) |
| C07D 471/04 | (2006.01) |
| C07D 213/68 | (2006.01) |
| C07D 401/12 | (2006.01) |
| C07D 213/61 | (2006.01) |
| C07D 213/70 | (2006.01) |
| C07D 213/71 | (2006.01) |
| C07D 213/81 | (2006.01) |
| C07D 217/14 | (2006.01) |
| C07D 239/34 | (2006.01) |
| C07D 239/42 | (2006.01) |
| C07D 405/12 | (2006.01) |

(56) References Cited

U.S. PATENT DOCUMENTS

| | | | |
|---|---|---|---|
| 2006/0030543 | A1 | 2/2006 | Malecha et al. |
| 2006/0258671 | A1 | 11/2006 | Desos et al. |
| 2007/0185136 | A1 | 8/2007 | Courtemanche et al. |
| 2007/0287708 | A1 | 12/2007 | Cole et al. |
| 2008/0039491 | A1 | 2/2008 | Ronan et al. |
| 2008/0167348 | A1 | 7/2008 | Banner et al. |

FOREIGN PATENT DOCUMENTS

| | | |
|---|---|---|
| WO | WO 2004/043917 | 5/2004 |
| WO | WO 2004/113279 | 12/2004 |
| WO | WO 2008/008375 | 1/2008 |
| WO | WO 2008/042867 | 4/2008 |
| WO | WO 2008/136378 | 11/2008 |
| WO | WO 2010/011868 | 1/2010 |

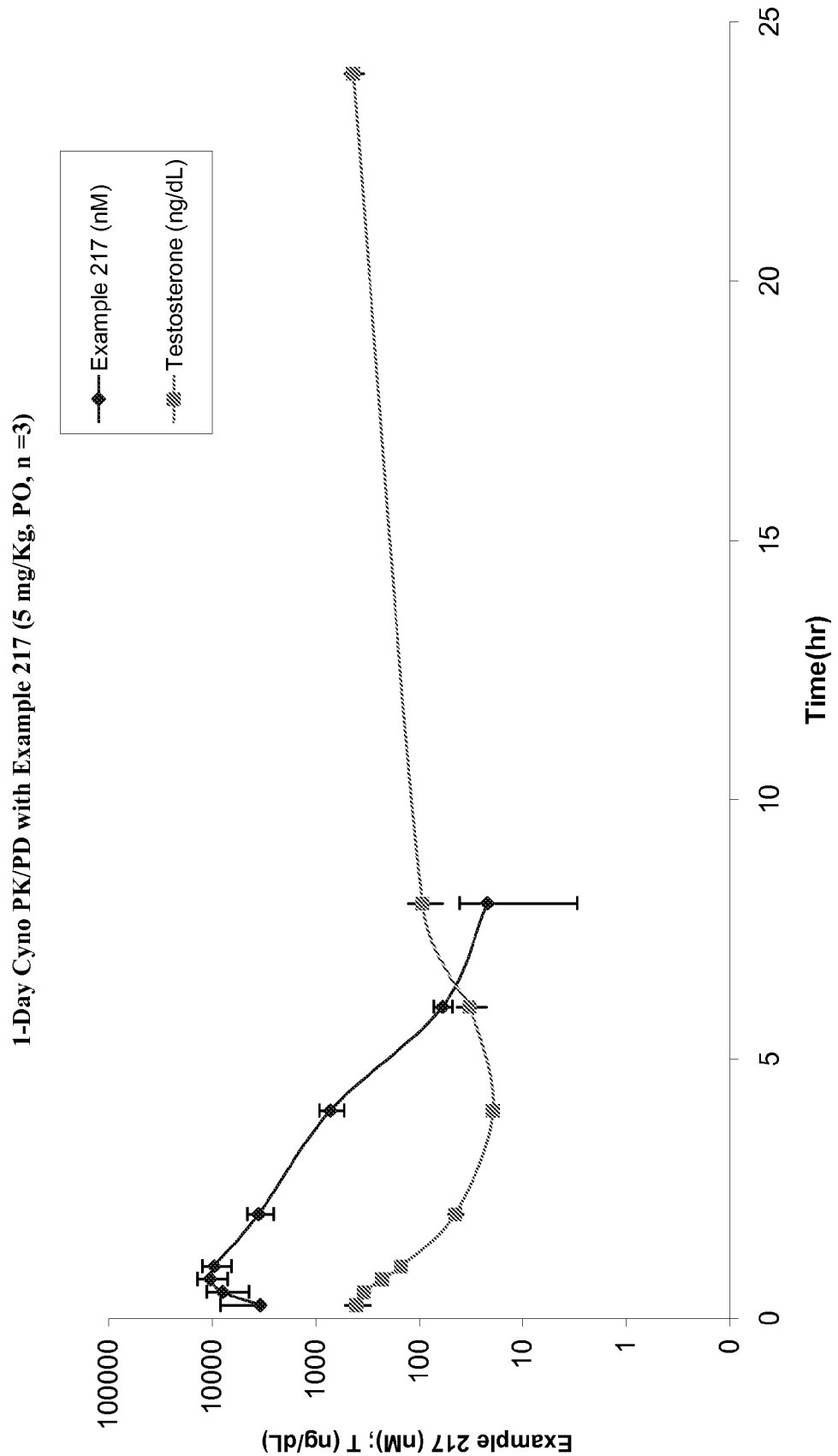

SULFONAMIDE COMPOUNDS USEFUL AS CYP17 INHIBITORS

CROSS-REFERENCE TO RELATED APPLICATION

This application claims the benefit of U.S. Provisional Application Ser. No. 61/367,612, filed Jul. 26, 2010, incorporated herein by reference in its entirety.

DESCRIPTION

The present invention generally relates to sulfonamide compounds useful as CYP17 inhibitors. Provided herein are sulfonamide compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with anti-androgens more difficult.

The cytochrome P450 monooxygenase 17α-hydroxylase/17,20-lyase (CYP17) is responsible for the biosynthesis of both dihydroepiandrostenedione and androstenedione which are precursors of both androgens and estrogen. Thus the production of androgens and estrogens in the human body is mediated by CYP17. Blocking this enzyme would inhibit the production of gonadal, adrenal, and tumoral androgens and could offer a new treatment option for prostate cancer and estrogen receptor-positive breast cancer patients. Clinical proof-of-concept for CYP17 as a target for prostate cancer has been achieved with the antifungal ketoconazole and the steroidal CYP17 inhibitor abiraterone, which has progressed to Phase III clinical trials for prostate cancer. Despite the advances recently made in the art, there is a clear need for new compounds that are useful as inhibitors of CYP17 enzymes.

Applicants have found potent sulfonamide compounds that have activity as CYP17 inhibitors, and these compounds may be useful for the treatment of conditions related to the CYP17 enzyme.

Certain sulfonamide compounds have been reported in patent publications. Such publications, for example, include the following: WO 01/82916; WO 2004/113279; U.S. 2007/0287708; U.S. 2008/003949; WO 2008/042867; WO 2008/136378; U.S. 2004/0048891; U.S. 2006/0030543; U.S. 2008/0167348; U.S. 2006/0258671; and WO 2010/005922. However, these publications do not disclose CYP17 activity for their compounds.

SUMMARY OF THE INVENTION

The present invention fills the foregoing need by providing sulfonamide compounds, which are useful as inhibitors of CYP17 enzymes, including stereoisomers, N-oxides, prodrugs, and pharmaceutically acceptable salts thereof.

The present invention also provides pharmaceutical compositions comprising a pharmaceutically acceptable carrier; and at least one compound of Formula (I), or stereoisomers, N-oxides, prodrugs, or pharmaceutically acceptable salts thereof.

The present invention also provides a method of treating a disease or disorder associated with the activity of the CYP17 enzyme, the method comprising administering to a mammalian patient a compound of Formula (I), or stereoisomers, N-oxides, prodrugs, or pharmaceutically acceptable salts thereof.

The present invention also provides processes and intermediates for making the compounds of Formula (I), or stereoisomers, N-oxides, prodrugs, or pharmaceutically acceptable salts thereof.

The present invention also provides the compounds of Formula (I), or stereoisomers, N-oxides, prodrugs, or pharmaceutically acceptable salts thereof, for use in therapy.

The present invention also provides use of the compounds of Formula (I), or stereoisomers, N-oxides, prodrugs, or pharmaceutically acceptable salts thereof, for the manufacture of a medicament for the treatment of cancer.

The compounds of Formula (I) and compositions comprising such compounds are inhibitors of CYP17 enzymes, and may be used in treating, prevention, or curing various CYP17 enzyme related conditions. Pharmaceutical compositions comprising the compounds of the present invention are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawing described below.

FIG. 1 shows the plasma pharmacokinetics of Example 217 and testosterone levels in cynomolgus monkeys after administration of Example 217. Example 217 was administered orally at a dose of 5 mg/kg. (◆) Example 217 (nM); (■) testosterone level after treatment with Example 217 (ng/dL).

DETAILED DESCRIPTION

In a first aspect, the present disclosure provides a compound of Formula (I):

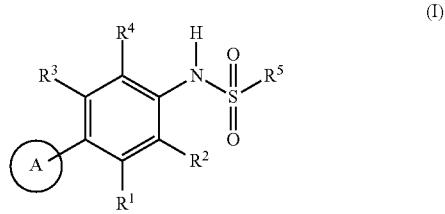

or a stereoisomer, an N-oxide, a prodrug, or a pharmaceutically acceptable salt thereof, wherein:

ring A is:

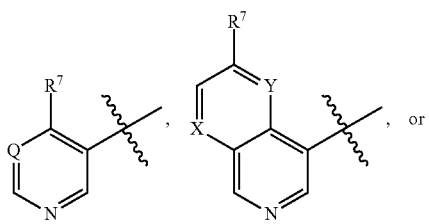

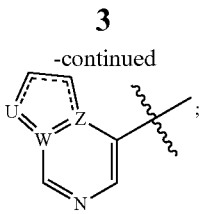

X, Y, and Q are independently N and/or CR$^6$;
U is independently N, NR$^8$, and/or CH;
W and Z are independently N and/or C;
provided that:
- (i) if U is NR$^8$, then W and Z are each C;
- (ii) if U is N or CH, then one of W and Z is N, and the other of W and Z is C;

the ═══ bond represents a single or double bond;
R$^1$ is H, halo, —OH, C$_{1-4}$alkyl, C$_{1-4}$haloalkyl, C$_{1-4}$alkoxy, C$_{1-4}$haloalkoxy, C$_{1-4}$hydroxyalkyl, or —C(O)O(C$_{1-4}$alkyl);
R$^2$ is H, halo, or C$_{1-3}$alkyl;
R$^3$ is H, halo, C$_{1-3}$alkyl, or C$_{1-3}$alkoxy;
R$^4$ is H, halo, C$_{1-3}$alkyl, C$_{1-3}$alkoxy, or C$_{1-3}$haloalkoxy;
R$^5$ is:
- (i) C$_{1-6}$alkyl substituted with zero to 3 substituents independently selected from halo, phenyl, isoindoline-1,3-dione, and/or camphor, wherein said phenyl may be substituted with zero to 3 R$^a$;
- (ii) C$_{2-6}$alkenyl substituted with zero to 3 substituents independently selected from halo and/or phenyl;
- (iii) C$_{3-6}$cycloalkyl substituted with zero to 2 substituents independently selected from halo, C$_{1-3}$alkyl, and/or C$_{1-3}$haloalkyl;
- (iv) adamantanyl;
- (v) —NR$^c$R$^d$;
- (vi) phenyl substituted with zero to 3 substituents independently selected from halo, —CN, —NO$_2$, C$_{1-6}$alkyl, C$_{1-4}$haloalkyl, C$_{1-4}$alkoxy, C$_{1-4}$haloalkoxy, —C(O)O(C$_{1-4}$alkyl), —NR$^b$C(O)(C$_{1-4}$alkyl), phenyl, and/or phenoxy;
- (vii) naphthalenyl substituted with zero to 3 substituents independently selected from halo, C$_{1-3}$alkyl, C$_{1-3}$haloalkyl, C$_{1-3}$alkoxy, and/or C$_{1-3}$haloalkoxy;
- (viii) 5- to 10-membered heteroaryl substituted with zero to 2 substituents independently selected from halo, —C(O)(C$_{1-3}$alkyl), —C(O)O(C$_{1-3}$alkyl), C$_{1-3}$alkyl, and/or C$_{1-3}$haloalkyl; or
- (ix) 5- to 6-membered heterocyclyl substituted with zero to 2 substituents independently selected from halo, —OH, C$_{1-3}$alkyl, and/or C$_{1-3}$haloalkyl;

wherein each of said heteroaryl or heterocyclyl groups comprises 1 to 2 heteroatoms;
R$^6$ is H, halo, —CN, C$_{1-3}$alkyl, C$_{1-3}$haloalkyl, C$_{1-3}$alkoxy, or C$_{1-3}$haloalkoxy;
R$^7$ is:
- (i) halo;
- (ii) —CN;
- (iii) C$_{1-4}$alkyl substituted with zero to 1 C$_{1-3}$alkoxy group;
- (iv) C$_{1-4}$haloalkyl or C$_{1-4}$hydroxyalkyl;
- (v) C$_{2-4}$alkenyl;
- (vi) C$_{1-4}$alkoxy substituted with zero to 2 substituents independently selected from halo, lNR$^b$R$^c$, phenyl, C$_{3-6}$cycloalkyl, and/or C$_{1-3}$alkoxy;
- (vii) C$_{3-6}$cycloalkyl substituted with zero to 2 substituents independently selected from halo, C$_{1-3}$alkyl, and/or C$_{1-3}$haloalkyl;
- (viii) —S(C$_{1-3}$alkyl);
- (ix) —NR$^b$R$^c$;
- (x) —C(O)M, wherein M is 5- to 6-membered heterocyclyl;
- (xi) phenyl substituted with zero to 4 substituents independently selected from halo, —CN, C$_{1-3}$alkyl, C$_{1-3}$haloalkyl, and/or C$_{1-3}$alkoxy; or
- (xii) 3- to 6-membered heterocyclyl substituted with zero to 4 substituents independently selected from halo, C$_{1-3}$alkyl, and/or C$_{1-3}$haloalkyl;

wherein each of said heterocyclyl groups comprises 1 to 3 heteroatoms;
R$^8$ is H, C$_{1-3}$alkyl, or —S(O)$_2$(phenyl);
each R$^a$ is independently halo, C$_{1-3}$alkyl, C$_{1-3}$haloalkyl, C$_{1-3}$alkoxy, and/or C$_{1-3}$haloalkoxy;
each R$^b$ is independently H and/or C$_{1-3}$alkyl;
each R$^c$ is independently H, C$_{1-3}$alkyl, and/or C$_{1-3}$haloalkyl; and
each R$^d$ is independently H, C$_{1-3}$alkyl, C$_{1-3}$haloalkyl, and/or phenyl substituted with zero to 2 substituents independently selected from halo, C$_{1-3}$alkyl, C$_{1-3}$haloalkyl, C$_{1-3}$alkoxy, and/or C$_{1-3}$haloalkoxy; or
R$^c$ and R$^d$ together with the nitrogen atom to which they are attached form a 5- to 6-membered heterocyclyl having zero to 1 additional heteroatom independently selected from N and/or O, wherein said heterocyclyl may be substituted with zero to 2 substituents independently selected from halo, C$_{1-3}$alkyl, and/or —OH.

In another embodiment, the present disclosure provides a compound of Formula (I), or a stereoisomer, an N-oxide, a prodrug, or a pharmaceutically acceptable salt thereof, wherein:
ring A is:

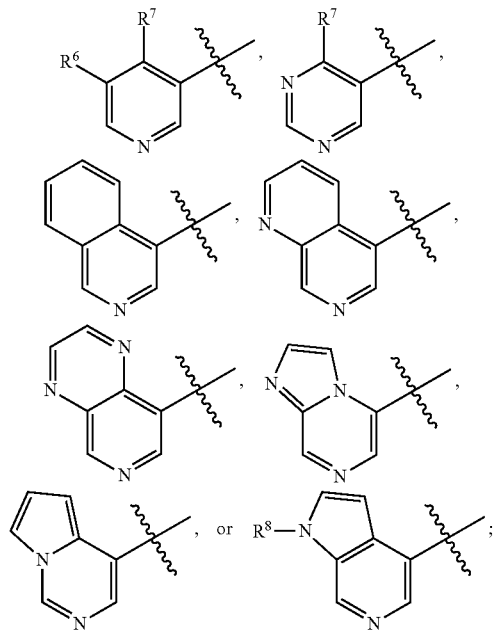

R$^1$ is H, halo, —OH, C$_{1-3}$alkyl, C$_{1-3}$fluoroalkyl, C$_{1-3}$alkoxy, C$_{1-3}$fluoroalkoxy, C$_{1-4}$hydroxyalkyl, or —C(O)O(C$_{1-3}$alkyl);
R$^2$ is H;
R$^3$ is H, C$_{1-3}$alkyl, or C$_{1-3}$alkoxy;
R$^4$ is H, halo, or C$_{1-3}$fluoroalkoxy;
R$^5$ is:
- (i) C$_{1-6}$alkyl substituted with zero to 3 substituents independently selected from halo, phenyl, isoindoline-1,3-dione, and/or camphor, wherein said phenyl may be substituted with zero to 3 R$^a$;
- (ii) C$_{2-6}$alkenyl substituted with phenyl;

(iii) C$_{3-6}$cycloalkyl;
(iv) adamantanyl;
(v) —NR$^c$R$^d$;
(vi) phenyl substituted with zero to 3 substituents independently selected from halo, —CN, —NO$_2$, C$_{1-4}$alkyl, C$_{1-4}$fluoroalkyl, C$_{1-4}$alkoxy, —C(O)O(C$_{1-4}$alkyl), —NHC(O)(C$_{1-4}$alkyl), phenyl, and/or phenoxy;
(vii) naphthalenyl; or
(viii) 5- to 10-membered heteroaryl substituted with zero to 2 substituents independently selected from —C(O)(C$_{1-3}$alkyl), —C(O)O(C$_{1-3}$alkyl), and/or C$_{1-3}$alkyl, wherein said heteroaryl comprises 1 to 2 heteroatoms;

R$^6$ is H, halo, or —CN;
R$^7$ is:
(i) halo;
(ii) —CN;
(iii) C$_{1-4}$alkyl with zero to 1 C$_{1-3}$alkoxy group;
(iv) C$_{1-4}$fluoroalkyl or C$_{1-4}$hydroxyalkyl;
(v) C$_{2-4}$alkenyl;
(vi) C$_{1-4}$alkoxy substituted with zero to 2 substituents independently selected from halo, —NR$^b$R$^c$, phenyl, C$_{3-6}$cycloalkyl, and/or C$_{1-3}$alkoxy;
(vii) C$_{3-6}$cycloalkyl;
(viii) —S(C$_{1-3}$alkyl);
(ix) —NH(C$_{1-3}$fluoroalkyl);
(x) —C(O)(pyrrolidinyl);
(xi) phenyl; or
(xii) 3- to 6-membered heterocyclyl substituted with zero to 2 substituents independently selected from halo and/or C$_{1-3}$alkyl, wherein said heterocyclyl group comprises 1 to 3 heteroatoms;

R$^8$ is —S(O)$_2$(phenyl);
each R$^a$ is independently halo and/or C$_{1-3}$fluoroalkyl;
each R$^b$ is independently H and/or C$_{1-3}$alkyl;
each R$^c$ is independently H and/or C$_{1-3}$alkyl; and
each R$^d$ is independently H, C$_{1-3}$alkyl, and/or phenyl substituted with zero to 2 substituents independently selected from halo and/or C$_{1-3}$alkoxy; or
R$^c$ and R$^d$ together with the nitrogen atom to which they are attached form a 5- to 6-membered heterocyclyl having zero to 1 additional heteroatom independently selected from N and/or O, wherein said heterocyclyl may be substituted with zero to 1 hydroxyl group.

In another embodiment, the present disclosure provides a compound of Formula (Ia):

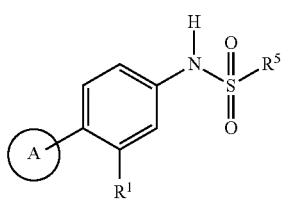

(Ia)

or a stereoisomer, an N-oxide, a prodrug, or a pharmaceutically acceptable salt thereof, wherein:
ring A is:

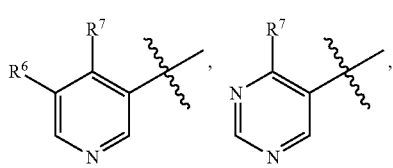

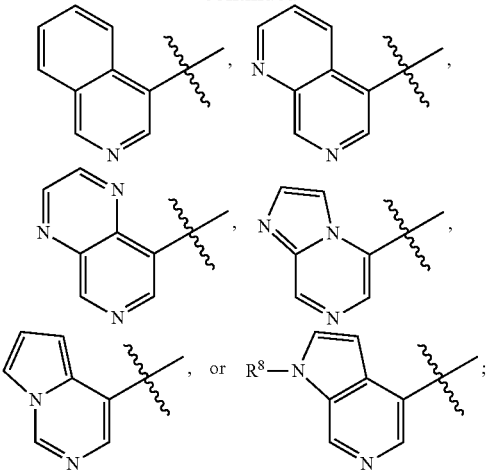

R$^1$ is H, halo, —OH, C$_{1-3}$alkyl, C$_{1-3}$fluoroalkyl, C$_{1-3}$alkoxy, C$_{1-3}$fluoroalkoxy, C$_{1-4}$hydroxyalkyl, or —C(O)O(C$_{1-3}$alkyl);

R$^5$ is:
(i) C$_{1-6}$alkyl substituted with zero to 3 substituents independently selected from halo, phenyl, isoindoline-1,3-dione, and/or camphor, wherein said phenyl may be substituted with zero to 3 R$^a$;
(ii) C$_{2-6}$alkenyl substituted with phenyl;
(iii) C$_{3-6}$cycloalkyl;
(iv) adamantanyl;
(v) —NR$^c$R$^d$;
(vi) phenyl substituted with zero to 3 substituents independently selected from halo, —CN, —NO$_2$, C$_{1-4}$alkyl, C$_{1-4}$fluoroalkyl, C$_{1-4}$alkoxy, —C(O)O(C$_{1-4}$alkyl), —NHC(O)(C$_{1-4}$alkyl), phenyl, and/or phenoxy;
(vii) naphthalenyl; or
(viii) 5- to 10-membered heteroaryl substituted with zero to 2 substituents independently selected from —C(O)(C$_{1-3}$alkyl), —C(O)O(C$_{1-3}$alkyl), and/or C$_{1-3}$alkyl, wherein said heteroaryl comprises 1 to 2 heteroatoms;

R$^6$ is H, halo, or —CN;
R$^7$ is:
(i) halo;
(ii) —CN;
(iii) C$_{1-4}$alkyl substituted with zero to 1 C$_{1-3}$alkoxy group;
(iv) C$_{1-4}$fluoroalkyl or C$_{1-4}$hydroxyalkyl;
(v) C$_{2-4}$alkenyl;
(vi) C$_{1-4}$alkoxy substituted with zero to 2 substituents independently selected from halo, —NR$^b$R$^c$, phenyl, C$_{3-6}$cycloalkyl, and/or C$_{1-3}$alkoxy;
(vii) C$_{3-6}$cycloalkyl;
(viii) —S(C$_{1-3}$alkyl);
(ix) —NH(C$_{1-3}$fluoroalkyl);
(x) —C(O)(pyrrolidinyl);
(xi) phenyl; or
(xii) pyrrolidinyl or morpholinyl;

R$^8$ is —S(O)$_2$(phenyl);
each R$^a$ is independently halo and/or C$_{1-3}$fluoroalkyl;
each R$^b$ is independently H and/or C$_{1-3}$alkyl;
each R$^c$ is independently H and/or C$_{1-3}$alkyl; and
each R$^d$ is independently H, C$_{1-3}$alkyl, and/or phenyl substituted with zero to 2 substituents independently selected from halo and/or C$_{1-3}$alkoxy; or
R$^c$ and R$^d$ together with the nitrogen atom to which they are attached form a 5- to 6-membered heterocyclyl having zero to 1 additional heteroatom independently selected from N and/or O, wherein said heterocyclyl may be substituted with zero to 1 hydroxyl group.

In another embodiment, the present disclosure provides a compound of Formula (Ia):

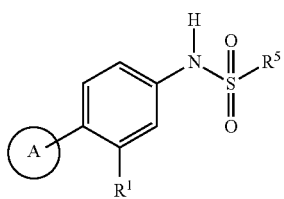

or a stereoisomer, an N-oxide, a prodrug, or a pharmaceutically acceptable salt thereof, wherein:
ring A is:

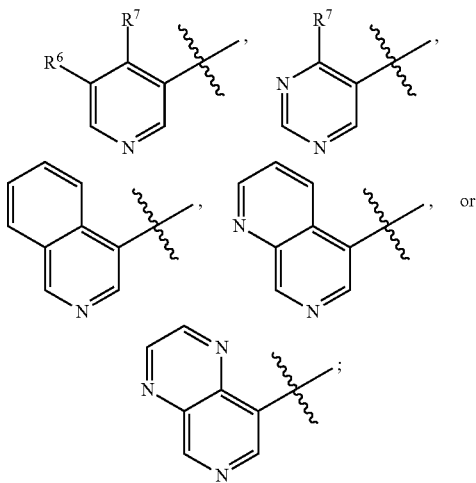

$R^1$ is H, halo, —OH, $C_{1-3}$alkyl, $C_{1-3}$fluoroalkyl, $C_{1-3}$alkoxy, $C_{1-3}$fluoroalkoxy, $C_{1-4}$hydroxyalkyl, or —C(O)O($C_{1-3}$alkyl);

$R^5$ is:
(i) $C_{1-6}$alkyl substituted with zero to 3 substituents independently selected from halo, phenyl, isoindoline-1,3-dione, and/or camphor, wherein said phenyl may be substituted with zero to 3 $R^a$;
(ii) $C_{2-6}$alkenyl substituted with phenyl;
(iii) $C_{3-6}$cycloalkyl;
(iv) adamantanyl;
(v) —$NR^cR^d$;
(vi) phenyl substituted with zero to 3 substituents independently selected from halo, —CN, —$NO_2$, $C_{1-4}$alkyl, $C_{1-4}$fluoroalkyl, $C_{1-4}$alkoxy, —C(O)O($C_{1-4}$alkyl), —NHC(O)($C_{1-4}$alkyl), phenyl, and/or phenoxy;
(vii) naphthalenyl; or
(viii) 5- to 10-membered heteroaryl substituted with zero to 2 substituents independently selected from —C(O)($C_{1-3}$alkyl), —C(O)O($C_{1-3}$alkyl), and/or $C_{1-3}$alkyl, wherein said heteroaryl comprises 1 to 2 heteroatoms;

$R^6$ is H, halo, or —CN;
$R^7$ is:
(i) halo;
(ii) —CN;
(iii) $C_{1-4}$alkyl substituted with zero to 1 $C_{1-3}$alkoxy group;
(iv) $C_{1-4}$fluoroalkyl or $C_{1-4}$hydroxyalkyl;
(v) $C_{2-4}$alkenyl;
(vi) $C_{1-4}$alkoxy substituted with zero to 2 substituents independently selected from halo, —$NR^bR^c$, phenyl, $C_{3-6}$cycloalkyl, and/or $C_{1-3}$alkoxy;
(vii) $C_{3-6}$cycloalkyl;
(viii) —S($C_{1-3}$alkyl);
(ix) —NH($C_{1-3}$fluoroalkyl);
(x) —C(O)(pyrrolidinyl);
(xi) phenyl; or
(xii) pyrrolidinyl or morpholinyl;

each $R^a$ is independently halo and/or $C_{1-3}$fluoroalkyl;
each $R^b$ is independently H and/or $C_{1-3}$alkyl;
each $R^c$ is independently H and/or $C_{1-3}$alkyl; and
each $R^d$ is independently H, $C_{1-3}$alkyl, and/or phenyl substituted with zero to 2 substituents independently selected from halo and/or $C_{1-3}$alkoxy; or
$R^c$ and $R^d$ together with the nitrogen atom to which they are attached form a 5- to 6-membered heterocyclyl having zero to 1 additional heteroatom independently selected from N and/or O, wherein said heterocyclyl may be substituted with zero to 1 hydroxyl group.

In another embodiment, the present disclosure provides a compound of Formula (Ia):

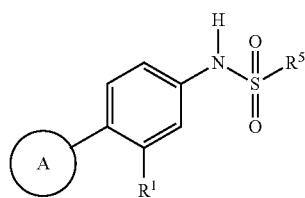

or a stereoisomer, an N-oxide, a prodrug, or a pharmaceutically acceptable salt thereof, wherein:
ring A is:

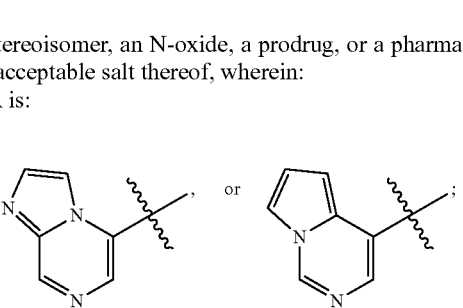

$R^1$ is H, halo, —OH, $C_{1-3}$alkyl, $C_{1-3}$fluoroalkyl, $C_{1-3}$alkoxy, $C_{1-3}$fluoroalkoxy, $C_{1-4}$hydroxyalkyl, or —C(O)O($C_{1-3}$alkyl);

$R^5$ is:
(i) $C_{1-6}$alkyl substituted with zero to 3 substituents independently selected from halo, phenyl, isoindoline-1,3-dione, and/or camphor, wherein said phenyl may be substituted with zero to 3 $R^a$;
(ii) $C_{2-6}$alkenyl substituted with phenyl;
(iii) $C_{3-6}$cycloalkyl;
(iv) adamantanyl;
(v) —$NR^cR^d$;
(vi) phenyl substituted with zero to 3 substituents independently selected from halo, —CN, —$NO_2$, $C_{1-4}$alkyl, $C_{1-4}$fluoroalkyl, $C_{1-4}$alkoxy, —C(O)O($C_{1-4}$alkyl), —NHC(O)($C_{1-4}$alkyl), phenyl, and/or phenoxy;
(vii) naphthalenyl; or
(viii) 5- to 10-membered heteroaryl substituted with zero to 2 substituents independently selected from —C(O)

(C$_{1-3}$alkyl), —C(O)O(C$_{1-3}$alkyl), and/or C$_{1-3}$alkyl, wherein said heteroaryl comprises 1 to 2 heteroatoms;

each R$^a$ is independently halo and/or C$_{1-3}$fluoroalkyl;

each R$^c$ is independently H and/or C$_{1-3}$alkyl; and each R$^d$ is independently H, C$_{1-3}$alkyl, and/or phenyl substituted with zero to 2 substituents independently selected from halo and/or C$_{1-3}$alkoxy; or R$^c$ and R$^d$ together with the nitrogen atom to which they are attached form a 5- to 6-membered heterocyclyl having zero to 1 additional heteroatom independently selected from N and/or O, wherein said heterocyclyl may be substituted with zero to 1 hydroxyl group.

In another embodiment, the present disclosure provides a compound having Formula (Ib), (Ic), or (Id), or a stereoisomer, an N-oxide, a prodrug, or a pharmaceutically acceptable salt thereof, wherein the substituents R$^1$, R$^5$, and R$^7$, as they appear, are selected from the designated groups as recited elsewhere herein:

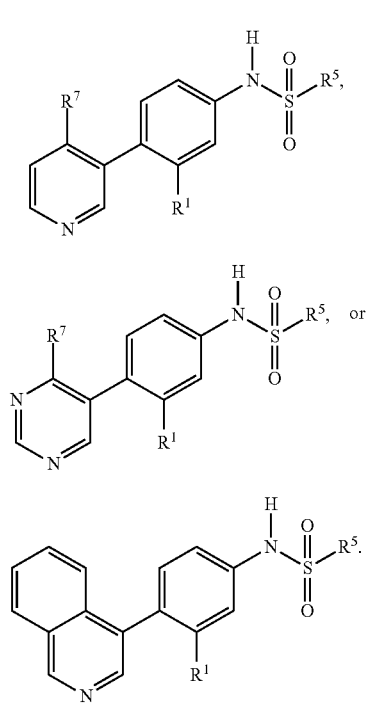

In another embodiment, the present disclosure provides a compound having Formula (Ia), (Ib), (Ic), or (Id), or a stereoisomer, an N-oxide, a prodrug, or a pharmaceutically acceptable salt thereof, wherein:

R$^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, —OCH$_2$CF$_3$, or —C(CH$_3$)$_2$OH;

R$^5$ is:
- (i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);
- (ii) —CH=CH$_2$(phenyl);
- (iii) cyclopropyl;
- (iv) adamantanyl;
- (v) —NH(CH$_3$), —NH(phenyl), —N(CH$_3$)(chlorophenyl), —NH(methoxyphenyl),

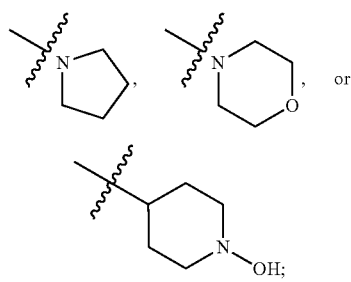

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;

(vii) naphthalenyl; or (viii)

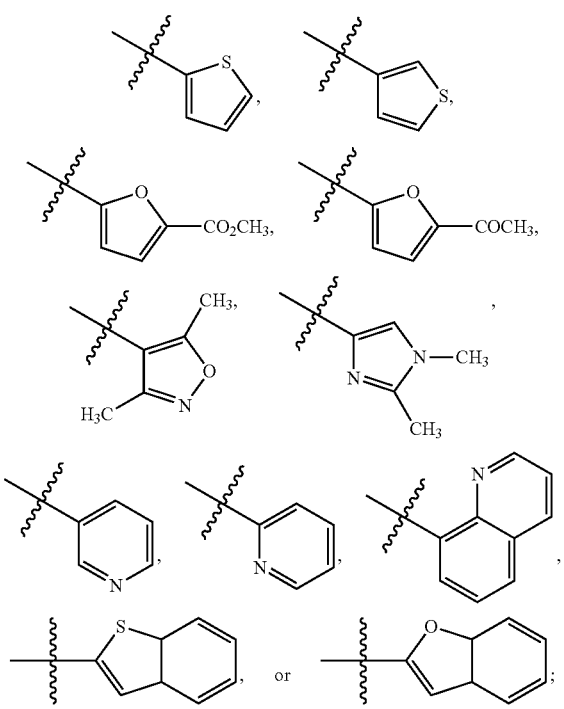

R$^6$ is H;

R$^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$, —CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), cyclopropyl, —O(CH$_2$)(cyclopropyl), cyclohexyl, phenyl,

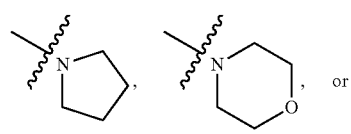

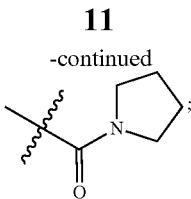

and

R⁸ is —S(O)₂(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein:

R¹ is H, Cl, —CH₃, —CF₃, —OH, —OCH₃, —OCH₂CH₃, —OCF₃, —OCH₂CH₂F, —OCH₂CHF₂, or —OCH₂CF₃;

R⁵ is:

(i) —CH₃, —CH₂CH₃, —(CH₂)₂CH₃, —CH(CH₃)₂, —(CH₂)₃CH₃, —CH₂CH(CH₃)₂, —CH₂CF₃, —CH₂(phenyl), —(CH₂)₂(phenyl), —CH₂(camphor), —CH₂(chlorophenyl), —CH₂(di-chlorophenyl), or —CH₂(trifluoromethylphenyl);

(ii) —CH=CH₂(phenyl);

(iii) cyclopropyl;

(iv) adamantanyl;

(v) —NH(CH₃), —NH(phenyl), —N(CH₃)(chlorophenyl), —NH(methoxyphenyl),

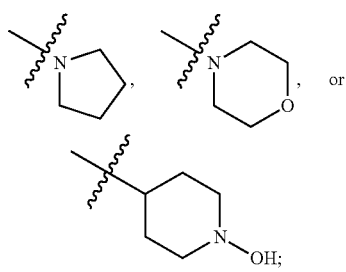

(vi) phenyl substituted with zero to 3 substituents independently selected from F, Cl, Br, —CH₃, —CF₃, —OCH₃, —CN, —NO₂, —CH(CH₃)₂, —C(O)OCH₃, —NHC(O)CH₃, phenyl, and/or phenoxy; or (vii)

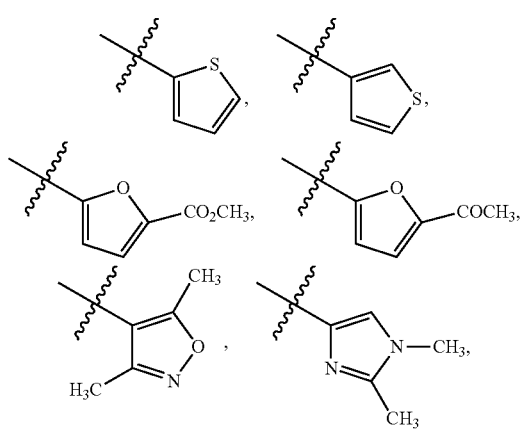

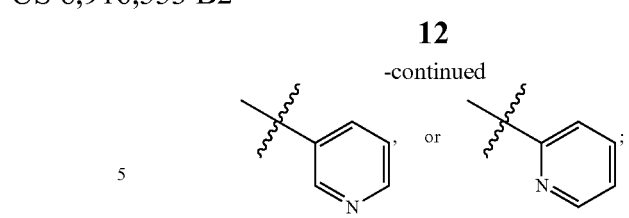

R⁶ is H;

R⁷ is F, Cl, —CN, —CH₃, —CH₂CH₃, —CH(CH₃)₂, —(CH₂)₂CH₃, —CF₃, —CHF₂, —CH₂OH, —CH₂OCH₃, —CH(CH₃)=CH₂, —SCH₃, —NHCH₂CF₃, —OCH₃, —OCH₂CH₃, —OCH(CH₃)₂, —OCH₂CF₃, —OCH₂CH₂F, —OCH₂CHF₂, —O(CH₂)₂N(CH₃)₂, —O(CH₂)₂OCH₃, —O(CH₂)₂(phenyl), —O(CH₂)(cyclopropyl), cyclopropyl, cyclohexyl,

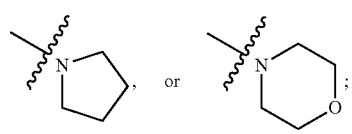

and

R⁸ is —S(O)₂(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein:

R¹ is H, Cl, —CH₃, —CF₃, —OH, —OCH₃, —OCH₂CH₃, —OCF₃, —OCH₂CH₂F, —OCH₂CHF₂, or —OCH₂CF₃;

R⁵ is:

(i) —CH₃, —CH₂CH₃, —(CH₂)₂CH₃, —CH(CH₃)₂, —(CH₂)₃CH₃, —CH₂CH(CH₃)₂, —CH₂CF₃, —CH₂(phenyl), —(CH₂)₂(phenyl), —CH₂(camphor), —CH₂(chlorophenyl), —CH₂(di-chlorophenyl), or —CH₂(trifluoromethylphenyl);

(ii) —CH=CH₂(phenyl);

(iii) cyclopropyl;

(iv) adamantanyl;

(v)

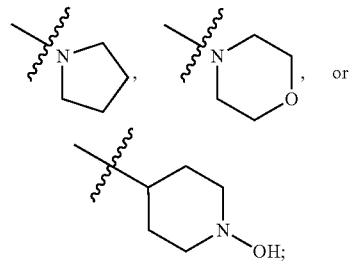

(vi) phenyl substituted with zero to 3 substituents independently selected from F, Cl, Br, —CH₃, —CF₃, —OCH₃, —CN, —NO₂, —CH(CH₃)₂, —C(O)OCH₃, —NHC(O)CH₃, phenyl, and/or phenoxy;

(vii) naphthalenyl; or (viii)

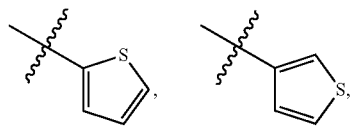

-continued

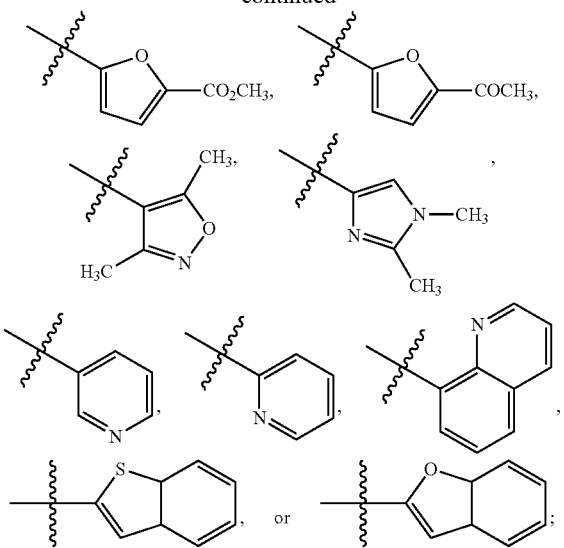

$R^6$ is H;
$R^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$, —CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), —O(CH$_2$)(cyclopropyl), cyclopropyl, cyclohexyl,

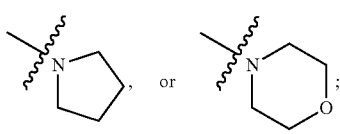

and
$R^8$ is —S(O)$_2$(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein:
$R^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;
$R^5$ is:
(i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);
(ii) —CH=CH$_2$(phenyl);
(iii) cyclopropyl;
(iv) adamantanyl;
(v) —NH(CH$_3$), —NH(phenyl), —N(CH$_3$)(chlorophenyl), or —NH(methoxyphenyl);
$R^6$ is H;
$R^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$, —CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), —O(CH$_2$)(cyclopropyl), cyclopropyl, cyclohexyl,

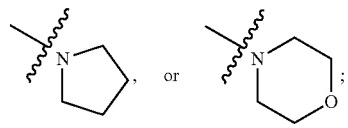

and
$R^8$ is —S(O)$_2$(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein:
$R^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;
$R^5$ is:
(i)

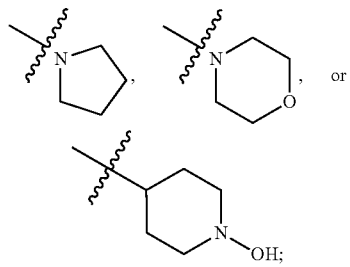

(ii) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;
(iii) naphthalenyl; or
(iv)

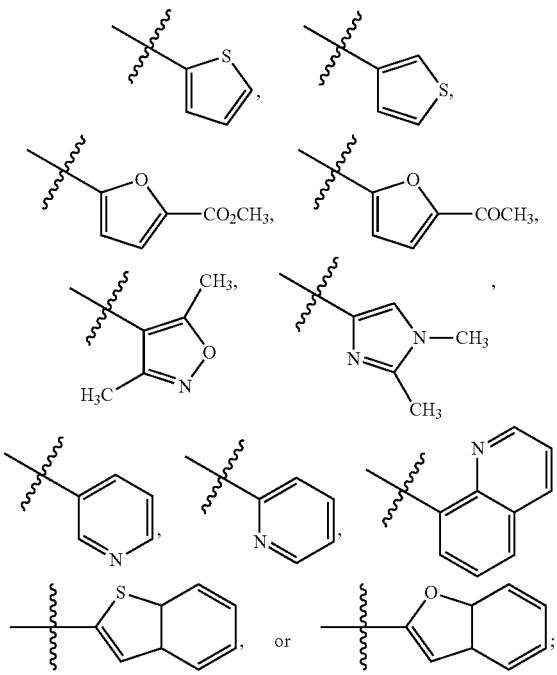

$R^6$ is H;
$R^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$,

—CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), —O(CH$_2$)(cyclopropyl), cyclopropyl, cyclohexyl,

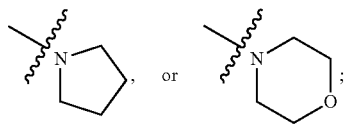

and

R$^8$ is —S(O)$_2$(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein:

R$^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;

R$^5$ is:

(i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);

(ii) —CH=CH$_2$(phenyl);

(iii) cyclopropyl;

(iv) adamantanyl;

(v) —NH(CH$_3$), —NH(phenyl), —N(CH$_3$)(chlorophenyl), —NH(methoxyphenyl),

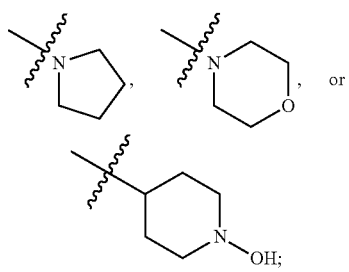

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;

(vii) naphthalenyl; or (viii)

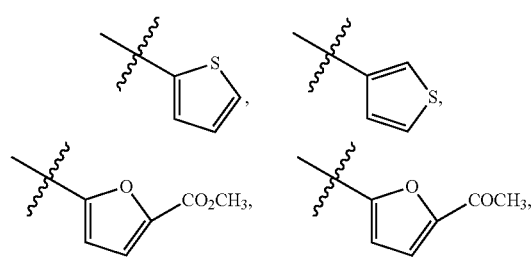

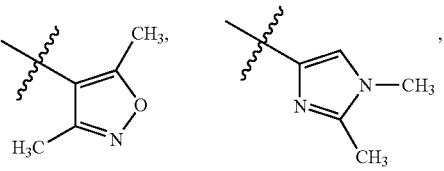

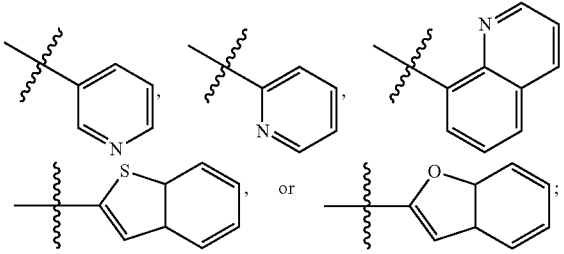

R$^6$ is H;

R$^7$ is —CH$_3$; and

R$^8$ is —S(O)$_2$(phenyl).

In another embodiment, the present disclosure provides a compound having Formula (Ia), (Ib), (Ic), or (Id), or a stereoisomer, an N-oxide, a prodrug, or a pharmaceutically acceptable salt thereof, wherein R$^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;

R$^5$ is phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;

R$^6$ is H; and

R$^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$, —CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), —O(CH$_2$)(cyclopropyl), cyclopropyl, cyclohexyl,

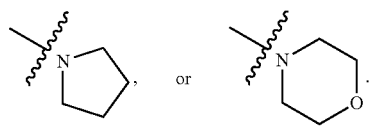

In another embodiment, the present disclosure provides a compound having Formula (Ia), (Ib), (Ic), or (Id), or a stereoisomer, an N-oxide, a prodrug, or a pharmaceutically acceptable salt thereof, wherein:

R$^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;

R$^5$ is —CH$_3$;

R$^6$ is H; and

R$^7$ is F, Cl, —CN, —CH$_3$, —CH$_2$CH$_3$, —CH(CH$_3$)$_2$, —(CH$_2$)$_2$CH$_3$, —CF$_3$, —CHF$_2$, —CH$_2$OH, —CH$_2$OCH$_3$, —CH(CH$_3$)=CH$_2$, —SCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)$_2$N(CH$_3$)$_2$, —O(CH$_2$)$_2$OCH$_3$, —O(CH$_2$)$_2$(phenyl), —O(CH$_2$)(cyclopropyl), cyclopropyl, cyclohexyl,

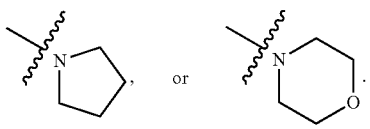

In another embodiment, the present disclosure provides a compound having Formula (Ib), (Ic), or (Id), or a stereoisomer, an N-oxide, a prodrug, or a pharmaceutically acceptable salt thereof, wherein:
$R^1$ is —CH$_3$, —OCH$_3$, —OCH$_2$CH$_2$F, or —OCH$_2$CHF$_2$;
$R^5$ is —CH$_3$; and
$R^7$ is Cl, —CH$_3$, —CH$_2$OH, —OCH$_3$, —OCH$_2$CF$_3$, or cyclopropyl.

In another embodiment, the present disclosure provides a compound having Formula (Ib), or a stereoisomer, an N-oxide, a prodrug, or a pharmaceutically acceptable salt thereof, wherein:
$R^1$ is H, Cl, —CH$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;
$R^5$ is:
(i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);
(ii) —CH=CH$_2$(phenyl);
(iii) cyclopropyl;
(iv) adamantanyl;
(v) —NH(CH$_3$), —NH(phenyl), —N(CH$_3$)(chlorophenyl), —NH(methoxyphenyl),

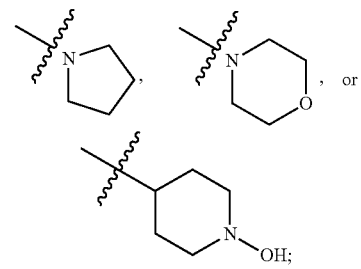

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;
(vii) naphthalenyl; or
(viii)

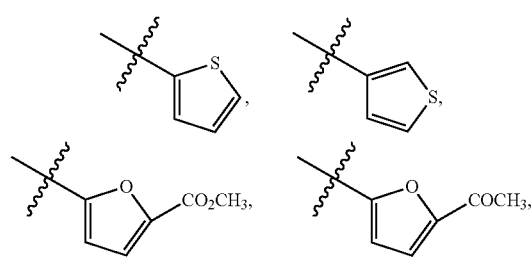

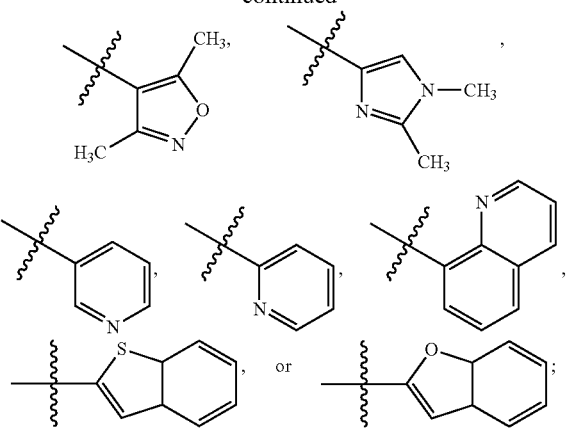

and
$R^7$ is F, Cl, —CH$_3$, —CH$_2$CH$_3$, —(CH$_2$)$_2$CH$_3$, —CF$_3$, —CHF$_2$, —CH$_2$OH, —CH$_2$OCH$_3$, —NHCH$_2$CF$_3$, —OCH$_3$, —OCH$_2$CH$_3$, —OCH$_2$CF$_3$, —OCH$_2$CH$_2$F, —OCH$_2$CHF$_2$, —O(CH$_2$)(cyclopropyl), or cyclopropyl.

In another embodiment, the present disclosure provides a compound having Formula (Ib), or a stereoisomer, an N-oxide, a prodrug, or a pharmaceutically acceptable salt thereof, wherein:
$R^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;
$R^5$ is —CH$_3$; and
$R^7$ is F, Cl, —CH$_3$, —CH$_2$CH$_3$, —(CH$_2$)$_2$CH$_3$, —CF$_3$, —CHF$_2$, —CH$_2$OH, —CH$_2$OCH$_3$, —NHCH$_2$CF$_3$, —OCH$_3$, —OCH$_2$CH$_3$, —OCH$_2$CF$_3$, —OCH$_2$CH$_2$F, —OCH$_2$CHF$_2$, —O(CH$_2$)(cyclopropyl), or cyclopropyl.

In another embodiment, the present disclosure provides a compound having Formula (Ib), or a stereoisomer, an N-oxide, a prodrug, or a pharmaceutically acceptable salt thereof, wherein:
$R^1$ is —CH$_3$, —OCH$_3$, —OCH$_2$CH$_2$F, or —OCH$_2$CHF$_2$;
$R^5$ is —CH$_3$; and
$R^7$ is F, Cl, —CH$_3$, —CH$_2$CH$_3$, —(CH$_2$)$_2$CH$_3$, —CF$_3$, —CHF$_2$, —CH$_2$OH, —CH$_2$OCH$_3$, —NHCH$_2$CF$_3$, —OCH$_3$, —OCH$_2$CH$_3$, —OCH$_2$CF$_3$, —OCH$_2$CH$_2$F, —OCH$_2$CHF$_2$, —O(CH$_2$)(cyclopropyl), or cyclopropyl.

In another embodiment, the present disclosure provides a compound having Formula (Ib), or a stereoisomer, an N-oxide, a prodrug, or a pharmaceutically acceptable salt thereof, wherein:
$R^1$ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, or —OCH$_2$CF$_3$;
$R^5$ is —CH$_3$; and
$R^7$ is Cl, —CH$_3$, —CH$_2$OH, —OCH$_3$, or —OCH$_2$CF$_3$.

In another embodiment, the present disclosure provides a compound having Formula (Ib), or a stereoisomer, an N-oxide, a prodrug, or a pharmaceutically acceptable salt thereof, wherein:
$R^1$ is —CH$_3$, —OCH$_3$, —OCH$_2$CH$_2$F, or —OCH$_2$CHF$_2$;
$R^5$ is —CH$_3$; and
$R^7$ is Cl, —CH$_3$, —CH$_2$OH, —OCH$_3$, or —OCH$_2$CF$_3$.

In another embodiment, the present disclosure provides a compound having Formula (Ic), or a stereoisomer, an N-oxide, a prodrug, or a pharmaceutically acceptable salt thereof, wherein:
$R^1$ is —OCH$_3$;
$R^5$ is:
(i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$ (phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);

(ii) —CH=CH$_2$(phenyl);

(iii) cyclopropyl;

(iv) adamantanyl;

(v) —NH(CH$_3$), —NH(phenyl), —N(CH$_3$)(chlorophenyl), —NH(methoxyphenyl),

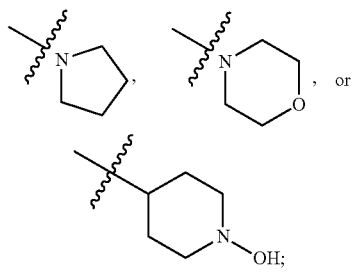

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy;

(vii) naphthalenyl; or (viii)

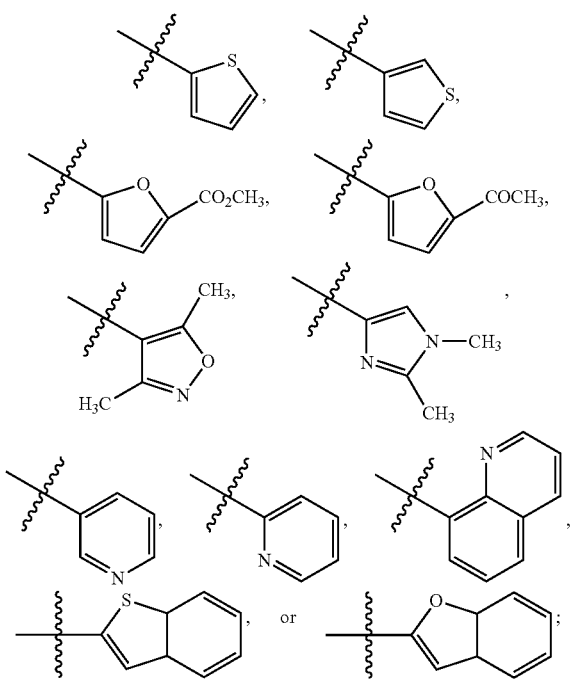

and

R$^7$ is —CH$_3$, —CH$_2$CH$_3$, —CH(CH$_3$)$_2$, —(CH$_2$)$_2$CH$_3$, —NHCH$_2$CF$_3$, —OCH$_3$, —OCH$_2$CH$_3$, —OCH$_2$CF$_3$, cyclopropyl, cyclohexyl,

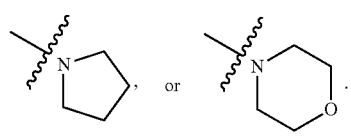

In another embodiment, the present disclosure provides a compound having Formula (Ic), or a stereoisomer, an N-oxide, a prodrug, or a pharmaceutically acceptable salt thereof, wherein:

R$^1$ is —OCH$_3$;

R$^5$ is:

(i) —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);

(ii) —CH=CH$_2$(phenyl);

(iii) cyclopropyl;

(iv) adamantanyl;

(v) —NH(CH$_3$), —NH(phenyl), —N(CH$_3$)(chlorophenyl), —NH(methoxyphenyl),

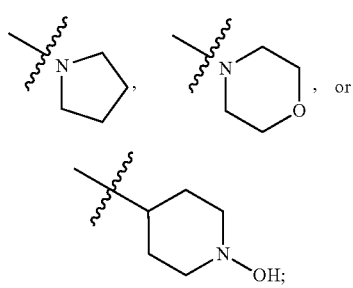

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy; or (vii)

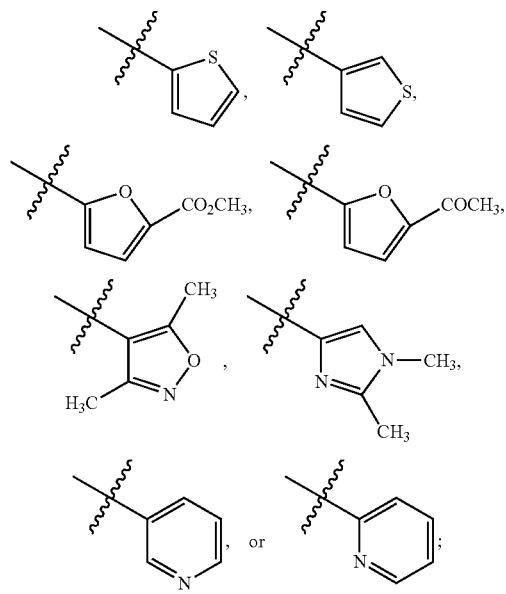

and

R$^7$ is —CH$_3$, —CH$_2$CH$_3$, —CH(CH$_3$)$_2$, —(CH$_2$)$_2$CH$_3$, —NHCH$_2$CF$_3$, —OCH$_3$, —OCH$_2$CH$_3$, —OCH$_2$CF$_3$, cyclopropyl, cyclohexyl,

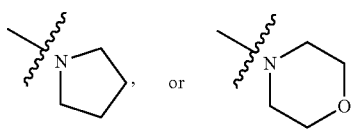

In another embodiment, the present disclosure provides a compound having Formula (Ic), or a stereoisomer, an N-oxide, a prodrug, or a pharmaceutically acceptable salt thereof, wherein:
$R^1$ is —$OCH_3$;
$R^5$ is —$CH_3$, —$(CH_2)_2CH_3$, —$CH_2CH(CH_3)_2$, —$CH_2CF_3$, —$CH_2$(phenyl), —$(CH_2)_2$(phenyl), —$CH_2$(chlorophenyl), naphthalenyl,

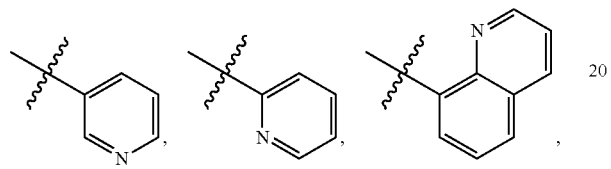

or phenyl substituted with zero to 1 substituents independently selected from Cl, —$OCH_3$, and/or phenoxy; and
$R^7$ is —$CH_3$, —$CH_2CH_3$, —$CH(CH_3)_2$, —$(CH_2)_2CH_3$, —$NHCH_2CF_3$, —$OCH_3$, —$OCH_2CH_3$, —$OCH_2CF_3$, cyclopropyl, cyclohexyl,

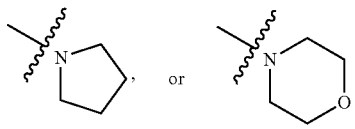

In another embodiment, the present disclosure provides a compound having Formula (Ic), or a stereoisomer, an N-oxide, a prodrug, or a pharmaceutically acceptable salt thereof, wherein:
$R^1$ is —$OCH_3$;
$R^5$ is —$CH_3$; and
$R^7$ is —$CH_3$, —$CH_2CH_3$, —$CH(CH_3)_2$, —$(CH_2)_2CH_3$, —$NHCH_2CF_3$, —$OCH_3$, —$OCH_2CH_3$, —$OCH_2CF_3$, cyclopropyl, cyclohexyl,

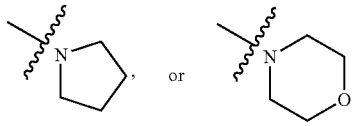

In another embodiment, the present disclosure provides a compound having Formula (Ic), or a stereoisomer, an N-oxide, a prodrug, or a pharmaceutically acceptable salt thereof, wherein:
$R^1$ is —$OCH_3$;
$R^5$ is —$CH_3$; and
$R^7$ is —$CH_3$, —$OCH_2CF_3$, or cyclopropyl.

In another embodiment, the present disclosure provides a compound having Formula (Id), or a stereoisomer, an N-oxide, a prodrug, or a pharmaceutically acceptable salt thereof, wherein:
$R^1$ is H, —$CH_3$, —$CF_3$, —$OCH_3$, —$OCF_3$, —$OCH_2CH_2F$, or —$OCH_2CF_3$; and $R^5$ is:
(i) —$CH_3$, —$CH_2CH_3$, —$(CH_2)_2CH_3$, —$CH(CH_3)_2$, —$(CH_2)_3CH_3$, —$CH_2CH(CH_3)_2$, —$CH_2CF_3$, —$CH_2$(phenyl), —$(CH_2)_2$(phenyl), —$CH_2$(camphor), —$CH_2$(chlorophenyl), —$CH_2$(di-chlorophenyl), or —$CH_2$(trifluoromethylphenyl);
(ii) —CH═$CH_2$(phenyl);
(iii) cyclopropyl;
(iv) adamantanyl;
(v) —NH($CH_3$), —NH(phenyl), —N($CH_3$)(chlorophenyl), —NH(methoxyphenyl),

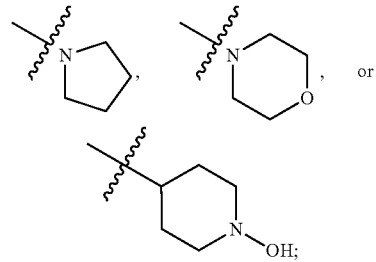

(vi) phenyl substituted with zero to 3 substituents independently selected from F, Cl, Br, —$CH_3$, —$CF_3$, —$OCH_3$, —CN, —$NO_2$, —$CH(CH_3)_2$, —$C(O)OCH_3$, —NHC(O)$CH_3$, phenyl, and/or phenoxy;
(vii) naphthalenyl; or
(viii)

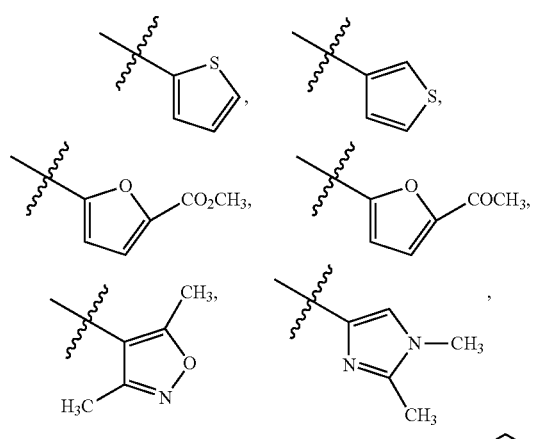

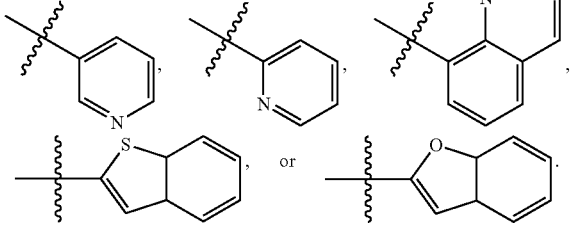

In another embodiment, the present disclosure provides a compound having Formula (Id), or a stereoisomer, an N-oxide, a prodrug, or a pharmaceutically acceptable salt thereof, wherein:
$R^1$ is H, —$CH_3$, —$CF_3$, —$OCH_3$, —$OCF_3$, —$OCH_2CH_2F$, or —$OCH_2CF_3$; and
$R^5$ is —$CH_3$, —$CH_2CH_3$, —$(CH_2)_2CH_3$, —$CH_2CH(CH_3)_2$, —$CH_2CF_3$, —$CH_2$(phenyl), —$(CH_2)_2$(phenyl), cyclopropyl, naphthalenyl,

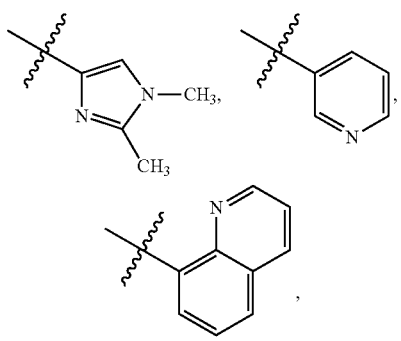

or phenyl substituted with zero to 1 substituents independently selected from Cl, —CN, —OCH$_3$, and/or phenoxy.

In another embodiment, the present disclosure provides a compound having Formula (Id), or a stereoisomer, an N-oxide, a prodrug, or a pharmaceutically acceptable salt thereof, wherein:

R$^1$ is H, —CH$_3$, —CF$_3$, —OCH$_3$, —OCF$_3$, —OCH$_2$CH$_2$F, or —OCH$_2$CF$_3$; and R$^5$ is —CH$_3$.

In another embodiment, the present disclosure provides a compound having Formula (Id), or a stereoisomer, an N-oxide, a prodrug, or a pharmaceutically acceptable salt thereof, wherein:

R$^1$ is —OCF$_3$, —OCH$_2$CH$_2$F, or —OCH$_2$CF$_3$; and

R$^5$ is —CH$_3$.

For each of the embodiments described in the present application, further and more particular values of the various groups used in each of the embodiments may be selected from the following definitions, these values may be used individually in any of the embodiments or in any combination.

In certain embodiments, the R$^1$ group of any of Formulae (I), (Ia), (Ib), (Ic), and (Id) is H, halo, —OH, C$_{1-3}$alkyl, C$_{1-3}$haloalkyl, C$_{1-3}$alkoxy, C$_{1-3}$haloalkoxy, C$_{1-4}$hydroxyalkyl, or —C(O)O(C$_{1-3}$alkyl).

In other embodiments, the R$^1$ group of any of Formulae (I), (Ia), (Ib), (Ic), and (Id) is H, halo, —OH, C$_{1-3}$alkyl, C$_{1-3}$fluoroalkyl, C$_{1-3}$alkoxy, or C$_{1-3}$fluoroalkoxy.

In other embodiments, the R$^1$ group of any of Formulae (I), (Ia), (Ib), (Ic), and (Id) is H, Cl, —OH, —CH$_3$, —CF$_3$, —CH$_3$O, —OCH$_2$CH$_3$, —OCF$_3$, —OCH$_2$CH$_2$F, —OCH$_2$CHF$_2$, or —OCH$_2$CF$_3$.

In other embodiments, the R$^1$ group of any of Formulae (I), (Ia), (Ib), (Ic), and (Id) is H, Cl, —CH$_3$, —CF$_3$, —CH$_3$O, —OCF$_3$, —OCH$_2$CH$_2$F, or —OCH$_2$CF$_3$.

In other embodiments, the R$^1$ group of any of Formulae (I), (Ia), (Ib), (Ic), and (Id) is —OCH$_3$.

In other embodiments, the R$^1$ group of any of Formulae (I), (Ia), (Ib), (Ic), and (Id) is —CH$_3$.

In other embodiments, the R$^1$ group of any of Formulae (I), (Ia), (Ib), (Ic), and (Id) is H.

In certain embodiments, the R$^5$ group of any of Formulae (I), (Ia), (Ib), (Ic), and (Id) is C$_{1-4}$alkyl, C$_{1-4}$fluoroalkyl, C$_{1-2}$alkyl(phenyl), C$_{1-2}$alkyl(chlorophenyl), C$_{1-2}$alkyl (trifluoromethylphenyl), —CH=CH$_2$(phenyl), C$_{3-6}$cycloalkyl, adamantanyl, —NH(CH$_3$), —NH(phenyl), —N(CH$_3$)(chlorophenyl), —NH(methoxyphenyl), naphthalenyl,

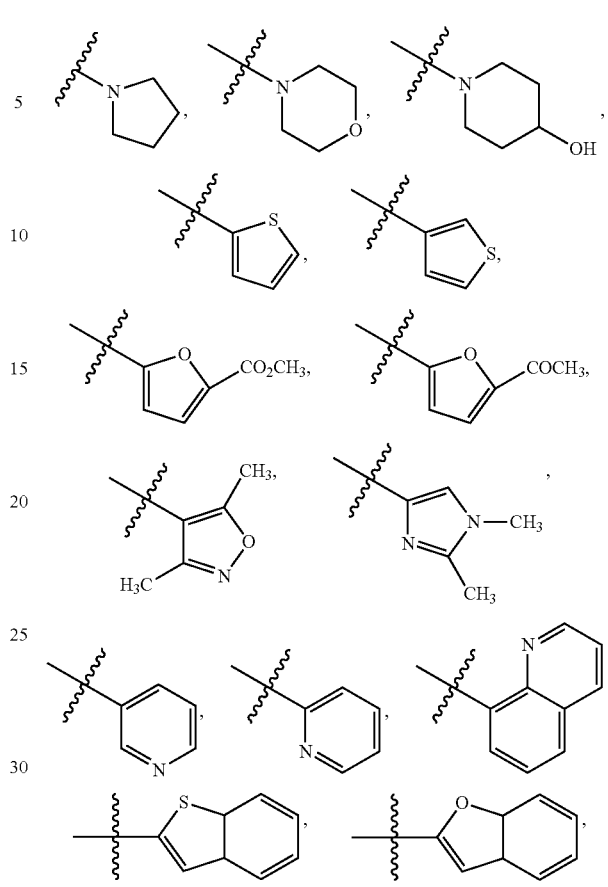

or phenyl substituted with zero to 3 substituents independently selected from halo, —CN, —NO$_2$, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy.

In other embodiments, the R$^5$ group of any of Formulae (I), (Ia), (Ib), (Ic), and (Id) is

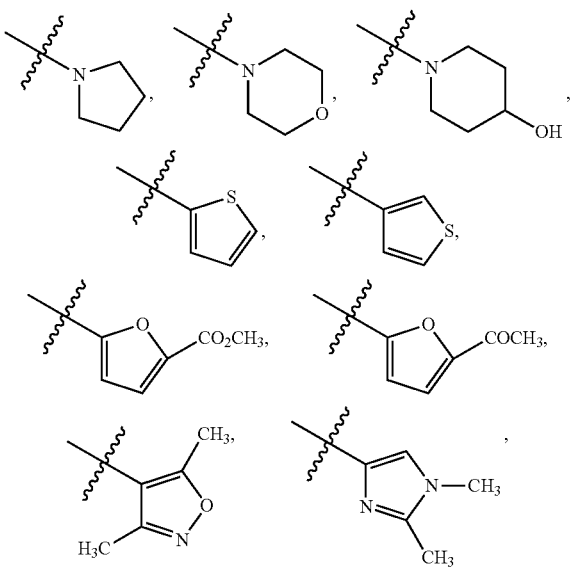

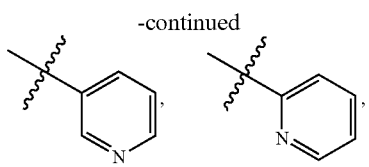

or phenyl substituted with zero to 2 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy.

In other embodiments, the R$^5$ group of any of Formulae (I), (Ia), (Ib), (Ic), and (Id) is phenyl substituted with zero to 2 substituents independently selected from F, Cl, Br, —CH$_3$, —CF$_3$, —OCH$_3$, —CN, —NO$_2$, —CH(CH$_3$)$_2$, —C(O)OCH$_3$, —NHC(O)CH$_3$, phenyl, and/or phenoxy.

In other embodiments, the R$^5$ group of any of Formulae (I), (Ia), (Ib), (Ic), and (Id) is C$_{1-4}$alkyl, C$_{1-4}$fluoroalkyl, C$_{1-2}$alkyl(phenyl), C$_{1-2}$alkyl(chlorophenyl), C$_{1-2}$alkyl(trifluoromethylphenyl), —CH═CH$_2$(phenyl), C$_{3-6}$cycloalkyl, adamantanyl, —NH(CH$_3$), —NH(phenyl), —N(CH$_3$)(chlorophenyl), or —NH(methoxyphenyl).

In other embodiments, the R$^5$ group of any of Formulae (I), (Ia), (Ib), (Ic), and (Id) is C$_{1-4}$alkyl, C$_{1-4}$fluoroalkyl, C$_{1-2}$alkyl(phenyl), C$_{1-2}$alkyl(chlorophenyl), or C$_{1-2}$alkyl(trifluoromethylphenyl).

In other embodiments, the R$^5$ group of any of Formulae (I), (Ia), (Ib), (Ic), and (Id) is C$_{1-4}$alkyl or C$_{1-4}$fluoroalkyl.

In other embodiments, the R$^5$ group of any of Formulae (I), (Ia), (Ib), (Ic), and (Id) is —CH$_3$.

In certain embodiments, the R$^7$ group of any of Formulae (I), (Ia), (Ib), and (Ic) is halo, —CN, C$_{1-3}$alkyl substituted with zero to 1 C$_{1-3}$alkoxy group, C$_{1-3}$fluoroalkyl, C$_{1-3}$hydroxyalkyl, C$_{1-3}$alkoxy, C$_{1-3}$fluoroalkoxy, —CH(CH$_3$)═CH$_2$, —SCH$_3$, —NHCH$_2$CF$_3$, —O(CH$_2$)$_2$N(CH$_3$)$_2$, —O(CH$_2$)$_2$OCH$_3$, —O(CH$_2$)$_2$(phenyl), —O(CH$_2$)cyclopropyl, C$_{3-6}$cycloalkyl, —C(O)(pyrrolidinyl), phenyl, pyrrolidinyl, or morpholinyl.

In other embodiments, the R$^7$ group of any of Formulae (I), (Ia), (Ib), and (Ic) is F, Cl, —CN, C$_{1-3}$alkyl substituted with zero to 1 C$_{1-3}$alkoxy group C$_{1-3}$fluoroalkyl, C$_{1-3}$hydroxyalkyl, C$_{1-3}$alkoxy, C$_{1-3}$fluoroalkoxy, —NHCH$_2$CF$_3$, —O(CH$_2$)$_2$N(CH$_3$)$_2$, —O(CH$_2$)$_2$OCH$_3$, —O(CH$_2$)$_2$(phenyl), —O(CH$_2$)cyclopropyl, cyclopropyl, cyclohexyl,

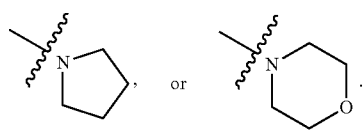

In other embodiments, the R$^7$ group of any of Formulae (I), (Ia), (Ib), and (Ic) is F, Cl, —CH$_3$, —CH$_2$CH$_3$—CF$_3$, —CHF$_2$, —CH$_2$OH, —CH$_2$OCH$_3$, —NHCH$_2$CF$_3$, —OCH$_3$, —OCH$_2$CH$_3$, —OCH(CH$_3$)$_2$, —OCH$_2$CF$_3$, —OCH$_2$CH$_2$F, —OCH$_2$CHF$_2$, —O(CH$_2$)(cyclopropyl), cyclopropyl, or cyclohexyl.

In other embodiments, the R$^7$ group of any of Formulae (I), (Ia), (Ib), and (Ic) is Cl, —CH$_3$, —CH$_2$OH, —OCH$_3$, —OCH$_2$CF$_3$, or cyclopropyl.

In other embodiments, the R$^7$ group of any of Formulae (I), (Ia), (Ib), and (Ic) is —CH$_3$.

One embodiment of the present disclosure provides a compound of Formula (I), (Ia), (Ib), (Ic), and/or (Id), or a stereoisomer, an N-oxide, a prodrug, or a pharmaceutically acceptable salt thereof, wherein said compound is selected from: N-(3-methyl-4-(4-methyl-3-pyridinyl)phenyl)methanesulfonamide (1); N-(4-(4-methoxypyridin-3-yl)-3-methylphenyl)methanesulfonamide (2); 4-chloro-N-(4-(4-methyl-3-pyridinyl)phenyl)benzenesulfonamide (3); 3,4-dichloro-N-(4-(4-methyl-3-pyridinyl)phenyl)benzenesulfonamide (4); 4-chloro-N-(3-methyl-4-(4-methyl-3-pyridinyl)phenyl)benzene sulfonamide (5); 1-((1S)-7,7-dimethyl-2-oxobicyclo[2.2.1]hept-1-yl)-N-(3-methyl-4-(4-methyl-3-pyridinyl)phenyl)methanesulfonamide (6); 4-chloro-N-(4-(4-methoxypyridin-3-yl)-3-methylphenyl)benzenesulfonamide (7); 4-chloro-N-(4-(4-phenyl-3-pyridinyl)phenyl)benzenesulfonamide (8); 1-phenyl-N-(4-(4-phenyl-3-pyridinyl)phenyl)methanesulfonamide (9); N-(3-methyl-4-(4-phenyl-3-pyridinyl)phenyl)-1-phenylmethane sulfonamide (10); N-(4-((3-methyl-4-(4-phenyl-3-pyridinyl)phenyl)sulfamoyl)phenyl) acetamide (11); N-(3-methyl-4-(4-phenyl-3-pyridinyl)phenyl) methanesulfonamide (12); N-(4-(4-cyclopropyl-3-pyridinyl)-3-methylphenyl)methanesulfonamide (13); methyl 2-(4-methyl-3-pyridinyl)-5-((methylsulfonyl)amino)benzoate (14); N-(3-(2-hydroxypropan-2-yl)-4-(4-methylpyridin-3-yl)phenyl)methanesulfonamide (15); N-(3-methoxy-4-(4-methoxy-3-pyridinyl)phenyl)methanesulfonamide (16); N-(3-ethoxy-4-(4-methyl-3-pyridinyl)phenyl)methanesulfonamide (17); 2,2,2-trifluoro-N-(3-methoxy-4-(4-methyl-3-pyridinyl)phenyl)ethane sulfonamide (18); N-(3-methoxy-4-(4-methyl-3-pyridinyl)phenyl)-2-propanesulfonamide (19); N-(5-methoxy-2-methyl-4-(4-methyl-3-pyridinyl)phenyl)methane sulfonamide (20); N-(3,5-dimethoxy-4-(4-methyl-3-pyridinyl)phenyl) methanesulfonamide (21); N-(3-(2-fluoroethoxy)-4-(4-methyl-3-pyridinyl)phenyl)methane sulfonamide (22); N-(3-(2,2-difluoroethoxy)-4-(4-methyl-3-pyridinyl)phenyl) methane sulfonamide (23); N-(4-(4-methyl-3-pyridinyl)-3-(2,2,2-trifluoroethoxy)phenyl)methane sulfonamide (24); N-(4-(4-fluoro-3-pyridinyl)-3-methylphenyl)methanesulfonamide (25); N-(4-(4-cyano-3-pyridinyl)phenyl)benzenesulfonamide (26); 4-chloro-N-(4-(4-cyanopyridin-3-yl)phenyl)benzenesulfonamide (27); N-(4-(4-cyano-3-pyridinyl)phenyl)methanesulfonamide (28); N-(2-fluoro-4-(4-methyl-3-pyridinyl)phenyl)methanesulfonamide (29); N-(4-(4-methyl-3-pyridinyl)phenyl)-1-adamantanesulfonamide (30); 4-chloro-N-(4-(4-methyl-3-pyridinyl)-2-(trifluoromethoxy)phenyl)benzenesulfonamide (31); N-(4-(4-methyl-3-pyridinyl)-2-(trifluoromethoxy)phenyl) methanesulfonamide (32); 3,4-dibromo-N-(3-methyl-4-(4-methylpyridin-3-yl)phenyl)benzenesulfonamide (33); N-(3-methyl-4-(4-methyl-3-pyridinyl)phenyl)-4-biphenylsulfonamide (34); N-(3-methyl-4-(4-methyl-3-pyridinyl)phenyl)-3-biphenylsulfonamide (35); N-(3-methyl-4-(4-methyl-3-pyridinyl)phenyl)-8-quinolinesulfonamide (36); 4-fluoro-N-(3-methyl-4-(4-methyl-3-pyridinyl)phenyl)benzenesulfonamide (37); N-(4-((3-methyl-4-(4-methyl-3-pyridinyl)phenyl)sulfamoyl) phenyl)acetamide (38); 4-methoxy-N-(3-methyl-4-(4-methyl-3-pyridinyl)phenyl)benzenesulfonamide (39); 2,2,2-trifluoro-N-(3-methyl-4-(4-methyl-3-pyridinyl)phenyl) ethanesulfonamide (40); N-(3-methyl-4-(4-methyl-3-pyridinyl)phenyl)-1-butanesulfonamide (41); 2,5-dimethoxy-N-(3-methyl-4-(4-methyl-3-pyridinyl)phenyl)benzenesulfonamide (42); 2-fluoro-N-(3-methyl-4-(4-methyl-3-pyridinyl)phenyl)benzenesulfonamide (43); 3-fluoro-N-(3-methyl-4-(4-methyl-3-pyridinyl)phenyl)benzenesulfonamide (44); 2-chloro-N-(3-methyl-4-(4-methyl-3-pyridinyl)phenyl)benzenesulfonamide (45); 3,4-dimethoxy-N-(3-methyl-4-(4-methyl-3-pyridinyl)phenyl)

benzenesulfonamide (46); 4-cyano-N-(3-methyl-4-(4-methyl-3-pyridinyl)phenyl)benzenesulfonamide (47); 3,5-dimethyl-N-(3-methyl-4-(4-methyl-3-pyridinyl)phenyl)-4-isoxazolesulfonamide (48); 3-methoxy-N-(3-methyl-4-(4-methyl-3-pyridinyl)phenyl)benzenesulfonamide (49); N-(3-methyl-4-(4-methyl-3-pyridinyl)phenyl)-3-thiophenesulfonamide (50); N-(3-methyl-4-(4-methyl-3-pyridinyl)phenyl)-3-pyridinesulfonamide (51); N-(3-methyl-4-(4-methyl-3-pyridinyl)phenyl)methanesulfonamide (52); 1,2-dimethyl-N-(3-methyl-4-(4-methyl-3-pyridinyl)phenyl)-1H-imidazole-4-sulfonamide (53); N-(3-methyl-4-(4-methyl-3-pyridinyl)phenyl)cyclopropanesulfonamide (54); N-(3-methyl-4-(4-methyl-3-pyridinyl) phenyl)-1-naphthalene sulfonamide (55); 2,5-dichloro-N-(3-methyl-4-(4-methyl-3-pyridinyl)phenyl)benzenesulfonamide (56); 4-methyl-N-(3-methyl-4-(4-methyl-3-pyridinyl)phenyl)benzenesulfonamide (57); N-(3-methyl-4-(4-methyl-3-pyridinyl)phenyl)-3-(trifluoromethyl)benzenesulfonamide (58); 2-methyl-N-(3-methyl-4-(4-methyl-3-pyridinyl)phenyl)benzenesulfonamide (59); 2,5-dimethyl-N-(3-methyl-4-(4-methyl-3-pyridinyl)phenyl)benzenesulfonamide (60); 3-chloro-N-(3-methyl-4-(4-methyl-3-pyridinyl)phenyl)benzenesulfonamide (61); 3-methyl-N-(3-methyl-4-(4-methyl-3-pyridinyl)phenyl)benzenesulfonamide (62); 1-(4-chlorophenyl)-N-(3-methyl-4-(4-methyl-3-pyridinyl)phenyl)methanesulfonamide (63); N-(3-methyl-4-(4-methyl-3-pyridinyl)phenyl)-2-biphenylsulfonamide (64); methyl 3-((3-methyl-4-(4-methyl-3-pyridinyl)phenyl)sulfamoyl)benzoate (65); N-(3-methyl-4-(4-methyl-3-pyridinyl)phenyl)-2-thiophenesulfonamide (66); N-(3-methyl-4-(4-methyl-3-pyridinyl)phenyl)ethanesulfonamide (67); N-(3-methyl-4-(4-methyl-3-pyridinyl)phenyl)-1-propanesulfonamide (68); 4-isopropyl-N-(3-methyl-4-(4-methyl-3-pyridinyl)phenyl)benzenesulfonamide (69); N-(3-methyl-4-(4-methyl-3-pyridinyl)phenyl)-4-phenoxybenzenesulfonamide (70); methyl 5-((3-methyl-4-(4-methyl-3-pyridinyl)phenyl)sulfamoyl)-2-furoate (71); N-(3-methyl-4-(4-methyl-3-pyridinyl)phenyl)-2-phenylethanesulfonamide (72); N-(3-methyl-4-(4-methyl-3-pyridinyl)phenyl)-2-naphthalenesulfonamide (73); N-(3-methyl-4-(4-methyl-3-pyridinyl)phenyl)benzenesulfonamide (74); N-(3-methyl-4-(4-methyl-3-pyridinyl)phenyl)-1-phenylmethanesulfonamide (75); 1-(3,4-dichlorophenyl)-N-(3-methyl-4-(4-methyl-3-pyridinyl)phenyl)methanesulfonamide (76); 1-(2-chlorophenyl)-N-(3-methyl-4-(4-methyl-3-pyridinyl)phenyl)methanesulfonamide (77); N-(3-methyl-4-(4-methyl-3-pyridinyl)phenyl)-1-(3-(trifluoromethyl)phenyl)methanesulfonamide (78); N-(3-methoxy-4-(4-methyl-3-pyridinyl)phenyl)benzenesulfonamide (79); 4-fluoro-N-(3-methoxy-4-(4-methyl-3-pyridinyl)phenyl)benzenesulfonamide (80); 4-chloro-N-(3-methoxy-4-(4-methyl-3-pyridinyl)phenyl)benzenesulfonamide (81); N-(3-methoxy-4-(4-methyl-3-pyridinyl)phenyl)-3-(trifluoromethyl)benzenesulfonamide (82); N-(3-methoxy-4-(4-methyl-3-pyridinyl)phenyl)-2-methylbenzenesulfonamide (83); N-(3-methoxy-4-(4-methyl-3-pyridinyl)phenyl)-2,5-dimethylbenzenesulfonamide (84); 3-chloro-4-fluoro-N-(3-methoxy-4-(4-methyl-3-pyridinyl)phenyl)benzenesulfonamide (85); 3-fluoro-N-(3-methoxy-4-(4-methyl-3-pyridinyl)phenyl)benzenesulfonamide (86); 3,5-dichloro-N-(3-methoxy-4-(4-methyl-3-pyridinyl)phenyl)benzenesulfonamide (87); N-(3-methoxy-4-(4-methyl-3-pyridinyl)phenyl)-3-methylbenzenesulfonamide (88); 3,4-dimethoxy-N-(3-methoxy-4-(4-methyl-3-pyridinyl)phenyl)benzenesulfonamide (89); 4-cyano-N-(3-methoxy-4-(4-methyl-3-pyridinyl)phenyl)benzenesulfonamide (90); 2-methoxy-N-(3-methoxy-4-(4-methyl-3-pyridinyl)phenyl)-5-methylbenzenesulfonamide (91); 2,5-difluoro-N-(3-methoxy-4-(4-methyl-3-pyridinyl)phenyl)benzenesulfonamide (92); 3,4-difluoro-N-(3-methoxy-4-(4-methyl-3-pyridinyl)phenyl)benzenesulfonamide (93); N-(3-methoxy-4-(4-methyl-3-pyridinyl)phenyl)-2,4-dimethylbenzenesulfonamide (94); 3-methoxy-N-(3-methoxy-4-(4-methyl-3-pyridinyl)phenyl)benzenesulfonamide (95); 3,5-difluoro-N-(3-methoxy-4-(4-methyl-3-pyridinyl)phenyl)benzenesulfonamide (96); N-(3-methoxy-4-(4-methyl-3-pyridinyl)phenyl)-1-benzothiophene-2-sulfonamide (97); N-(3-methoxy-4-(4-methyl-3-pyridinyl)phenyl)-1-benzofuran-2-sulfonamide (98); 3-chloro-N-(3-methoxy-4-(4-methyl-3-pyridinyl)phenyl)benzenesulfonamide (99); N-(4-(4-methyl-3-pyridinyl)phenyl)-2-thiophenesulfonamide (100); 4-fluoro-N-(4-(4-methyl-3-pyridinyl)phenyl)benzenesulfonamide (101); N-(4-((4-(4-methyl-3-pyridinyl)phenyl)sulfamoyl)phenyl)acetamide (102); N-(4-(4-methyl-3-pyridinyl)phenyl)-4-nitrobenzenesulfonamide (103); 4-methoxy-N-(4-(4-methyl-3-pyridinyl)phenyl)benzenesulfonamide (104); 3-chloro-4-fluoro-N-(4-(4-methyl-3-pyridinyl)phenyl)benzenesulfonamide (105); 2-chloro-N-(4-(4-methyl-3-pyridinyl)phenyl)benzenesulfonamide (106); 3-chloro-N-(4-(4-methyl-3-pyridinyl)phenyl)benzenesulfonamide (107); 3,5-dichloro-N-(4-(4-methyl-3-pyridinyl)phenyl)benzenesulfonamide (108); 3-methyl-N-(4-(4-methyl-3-pyridinyl)phenyl)benzenesulfonamide (109); 4-cyano-N-(4-(4-methyl-3-pyridinyl)phenyl)benzenesulfonamide (110); N-(4-(4-methyl-3-pyridinyl)phenyl)-4-biphenylsulfonamide (111); 3,4-difluoro-N-(4-(4-methyl-3-pyridinyl)phenyl)benzenesulfonamide (112); N-(4-(4-methyl-3-pyridinyl)phenyl)cyclopropanesulfonamide (113); N-(4-(4-methyl-3-pyridinyl)phenyl)-3-pyridinesulfonamide (114); 3-methoxy-N-(4-(4-methyl-3-pyridinyl)phenyl)benzenesulfonamide (115); N-(4-(4-methyl-3-pyridinyl)phenyl)-2-phenylethanesulfonamide (116); methyl 3-((4-(4-methyl-3-pyridinyl)phenyl)sulfamoyl)benzoate (117); (E)-N-(4-(4-methyl-3-pyridinyl)phenyl)-2-phenylethenesulfonamide (118); 2,2,2-trifluoro-N-(4-(4-methyl-3-pyridinyl)phenyl)ethanesulfonamide (119); N-(4-(4-methyl-3-pyridinyl)phenyl)-1-propanesulfonamide (120); N-(4-(4-methyl-3-pyridinyl)phenyl)-1-butanesulfonamide (121); 1-(3-chlorophenyl)-N-(4-(4-methyl-3-pyridinyl)phenyl)methanesulfonamide (122); 1,2-dimethyl-N-(4-(4-methyl-3-pyridinyl)phenyl)-1H-imidazole-4-sulfonamide (123); 2-methyl-N-(4-(4-methyl-3-pyridinyl)phenyl)benzenesulfonamide (124); N-(4-(4-methyl-3-pyridinyl)phenyl)-1-naphthalenesulfonamide (125); N-(4-(4-methyl-3-pyridinyl)phenyl)-2-naphthalenesulfonamide (126); 4-bromo-N-(4-(4-methyl-3-pyridinyl)phenyl)benzenesulfonamide (127); 4-chloro-N-(4-(4-methyl-3-pyridinyl)phenyl)-3-nitrobenzenesulfonamide (128); 4-methyl-N-(4-(4-methyl-3-pyridinyl)phenyl)benzenesulfonamide (129); N-(4-(4-methyl-3-pyridinyl)phenyl)methanesulfonamide (130); N-(4-(4-methyl-3-pyridinyl)phenyl)-4-phenoxybenzenesulfonamide (131); 1-(4-chlorophenyl)-N-(4-(4-methyl-3-pyridinyl)phenyl)methanesulfonamide (132); 2-(1,3-dioxo-1,3-dihydro-2H-isoindol-2-yl)-N-(4-(4-methyl-3-pyridinyl)phenyl)ethanesulfonamide (133); methyl 5-((4-(4-methyl-3-pyridinyl)phenyl)sulfamoyl)-2-furoate (134); N-(4-(4-methyl-3-pyridinyl)phenyl)-2-biphenylsulfonamide (135); N-(4-(4-methyl-3-pyridinyl)phenyl)-3-thiophenesulfonamide (136); N-(4-(4-methyl-3-pyridinyl)phenyl)-3-biphenylsulfonamide (137); N-(4-(4-methyl-3-pyridinyl)phenyl)-3-(trifluoromethyl)benzenesulfonamide (138); 3-cyano-N-(4-(4-methyl-3-pyridinyl)phenyl)benzenesulfonamide (139); N-(4-(4-methyl-3-pyridinyl)phenyl)ethanesulfonamide (140); 2-methyl-N-(4-(4-methyl-3-pyridinyl)phenyl)-1-propanesulfonamide (141); N-(4-(isoquinolin-4-yl)-3-methoxyphenyl)methanesulfonamide (142); N-(4-(isoquinolin-4-yl)-3-methoxyphenyl)benzenesulfonamide (143); N-(4-(isoquinolin-4-yl)-3-methoxyphenyl)naphthalene-1-sulfonamide (144); N-(4-(isoquinolin-4-yl)-3-methoxyphenyl)naphthalene-2-sulfonamide (145); 4-chloro-N-(4-(isoquinolin-4-yl)-3-methoxyphenyl)benzenesulfonamide (146); N-(4-(isoquinolin-4-yl)-3-methoxyphenyl)-4-methoxybenzenesulfonamide (147); N-(4-(isoquinolin-4-yl)-3-methoxyphenyl)-1-phenylmethanesulfonamide (148); 2-chloro-N-(4-(isoquinolin-4-yl)-3-methoxyphenyl)benzenesulfonamide (149); 4-cyano-N-(4-(isoquinolin-4-yl)-3-methoxyphenyl)benzenesulfonamide (150); N-(4-(isoquinolin-4-yl)-3-methoxyphenyl)-2-phenylethanesulfonamide (151); N-(4-(isoquinolin-4-yl)-3-methoxyphenyl)-2-methylpropane-1-sulfonamide (152); N-(4-(isoquinolin-4-yl)-3-methoxyphenyl)-4-phenoxybenzenesulfonamide (153); N-(4-(isoquinolin-4-yl)-3-methoxyphenyl)quinoline-8-sulfonamide (154); 2,2,2-trifluoro-N-(4-(isoquinolin-4-yl)-3-methoxyphenyl)ethanesulfonamide (155); N-(4-(isoquinolin-4-yl)-3-methoxyphenyl)ethanesulfonamide (156); N-(4-(isoquinolin-4-yl)-3-methoxyphenyl)propane-1-sulfonamide (157); N-(4-(isoquinolin-4-yl)-3-methoxyphenyl)-1,2-dimethyl-1H-imidazole-4-sulfonamide (158); N-(4-(isoquinolin-4-yl)-3-methoxyphenyl)cyclopropanesulfonamide (159); N-(4-(isoquinolin-4-yl)-3-methoxyphenyl)pyridine-2-sulfonamide (160); N-(3-methoxy-4-(4-methylpyrimidin-5-yl)phenyl)methanesulfonamide (161); N-(3-methoxy-4-(4-methylpyrimidin-5-yl)phenyl)cyclopropanesulfonamide (162); N-(3-methoxy-4-(4-methylpyrimidin-5-yl)phenyl)propane-1-sulfonamide (163); N-(3-methoxy-4-(4-methylpyrimidin-5-yl)phenyl)methanesulfonamide (164); N-(3-methoxy-4-(4-methylpyrimidin-5-yl)phenyl)benzenesulfonamide (165); N-(3-methoxy-4-(4-methylpyrimidin-5-yl)phenyl)pyridine-3-sulfonamide (166); 2,2,2-trifluoro-N-(3-methoxy-4-(4-methylpyrimidin-5-yl)phenyl)ethanesulfonamide (167); N-(3-methoxy-4-(4-methylpyrimidin-5-yl)phenyl)-1-phenylmethanesulfonamide (168); N-(3-methoxy-4-(4-methylpyrimidin-5-yl)phenyl)-2-phenylethanesulfonamide (169); 4-methoxy-N-(3-methoxy-4-(4-methylpyrimidin-5-yl)phenyl)benzenesulfonamide (170); 2-chloro-N-(3-methoxy-4-(4-methylpyrimidin-5-yl)phenyl)benzenesulfonamide (171); 4-chloro-N-(3-methoxy-4-(4-methylpyrimidin-5-yl)phenyl)benzenesulfonamide (172); 1-(4-chlorophenyl)-N-(3-methoxy-4-(4-methylpyrimidin-5-yl)phenyl)methanesulfonamide (173); N-(3-methoxy-4-(4-methylpyrimidin-5-yl)phenyl)naphthalene-1-sulfonamide (174); N-(3-methoxy-4-(4-methylpyrimidin-5-yl)phenyl)naphthalene-2-sulfonamide (175); N-(3-methoxy-4-(4-methylpyrimidin-5-yl)phenyl)quinoline-8-sulfonamide (176); N-(3-methoxy-4-(4-methylpyrimidin-5-yl)phenyl)naphthalene-2-sulfonamide (177); N-(3-chloro-4-(4-methylpyridin-3-yl)phenyl)methanesulfonamide (178); 4-chloro-N-(4-(4-isoquinolinyl)phenyl)benzenesulfonamide (179); 4-chloro-N-(4-(4-(1-pyrrolidinylcarbonyl)-3-pyridinyl)phenyl) benzene sulfonamide (180); N-(4-(1-(phenylsulfonyl)-1H-pyrrolo[2,3-c]pyridin-4-yl)phenyl)benzenesulfonamide (181); 4-chloro-N-(4-(4-isoquinolinyl)-3-methylphenyl) benzenesulfonamide (182); N-(4-(4-methylpyridin-3-yl)-3-(2,2,2-trifluoroethoxy)phenylbenzenesulfonamide (183); N-(4-(4-methylpyridin-3-yl)-3-(2,2,2-trifluoroethoxy)phenylcyclopropylsulfonamide (184); N-(4-(5-bromo-4-methoxypyridin-3-yl)-3-methylphenyl)methane sulfonamide (185); N-(4-(5-bromo-4-isopropoxy-3-pyridinyl)-3-methylphenyl) methanesulfonamide (186); N-(4-(5-bromo-4-ethoxy-3-pyridinyl)-3-methylphenyl)methane sulfonamide (187); N-(4-(5-bromo-4-(2,2,2-trifluoroethoxy)-3-pyridinyl)-3-methylphenyl) methanesulfonamide (188); N-(4-(5-bromo-4-(2-fluoroethoxy)-3-pyridinyl)-3-methylphenyl) methanesulfonamide (189); N-(4-(5-bromo-4-(2,2-difluoroethoxy)-3-pyridinyl)-3-methylphenyl) methanesulfonamide (190); N-(4-(5-bromo-4-(2-phenylethoxy)-3-pyridinyl)-3-methylphenyl) methanesulfonamide (191); N-(4-(5-bromo-4-(2-(dimethylamino)ethoxy)-3-pyridinyl)-3-methylphenyl) methanesulfonamide (192); N-(4-(5-bromo-4-(2-methoxyethoxy)-3-pyridinyl)-3-methylphenyl) methanesulfonamide (193); N-(4-(5-bromo-4-(methylsulfanyl)-3-pyridinyl)-3-methylphenyl) methanesulfonamide (194); N-(4-(4-chloro-3-pyridinyl)-3-methylphenyl)methanesulfonamide (195); N-(4-(4-isopropoxy-3-pyridinyl)-3-methylphenyl)methanesulfonamide (196); N-(4-(4-ethoxy-3-pyridinyl)-3-methylphenyl)methanesulfonamide (197); N-(3-methyl-4-(4-(2,2,2-trifluoroethoxy)-3-pyridinyl)phenyl) methane sulfonamide (198); N-(4-(4-(2-fluoroethoxy)-3-pyridinyl)-3-methylphenyl)methane sulfonamide (199); N-(4-(4-(2,2-difluoroethoxy)-3-pyridinyl)-3-methylphenyl) methane sulfonamide (200); N-(3-methyl-4-(4-(2-phenylethoxy)-3-pyridinyl)phenyl)methanesulfonamide (201); N-(4-(4-(2-(dimethylamino)ethoxy)-3-pyridinyl)-3-methylphenyl) methanesulfonamide (202); N-(4-(4-(2-methoxyethoxy)-3-pyridinyl)-3-methylphenyl)methanesulfonamide (203); N-(3-methyl-4-(4-(methylsulfanyl)-3-pyridinyl)phenyl)methanesulfonamide (204); N-(4-(4-methyl-3-pyridinyl) phenyl)-N'-phenylsulfamide (205); N-(4-chlorophenyl)-N-methyl-N'-(4-(4-methyl-3-pyridinyl)phenyl) sulfamide (206); N-(4-methoxyphenyl)-N'-(4-(4-methyl-3-pyridinyl)phenyl)sulfamide (207); N-(3-methyl-4-(4-methyl-3-pyridinyl)phenyl)-4-morpholine sulfonamide (208); N-(3-methyl-4-(4-methyl-3-pyridinyl)phenyl)-1-pyrrolidinesulfonamide (209); N-methyl-N'-(3-methyl-4-(4-methyl-3-pyridinyl)phenyl)sulfamide (210); 4-hydroxy-N-(3-methyl-4-(4-methylpyridin-3-yl)phenyl)piperidine-1-sulfonamide (211); N-(3-chloro-4-(4-methoxypyridin-3-yl)phenyl)methanesulfonamide (212); N-(3-methoxy-4-(4-(2,2,2-trifluoroethoxy)pyridine-3-yl)phenyl)methanesulfonamide (213); N-(4-(4-cyclopropylpyrimidin-5-yl)-3-methoxyphenyl) methanesulfonamide (214); N-(3-hydroxy-4-(4-methyl-3-pyridinyl)phenyl)methanesulfonamide (215); N-(4-(5-cyano-4-methoxy-3-pyridinyl)-3-methylphenyl)methane sulfonamide (216); N-(3-methoxy-4-(4-methyl-3-pyridinyl) phenyl)methanesulfonamide (217); N-(4-(4-ethylpyrimidin-5-yl)-3-methoxyphenyl) methanesulfonamide (218); N-(3-methoxy-4-(4-propylpyrimidin-5-yl)phenyl) methanesulfonamide (219); N-(4-(4-isopropylpyrimidin-5-yl)-3-methoxyphenyl) methanesulfonamide (220); N-(4-(4-cyclohexylpyrimidin-5-yl)-3-methoxyphenyl) methanesulfonamide (221); N-(3-methoxy-4-(1,7-naphthyridin-5-yl)phenyl)methanesulfonamide (222); N-(3-methoxy-4-(4-(pyrrolidin-1-yl)pyrimidin-5-yl)phenyl) methanesulfonamide (223); N-(3-methoxy-4-(4-morpholinopyrimidin-5-yl)phenyl)methanesulfonamide (224); N-(4-(4-cyclopropylpyridin-3-yl)-3-methoxyphenyl) methanesulfonamide (225); N-(4-(4-(difluoromethyl)pyridin-3-yl)-3-methoxyphenyl)methanesulfonamide (226); N-(3-methoxy-4-(4-(prop-1-en-2-yl)pyridin-3-yl)phenyl) methanesulfonamide (227); N-(4-(isoquinolin-4-yl)-3-(trifluoromethoxy)phenyl)methanesulfonamide (228); N-(4-(4-methylpyridin-3-yl)-3-(trifluoromethoxy)phenyl) methanesulfonamide (229); N-(4-chloropyridin-3-yl)-3-(trifluoromethoxy)phenyl)methanesulfonamide (230); N-(4-(4-methoxypyridin-3-yl)-3-(trifluoromethoxy)phenyl)

methanesulfonamide (231); N-(4-(isoquinolin-4-yl)-3-(2,2,2-trifluoroethoxy)phenyl)methanesulfonamide (232); N-(4-(4-methoxypyridin-3-yl)-3-(2,2,2-trifluoroethoxy)phenyl) methanesulfonamide (233); N-(3-(2-fluoroethoxy)-4-(isoquinolin-4-yl)phenyl)methanesulfonamide (234); N-(3-(2-fluoroethoxy)-4-(4-methoxypyridin-3-yl)phenyl) methanesulfonamide (235); N-(4-(4-chloropyridin-3-yl)-3-(2-fluoroethoxy)phenyl)methanesulfonamide (236); N-(3-(2-fluoroethoxy)-4-(4-(trifluoromethyl) pyridin-3-yl)phenyl) methanesulfonamide (237); N-(3-(2-fluoroethoxy)-4-(pyrido[4,3-b]pyrazin-8-yl)phenyl) methanesulfonamide (238); N-(3-(2-fluoroethoxy)-4-(1,7-naphthyridin-5-yl)phenyl) methanesulfonamide (239); N-(4-(4-methylpyridin-3-yl)-3-(trifluoromethyl)phenyl)methanesulfonamide (240); N-(4-(isoquinolin-4-yl)-3-(trifluoromethyl)phenyl) methanesulfonamide (241); N-(4-(4-chloropyridin-3-yl)-3-(trifluoromethyl)phenyl)methanesulfonamide (242); N-(4-(4-cyclopropylpyridin-3-yl)-3-(trifluoromethyl)phenyl) methanesulfonamide (243); N-(4-(4-isopropylpyridin-3-yl)-3-)methoxyphenyl)methanesulfonamide (244); N-(3-Methoxy-4-(4-methoxypyrimidin-5-yl)methanesulfonamide (245); N-(3,5-dimethyl-4-(4-methyl-3-pyridinyl)phenyl)methanesulfonamide (246); N-(3-methoxy-4-(4-(2,2,2-trifluoroethoxy)-5-pyrimidinyl)phenyl)methanesulfonamide (247); N-(3-methoxy-4-(4-(2,2,2-trifluoroethylamino)pyrimidin-5-yl)phenyl)methanesulfonamide (248); N-(4-(4-ethoxy-5-pyrimidinyl)-3-methoxyphenyl)methanesulfonamide (249); N-(3-methoxy-4-(pyrrolo[1,2-c]pyrimidin-4-yl)phenyl)methanesulfonamide (250); N-(4-(imidazo[1,2-a]pyrazin-5-yl)-3-methoxyphenyl)methanesulfonamide (251); N-(4-(4-cyanopyridin-3-yl)-3-methoxyphenyl)methanesulfonamide (252); N-(4-(4-(hydroxymethyl)pyridin-3-yl)-3-methoxyphenyl)methanesulfonamide (253); N-(3-methoxy-4-(4-(methoxymethyl)pyridin-3-yl)phenyl) methanesulfonamide (254); and N-(4-(4-(cyclopropylmethoxy)pyridin-3-yl)-3-methoxyphenyl) methanesulfonamide (255).

One embodiment of the present disclosure provides a compound of Formula (I), (Ia), and/or (Ib), or a stereoisomer, an N-oxide, a prodrug, or a pharmaceutically acceptable salt thereof, wherein said compound is selected from: N-(3-methyl-4-(4-methyl-3-pyridinyl)phenyl)methanesulfonamide (1); N-(4-(4-methoxypyridin-3-yl)-3-methylphenyl)methanesulfonamide (2); 4-chloro-N-(4-(4-methyl-3-pyridinyl)phenyl)benzenesulfonamide (3); 3,4-dichloro-N-(4-(4-methyl-3-pyridinyl)phenyl)benzenesulfonamide (4); 4-chloro-N-(3-methyl-4-(4-methyl-3-pyridinyl)phenyl)benzene sulfonamide (5); 1-((1S)-7,7-dimethyl-2-oxobicyclo[2.2.1]hept-1-yl)-N-(3-methyl-4-(4-methyl-3-pyridinyl)phenyl) methanesulfonamide (6); 4-chloro-N-(4-(4-methoxypyridin-3-yl)-3-methylphenyl)benzenesulfonamide (7); 4-chloro-N-(4-(4-phenyl-3-pyridinyl)phenyl)benzenesulfonamide (8); 1-phenyl-N-(4-(4-phenyl-3-pyridinyl)phenyl)methanesulfonamide (9); N-(3-methyl-4-(4-phenyl-3-pyridinyl)phenyl)-1-phenylmethane sulfonamide (10); N-(4-((3-methyl-4-(4-phenyl-3-pyridinyl)phenyl)sulfamoyl)phenyl) acetamide (11); N-(3-methyl-4-(4-phenyl-3-pyridinyl)phenyl)methanesulfonamide (12); N-(4-(4-cyclopropyl-3-pyridinyl)-3-methylphenyl)methanesulfonamide (13); methyl 2-(4-methyl-3-pyridinyl)-5-((methylsulfonyl)amino)benzoate (14); N-(3-(2-hydroxypropan-2-yl)-4-(4-methylpyridin-3-yl)phenyl)methanesulfonamide (15); N-(3-methoxy-4-(4-methoxy-3-pyridinyl)phenyl)methanesulfonamide (16); N-(3-ethoxy-4-(4-methyl-3-pyridinyl)phenyl) methanesulfonamide (17); 2,2,2-trifluoro-N-(3-methoxy-4-(4-methyl-3-pyridinyl)phenyl)ethane sulfonamide (18); N-(3-methoxy-4-(4-methyl-3-pyridinyl)phenyl)-2-propanesulfonamide (19); N-(5-methoxy-2-methyl-4-(4-methyl-3-pyridinyl)phenyl)methane sulfonamide (20); N-(3,5-dimethoxy-4-(4-methyl-3-pyridinyl)phenyl) methanesulfonamide (21); N-(3-(2-fluoroethoxy)-4-(4-methyl-3-pyridinyl)phenyl)methane sulfonamide (22); N-(3-(2,2-difluoroethoxy)-4-(4-methyl-3-pyridinyl)phenyl) methane sulfonamide (23); N-(4-(4-methyl-3-pyridinyl)-3-(2,2,2-trifluoroethoxy)phenyl)methane sulfonamide (24); N-(4-(4-fluoro-3-pyridinyl)-3-methylphenyl)methanesulfonamide (25); N-(4-(4-cyano-3-pyridinyl)phenyl)benzenesulfonamide (26); 4-chloro-N-(4-(4-cyanopyridin-3-yl)phenyl)benzenesulfonamide (27); N-(4-(4-cyano-3-pyridinyl)phenyl)methanesulfonamide (28); N-(2-fluoro-4-(4-methyl-3-pyridinyl)phenyl)methanesulfonamide (29); N-(4-(4-methyl-3-pyridinyl)phenyl)-1-adamantanesulfonamide (30); 4-chloro-N-(4-(4-methyl-3-pyridinyl)-2-(trifluoromethoxy)phenyl)benzenesulfonamide (31); N-(4-(4-methyl-3-pyridinyl)-2-(trifluoromethoxy)phenyl) methanesulfonamide (32); 3,4-dibromo-N-(3-methyl-4-(4-methylpyridin-3-yl)phenyl)benzenesulfonamide (33); N-(3-methyl-4-(4-methyl-3-pyridinyl)phenyl)-4-biphenylsulfonamide (34); N-(3-methyl-4-(4-methyl-3-pyridinyl)phenyl)-3-biphenylsulfonamide (35); N-(3-methyl-4-(4-methyl-3-pyridinyl)phenyl)-8-quinolinesulfonamide (36); 4-fluoro-N-(3-methyl-4-(4-methyl-3-pyridinyl)phenyl)benzenesulfonamide (37); N-(4-((3-methyl-4-(4-methyl-3-pyridinyl)phenyl)sulfamoyl) phenyl)acetamide (38); 4-methoxy-N-(3-methyl-4-(4-methyl-3-pyridinyl)phenyl)benzenesulfonamide (39); 2,2,2-trifluoro-N-(3-methyl-4-(4-methyl-3-pyridinyl)phenyl) ethanesulfonamide (40); N-(3-methyl-4-(4-methyl-3-pyridinyl)phenyl)-1-butanesulfonamide (41); 2,5-dimethoxy-N-(3-methyl-4-(4-methyl-3-pyridinyl)phenyl) benzenesulfonamide (42); 2-fluoro-N-(3-methyl-4-(4-methyl-3-pyridinyl)phenyl)benzenesulfonamide (43); 3-fluoro-N-(3-methyl-4-(4-methyl-3-pyridinyl)phenyl)benzenesulfonamide (44); 2-chloro-N-(3-methyl-4-(4-methyl-3-pyridinyl)phenyl)benzenesulfonamide (45); 3,4-dimethoxy-N-(3-methyl-4-(4-methyl-3-pyridinyl)phenyl) benzenesulfonamide (46); 4-cyano-N-(3-methyl-4-(4-methyl-3-pyridinyl)phenyl)benzenesulfonamide (47); 3,5-dimethyl-N-(3-methyl-4-(4-methyl-3-pyridinyl)phenyl)-4-isoxazolesulfonamide (48); 3-methoxy-N-(3-methyl-4-(4-methyl-3-pyridinyl)phenyl)benzenesulfonamide (49); N-(3-methyl-4-(4-methyl-3-pyridinyl)phenyl)-3-thiophenesulfonamide (50); N-(3-methyl-4-(4-methyl-3-pyridinyl)phenyl)-3-pyridinesulfonamide (51); N-(3-methyl-4-(4-methyl-3-pyridinyl)phenyl) methanesulfonamide (52); 1,2-dimethyl-N-(3-methyl-4-(4-methyl-3-pyridinyl)phenyl)-1H-imidazole-4-sulfonamide (53); N-(3-methyl-4-(4-methyl-3-pyridinyl)phenyl)cyclopropanesulfonamide (54); N-(3-methyl-4-(4-methyl-3-pyridinyl) phenyl)-1-naphthalene sulfonamide (55); 2,5-dichloro-N-(3-methyl-4-(4-methyl-3-pyridinyl)phenyl) benzenesulfonamide (56); 4-methyl-N-(3-methyl-4-(4-methyl-3-pyridinyl)phenyl)benzenesulfonamide (57); N-(3-methyl-4-(4-methyl-3-pyridinyl)phenyl)-3-(trifluoromethyl) benzenesulfonamide (58); 2-methyl-N-(3-methyl-4-(4-methyl-3-pyridinyl)phenyl)benzenesulfonamide (59); 2,5-dimethyl-N-(3-methyl-4-(4-methyl-3-pyridinyl)phenyl) benzenesulfonamide (60); 3-chloro-N-(3-methyl-4-(4-methyl-3-pyridinyl)phenyl)benzenesulfonamide (61); 3-methyl-N-(3-methyl-4-(4-methyl-3-pyridinyl)phenyl)benzenesulfonamide (62); 1-(4-chlorophenyl)-N-(3-methyl-4-(4-methyl-3-pyridinyl)phenyl)methanesulfonamide (63); N-(3-methyl-4-(4-methyl-3-pyridinyl)phenyl)-2-biphenylsulfonamide (64); methyl 3-((3-methyl-4-(4-methyl-3-pyridinyl)phenyl)sulfamoyl)benzoate (65); N-(3-methyl-4-(4-methyl-3-pyridinyl)phenyl)-2-thiophenesulfonamide (66); N-(3-methyl-4-(4-methyl-3-pyridinyl)phenyl)ethanesulfonamide (67); N-(3-methyl-4-(4-methyl-3-pyridinyl)phenyl)-1-propanesulfonamide (68); 4-isopropyl-N-(3-methyl-4-(4-methyl-3-pyridinyl)phenyl)benzenesulfonamide (69); N-(3-methyl-4-(4-methyl-3-pyridinyl)phenyl)-4-phenoxybenzenesulfonamide (70); methyl 5-((3-methyl-4-(4-methyl-3-pyridinyl)phenyl)sulfamoyl)-2-furoate (71); N-(3-methyl-4-(4-methyl-3-pyridinyl)phenyl)-2-phenylethanesulfonamide (72); N-(3-methyl-4-(4-methyl-3-pyridinyl)phenyl)-2-naphthalenesulfonamide (73); N-(3-methyl-4-(4-methyl-3-pyridinyl)phenyl)benzenesulfonamide (74); N-(3-methyl-4-(4-methyl-3-pyridinyl)phenyl)-1-phenylmethanesulfonamide (75); 1-(3,4-dichlorophenyl)-N-(3-methyl-4-(4-methyl-3-pyridinyl)phenyl)methanesulfonamide (76); 1-(2-chlorophenyl)-N-(3-methyl-4-(4-methyl-3-pyridinyl)phenyl)methanesulfonamide (77); N-(3-methyl-4-(4-methyl-3-pyridinyl)phenyl)-1-(3-(trifluoromethyl)phenyl)methanesulfonamide (78); N-(3-methoxy-4-(4-methyl-3-pyridinyl)phenyl)benzenesulfonamide (79); 4-fluoro-N-(3-methoxy-4-(4-methyl-3-pyridinyl)phenyl)benzenesulfonamide (80); 4-chloro-N-(3-methoxy-4-(4-methyl-3-pyridinyl)phenyl)benzenesulfonamide (81); N-(3-methoxy-4-(4-methyl-3-pyridinyl)phenyl)-3-(trifluoromethyl)benzenesulfonamide (82); N-(3-methoxy-4-(4-methyl-3-pyridinyl)phenyl)-2-methylbenzenesulfonamide (83); N-(3-methoxy-4-(4-methyl-3-pyridinyl)phenyl)-2,5-dimethylbenzenesulfonamide (84); 3-chloro-4-fluoro-N-(3-methoxy-4-(4-methyl-3-pyridinyl)phenyl)benzenesulfonamide (85); 3-fluoro-N-(3-methoxy-4-(4-methyl-3-pyridinyl)phenyl)benzenesulfonamide (86); 3,5-dichloro-N-(3-methoxy-4-(4-methyl-3-pyridinyl)phenyl)benzenesulfonamide (87); N-(3-methoxy-4-(4-methyl-3-pyridinyl)phenyl)-3-methylbenzenesulfonamide (88); 3,4-dimethoxy-N-(3-methoxy-4-(4-methyl-3-pyridinyl)phenyl)benzenesulfonamide (89); 4-cyano-N-(3-methoxy-4-(4-methyl-3-pyridinyl)phenyl)benzenesulfonamide (90); 2-methoxy-N-(3-methoxy-4-(4-methyl-3-pyridinyl)phenyl)-5-methylbenzenesulfonamide (91); 2,5-difluoro-N-(3-methoxy-4-(4-methyl-3-pyridinyl)phenyl)benzenesulfonamide (92); 3,4-difluoro-N-(3-methoxy-4-(4-methyl-3-pyridinyl)phenyl)benzenesulfonamide (93); N-(3-methoxy-4-(4-methyl-3-pyridinyl)phenyl)-2,4-dimethylbenzenesulfonamide (94); 3-methoxy-N-(3-methoxy-4-(4-methyl-3-pyridinyl)phenyl)benzenesulfonamide (95); 3,5-difluoro-N-(3-methoxy-4-(4-methyl-3-pyridinyl)phenyl)benzenesulfonamide (96); N-(3-methoxy-4-(4-methyl-3-pyridinyl)phenyl)-1-benzothiophene-2-sulfonamide (97); N-(3-methoxy-4-(4-methyl-3-pyridinyl)phenyl)-1-benzofuran-2-sulfonamide (98); 3-chloro-N-(3-methoxy-4-(4-methyl-3-pyridinyl)phenyl)benzenesulfonamide (99); N-(4-(4-methyl-3-pyridinyl)phenyl)-2-thiophenesulfonamide (100); 4-fluoro-N-(4-(4-methyl-3-pyridinyl)phenyl)benzenesulfonamide (101); N-(4-((4-(4-methyl-3-pyridinyl)phenyl)sulfamoyl)phenyl) acetamide (102); N-(4-(4-methyl-3-pyridinyl)phenyl)-4-nitrobenzenesulfonamide (103); 4-methoxy-N-(4-(4-methyl-3-pyridinyl)phenyl)benzenesulfonamide (104); 3-chloro-4-fluoro-N-(4-(4-methyl-3-pyridinyl)phenyl)benzenesulfonamide (105); 2-chloro-N-(4-(4-methyl-3-pyridinyl)phenyl)benzenesulfonamide (106); 3-chloro-N-(4-(4-methyl-3-pyridinyl)phenyl)benzenesulfonamide (107); 3,5-dichloro-N-(4-(4-methyl-3-pyridinyl)phenyl)benzenesulfonamide (108); 3-methyl-N-(4-(4-methyl-3-pyridinyl)phenyl)benzenesulfonamide (109); 4-cyano-N-(4-(4-methyl-3-pyridinyl)phenyl)benzenesulfonamide (110); N-(4-(4-methyl-3-pyridinyl)phenyl)-4-biphenylsulfonamide (111); 3,4-difluoro-N-(4-(4-methyl-3-pyridinyl)phenyl)benzenesulfonamide (112); N-(4-(4-methyl-3-pyridinyl)phenyl) cyclopropanesulfonamide (113); N-(4-(4-methyl-3-pyridinyl)phenyl)-3-pyridinesulfonamide (114); 3-methoxy-N-(4-(4-methyl-3-pyridinyl)phenyl)benzenesulfonamide (115); N-(4-(4-methyl-3-pyridinyl)phenyl)-2-phenylethanesulfonamide (116); methyl 3-((4-(4-methyl-3-pyridinyl)phenyl)sulfamoyl)benzoate (117); (E)-N-(4-(4-methyl-3-pyridinyl)phenyl)-2-phenylethenesulfonamide (118); 2,2,2-trifluoro-N-(4-(4-methyl-3-pyridinyl)phenyl)ethanesulfonamide (119); N-(4-(4-methyl-3-pyridinyl)phenyl)-1-propanesulfonamide (120); N-(4-(4-methyl-3-pyridinyl)phenyl)-1-butanesulfonamide (121); 1-(3-chlorophenyl)-N-(4-(4-methyl-3-pyridinyl)phenyl)methanesulfonamide (122); 1,2-dimethyl-N-(4-(4-methyl-3-pyridinyl)phenyl)-1H-imidazole-4-sulfonamide (123); 2-methyl-N-(4-(4-methyl-3-pyridinyl)phenyl)benzenesulfonamide (124); N-(4-(4-methyl-3-pyridinyl)phenyl)-1-naphthalenesulfonamide (125); N-(4-(4-methyl-3-pyridinyl)phenyl)-2-naphthalenesulfonamide (126); 4-bromo-N-(4-(4-methyl-3-pyridinyl)phenyl)benzenesulfonamide (127); 4-chloro-N-(4-(4-methyl-3-pyridinyl)phenyl)-3-nitrobenzenesulfonamide (128); 4-methyl-N-(4-(4-methyl-3-pyridinyl)phenyl)benzenesulfonamide (129); N-(4-(4-methyl-3-pyridinyl)phenyl)methanesulfonamide (130); N-(4-(4-methyl-3-pyridinyl)phenyl)-4-phenoxybenzenesulfonamide (131); 1-(4-chlorophenyl)-N-(4-(4-methyl-3-pyridinyl)phenyl) methanesulfonamide (132); 2-(1,3-dioxo-1,3-dihydro-2H-isoindol-2-yl)-N-(4-(4-methyl-3-pyridinyl)phenyl)ethanesulfonamide (133); methyl 5-((4-(4-methyl-3-pyridinyl)phenyl)sulfamoyl)-2-furoate (134); N-(4-(4-methyl-3-pyridinyl)phenyl)-2-biphenylsulfonamide (135); N-(4-(4-methyl-3-pyridinyl)phenyl)-3-thiophenesulfonamide (136); N-(4-(4-methyl-3-pyridinyl)phenyl)-3-biphenylsulfonamide (137); N-(4-(4-methyl-3-pyridinyl)phenyl)-3-(trifluoromethyl)benzenesulfonamide (138); 3-cyano-N-(4-(4-methyl-3-pyridinyl)phenyl)benzenesulfonamide (139); N-(4-(4-methyl-3-pyridinyl)phenyl)ethanesulfonamide (140); 2-methyl-N-(4-(4-methyl-3-pyridinyl)phenyl)-1-propanesulfonamide (141); N-(3-chloro-4-(4-methylpyridin-3-yl)phenyl)methanesulfonamide (178); 4-chloro-N-(4-(4-(1-pyrrolidinylcarbonyl)-3-pyridinyl)phenyl)benzene sulfonamide (180); N-(4-(4-methylpyridin-3-yl)-3-(2,2,2-trifluoroethoxy)phenylbenzenesulfonamide (183); N-(4-(4-methylpyridin-3-yl)-3-(2,2,2-trifluoroethoxy)phenylcyclopropylsulfonamide (184); N-(4-(5-bromo-4-methoxypyridin-3-yl)-3-methylphenyl)methane sulfonamide (185); N-(4-(5-bromo-4-isopropoxy-3-pyridinyl)-3-methylphenyl) methanesulfonamide (186); N-(4-(5-bromo-4-ethoxy-3-pyridinyl)-3-methylphenyl)methane sulfonamide (187); N-(4-(5-bromo-4-(2,2,2-trifluoroethoxy)-3-pyridinyl)-3-methylphenyl) methanesulfonamide (188); N-(4-(5-bromo-4-(2-fluoroethoxy)-3-pyridinyl)-3-methylphenyl) methanesulfonamide (189); N-(4-(5-bromo-4-(2,2-difluoroethoxy)-3-pyridinyl)-3-methylphenyl) methanesulfonamide (190); N-(4-(5-bromo-4-(2-phenylethoxy)-3-pyridinyl)-3-methylphenyl) methanesulfonamide (191); N-(4-(5-bromo-4-(2-(dimethylamino)ethoxy)-3-pyridinyl)-3-methylphenyl)methanesulfonamide (192); N-(4-(5-bromo-4-(2-methoxyethoxy)-3-pyridinyl)-3-methylphenyl) methanesulfonamide (193); N-(4-(5-bromo-4-(methylsulfanyl)-3-pyridinyl)-3-methylphenyl) methanesulfonamide (194); N-(4-(4-chloro-3-pyridinyl)-3-methylphenyl)methanesulfonamide (195); N-(4-(4-isopropoxy-3-pyridinyl)-3-methylphenyl) methanesulfonamide (196); N-(4-(4-ethoxy-3-pyridinyl)-3- methylphenyl)methanesulfonamide (197); N-(3-methyl-4-(4-(2,2,2-trifluoroethoxy)-3-pyridinyl)phenyl) methane sulfonamide (198); N-(4-(4-(2-fluoroethoxy)-3-pyridinyl)-3-methylphenyl)methane sulfonamide (199); N-(4-(4-(2,2-difluoroethoxy)-3-pyridinyl)-3-methylphenyl)methane sulfonamide (200); N-(3-methyl-4-(4-(2-phenylethoxy)-3-pyridinyl)phenyl)methanesulfonamide (201); N-(4-(4-(2-(dimethylamino)ethoxy)-3-pyridinyl)-3-methylphenyl) methanesulfonamide (202); N-(4-(4-(2-methoxyethoxy)-3-pyridinyl)-3-methylphenyl)methanesulfonamide (203); N-(3-methyl-4-(4-(methylsulfanyl)-3-pyridinyl)phenyl) methanesulfonamide (204); N-(4-(4-methyl-3-pyridinyl) phenyl)-N'-phenylsulfamide (205); N-(4-chlorophenyl)-N-methyl-N'-(4-(4-methyl-3-pyridinyl)phenyl) sulfamide (206); N-(4-methoxyphenyl)-N'-(4-(4-methyl-3-pyridinyl) phenyl)sulfamide (207); N-(3-methyl-4-(4-methyl-3-pyridinyl)phenyl)-4-morpholine sulfonamide (208); N-(3-methyl-4-(4-methyl-3-pyridinyl)phenyl)-1-pyrrolidinesulfonamide (209); N-methyl-N'-(3-methyl-4-(4-methyl-3-pyridinyl)phenyl)sulfamide (210); 4-hydroxy-N-(3-methyl-4-(4-methylpyridin-3-yl)phenyl)piperidine-1-sulfonamide (211); N-(3-chloro-4-(4-methoxypyridin-3-yl)phenyl)methanesulfonamide (212); N-(3-methoxy-4-(4-(2,2,2-trifluoroethoxy)pyridine-3-yl)phenyl)methanesulfonamide (213); N-(3-hydroxy-4-(4-methyl-3-pyridinyl)phenyl)methanesulfonamide (215); N-(4-(5-cyano-4-methoxy-3-pyridinyl)-3-methylphenyl)methane sulfonamide (216); N-(3-methoxy-4-(4-methyl-3-pyridinyl)phenyl)methanesulfonamide (217); N-(4-(4-cyclopropylpyridin-3-yl)-3-methoxyphenyl)methanesulfonamide (225); N-(4-(4-(difluoromethyl)pyridin-3-yl)-3-methoxyphenyl)methanesulfonamide (226); N-(3-methoxy-4-(4-(prop-1-en-2-yl)pyridin-3-yl)phenyl) methanesulfonamide (227); N-(4-(4-methylpyridin-3-yl)-3-(trifluoromethoxy)phenyl)methanesulfonamide (229); N-(4-(4-chloropyridin-3-yl)-3-(trifluoromethoxy)phenyl) methanesulfonamide (230); N-(4-(4-methoxypyridin-3-yl)-3-(trifluoromethoxy)phenyl)methanesulfonamide (231); N-(3-(2-fluoroethoxy)-4-(4-methoxypyridin-3-yl)phenyl) methanesulfonamide (235); N-(4-(4-chloropyridin-3-yl)-3-(2-fluoroethoxy)phenyl)methanesulfonamide (236); N-(3-(2-fluoroethoxy)-4-(4-(trifluoromethyl)pyridin-3-yl)phenyl) methanesulfonamide (237); N-(4-(4-methylpyridin-3-yl)-3-(trifluoromethyl)phenyl)methanesulfonamide (240); N-(4-(4-chloropyridin-3-yl)-3-(trifluoromethyl)phenyl)methanesulfonamide (242); N-(4-(4-cyclopropylpyridin-3-yl)-3-(trifluoromethyl)phenyl)methanesulfonamide (243); N-(4-(4-isopropylpyridin-3-yl)-3-)methoxyphenyl) methanesulfonamide (244); N-(3,5-dimethyl-4-(4-methyl-3-pyridinyl)phenyl)methanesulfonamide (246); N-(4-(4-cyanopyridin-3-yl)-3-methoxyphenyl)methanesulfonamide (252); N-(4-(4-(hydroxymethyl)pyridin-3-yl)-3-methoxyphenyl)methanesulfonamide (253); N-(3-methoxy-4-(4-(methoxymethyl)pyridin-3-yl)phenyl)methanesulfonamide (254); and N-(4-(4-(cyclopropylmethoxy)pyridin-3-yl)-3-methoxyphenyl)methanesulfonamide (255).

One embodiment of the present disclosure provides a compound of Formula (I), (Ia), and/or (Ic), or a stereoisomer, an N-oxide, a prodrug, or a pharmaceutically acceptable salt thereof, wherein said compound is selected from: N-(3-methoxy-4-(4-methylpyrimidin-5-yl)phenyl)methanesulfonamide (161); N-(3-methoxy-4-(4-methylpyrimidin-5-yl)phenyl)cyclopropanesulfonamide (162); N-(3-methoxy-4-(4-methylpyrimidin-5-yl)phenyl)propane-1-sulfonamide (163); N-(3-methoxy-4-(4-methylpyrimidin-5-yl)phenyl)methanesulfonamide (164); N-(3-methoxy-4-(4-methylpyrimidin-5-yl)phenyl)benzenesulfonamide (165); N-(3-methoxy-4-(4-methylpyrimidin-5-yl)phenyl)pyridine-3-sulfonamide (166); 2,2,2-trifluoro-N-(3-methoxy-4-(4-methylpyrimidin-5-yl)phenyl)ethanesulfonamide (167); N-(3-methoxy-4-(4-methylpyrimidin-5-yl)phenyl)-1-phenylmethanesulfonamide (168); N-(3-methoxy-4-(4-methylpyrimidin-5-yl) phenyl)-2-phenylethanesulfonamide (169); 4-methoxy-N-(3-methoxy-4-(4-methylpyrimidin-5-yl)phenyl) benzenesulfonamide (170); 2-chloro-N-(3-methoxy-4-(4-methylpyrimidin-5-yl)phenyl)benzenesulfonamide (171); 4-chloro-N-(3-methoxy-4-(4-methylpyrimidin-5-yl)phenyl) benzenesulfonamide (172); 1-(4-chlorophenyl)-N-(3-methoxy-4-(4-methylpyrimidin-5-yl)phenyl)methanesulfonamide (173); N-(3-methoxy-4-(4-methylpyrimidin-5-yl) phenyl)naphthalene-1-sulfonamide (174); N-(3-methoxy-4-(4-methylpyrimidin-5-yl)phenyl)naphthalene-2-sulfonamide (175); N-(3-methoxy-4-(4-methylpyrimidin-5-yl)phenyl)quinoline-8-sulfonamide (176); N-(3-methoxy-4-(4-methylpyrimidin-5-yl)phenyl)naphthalene-2-sulfonamide (177); N-(4-(4-cyclopropylpyrimidin-5-yl-)-3-methoxyphenyl)methanesulfonamide (214); N-(4-(4-ethylpyrimidin-5-yl)-3-methoxyphenyl) methanesulfonamide (218); N-(3-methoxy-4-(4-propylpyrimidin-5-yl)phenyl)methanesulfonamide (219); N-(4-(4-isopropylpyrimidin-5-yl)-3-methoxyphenyl) methanesulfonamide (220); N-(4-(4-cyclohexylpyrimidin-5-yl)-3-methoxyphenyl)methanesulfonamide (221); N-(3-methoxy-4-(4-(pyrrolidin-1-yl)pyrimidin-5-yl)phenyl) methanesulfonamide (223); N-(3-methoxy-4-(4-morpholinopyrimidin-5-yl)phenyl)methanesulfonamide (224); N-(3-Methoxy-4-(4-methoxypyrimidin-5-yl)methanesulfonamide (245); N-(3-methoxy-4-(4-(2,2,2-trifluoroethoxy)-5-pyrimidinyl)phenyl)methanesulfonamide (247); N-(3-methoxy-4-(4-(2,2,2-trifluoroethylamino)pyrimidin-5-yl)phenyl)methanesulfonamide (248); and N-(4-(4-ethoxy-5-pyrimidinyl)-3-methoxyphenyl)methanesulfonamide (249).

One embodiment of the present disclosure provides a compound of Formula (I), (Ia), and/or (Id), or a stereoisomer, an N-oxide, a prodrug, or a pharmaceutically acceptable salt thereof, wherein said compound is selected from: N-(4-(isoquinolin-4-yl)-3-methoxyphenyl)methanesulfonamide (142); N-(4-(isoquinolin-4-yl)-3-methoxyphenyl)benzenesulfonamide (143); N-(4-(isoquinolin-4-yl)-3-methoxyphenyl)naphthalene-1-sulfonamide (144); N-(4-(isoquinolin-4-yl)-3-methoxyphenyl)naphthalene-2-sulfonamide (145); 4-chloro-N-(4-(isoquinolin-4-yl)-3-methoxyphenyl)benzenesulfonamide (146); N-(4-(isoquinolin-4-yl)-3-methoxyphenyl)-4-methoxybenzenesulfonamide (147); N-(4-(isoquinolin-4-yl)-3-methoxyphenyl)-1-phenylmethanesulfonamide (148); 2-chloro-N-(4-(isoquinolin-4-yl)-3-methoxyphenyl)benzenesulfonamide (149); 4-cyano-N-(4-(isoquinolin-4-yl)-3-methoxyphenyl) benzenesulfonamide (150); N-(4-(isoquinolin-4-yl)-3-methoxyphenyl)-2-phenylethanesulfonamide (151); N-(4-(isoquinolin-4-yl)-3-methoxyphenyl)-2-methylpropane-1-sulfonamide (152); N-(4-(isoquinolin-4-yl)-3-methoxyphenyl)-4-phenoxybenzenesulfonamide (153); N-(4-(isoquinolin-4-yl)-3-methoxyphenyl)quinoline-8-sulfonamide (154); 2,2,2-trifluoro-N-(4-(isoquinolin-4-yl)-3-methoxyphenyl)ethanesulfonamide (155); N-(4-(isoquinolin-4-yl)-3-methoxyphenyl)ethanesulfonamide (156); N-(4-(isoquinolin-4-yl)-3-methoxyphenyl)propane-1-sulfonamide (157); N-(4-(isoquinolin-4-yl)-3-methoxyphenyl)-1,2-dimethyl-1H-imidazole-4-sulfonamide (158); N-(4-(isoquinolin-4-yl)-3-methoxyphenyl)cyclopropanesulfonamide (159); N-(4-(isoquinolin-4-yl)-3-methoxyphenyl)pyridine-2-sulfonamide (160); 4-chloro-N-(4-(4-isoquinolinyl)phenyl)benzenesulfonamide (179); 4-chloro-N-(4-(4-isoquinolinyl)-3-methylphenyl) benzenesulfonamide (182); N-(4-(isoquinolin-4-yl)-3-(trifluoromethoxy)phenyl)methanesulfonamide (228); N-(4-

(isoquinolin-4-yl)-3-(2,2,2-trifluoroethoxy)phenyl) methanesulfonamide (232); N-(3-(2-fluoroethoxy)-4-(isoquinolin-4-yl)phenyl)methanesulfonamide (234); and N-(4-(isoquinolin-4-yl)-3-(trifluoromethyl)phenyl)methanesulfonamide (241).

One embodiment of the present disclosure provides a compound of Formula (I), (Ia), (Ib), (Ic), and/or (Id), or a stereoisomer, an N-oxide, a prodrug, or a pharmaceutically acceptable salt thereof, wherein said compound is selected from: N-(4-(4-methoxypyridin-3-yl)-3-methylphenyl)methanesulfonamide (2); N-(3-(2-fluoroethoxy)-4-(4-methyl-3-pyridinyl)phenyl)methane sulfonamide (22); N-(3-(2,2-difluoroethoxy)-4-(4-methyl-3-pyridinyl)phenyl)methane sulfonamide (23); N-(3-methoxy-4-(4-methylpyrimidin-5-yl)phenyl)methanesulfonamide (161); N-(4-(4-chloro-3-pyridinyl)-3-methylphenyl)methanesulfonamide (195); N-(3-methoxy-4-(4-(2,2,2-trifluoroethoxy)pyridine-3-yl)phenyl) methanesulfonamide (213); N-(4-(4-cyclopropylpyrimidin-5-yl-)3-methoxyphenyl)methanesulfonamide (214); N-(3-methoxy-4-(4-methyl-3-pyridinyl)phenyl) methanesulfonamide (217); N-(3-(2-fluoroethoxy)-4-(isoquinolin-4-yl)phenyl)methanesulfonamide (234); N-(3-methoxy-4-(4-(2,2,2-trifluoroethoxy)-5-pyrimidinyl) phenyl)methanesulfonamide (247); and N-(4-(4-(hydroxymethyl)pyridin-3-yl)-3-methoxyphenyl) methanesulfonamide (253).

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural Formulae herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The term "alkenyl" as used herein, refers to both branched and straight-chain unsaturated aliphatic hydrocarbon groups, which have one or more carbon-carbon double bonds that may occur at any stable point along the chain. The term "$C_{2-4}$alkenyl" is intended to include $C_2$, $C_3$, and $C_4$ alkenyl groups.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$), and 2,2,2-trfluoroethyl (—$CH_2CF_3$). When numbers appear in a subscript after the symbol "C", the subscript defines with more specificity the number of carbon atoms that a particular haloalkyl group may contain. For example, "$C_{1-4}$haloalkyl" denotes straight and branched chain haloalkyl groups with one to four carbon atoms.

The term "fluoroalkyl" as used herein is intended to include both branched and straight-chain alkyl groups substituted with one or more fluorine atoms. For example, "$C_{1-4}$fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain alkyl groups substituted with one or more hydroxyl groups. For example, "$C_{1-4}$hydroxyalkyl" is intended to include $C_1$, $C_2$, $C_3$, and $C_4$ alkyl groups substituted with one or more hydroxyl groups. Representative examples of hydroxyalkyl groups include, but are not limited to, —$CH_2OH$, and $CH_2CH_2OH$.

The term "cycloalkyl," as used herein, refers to cyclized alkyl groups, including mono-, bi- or poly-cyclic ring systems. Representative examples of cycloalkyl groups include, but are not limited to, cyclopropyl, cyclopentyl, cyclohexyl, and adamantanyl. When numbers appear in a subscript after the symbol "C", the subscript defines with more specificity the number of carbon atoms that a particular cycloalkyl group may contain. For example, "$C_3$-$C_6$cycloalkyl" denotes cycloalkyl groups with three to six carbon atoms.

The term "alkoxy," as used herein, refers to an alkyl group attached to the parent molecular moiety through an oxygen atom. For example, "$C_{1-4}$alkoxy" is intended to include $C_1$, $C_2$, $C_3$, and $C_4$ alkoxy groups.

The term "haloalkoxy" as used herein, refers a haloalkyl group as defined above attached to the parent molecular moiety through an oxygen atom. For example, "$C_{1-4}$haloalkoxy" is intended to include $C_1$, $C_2$, $C_3$, and $C_4$ haloalkoxy groups.

The term "fluoroalkoxy" as used herein, refers a fluoroalkyl group as defined above attached to the parent molecular moiety through an oxygen atom. For example, "$C_{1-4}$fluoroalkoxy" is intended to include $C_1$, $C_2$, $C_3$, and $C_4$ fluoroalkoxy groups.

The term "aryl," as used herein, refers to a group derived from a molecule containing aromatic ring(s) by removing one hydrogen that is bonded to the aromatic ring(s). Representative examples of aryl groups include, but are not limited to, phenyl, naphthalenyl, and indanyl.

The term "phenoxy" as used herein, refers to a group having the structure:

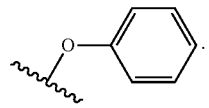 [SMILES: *Oc1ccccc1]

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups that are bicyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivatives.

As referred to herein, the term "substituted" means that at least one hydrogen atom is replaced with a non-hydrogen group, provided that normal valencies are maintained and that the substitution results in a stable compound.

The term "stereoisomer" refers to a compound which has identical chemical constitution, but differs with regard to the arrangement of the atoms or groups in space.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

The term "protecting group" refers to a substituent that is commonly employed to block or protect a particular functionality while reacting with other functional group on the compound. For a general description of protection groups and their use, see Greene, T.W., *Protective Groups In Organic Synthesis*", John Wiley & Sons, New York (1991).

Compounds of the Formula (I) may also have prodrug forms. Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound of the Formula (I)), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as a CYP17 inhibitor, or effective to treat or prevent cancer or other proliferative diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compounds of Formula (I), or stereoisomers, or pharmaceutically acceptable salts thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.05 to 2000 mg, preferably from about 0.05 to 500 mg, more preferably from about 0.05 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably about 0.05 to 50 mg/kg body weight, and most preferably about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a stereoisomer, or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a stereoisomer, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the Formulae described herein.

The terms "compound of this invention", "compounds of the present invention", "compound of Formula (I)", and "compounds of Formula (I)" include compounds of Formulae (I), (Ia), (Ib), (Ic) and (Id), and stereoisomers, N-oxides, prodrugs, and a pharmaceutically acceptable salts thereof

UTILITY

The compounds of Formula (I) are useful for the treatment of cancer, for example, cancers dependent upon androgen receptor signaling. These compounds inhibit the activity of the CYP17 enzyme, which is involved in biosynthesis of androgens. Blocking this enzyme would inhibit the production of gonadal, adrenal, and tumoral androgens and could offer a new treatment option for cancers dependent upon androgen receptor signaling, such as prostate cancer and estrogen receptor-positive breast cancer patients. Thus, the treatment comprises administering to the patient a compound of Formula (I), or a stereoisomer, or a pharmaceutically acceptable salt thereof.

In one embodiment, a method is provided for treating cancer comprising administering a compound of Formula (I), a stereoisomer, or a pharmaceutically acceptable salt thereof. The method of this embodiment can be used to treat a variety of cancers, including, but not limited to, breast cancer, ovarian cancer, and prostate cancer. Preferably, the method of this embodiment is used to treat prostate cancer and/or breast cancer. In one method of this embodiment, the compound of Formula (I), a stereoisomer, or a pharmaceutically acceptable salt thereof is administered in a therapeutically effective amount.

In one embodiment, provided are methods for treating cancer in a patient wherein the cancer is dependent upon CYP17 activation, comprising administering to the patient in need thereof a therapeutically effective amount of a compound of Formula (I), a stereoisomer, or a pharmaceutically acceptable salt thereof. In one method of this embodiment, a compound of Formula (I), a stereoisomer, or a pharmaceutically acceptable salt thereof is administered to treat prostate cancer. In another method of this embodiment, a compound of Formula (I), a stereoisomer, or a pharmaceutically acceptable salt thereof is administered to treat breast cancer. Preferably, a therapeutically effective amount of Compound (I), a stereoisomer, or a pharmaceutically acceptable salt thereof is administered.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably about 0.05 to 50 mg/kg body weight, and most preferably about 0.05 to 20 mg/kg body weight, may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phases of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the Physicians' Desk Reference (PDR) or as otherwise determined by one of ordinary skill in the art.

In one embodiment, a method is provided for treating cancer comprising administering to a mammal in need thereof a compound of Formula (I), a stereoisomer, or a pharmaceutically acceptable salt thereof; and a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I), a stereoisomer, or a pharmaceutically acceptable salt thereof; and a mineralocorticoid receptor antagonist; and optionally, one or more additional anticancer agent. Examples of suitable mineralocorticoid receptor antagonists include, but are not limited to, eplerenone.

In another embodiment, a compound of Formula (I), or a stereoisomer, or a pharmaceutically acceptable salt thereof is used to treat prostate cancer.

In another embodiment, a compound of Formula (I), or a stereoisomer, or a pharmaceutically acceptable salt thereof is used to treat breast cancer.

In one embodiment, the patient is a human.

In another embodiment, the patient is a mammalian species including, but not limited to, for example, humans and domestic animals, such as, for example, dogs, cats, and horses.

In one embodiment, the present disclosure provides a compound of Formula (I), or a stereoisomer, or a pharmaceutically acceptable salt thereof for use in therapy.

In one embodiment, the present disclosure provides a compound of Formula (I), or a stereoisomer, or a pharmaceutically acceptable salt thereof for use in therapy for the treatment of prostate cancer.

In one embodiment, the present disclosure provides a compound of Formula (I), or a stereoisomer, or a pharmaceutically acceptable salt thereof for use in therapy for the treatment of breast cancer.

In one embodiment, the present disclosure provides use of a compound of Formula (I), or a stereoisomer, or a pharmaceutically acceptable salt thereof for the manufacture of a medicament for the treatment of cancer.

In one embodiment, the present disclosure provides use of a compound of Formula (I), or a stereoisomer, or a pharmaceutically acceptable salt thereof for the manufacture of a medicament for the treatment of prostate cancer.

In one embodiment, the present disclosure provides use of a compound of Formula (I), or a stereoisomer, or a pharmaceutically acceptable salt thereof for the manufacture of a medicament for the treatment of breast cancer.

METHODS OF PREPARATION

The compounds of the present invention may be prepared by synthetic routes that include processes analogous to those well-known in the chemical arts, particularly in light of the description provided herein. For illustrative purposes, general Schemes 1 to 8 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting material and reagents are depicted in the Schemes and discussed below, other starting materials and reagents can be easily substituted to provide a variety of compounds of the present invention. In addition, many of the compounds prepared by the methods below can be further modified in light of this disclosure using conventional chemistry well known to those skilled in the art.

As shown in Scheme 1, for instance a 3-pyridylboronic acid or ester II can be coupled to an aryl halide of type III, where P is a common protecting group known to those skilled in the art, via standard Suzuki coupling conditions to give a coupled product of general structure IV. Removal of protecting group via standard conditions gives the aniline of general structure V. Treatment of the aniline with a sulfonyl chloride VI in the presence of an organic base such as triethylamine, will give the desired sulfonamide of general structure (I).

Scheme 1

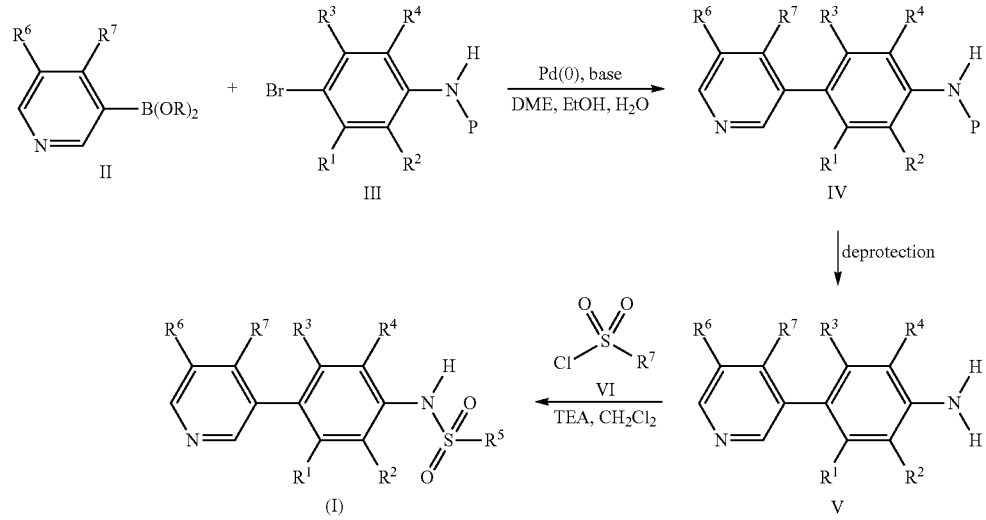

Alternatively, the boronic acid or ester of general structure II (Scheme 2) can be coupled with an aryl halide of general structure VII where the sulfonamide functionality is already present under standard Suzuki coupling conditions to give products of general structure (I).

with the boronic acid/ester VIII will give compounds of general structure XIII. Functionalization at the 5-position of the pyridine in XIII via Suzuki or Buchwald coupling will give compounds of general structure (I).

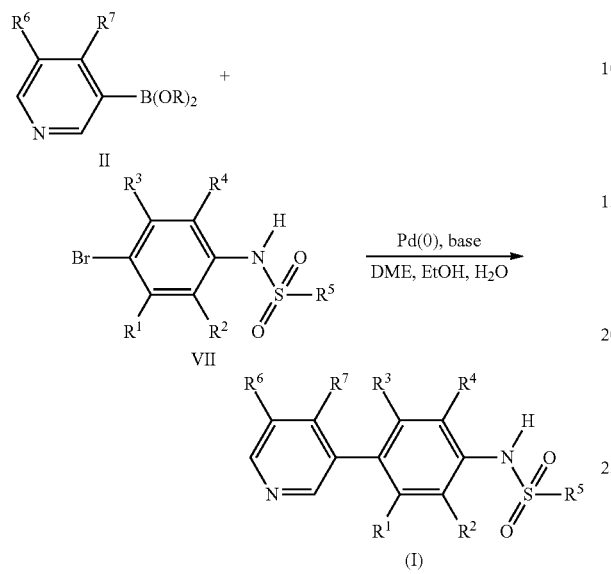

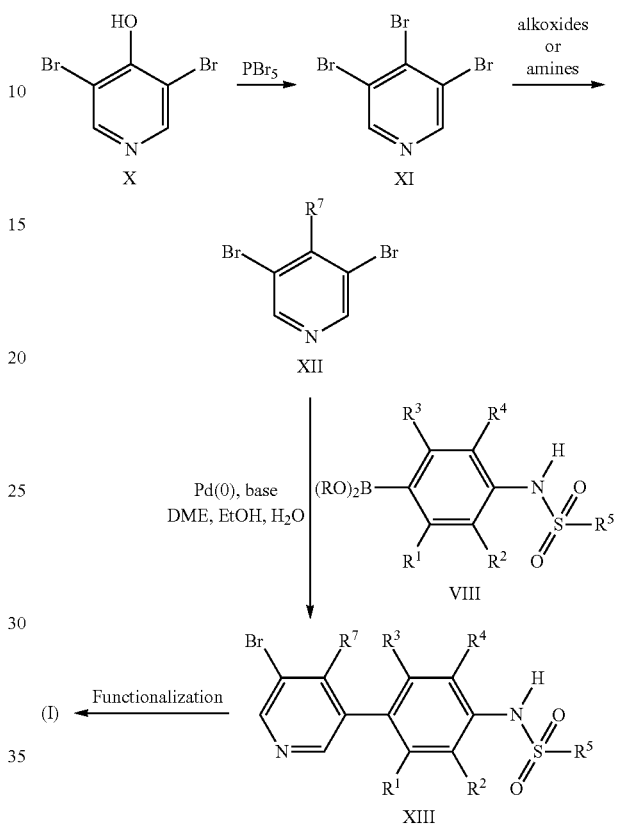

Scheme 3 depicts another preparation beginning with sulfonamides of general structure VII where G is bromo or iodo. Treatment of the halide at low temperature with excess alkyl lithium, such as tertiary butyl lithium, followed by trapping of the resultant anion with a boronic ester such as pinacol borane, will give products of general structure VIII with a boronic ester para to the sulfonamide. This boronic ester can then be coupled to the 3-bromopyridine of general structure IX under standard Suzuki conditions to afford compounds of general structure (I).

An alternative coupling strategy is shown in Scheme 5. Treatment of optionally substituted pyridines of general structure XIV with an organolithium such as LDA followed by addition of $ZnCl_2$ and Pd(O) in the presence of an aryl halide such as the bromide of general structure XV, will afford the coupled product of general structure XVI. The 4-position of the pyridine can then be further functionalized by chemistry well-known to one skilled in the art such as Suzuki couplings with aryl boronic acids to afford compounds of general structure XVII. Reduction of the nitro group under standard conditions such as iron/acetic acid or Pd catalyzed hydrogenation will afford the aniline of general structure V which can be converted to the sulfonamide of general structure (I) by methods discussed previously.

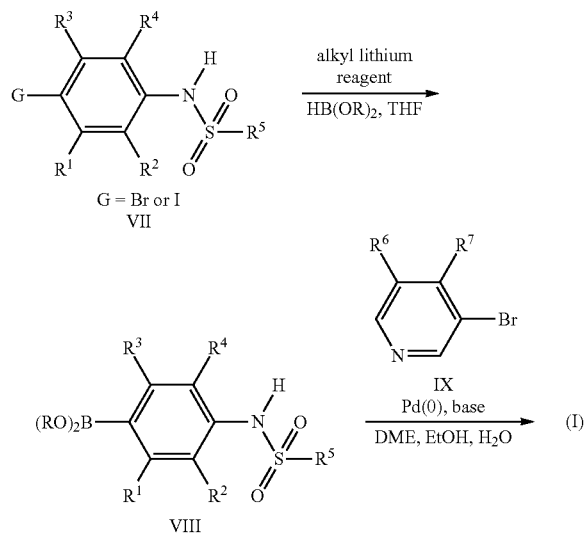

Starting with the commercial pyridine X, treatment with $PBr_5$ will afford the tribromide XI. Substitution at the 4-position of XI with various alkoxides and amines under conditions well-known to one skilled in the art will afford compounds of general structure XII. Standard Suzuki coupling

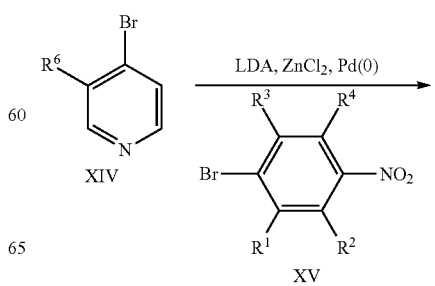

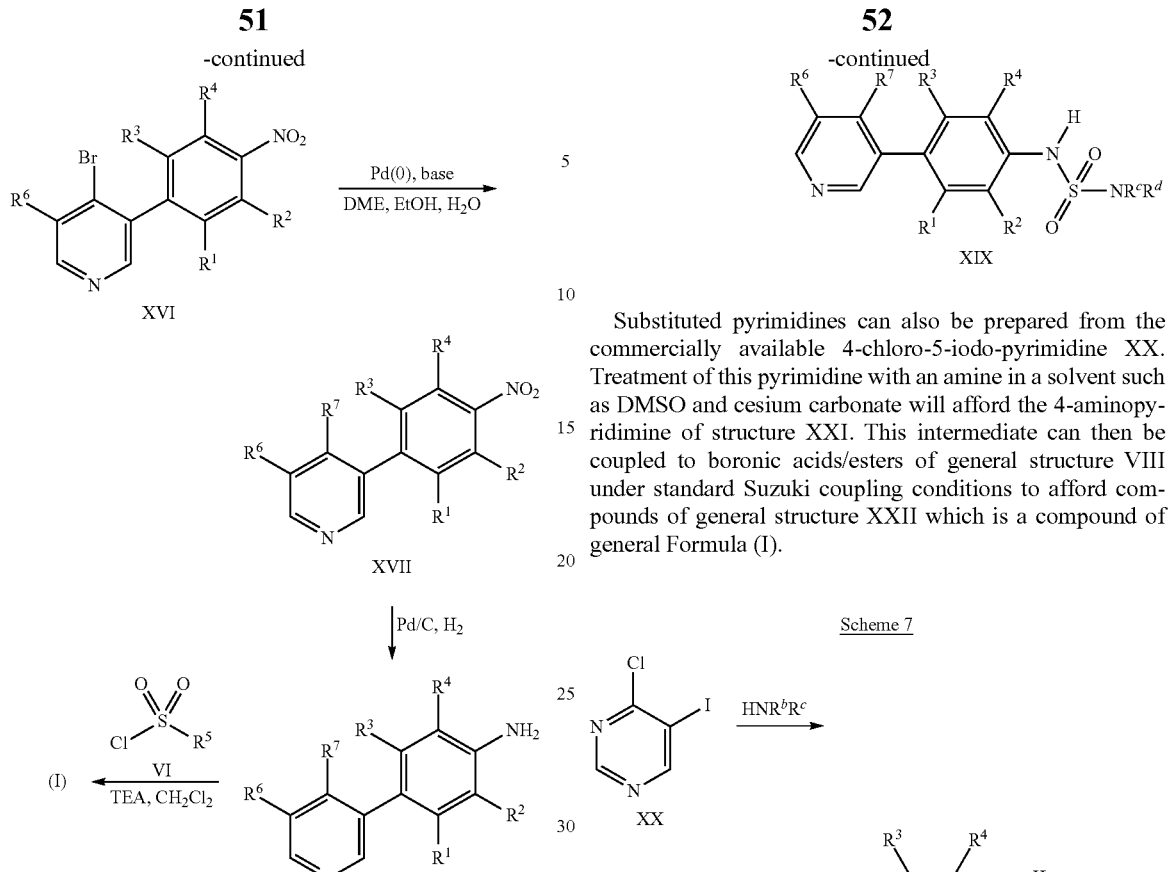

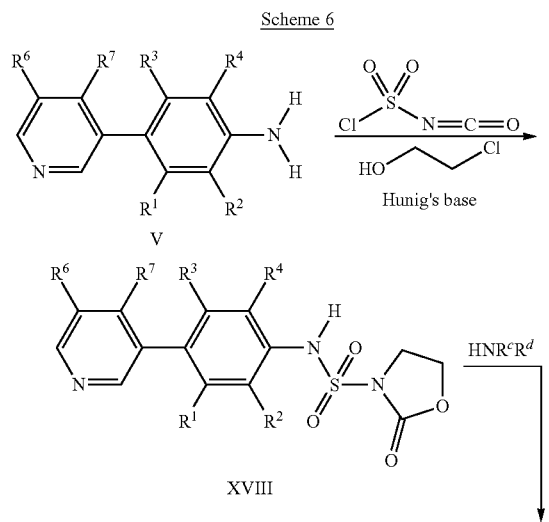

Sulfamides can were also prepared and are encompassed by general Formula (I). Treatment of the aniline V with chlorosulfonylisocyanate and 2-hydroxychloroethane in the presence of Hunig's base gives the intermediate oxazolidinone of structure XVIII. Subsequent treatment with an amine at high temperatures, such as 80° C. in $CH_3CN$, will give the sulfamide of general structure XIX, which is a structure of general Formula (I).

Substituted pyrimidines can also be prepared from the commercially available 4-chloro-5-iodo-pyrimidine XX. Treatment of this pyrimidine with an amine in a solvent such as DMSO and cesium carbonate will afford the 4-aminopyridimine of structure XXI. This intermediate can then be coupled to boronic acids/esters of general structure VIII under standard Suzuki coupling conditions to afford compounds of general structure XXII which is a compound of general Formula (I).

In a similar manner, the 4-alkoxy-pyrimidines of general structure XXIII can be prepared leading to compounds of general structure XXIV which is a compound of general Formula (I).

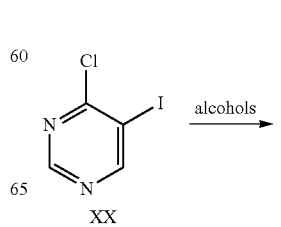

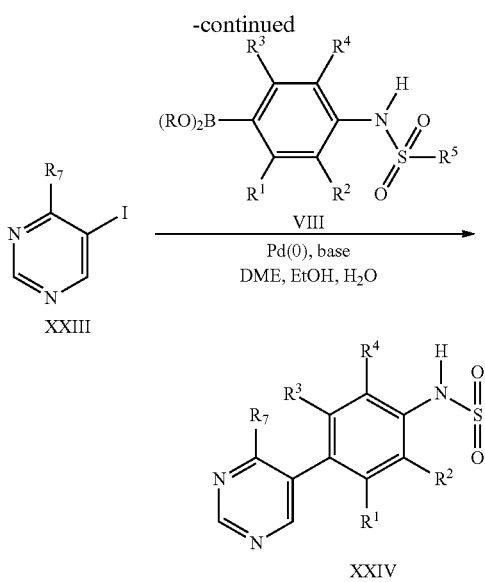

EXAMPLES

The following Examples are offered as illustrative as a partial scope and particular embodiment of the invention and are not to be limiting of the scope of the invention.

Abbreviations

The following abbreviations are employed in the Example section below and elsewhere herein:
AcOH acetic acid
$Ac_2O$ acetic anhydride
$CH_2Cl_2$ or DCM dichloromethane
DCE dichloroethane
DMAP dimethylaminopyridine
DME dimethoxyethane
DIEA or Hunig's base diisopropylethylamine
DMF dimethylformamide
DMSO dimethylsulfoxide
EDC 1-ethyl-3-[3-dimethylaminopropyl]carbodiimide hydrochloride
Et ethyl
$Et_2O$ diethyl ether
EtOAc ethyl acetate
EtOH ethanol
$Et_3N$ or TEA triethylamine
$Et_3SiH$ triethylsilane
HCl hydrochloric acid
HOBT 1-hydroxybenzotriazole
iPr isopropyl
iPrOH isopropanol
LDA lithium diisopropylamide
Me methyl
MeOH methanol
NBS N-bromosuccinimide
n-BuLi n-butyl lithium
NaOMe sodium methoxide
NaOH sodium hydroxide
$PMe_3$ trimethyl phosphine
$Pd(Ph_3P)_4$ tetrakis(triphenylphosphine)palladium(0)
TBSCl tert-butyldimethylsilylchloride
TFA trifluoroacetic acid
$Tf_2O$ trifluoromethylsulfonic anhydride
THF tetrahydrofuran
VCD vibrational circular dichroism
h hour(s)
min minute(s)
L liter
mL milliliter
αL microliter
g gram(s)
mg milligram(s)
mol mole(s)
mmol millimole(s)
rt room temperature
Ret time HPLC/LC-MS retention time
sat or sat'd saturated
aq. aqueous
TLC thin layer chromatography
HPLC high performance liquid chromatography
Prep HPLC preparative reverse phase HPLC
LC/MS liquid chromatography/mass spectrometry
MS mass spectrometry
NMR nuclear magnetic resonance
mp melting point Analytical HPLC/LC-MS Retention Time Retention time data reported for each example and intermediate uses one of the following general Analytical HPLC/LC-MS methods:

Method A: YMC S-5 ODS-A 4.6×50 mm column; flow rate 4 mL/min; gradient time 4 min; 100% Solvent A to 100% Solvent B and holding 100% Solvent B for 1 min; monitoring at 220 nm (Solvent A: 10% MeOH, 90% $H_2O$, 0.2% $H_3PO_4$; Solvent B: 90% MeOH, 10% $H_2O$, 0.2% $H_3PO_4$). (HPLC Ret time[a]).

Method B: PHENOMENEX® 5u C18 4.6×50 mm column; flow rate 4 mL/min; gradient time 4 min; 100% Solvent A to 100% Solvent B and holding 100% Solvent B for 1 min; monitoring at 220 nm (Solvent A: 10% MeOH, 90% $H_2O$, 0.1% TFA; Solvent B: 90% MeOH, 10% $H_2O$, 0.1% TFA). (HPLC Ret time[b]).

Method C: CHROMOLITH® S5 ODS 4.6×50 mm column; flow rate 4 mL/min; gradient time 4 min; 100% Solvent A to 100% Solvent B and holding 100% Solvent B for 1 min; monitoring at 220 nm (Solvent A: 10% MeOH, 90% $H_2O$, 0.1% TFA; Solvent B: 90% MeOH, 10% $H_2O$, 0.1% TFA). (HPLC Ret time[c]).

Method D: Xbridge 4.6×50 mm S10 column; flow rate 4 mL/min; gradient time 3 min;, 100% Solvent A to 100% Solvent B and holding 100% Solvent B for 1 min; monitoring at 254 nm (Solvent A: 95% MeOH, 5% $H_2O$, 0.1% TFA; Solvent B: 5% MeOH, 95% $H_2O$, 0.1% TFA). (HPLC Ret time[d]).

Method E: PHENOMENEX® Luna C18, 50×2, 3u column; flow rate 0.8 mL/min; gradient time 4 min; 100% Solvent A to 100% Solvent B and holding 100% Solvent B for 1 min; monitoring at 250 nm (Solvent A: 5% MeOH, 95% $H_2O$, 10 mM Ammonium Acetate; Solvent B: 95% MeOH, 5% $H_2O$, 10 mM Ammonium Acetate). (HPLC Ret time[e]).

Method F: SUPELCO® Ascentis Express 4.6×50 mm 2.7 um C18; gradient time 4 min; 100% Solvent A to 100% Solvent B and holding 100% Solvent B for 1 min; monitoring at 220 nm (Solvent A: 5% Acetonitrile, 95% $H_2O$, 10 mM Ammonium Acetate; Solvent B: 95% Acetonitrile, 5% $H_2O$, 10 mM Ammonium Acetate). (HPLC Ret time[f]).

Method G: Xbridge 4.6×50 mm S5 column; flow rate 5 mL/min; gradient time 4 min; 100% Solvent A to 100% Solvent B and holding 100% Solvent B for 1 min; monitoring at 254 nm (Solvent A: 10% MeOH, 90% H$_2$O, 0.1% TFA; Solvent B: 90% MeOH, 10% H$_2$O, 0.1% TFA). (HPLC Ret time$^g$).

Method H: PHENOMENEX® Luna 4.6×30 mm S10 column; flow rate 3 mL/min; gradient time 4 min; 100% Solvent A to 100% Solvent B and holding 100% Solvent B for 1 min; monitoring at 220 nm (Solvent A: 10% MeOH, 90% H$_2$O, 0.1% TFA; Solvent B: 90% MeOH, 10% H$_2$O, 0.1% TFA). (HPLC Ret time$^h$).

Method I: Mac-mod Halo C18, 4.6×50 mm 2.7-µm particles; flow rate 4 mL/min; gradient time 4 min; 100% Solvent A to 100% Solvent B and holding 100% Solvent B for 1 min; monitoring at 220 nm (Solvent A: 5% Acetonitrile, 95% H$_2$O, 10 mM ammonium acetate; Solvent B: 90% Acetonitrile, 10% H$_2$O, 10 mM ammonium acetate). (HPLC Ret time$^i$).

Method J: PHENOMENEX® Luna C18 4.6×30 mm 3u column; flow rate 4 mL/min; monitoring at 220 nm; Solvent A:10:90 H$_2$O:ACN NH$_4$OAc; Solvent B:10:90 H$_2$O:ACN NH$_4$OAc; 0%-95% B in 2 min. (HPLC Ret time$^j$).

Intermediate 1

3-Methyl-4-(4-methylpyridin-3-yl)aniline

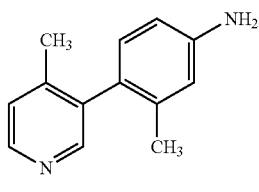

Intermediate 1A: 4-Methylpyridin-3-ylboronic acid

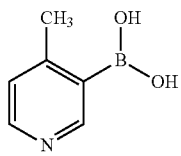

To a stirring solution of 3-bromo-4-methylpyridine (5.9 g, 34.3 mmol) in toluene (30 mL) and THF (7.5 mL) was added triisopropyl borate (10.3 mL, 44.6 mmol). The resulting mixture was cooled to −78° C. under a nitrogen atmosphere followed by the addition of n-butyllithium (17.83 mL, 44.6 mmol, 2.5 M in hexanes) over a period of 1 hour. The reaction mixture was allowed to stir for an additional 30 min and then the dry ice bath was removed. The reaction mixture was quenched by the addition of 2N HCl (60 mL). Upon reaching room temperature, the resulting yellow solution was transferred to a 500 mL separatory funnel and the layers were separated. The aqueous layer was neutralized to pH 7.0 with sodium hydroxide and then extracted with THF (3×60 mL). The combined organics were washed with brine, dried over anhydrous sodium sulfate, and concentrated under reduced pressure. The resulting solid material was vigorously stirred with acetonitrile and filtered to yield Intermediate 1A (2.2 g, 16.06 mmol, 48.8% yield) as an off-white solid. MS (ES): m/z=138.0 [M+H]$^+$. $^1$H NMR (400 MHz, MeOD) δ ppm 8.45 (1 H, s), 8.33 (1 H, d, J=5.77 Hz), 7.50 (1 H, d, J=5.27 Hz), 2.62 (3 H, s).

Intermediate 1B:
N-(4-Bromo-3-methylphenyl)acetamide

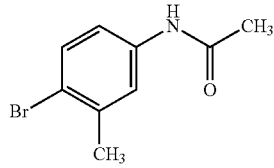

To a stirring solution of 4-bromo-3-methylaniline (4.3 g, 23.11 mmol) in acetic acid (2 mL, 23.11 mmol) at room temperature was added acetic anhydride (2.62 mL, 27.7 mmol). The reaction mixture was refluxed for 30 min, cooled to room temperature and then poured into 20 mL of ice water while allowing to stir for 5 min. The aqueous suspension was filtered, and the solid was washed with water, dissolved in CH$_2$Cl$_2$ and then dried over sodium sulfate. The organic layer was filtered and concentrated under reduced pressure to yield Intermediate 1B (4.96 g, 21.73 mmol, 94% yield) as an off-white solid. MS (ES): m/z=229.9 [M+H]$^+$.

Intermediate 1C:
4-(4-Methylpyridin-3-yl)-1H-indazole

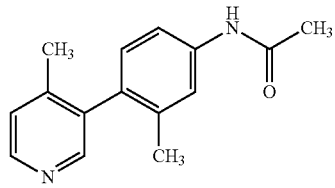 [SMILES: CC(=O)Nc1ccc(-c2cnccc2C)c(C)c1]

A pressure vessel charged with tetrakis(triphenylphosphine)palladium(0) (1.013 g, 0.877 mmol), Intermediate 1B (4 g, 17.54 mmol), sodium carbonate (9.29 g, 88 mmol), and Intermediate 1A (3.12 g, 22.80 mmol) was stirred at room temperature for 10 min under a nitrogen atmosphere, followed by the sequential addition of ethanol (5 mL), DME (10 mL), and water (5 mL). The resulting mixture was stirred under a nitrogen atmosphere for 30 min and then heated at 90° C. for 3 hours. The reaction mixture was cooled, filtered, and rinsed with excess MeOH. The filtrate was concentrated under reduced pressure and then purified by silica gel chromatography (120 g ISCO column, eluting with 0% to 10% MeOH in CH$_2$Cl$_2$) to provide Intermediate 1C (3.2 g, 76% yield) as a pale yellow solid. MS (ES): m/z=241.1 [M+H]$^+$.

Intermediate 1:
3-Methyl-4-(4-methylpyridin-3-yl)aniline

Intermediate 1C (6.79 g, 28.3 mmol) was dissolved in MeOH (10 mL) followed by the addition of concentrated HCl (10 mL, 329 mmol). The resulting mixture was refluxed for 2 hours and then evaporated under reduced pressure to remove the volatile organics. The crude material was dissolved in a saturated aqueous solution of sodium bicarbonate (200 mL) and extracted with EtOAc (2×200 mL). The combined organics were washed with brine, dried over anhydrous sodium sulfate, and concentrated under reduced pressure to yield Intermediate 1 (5.6 g, 99% yield) as a pale yellow semi solid. HPLC Ret time$^a$: 0.170 min. MS (ES): m/z=199.0 [M+H]$^+$. $^1$H NMR (400 MHz, MeOD) δ ppm 1.96 (s, 3 H) 2.14 (s, 3 H) 6.65 (dd, J=8.06, 2.52 Hz, 1 H) 6.71 (d, J=2.27 Hz, 1 H) 6.83 (d, J=8.06 Hz, 1 H) 7.35 (d, J=5.04 Hz, 1 H) 8.18 (s, 1 H) 8.34

(d, J=5.04 Hz, 1 H). Intermediate 1 was used in the synthesis of Examples 5, 6 and 33 to 78.

Intermediate 2

3-Ethoxy-4-(4-methylpyridin-3-yl)aniline

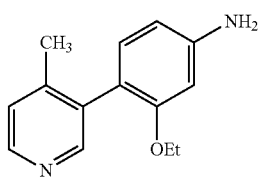 [SMILES: CCOc1cc(N)ccc1-c1cnccc1C]

Intermediate 2 was prepared from Intermediate 1A and N-(4-bromo-3-ethoxyphenyl)acetamide by the procedures described for the preparation of Intermediate 1. (60% yield). MS (ES): m/z=229.2 [M+1-1]⁺. Intermediate 2 was used in the synthesis of Example 17.

Intermediates 3 to 6

The following Intermediates in Table 1 were prepared by the procedures described in the preparation of Intermediate 1 or Intermediate 2.

TABLE 1

| Intermediate No. | Structure | Used for Ex. No. | Name | [M + H]⁺ | Ret time |
|---|---|---|---|---|---|
| 3 | 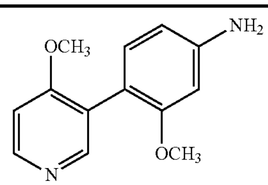 | 16 | 3-methoxy-4-(4-methoxypyridin-3-yl)aniline | 231.1 | 0.242$^c$ |
| 4 | 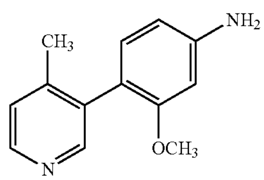 [SMILES: COc1cc(N)ccc1-c1cnccc1C] | 18-19, 79-99 | 3-methoxy-4-(4-methylpyridin-3-yl)aniline | 215.1 | 0.175$^a$ |
| 5 | 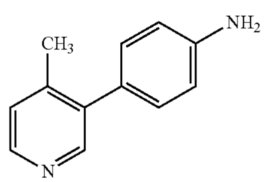 | 3, 4, 30, 100-141 | 4-(4-methylpyridin-3-yl)aniline | 185.1 | 0.171$^a$ |
| 6 | 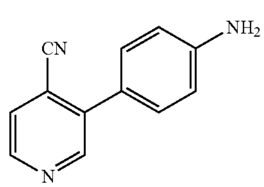 [SMILES: N#Cc1ccncc1-c1ccc(N)cc1] | 26-28 | 3-(4-aminophenyl)isonicotinonitrile | 196.1 | |

Intermediates 7 and 8

The following Intermediates in Table 2 were prepared by the procedure described for the preparation of Intermediate 1C using Intermediate 1A and corresponding bromides.

TABLE 2

| Intermediate No. | Structure | Used for Ex. No. | Name | [M + H]+ | Ret time |
|---|---|---|---|---|---|
| 7 | 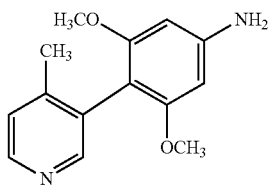 [SMILES: COc1cc(N)cc(OC)c1-c1cnccc1C] | 29 | 2-fluoro-4-(4-methylpyridin-3-yl)aniline | 203.1 | 0.600[a] |
| 8 | 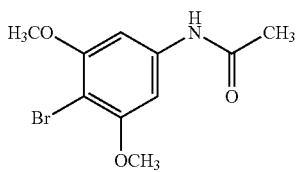 | 31-32 | 4-(4-methylpyridin-3-yl)-2-(trifluoromethoxy)aniline | 269.2 | |

Intermediate 9

3,5-Dimethoxy-4-(4-methylpyridin-3-yl)aniline

[structure]

Intermediate 9A:
N-(4-Bromo-3,5-dimethoxyphenyl)acetamide

[structure]

N-(3,5-Dimethoxyphenyl)acetamide (500 mg, 2.56 mmol) was suspended in CCl$_4$ (3 mL) followed by the addition of NBS (456 mg, 2.56 mmol) at room temperature. The reaction mixture was stirred at room temperature for 0.5 hour, heated at 80° C. for 2 hours and then concentrated under reduced pressure. The crude material was purified by silica gel chromatography (80 g ISCO column, eluting with 0% to 20% EtOAc in CH$_2$Cl$_2$) to provide Intermediate 9A (178 mg, 0.649 mmol, 25.4% yield) as a white solid. MS (ES): m/z=276.0 [M+H]+. $^1$H NMR (400 MHz, MeOD) δ ppm 2.14 (s, 3 H) 3.85 (s, 6 H) 7.01 (s, 2 H).

Intermediate 9:
3,5-Dimethoxy-4-(4-methylpyridin-3-yl)aniline

Intermediate 9 was prepared by the procedure described for the preparation of Intermediate 1 using Intermediate 9A and Intermediate 1A. (43% yield). MS (ES): m/z=245.1 [M+H]+. Intermediate 9 was used in the synthesis of Example 21.

Intermediate 10

4-(Isoquinolin-4-yl)aniline

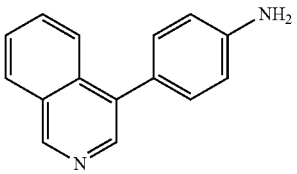 [SMILES: Nc1ccc(-c2cncc3ccccc23)cc1]

Intermediate 10A: tert-Butyl 4-(isoquinolin-4-yl)phenylcarbamate

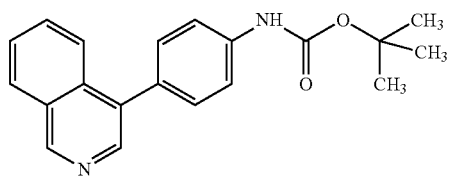 [SMILES: CC(C)(C)OC(=O)Nc1ccc(-c2cncc3ccccc23)cc1]

Intermediate 10A was prepared from 4-bromoisoquinoline and 4-(tert-butoxy carbonylamino)phenylboronic acid by the procedure described for the preparation of Intermediate 1C, and was obtained as an off-white foam (63% yield). MS (ES): m/z=321.2 [M+H]+. HPLC Ret time[a]: 2.432 min. $^1$H NMR (400 MHz, DMSO-d$_6$) δ ppm 1.51 (s, 9 H) 7.44 (d, J=8.53 Hz, 2 H) 7.65 (d, J=8.53 Hz, 2 H) 7.68-7.75 (m, 1 H) 7.75-7.82 (m, 1 H) 7.88 (d, J=8.53 Hz, 1 H) 8.20 (d, J=7.78 Hz, 1 H) 8.40 (s, 1 H) 9.31 (s, 1 H) 9.57 (s, 1 H).

Intermediate 10: 4-(Isoquinolin-4-yl)aniline

To a solution of Intermediate 10A (0.075 g, 0.234 mmol) in CH$_2$Cl$_2$ (2.0 mL) was added TFA (1.0 mL, 12.98 mmol). The mixture was stirred at room temperature for 1 hour. The volatiles were removed by a stream of nitrogen. The crude material was dissolved in a saturated aqueous solution of sodium bicarbonate (10 mL) and extracted with CH$_2$Cl$_2$ (2×10 mL). The combined organics were washed with brine, dried over anhydrous sodium sulfate and concentrated under reduced pressure to yield a pale semi solid. MS (ES): m/z=220.9 [M+H]$^+$. Intermediate 10 was used in the synthesis of Example 179.

Intermediate 11

4-(1H-Pyrrolo[2,3-c]pyridin-4-yl)aniline

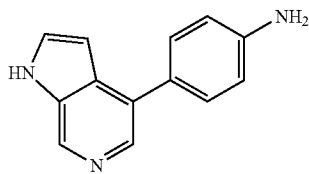 [SMILES: Nc1ccc(-c2cncc3[nH]ccc23)cc1]

Intermediate 11 was prepared from 4-bromo-1H-pyrrolo[2,3-c]pyridine and 4-(tert-butoxycarbonylamino)phenylboronic acid by the procedures described for the preparation of Intermediate 10. MS (ES): m/z=210.1 [M+H]$^+$. Intermediate 11 was used in the synthesis of Example 181.

Intermediate 12

(3-(4-Aminophenyl)pyridin-4-yl)(pyrrolidin-1-yl)methanone

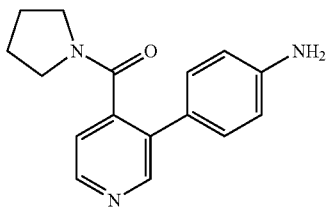 [SMILES: Nc1ccc(-c2cnccc2C(=O)N2CCCC2)cc1]

Intermediate 12A:
(3-Bromopyridin-4-yl)(pyrrolidin-1-yl)methanone

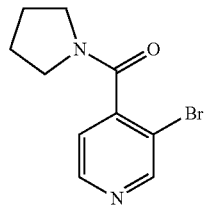 [SMILES: O=C(c1ccncc1Br)N1CCCC1]

To a solution of 3-bromoisonicotinic acid (0.250 g, 1.238 mmol) in DMF (1.5 mL) was added pyrrolidine (0.097 g, 1.361 mmol), EDC (0.285 g, 1.485 mmol), and HOBt (0.227 g, 1.485 mmol) resulting in a homogenous solution. After stirring at room temperature 3 hours, the reaction mixture was dissolved in a saturated aqueous solution of sodium bicarbonate (20 mL) and extracted with EtOAc (2×20 mL). The combined organics were washed with brine, dried over anhydrous sodium sulfate, and concentrated under reduced pressure to provide Intermediate 12A as a colorless oil (0.219 g, 0.850 mmol, 68.7% yield). HPLC Ret time$^a$: 1.463 min. MS (ES): m/z=257.0 [M+H]$^+$. $^1$H NMR (400 MHz, acetone) δ ppm 1.77-2.03 (m, 4 H) 3.20 (t, J=6.40 Hz, 2 H) 3.55 (t, J=6.65 Hz, 2 H) 7.38 (d, J=4.27 Hz, 1 H) 8.63 (d, J=4.77 Hz, 1 H) 8.78 (s, 1 H).

Intermediate 12B: tert-Butyl 4-(4-(pyrrolidine-1-carbonyl)pyridin-3-yl)phenyl carbamate

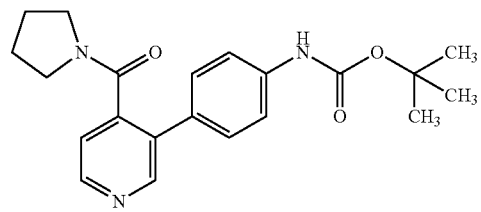 [SMILES: CC(C)(C)OC(=O)Nc1ccc(-c2cnccc2C(=O)N2CCCC2)cc1]

Intermediate 12B was prepared from 4-(tert-butoxycarbonylamino) phenylboronic acid and Intermediate 12A by the procedure described for the preparation of Intermediate 1C, and was obtained as a white foam (86% yield). HPLC Ret time$^a$: 2.365 min. MS (ES): m/z=368.3 [M+H]$^+$. $^1$H NMR (500 MHz, DMSO-d$_6$) δ ppm 1.47 (s, 9 H) 1.53 (d, J=6.05 Hz, 2 H) 1.61-1.72 (m, 2 H) 2.70-2.88 (m, 2 H) 3.23-3.30 (m, 2H) 7.23-7.46 (m, 3 H) 7.53 (d, J=8.25 Hz, 2 H) 8.58 (d, J=4.95 Hz, 1 H) 8.65 (s, 1 H) 9.51 (s, 1 H).

Intermediate 12: (3-(4-Aminophenyl)pyridin-4-yl)(pyrrolidin-1-yl)methanone

Intermediate 12 was prepared from Intermediate 12B by the procedure described for the preparation of Intermediate 10. Intermediate 12 was used in the synthesis of Example 180.

Intermediate 13

4-(4-Phenylpyridin-3-yl)aniline

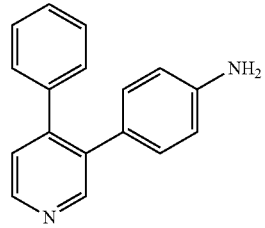

Intermediate 13A:
4-Bromo-3-(4-nitrophenyl)pyridine

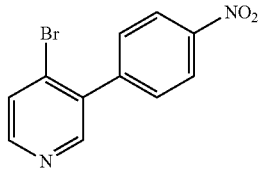

A solution of LDA (2.86 mL, 5.14 mmol) in THF (2.5 mL) was transferred to a solution of 4-bromopyridine hydrochloride (500 mg, 2.57 mmol) in THF (5 mL) at −78° C. and stirred for 30 min. Zinc chloride (350 mg, 2.57 mmol) in THF (2.5 mL) was added to the above reaction mixture. A precipitate was formed and the mixture was allowed to warm to room temperature. Next, 1-bromo-4-nitrobenzene (1039 mg, 5.14 mmol) and tetrakis(triphenylphosphine)palladium(0) (149 mg, 0.129 mmol) were added, and the reaction mixture was heated to reflux for 3 hours and then cooled to room temperature. The resulting reaction mixture was diluted with saturated solution of ammonium chloride (25 mL) and extracted with EtOAc (2×25 mL). The combined organics were washed with brine, dried over anhydrous sodium sulfate, and concentrated under reduced pressure. The crude material was purified by silica gel chromatography (40 g ISCO column, eluting with 0% to 50% EtOAc in $CH_2Cl_2$) to afford Intermediate 13A (300 mg, 1.023 mmol, 10.47% yield) as a pale yellow solid. MS (ES): m/z=280.9 $[M+H]^+$. $^1H$ NMR (400 MHz, DMSO-$d_6$) δ ppm 7.84 (s, 1 H) 7.87 (s, 1 H) 7.97 (d, J=5.29 Hz, 1 H) 8.41 (s, 1 H) 8.43 (s, 1 H) 8.57 (d, J=5.29 Hz, 1 H) 8.66 (s, 1 H).

Intermediate 13B:
3-(4-Nitrophenyl)-4-phenylpyridine

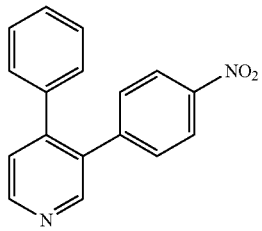 [SMILES: Nc1ccc(-c2cnccc2-c2ccccc2)cc1]

Intermediate 13B was prepared from Intermediate 13A and phenylboronic acid by the procedure described for the preparation of Intermediate 1C. The crude material was purified by silica gel chromatography (12 g ISCO column, eluting with 0 to 40% EtOAc in $CH_2Cl_2$) to yield Intermediate 13B. MS (ES): m/z=277.0 $[M+H]^+$.

Intermediate 13: 4-(4-Phenylpyridin-3-yl)aniline

To a solution of Intermediate 13B in MeOH (3 mL) was added Pd/C (33.2 mg, 0.031 mmol). The resulting mixture was stirred under $H_2$ atmosphere for 2 hours and then filtered through a pad of CELITE®/silica. The filtrate was concentrated to yield the Intermediate 13 (100 mg, 0.406 mmol, 78% yield). MS (ES): m/z=247.0 $[M+H]^+$. Intermediate 13 was used in the synthesis of the compounds of Examples 8 and 9.

Intermediates 14 and 15

The following Intermediates in Table 3 were prepared by the procedures described for the preparation of Intermediate 13 using 1-iodo-2-methyl-4-nitrobenzene and corresponding boronic acids

TABLE 3

| Intermediate No. | Structure | Used for Ex. No. | Name | $[M+H]^+$ | Ret time |
|---|---|---|---|---|---|
| 14 | 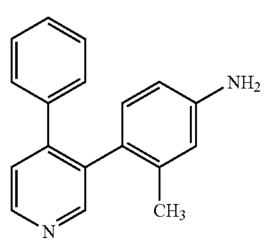 [SMILES: Cc1cc(N)ccc1-c1cnccc1-c1ccccc1] | 11-12 | 3-methyl-4-(4-phenylpyridin-3-yl)aniline | 261.0 | 1.12/1.19[b] |
| 15 | 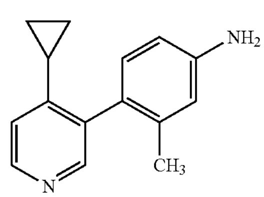 [SMILES: Cc1cc(N)ccc1-c1cnccc1C1CC1] | 13 | 4-(4-cyclopropylpyridin-3-yl)-3-methylaniline | 225.1 | |

Intermediate 16

3-(2-Fluoroethoxy)-4-(4-methylpyridin-3-yl)aniline

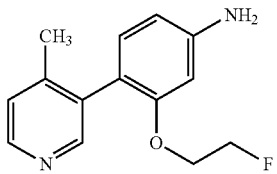 [SMILES: Cc1ccncc1-c1ccc(N)cc1OCCF]

Intermediate 16A: 2-Bromo-5-nitrophenol

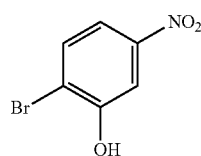 [SMILES: O=[N+]([O-])c1ccc(Br)c(O)c1]

To a solution of 1-bromo-2-methoxy-4-nitrobenzene (3 g, 12.93 mmol) in $CH_2Cl_2$ (5 mL) at −78° C. was added tribromoborane (38.8 mL, 38.8 mmol). The resulting mixture was stirred at room temperature overnight and then diluted with EtOAc and water. The separated organic layer was washed with brine, dried over sodium sulfate and concentrated. The residue was purified by flash chromatography on silica to yield 16A (2.0 g, 71% yield). MS (ES): m/z=218.0 [M+H]+. $^1$H NMR (500 MHz, DMSO-$d_6$) δ ppm 7.55-7.60 (m, 1 H) 7.61-7.66 (m, 1 H) 7.79 (d, J=2.20 Hz, 1 H).

Intermediate 16B: 1-Bromo-2-(2-fluoroethoxy)-4-nitrobenzene

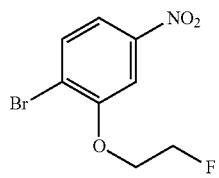 [SMILES: O=[N+]([O-])c1ccc(Br)c(OCCF)c1]

Intermediate 16A (475 mg, 2.179 mmol) was dissolved in DMF (1 mL) and to this solution was added potassium carbonate (903 mg, 6.54 mmol) and 1-bromo-2-fluoroethane (415 mg, 3.27 mmol). The reaction mixture was stirred at 100° C. for 3 hours, cooled, diluted with water (20 mL) and then extracted with EtOAc (2×20 mL). The combined organics were washed with brine, dried over anhydrous sodium sulfate, and concentrated under reduced pressure. Intermediate 16B was obtained as a pale yellow semi-solid (570 mg, 2.159 mmol, 99% yield). MS (ES): m/z=199.0 [M+H]+. $^1$H NMR (400 MHz, DMSO-$d_6$) δ ppm 4.47-4.51 (m, 1 H) 4.55-4.59 (m, 1 H) 4.73-4.78 (m, 1 H) 4.85-4.91 (m, 1 H) 7.77-7.83 (m, 1 H) 7.91 (d, J=2.51 Hz, 1 H) 7.94 (d, J=8.53 Hz, 1 H).

Intermediate 16C: 3-(2-(2-Fluoroethoxy)-4-nitrophenyl)-4-methylpyridine

Intermediate 16C was prepared from Intermediate 1A and Intermediate 16B by the procedure described for the preparation of Intermediate 1C, and was obtained as a beige solid (254 mg, 61% yield). MS (ES): m/z=277.0 [M+H]+.

Intermediate 16: 3-(2-Fluoroethoxy)-4-(4-methylpyridin-3-yl)aniline

Intermediate 16C (254 mg, 0.919 mmol), Zinc (361 mg, 5.52 mmol), and ammonium chloride (344 mg, 6.44 mmol) were taken in a flask followed by addition of EtOH (2 mL) and THF (2 mL). The reaction mixture was stirred at room temperature for 2 hours and filtered through a pad of CELITE®. The filtrate was concentrated to give Intermediate 16 (220 mg, 0.893 mmol, 97% yield) as a yellow solid. MS (ES): m/z=247.1 [M+H]+. $^1$H NMR (400 MHz, DMSO-$d_6$) δ ppm 2.13 (s, 3 H) 4.07 (dd, J=7.40, 3.39 Hz, 1 H) 4.13-4.20 (m, 1 H) 4.53 (dd, J=4.64, 3.14 Hz, 1 H) 4.65 (dd, J=4.77, 3.26 Hz, 1 H) 5.29 (s, 2 H) 6.28 (dd, J=8.03, 2.01 Hz, 1 H) 6.33 (d, J=2.01 Hz, 1 H) 6.81 (d, J=8.03 Hz, 1 H) 7.23 (d, J=5.02 Hz, 1 H) 8.22 (s, 1 H) 8.32 (d, J=4.77 Hz, 1 H). Intermediate 16 was used in the synthesis of Example 22.

Intermediates 17 and 18

The following Intermediates in Table 4 were prepared by the procedures described for the preparation of Intermediate 16 using 2-bromo-1,1-difluoroethane and 1,1,1-trifluoro-2-iodoethane, respectively.

TABLE 4

| Intermediate No. | Structure | Used for Ex. No. | Name | [M + H]+ | Ret time |
|---|---|---|---|---|---|
| 17 | 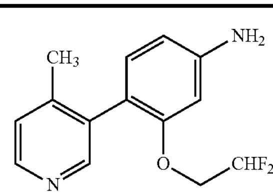 | 23 | 3-(2,2-difluoroethoxy)-4-(4-methylpyridin-3-yl)aniline | 265.0 | 0.633/0.748[b] |

TABLE 4-continued

| Intermediate No. | Structure | Used for Ex. No. | Name | [M + H]⁺ | Ret time |
|---|---|---|---|---|---|
| 18 | 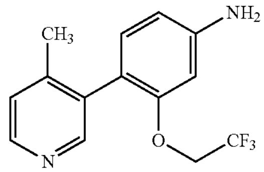 [SMILES: Cc1ccncc1-c1ccc(N)cc1OCC(F)(F)F] | 24 | 4-(4-methylpyridin-3-yl)-3-(2,2,2-trifluoroethoxy)aniline | 283.1 | 1.013ᵉ |

Intermediate 19

4-(4-Fluoropyridin-3-yl)-3-methylaniline

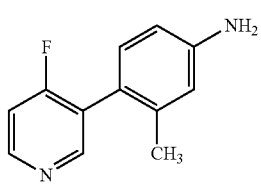

Intermediate 19A:
3-(2-Methyl-4-nitrophenyl)pyridin-4-amine

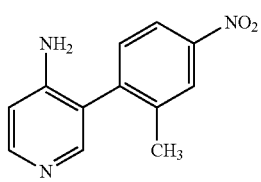 [SMILES: Cc1cc([N+](=O)[O-])ccc1-c1cnccc1N]

Intermediate 19A was prepared from 3-bromopyridin-4-amine and Intermediate 26A by the procedure described for the preparation of Intermediate 1C, and was obtained as a bright yellow solid (43% yield). MS (ES): m/z=230.0 [M+H]⁺. ¹H NMR (400 MHz, DMSO-d₆) δ ppm 2.25 (s, 3 H) 6.07 (s, 2 H) 6.71 (d, J=6.02 Hz, 1 H) 7.46 (d, J=8.53 Hz, 1 H) 7.91 (s, 1 H) 8.09 (d, J=5.77 Hz, 1 H) 8.14 (dd, J=8.53, 2.01 Hz, 1 H) 8.25 (d, J=2.51 Hz, 1 H).

Intermediate 19B:
4-Fluoro-3-(2-methyl-4-nitrophenyl)pyridine

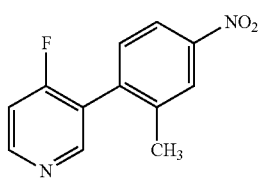 [SMILES: Cc1cc([N+](=O)[O-])ccc1-c1cnccc1F]

To a solution of Intermediate 19A (340 mg, 1.483 mmol) in tetrafluoroboric acid (1 mL, 7.65 mmol) at −10° C. was added sodium nitrite (179 mg, 2.60 mmol) in small portions, keeping the temperature below −5° C. After the addition was complete, the mixture was stirred at 0° C. for 45 min and then warmed slowly to room temperature over a period of 30 min to decompose the preparation of diazonium salt. The temperature of the mixture was rose to 30-35° C. and nitrogen was evolved for about 30 min. The resulting mixture was cooled to −10° C. and neutralized with 1M sodium hydroxide precooled to 0-5° C. The mixture was extracted with ethyl acetate (2×25 mL), washed with cooled water (25 mL), and dried over magnesium sulfate. The crude material was purified by silica gel chromatography (40 g ISCO column, eluting with 100% hexanes to 100% CH₂Cl₂) to provide Intermediate 19B (60 mg, 0.258 mmol, 17.42% yield) as a yellow solid. MS (ES): m/z=233.0 [M+H]⁺. ¹H NMR (400 MHz, MeOD) δ ppm 2.34 (s, 3 H) 7.44 (dd, J=9.66, 5.65 Hz, 1 H) 7.55 (d, J=8.28 Hz, 1 H) 8.20 (dd, J=8.16, 2.13 Hz, 1 H) 8.28 (d, J=2.26 Hz, 1 H) 8.57 (d, J=9.79 Hz, 1 H) 8.70 (dd, J=7.65, 5.65 Hz, 1 H).

Intermediate 19:
4-(4-Fluoropyridin-3-yl)-3-methylaniline

Intermediate 19 was prepared from Intermediate 19B by the procedure described for the preparation of Intermediate 16, and was obtained as a yellow solid. MS (ES): m/z=203.1 [M+H]⁺. Intermediate 19 was used in the synthesis of Example 25.

Intermediate 20

Methyl 5-amino-2-(4-methylpyridin-3-yl)benzoate

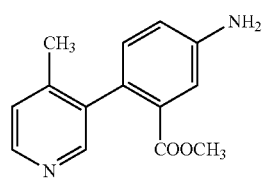 [SMILES: COC(=O)c1cc(N)ccc1-c1cnccc1C]

Intermediate 20A: Methyl 2-(4-methylpyridin-3-yl)-5-nitrobenzoate

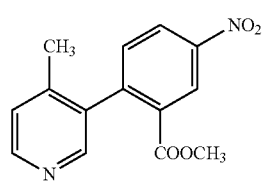 [SMILES: COC(=O)c1cc([N+](=O)[O-])ccc1-c1cnccc1C]

Intermediate 20A was prepared from Intermediate 1A and methyl 2-bromo-5-nitrobenzoate by the procedure described for the preparation of Intermediate 1C. MS (ES): m/z=273.1 [M+H]⁺.

Intermediate 20: Methyl 5-amino-2-(4-methylpyridin-3-yl)benzoate

Intermediate 20 was prepared from Intermediate 20A by the procedure described for the preparation of Intermediate 13. (9% yield). MS (ES): m/z=243.1 [M+H]⁺. Intermediate 20 was used in the synthesis of Example 14.

Intermediate 21

2-(5-Amino-2-(4-methylpyridin-3-yl)phenyl)propan-2-ol

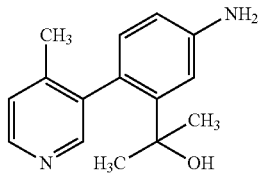

To a solution of methylmagnesium bromide (0.206 mL, 0.619 mmol) in THF (2 mL) at −78° C. was added slowly a solution of Intermediate 20 (50 mg, 0.206 mmol) in THF (2 mL). After stirring at −78° C. for 2 hours, the reaction mixture was warmed up to about −15° C. and methylmagnesium bromide (3 eq) was added and stirred for additional 2 hours. The reaction mixture was warmed up to room temperature and additional methylmagnesium bromide (3 eq) was added. The reaction mixture was stirred for 1 hour, slowly poured into a saturated solution of ammonium chloride (10 mL) and then extracted with EtOAc (2×10 mL). The combined organics were washed with brine, dried over anhydrous sodium sulfate, and concentrated under reduced pressure. The crude material was purified by silica gel chromatography (12 g ISCO column, eluting with 0% to 10% MeOH in $CH_2Cl_2$) to afford Intermediate 21 (10 mg, 0.041 mmol, 20.00% yield). MS (ES): m/z=243.2 [M+H]⁺. $^1$H NMR (400 MHz, MeOD) δ ppm 1.30 (s, 3 H) 1.37 (s, 3 H) 2.14 (s, 3 H) 6.68 (s, 2 H) 7.15 (s, 1 H) 7.30 (d, J=5.04 Hz, 1 H) 8.25 (s, 1 H) 8.30 (d, J=5.04 Hz, 1 H). Intermediate 21 was used in the synthesis of Example 15.

Intermediate 22

5-Methoxy-2-methyl-4-(4-methylpyridin-3-yl)aniline

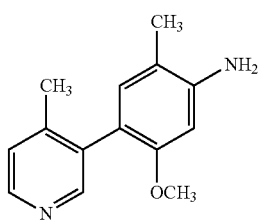 [SMILES: COc1cc(N)c(C)cc1-c1cnccc1C]

Intermediate 22A: N-(4-Bromo-5-methoxy-2-methylphenyl)acetamide

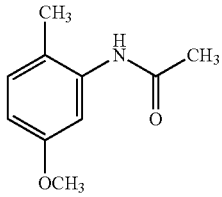

Intermediate 22A was prepared from 5-methoxy-2-methylaniline by the procedure described for the preparation of Intermediate 1B, and was obtained as a beige solid (84% yield). MS (ES): m/z=180.1 [M+H]⁺.

Intermediate 22B: N-(4-Bromo-5-methoxy-2-methylphenyl)acetamide

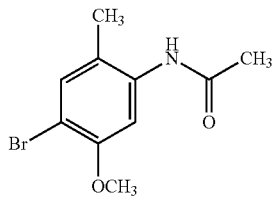

Intermediate 22A (500 mg, 2.79 mmol) was dissolved in acetic acid (3 mL) and the mixture was cooled to 15° C. To the mixture was added bromine (0.431 mL, 8.37 mmol), and the resulting mixture was maintained at 15° C. for 15-20 min, warmed up to room temperature and stirred for 1 hour. The reaction mixture was poured over ice, and the precipitates were filtered and washed with ice water. The wet solid was dissolved in EtOAc, dried over sodium sulfate and filtered. The filtrate was concentrated under reduced pressure to provide Intermediate 22B (587 mg, 2.274 mmol, 82% yield) as a yellow solid. MS (ES): m/z=258.1 [M+H]⁺. $^1$H NMR (500 MHz, MeOD) δ ppm 2.15 (s, 3 H) 2.16 (s, 3 H) 3.82 (s, 3 H) 7.14 (s, 1 H) 7.37 (s, 1 H).

Intermediate 22: 5-Methoxy-2-methyl-4-(4-methylpyridin-3-yl)aniline

Intermediate 22 was prepared from Intermediate 1A and Intermediate 22B by the procedures described for the preparation of Intermediate 1, and was obtained as a pale yellow solid (55% yield). MS (ES): m/z=229.3 [M+H]⁺. Intermediate 22 was used in the synthesis of Example 20.

Intermediate 23

4-(4-Methoxypyridin-3-yl)-3-methylaniline

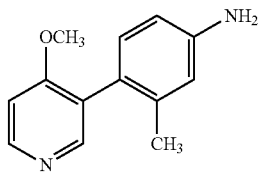 [SMILES: COc1ccncc1-c1ccc(N)cc1C]

Intermediate 23 was prepared by the procedure described for the preparation of Intermediate 1C using 4-bromo-3-methylaniline and 4-methoxypyridin-3-ylboronic acid, and was obtained as a yellow solid (44.3% yield). MS (ES): m/z=215.1 [M+H]$^+$. Intermediate 23 was used in the synthesis of Examples 2 and 7.

Intermediate 24

4-(Isoquinolin-4-yl)-3-methoxyaniline

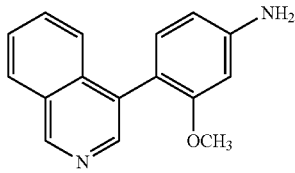 [SMILES: COc1cc(N)ccc1-c1cncc2ccccc12]

Intermediate 24 was prepared by the procedure described for the preparation of Intermediate 1C using (4,4,5,5-tetramethyl-1,3,2-dioxaborolan-2-yl)isoquinoline and 4-bromo-3-methoxyaniline, and was obtained as an off yellow solid (80% yield). HPLC Ret time$^a$: 1.243 min. MS (ES): m/z=251.2 [M+H]$^+$. Intermediate 24 was used in the synthesis of Examples 142 to 160.

Intermediate 25

3-Methoxy-4-(4-methylpyrimidin-5-yl)aniline

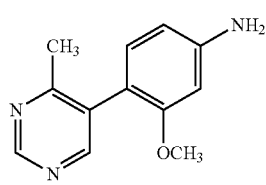 [SMILES: COc1cc(N)ccc1-c1cncnc1C]

Intermediate 25 was prepared by the procedure described for the preparation of Intermediate 1C using 3-methoxy-4-(4,4,5,5-tetramethyl-1,3,2-dioxaborolan-2-yl)aniline and 5-bromo-4-methylpyrimidine, and was obtained as a black oil (34.1% yield). MS (ES): m/z=216.2 [M+H]$^+$. Intermediate 25 was used in the synthesis of Examples 161 to 177.

Intermediate 26

3-Methyl-4-(4,4,5,5-tetramethyl-1,3,2-dioxaborolan-2-yl)aniline

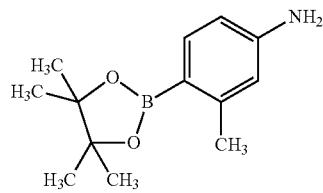 [SMILES: Cc1cc(N)ccc1B1OC(C)(C)C(C)(C)O1]

Intermediate 26A: 4,4,5,5-Tetramethyl-2-(2-methyl-4-nitrophenyl)-1,3,2-dioxaborolane

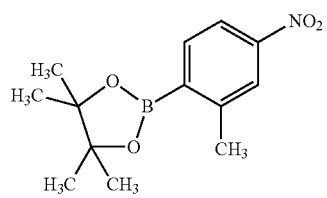 [SMILES: Cc1cc([N+](=O)[O-])ccc1B1OC(C)(C)C(C)(C)O1]

A mixture of 1-bromo-2-methyl-4-nitrobenzene (5 g, 23.14 mmol), [1,1'-bis(diphenylphosphino)ferrocene]dichloropalladium(II) (0.169 g, 0.231 mmol), potassium acetate (2.95 g, 30.1 mmol), and bis(pinacolato)diboron (6.47 g, 25.5 mmol) in DMSO (15 mL) was heated at 80° C. overnight. The reaction mixture was poured into 25 mL ice-water mixture and extracted with ethyl acetate (2×300 mL). The combined organics were dried over sodium sulfate, filtered, and concentrated under reduced pressure. The crude material was purified by silica gel chromatography to provide Intermediate 26A (3.45 g, 13.11 mmol, 56.7% yield) as a lemon yellow solid. MS (ES): m/z=296.2 [M+MeOH]$^+$. $^1$H NMR (400 MHz, chloroform-d) δ ppm 1.39 (s, 12 H) 2.65 (s, 3 H) 7.91 (d, 1 H) 7.97-8.01 (m, 1 H) 8.02 (s, 1 H).

Intermediate 26: 3-Methyl-4-(4,4,5,5-tetramethyl-1,3,2-dioxaborolan-2-yl)aniline Intermediate 26A (1 g, 3.80 mmol), ammonium chloride (1.432 g, 26.6 mmol), and zinc (1.491 g, 22.81 mmol) were added to a flask, followed by the addition of EtOH (10.0 mL) and THF (10.0 mL). The reaction mixture was stirred at room temperature for 2 hours and filtered through a pad of CELITE®. The filtrate was concentrated under reduced pressure to yield Intermediate 26 (885 mg, 100% yield). MS (ES): m/z=234.2 [M+H]$^+$.

Intermediate 27

3-Chloro-4-(4-methylpyridin-3-yl)aniline

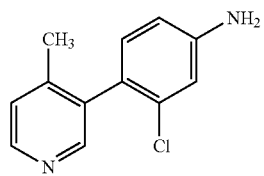

Intermediate 27A: 3-(2-Chloro-4-nitrophenyl)-4-methylpyridine

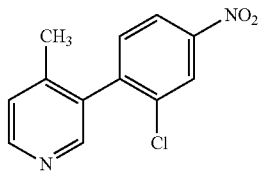 [SMILES: Cc1ccncc1-c1ccc([N+](=O)[O-])cc1Cl]

Intermediate 27A was prepared from Intermediate 1A and 1-bromo-2-chloro-4-nitrobenzene by the procedure described for the preparation of Intermediate 1C. HPLC Ret time$^j$:1.30 min. MS (ES): m/z=249.0 [M+H]$^+$.

Intermediate 27: 3-Chloro-4-(4-methylpyridin-3-yl)aniline

To a solution of Intermediate 27A (0.136 g, 0.547 mmol) in EtOAc (2.73 mL) was added Pd/C (0.058 g, 0.055 mmol). The mixture was placed under an atmosphere of H$_2$ for 18 hours. The reaction mixture was filtered through CELITE® and the filter cake was washed with CH$_2$Cl$_2$. The solvent was evaporated and the crude material re-dissolved in a minimal amount of CH$_2$Cl$_2$ and chromatographed. Purification of the crude material by silica gel chromatography using an ISCO machine (40 g column, 1-20% MeOH in CH$_2$Cl$_2$ over 25 min) gave the title compound (0.106 g, 0.485 mmol, 89% yield) as an orange residue. HPLC Ret time$^j$:1.06 min. MS (ES): m/z=219.1 [M+H]$^+$. Intermediate 27 was used in the synthesis of Example 178.

Intermediate 28

4-(Isoquinolin-4-yl)-3-methylaniline

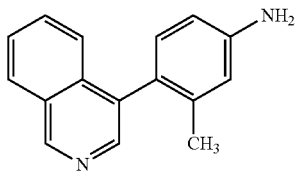 [SMILES: Cc1cc(N)ccc1-c1cncc2ccccc12]

Intermediate 28 was prepared by the procedure described for the preparation of Intermediate 1C using Intermediate 26 and 4-bromoisoquinoline. HPLC Ret time$^a$: 0.488 min. MS (ES): m/z=235.2 [M+H]$^+$. Intermediate 28 was used in the synthesis of Example 182.

Intermediate 29

4-(4-Methylpyridin-3-yl)-3-(2,2,2-trifluoroethoxy) aniline

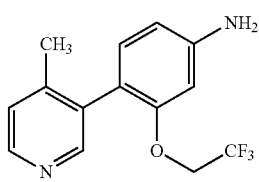 [SMILES: Cc1ccncc1-c1ccc(N)cc1OCC(F)(F)F]

Intermediate 29A: tert-Butyl 3-(2,2,2-trifluoroethoxy)phenylcarbamate

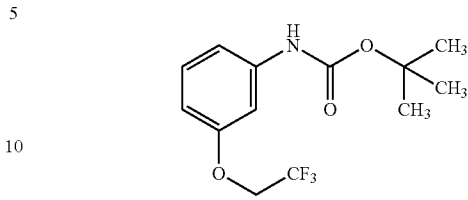

To a stirred solution of tert-butyl 3-hydroxyphenylcarbamate (2 g, 9.56 mmol) in acetone (38 mL) were added potassium carbonate (6.61 g, 47.8 mmol) and 2,2,2-trifluoroethyl trifluoromethanesulfonate (2.07 mL, 14.34 mmol). The reaction mixture was heated at 50° C. overnight, cooled and filtered. The filtrate was concentrated, and the residue was dissolved in CH$_2$Cl$_2$, washed with brine, dried over anhydrous sodium sulfate and concentrated to yield the title compound (2.7 g, 97% yield). MS (ES): m/z=314.25 [M+Na]$^+$.

Intermediate 29B: 3,5-Dibromo-4-phenethoxypyridine

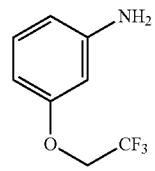

Intermediate 29A (2.7 g, 9.27 mmol) was taken in CH$_2$Cl$_2$ (20 mL) and trifluoroacetic acid (4 mL) was added. The reaction mixture was stirred at room temperature overnight, basified with saturated aqueous sodium bicarbonate and then extracted with CH$_2$Cl$_2$ (2×20 mL). The combined organics were washed with brine, dried over anhydrous sodium sulfate and concentrated under reduced pressure to provide Intermediate 29B (1.4 g, 79% yield). MS (ES): m/z=192.1 [M+H]$^+$.

Intermediate 29C: 4-Iodo-3-(2,2,2-trifluoroethoxy)aniline

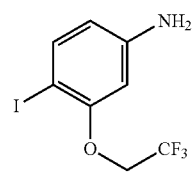 [SMILES: Nc1ccc(I)c(OCC(F)(F)F)c1]

To a stirred solution of the Intermediate 29B (1.4 g, 7.32 mmol) in pyridine (7.4 mL) at 0° C. was added iodine (2.231 g, 8.79 mmol). The resulting mixture was stirred at room temperature overnight, quenched with saturated aqueous sodium thiosulfate and then extracted with CH$_2$Cl$_2$ (2×15 mL). The combined organics were washed with brine, dried over anhydrous sodium sulfate and concentrated under reduced pressure. The crude material was purified by silica gel chromatography (80 g BIOTAGE® column, eluting with 30% EtOAc in hexane) to yield Intermediate 29C (1.075 g, 46.3% yield) as a brown oil. MS (ES): m/z=318.05 [M+H]$^+$.

Intermediate 29: 4-(4-Methylpyridin-3-yl)-3-(2,2,2-trifluoroethoxy)aniline

A pressure vessel charged with a mixture of tetrakis(triphenylphosphine) palladium(0) (200 mg, 0.173 mmol), Intermediate 29C (550 mg, 1.735 mmol), potassium phosphate tribasic (1.103 g, 5.2 mmol) and Intermediate 1A (356 mg, 2.6 mmol) was stirred at room temperature for 5 min under a nitrogen atmosphere, followed by addition of 1,4-dioxane (6.7 mL) and water (2.6 mL). The reaction mixture was degassed for 2 min, heated at 85° C. overnight and then cooled to room temperature. The mixture was filtered, and the filtrate was concentrated under reduced pressure. The crude material was purified by preparative HPLC using a PHENOMENEX® Luna 30×100 mm S5 column eluting with aqueous MeOH containing 0.1% TFA, gradient 20 to 70%, gradient time 12 min) The collected fractions were concentrated and then applied on a 1 g MCX cartridge. The cartridge was washed with methanol, and then eluted with 2M solution of ammonia in methanol (30 mL). The evaporation of the collected eluent under reduced pressure provided Intermediate 29 (117 mg, 23.9% yield) as a beige powder. MS (ES): m/z=283.14 [M+H]$^+$. Intermediate 29 was used in the synthesis of Examples 183 and 184.

Intermediate 30

3-Methoxy-4-(4-methoxypyrimidin-5-yl)aniline

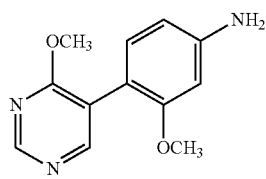 [SMILES: COc1cc(N)ccc1-c1cncnc1OC]

Intermediate 30A: 5-Iodo-4-methoxypyrimidine

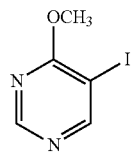

Into a tube capable of withstanding high pressure was added 4-Cl-5-iodopyrimidine (200 mg, 0.832 mmol) and cesium carbonate (542 mg, 1.664 mmol). These solids were dissolved in DMF (2 mL), to this solution was added methanol (0.083 mL, 2.057 mmol). The vessel was sealed and heated to 90° C. overnight and then cooled to room temperature. The mixture was filtered, and diluted with water (5 mL) and extracted with EtOAc. The organic layer was washed twice with a lithium chloride solution of (10%), dried (Na$_2$SO$_4$) and concentrated under reduced pressure. The crude material was used directly for subsequent reactions (70 mg, 25.7% yield). MS (ES): m/z=236.80 [M+H]$^+$; $^1$H NMR (400 MHz, DMSO-d$_6$) δ ppm 8.86 (1 H, s), 8.72 (1 H, s), 3.98 (4 H, s).

Intermediate 30B: 4-Methoxy-5-(2-methoxy-4-nitrophenyl)pyrimidine

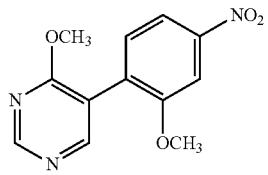

Intermediate 30B was prepared by the procedure described for the preparation of Intermediate 1C using Intermediate 30A and 2-(2-methoxy-4-nitrophenyl)-4,4,5,5-tetramethyl-1,3,2-dioxaborolane (prepared by the procedure described for the preparation of Intermediate 26A), and was obtained as a gummy yellow solid. The solid was dissolved in DMF and purified by reverse phase preparative HPLC (PHENOMENEX® Luna 30×100 mm column with a linear gradient of Solvent A (10% methanol/90% water with 0.1% TFA) and Solvent B (90% methanol/10% water with 0.1% TFA) over 12 min; monitored at 254 nM). The collected fractions were then applied to a 1 g Waters OASIS® MCX cation exchange cartridge, which was washed with methanol, and the product was then eluted off with 15 mL of 2 M ammonia in methanol. Evaporation of the collected eluent provided Intermediate 30B (46 mg, 25% yield) as a solid. HPLC Ret time$^d$: 1.34 min. MS: m/z=262 [M+H]$^+$; $^1$H NMR (500 MHz, CD$_3$OD) δ ppm 8.48 (s, 1 H), 8.05 (s, 1 H), 7.94-7.90 (m, 2 H), 7.57 (d, 1 H), 3.93 (s, 3 H), 3.61 (s, 3 H).

Intermediate 30: 3-Methoxy-4-(4-methoxypyrimidin-5-yl)aniline

Intermediate 30 was prepared by the procedure described for the preparation of Intermediate 13 using Intermediate 30B (99% yield). HPLC Ret time$^d$: 0.32 min. MS: m/z=232 [M+H]$^+$. Intermediate 30 was used in the synthesis of Example 245.

Intermediate 31

3,5-Dibromo-4-methoxypyridine

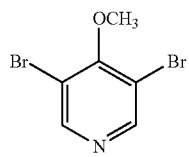

Intermediate 31A: 3,5-Dibromopyridin-4-ol

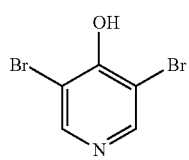

To a stirring solution of pyridine-4-ol (5 g, 52.6 mmol) in CCl$_4$ (100 mL) at room temperature was added N-bromosuccinimide (18.72 g, 105 mmol). The reaction mixture was allowed to stir under cover of darkness for 24 hours. The solvent was removed under reduced pressure, and the obtained solid was dissolved with acetone (100 mL) and MeOH (30 mL) and stirred for 5 min. The resulting slurry was filtered and the solid was rinsed with excess acetone/$CH_2Cl_2$. The solid material was vigorously stirred with acetonitrile, and filtered to yield Intermediate 31A (9.04 g, 35.7 mmol, 68% yield) as an off-white solid. MS (ES): m/z=253.8 [M+H]+. $^1$H NMR (400 MHz, MeOD) δ ppm 8.30 (2 H, s).

Intermediate 31B: 3,4,5-Tribromopyridine

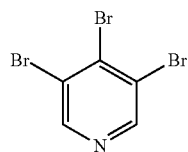

A vessel was charged with a mixture of Intermediate 31A (3.08 g, 12.18 mmol) and phosphorous pentabromide (2.5 g, 5.81 mmol). The vessel was sealed and heated to 180° C. for 3 hours. Upon cooling, the reaction mixture was diluted with water (10 mL) and filtered. The solid material was washed with successive quantities of water until the filtrate was a neutral pH. Intermediate 31B was obtained as a grey solid (3.7 g, 11.60 mmol, 95% yield). MS (ES): m/z=317.7 [M+H]+. $^1$H NMR (400 MHz, MeOD) 6 ppm 8.71 (2 H, s).

Intermediate 31: 3,5-Dibromo-4-methoxypyridine

To a solution of MeOH (0.115 mL, 2.85 mmol) and THF (0.5 mL) at 0° C. was added sodium hydride (60% dispersion, 114 mg, 2.85 mmol). After stirring for 15 min, Intermediate 31B (600 mg, 1.900 mmol) was added, and the resulting mixture was stirred at room temperature for 19 hours, diluted with water (3 mL) and extracted with EtOAc (2×10 mL). The combined organics were washed with brine, dried over anhydrous sodium sulfate, and concentrated under reduced pressure to yield Intermediate 31 (0.480 g, 1.798 mmol, 95% yield) as a beige color solid. MS (ES): m/z=267.9 [M+H]+. $^1$H NMR (400 MHz, MeOD) δ ppm 8.68 (2 H, s), 3.99 (3 H, s). Intermediate 31 was used in the synthesis of Example 185.

Intermediates 32 to 39

The following Intermediates in Table 5 were prepared by the procedures described for the preparation of Intermediate 31 using corresponding alcohols.

TABLE 5

| Intermediate No. | Structure | Used for Ex. No. | Name | [M + H]+ | Ret time |
|---|---|---|---|---|---|
| 32 | 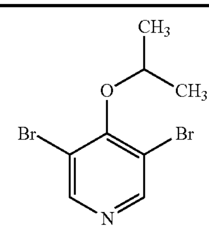 | 186 | 3,5-dibromo-4-isopropoxypyridine | 296.0 | 2.81$^c$ |
| 33 | 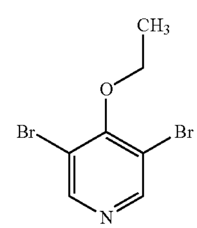 | 187 | 3,5-dibromo-4-ethoxypyridine | 281.94 | 2.532$^c$ |
| 34 | 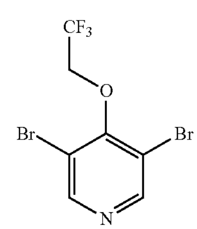 | 188 | 3,5-dibromo-4-(2,2,2-trifluoroethoxy)pyridine | 335.9 | 2.650$^c$ |
| 35 | 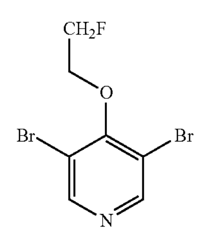 | 189 | 3,5-dibromo-4-(2-fluoroethoxy)pyridine | 299.9 | 1.880$^c$ |

TABLE 5-continued

| Intermediate No. | Structure | Used for Ex. No. | Name | [M + H]+ | Ret time |
|---|---|---|---|---|---|
| 36 | ![structure] | 190 | 3,5-dibromo-4-(2,2-difluoroethoxy)pyridine | 317.9 | 2.167<sup>c</sup> |
| 37 | ![structure] | 191 | 3,5-dibromo-4-phenethoxypyridine | 357.9 | 3.316<sup>c</sup> |
| 38 | ![structure] | 192 | 2-(3,5-dibromopyridin-4-yloxy)-N,N-dimethylethanamine | 324.9 | 0.768<sup>c</sup> |
| 39 | ![structure] | 193 | 3,5-dibromo-4-(2-methoxyethoxy)pyridine | 311.9 | |

Intermediate 40

3,5-Dibromo-4-(methylthio)pyridine

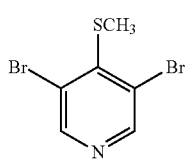

To a solution of Intermediate 31B (300 mg, 0.950 mmol) in DMSO (6 mL) at room temperature was added sodium methanethiolate (80 mg, 1.140 mmol). The dark brown mixture was stirred for 30 min, followed by addition of water and then filtered. The solid was collected and dried on a high vacuum apparatus. Intermediate 40 was obtained (170 mg, 0.601 mmol, 63.2% yield) as a black solid. MS (ES): m/z=283.8 [M+H]+. $^1$H NMR (400 MHz, MeOD) δ ppm 2.58 (s, 3 H) 8.69 (s, 2 H). Intermediate 40 was used in the synthesis of Example 194.

Intermediate 41

2-Methyl-3-(4-methylpyridin-3-yl)aniline

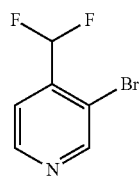

To a stirred solution of 3-bromoisonicotinaldehyde (100 mg, 0.538 mmol) in CH$_2$Cl$_2$ (5 mL) at 0° C. was added dropwise [bis(2-methoxyethyl)amino]sulfur trifluoride (0.38 mL, 2.06 mmol). The reaction mixture was stirred at 0° C. for 2 hours, quenched with saturated aqueous sodium bicarbonate (3 mL) and extracted with CH$_2$Cl$_2$ (2×5 mL). The combined organics were washed with brine, dried over anhydrous sodium sulfate and concentrated under reduced pressure to give Intermediate 41 (78 mg, 70% yield). MS (ES): m/z=208.2) [M+H]+. Intermediate 41 was used in the synthesis of Example 226.

Intermediate 42

3-Bromo-4-(prop-1-en-2-yl)pyridine

Intermediate 42A:
2-(3-Bromopyridin-4-yl)propan-2-ol

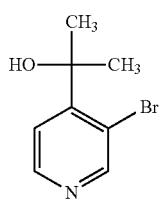

To a stirred solution of methyl 3-bromoisonicotinate (2.5 g, 11.57 mmol) in THF (46 mL) at −78° C. was added methylmagnesium bromide (7.91 mL, 23.72 mmol, 3M in Et$_2$O). The reaction mixture was then stirred at room temperature overnight, quenched with saturated aqueous NH$_4$Cl and extracted with CH$_2$Cl$_2$ (2×20 mL). The combined organics were washed with brine, dried over anhydrous sodium sulfate and concentrated under reduced pressure. The crude material was purified by silica gel chromatography (80 g BIOTAGE® column, eluting with CH$_2$Cl$_2$:EtOAc/85:15) to provide Intermediate 42A (1.62 g, 65% yield). MS (ES): m/z=216.09 [M+H]$^+$.

Intermediate 42:
3-Bromo-4-(prop-1-en-2-yl)pyridine

To a stirred solution of Intermediate 42A (1.25 g) in pyridine (38 mL) at 0° C. was added thionyl chloride (38.5 mL, 526.5 mmol). The reaction mixture was then stirred at room temperature overnight, quenched with saturated aqueous sodium bicarbonate solution and extracted with CH$_2$Cl$_2$ (2×20 mL). The combined organics were washed with brine, dried over anhydrous sodium sulfate and concentrated under reduced pressure. The crude material was purified by silica gel chromatography (80 g BIOTAGE® column, eluting with hexane:CH$_2$Cl$_2$/4:6) to provide Intermediate 42 (705 mg, 61.5% yield). MS (ES): m/z=198.1 [M+H]$^+$. Intermediate 42 was used in the synthesis of Example 227.

Intermediate 43

3-Bromo-4-cyclopropylpyridine

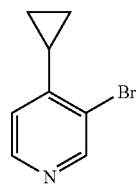

A solution of 2,2,6,6-tetramethylpiperidine (2.14 mL, 12.7 mmol) in THF (20 mL) was cooled under nitrogen to −78° C. and treated slowly with n-butyllithium (2.5 M in hexanes; 5.1 mL, 12.8 mmol). The reaction mixture was stirred at −78° C. for 10 min, followed by the dropwise addition of a solution of 3-bromopyridine (2.00 g, 12.7 mmol) and 1,3-dibromopropane (2.81 g, 13.9 mmol) over a period of 1 hour. The resulting mixture was allowed to warm slowly from −78 C to room temperature overnight, quenched with aqueous ammonium chloride and water, and extracted with EtOAc. The organic phase was dried over sodium sulfate, filtered and evaporated. The residue was purified by silica gel chromatography (eluting with 0% to 20% diethyl ether in hexanes) to afford Intermediate 43 (220 mg, 8% yield) as a light yellow liquid: HPLC Ret time$^d$: 0.96 min. MS: m/z=198, 200 [M+H]$^+$; $^1$H NMR (500 MHz, CDCl$_3$) δ ppm 8.64 (s, 1 H), 8.36 (d, 1 H, J=5.4 Hz), 6.81 (d, 1H, J=5.4 Hz), 2.39-2.19 (1 H, m), 1.31-1.13 (2 H, m), 0.87-0.74 (2 H, m). Intermediate 43 was used in the synthesis of Examples 225 and 243.

Intermediate 44

4-(5-Iodopyrimidin-4-yl)morpholine

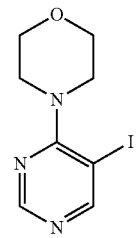 [SMILES: Ic1cncnc1N1CCOCC1]

To a stirred solution of 4-chloro-5-iodopyrimidine (300 mg, 1.248 mmol) in DMF (2 mL) was added cesium carbonate (813 mg, 2.496 mmol) and morpholine (0.435 mL, 4.99 mmol). The reaction was purged with N$_2$, heated to 90° C. for 12 hours and then concentrated to give the crude Intermediate 44, which was used directly in subsequent reaction. MS (ES): m/z=292.1 [M+H]$^+$. $^1$H NMR (400 MHz, MeOD) δ ppm 8.69 (1 H, s), 8.56 (1 H, s), 3.76-3.86 (5 H, m), 3.61-3.71 (5 H, m). Intermediate 44 was used in the synthesis of Example 224.

Intermediate 45

N-(4-Bromo-3-methoxyphenyl)methanesulfonamide

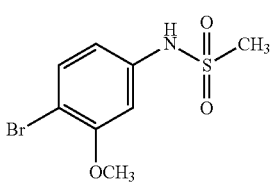

To a solution of 4-bromo-3-methoxyaniline (3 g, 14.85 mmol) in THF (10 mL) at 0° C. was added pyridine (12.01 mL, 148 mmol), followed by addition of methanesulfonyl chloride (1.494 mL, 19.30 mmol). The reaction mixture was stirred at room temperature overnight, diluted with saturated solution of sodium bicarbonate (50 mL) and extracted with EtOAc (2×50 mL). The combined organics were washed with brine, dried over anhydrous sodium sulfate, and concentrated under reduced pressure. The crude material was purified by silica gel chromatography (80 g ISCO column, eluting with 0% to 50% EtOAc in $CH_2Cl_2$) to provide Intermediate 45 (3.4 g, 82% yield) as a beige solid. MS (ES): m/z=281.9 $[M+H]^+$. Intermediate 45 was used in the synthesis of Example 217.

Intermediates 46 and 47

The following Intermediates in Table 6 were prepared by the procedure described for the preparation of Intermediate 45 using the corresponding anilines.

Intermediate 48A:
4-Bromo-3-(2-fluoroethoxy)aniline

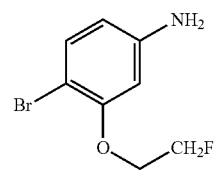

To a mixture of 1-bromo-2-(2-fluoroethoxy)-4-nitrobenzene (8.3 g, 31.4 mmol), and zinc (12.33 g, 189 mmol), ammonium chloride (11.77 g, 220 mmol) was added EtOH (70 mL) and THF (70 mL). The reaction mixture was stirred at room temperature overnight and filtered through a pad of CELITE®. The filtrate was concentrated to give the crude Intermediate 48A (7.1 g, 30.3 mmol, 96% yield).

Intermediate 48: N-(4-Bromo-3-(2-fluoroethoxy)phenyl)methanesulfonamide

Intermediate 48 was prepared by the procedures described for the preparation of Intermediate 45 using Intermediate 48A. $^1$H NMR (400 MHz, DMSO-$d_6$) δ ppm 9.90 (1 H, br. s.), 7.52 (1 H, d, J=8.53 Hz), 6.93 (1 H, d, J=2.26 Hz), 6.76 (1 H, dd, J=8.53, 2.26 Hz), 4.80-4.86 (1 H, m), 4.71 (1 H, dd, J=4.77, 3.01 Hz), 4.28-4.34 (1 H, m), 4.19-4.25 (1 H, m), 3.02 (4 H, s). Intermediate 48 was used in the synthesis of Examples 234 to 236.

TABLE 6

| Intermediate No. | Structure | Used for Ex. No. | Name | [M + H]$^+$ | Ret time |
|---|---|---|---|---|---|
| 46 | 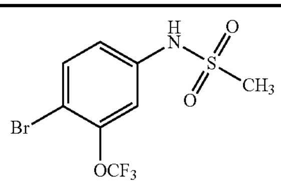 | 228-231 | N-(4-bromo-3-(trifluoromethoxy)phenyl)methanesulfonamide | 334.1 | 3.428$^e$ |
| 47 | 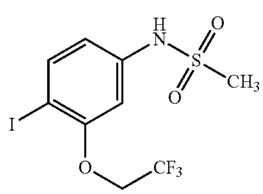 [SMILES: CS(=O)(=O)Nc1ccc(I)c(OCC(F)(F)F)c1] | 232-233 | 4-iodo-3-(2,2,2-trifluoroethoxy)aniline | 418.0 [M + Na] | 3.041$^g$ |

Intermediate 48

N-(4-Bromo-3-(2-fluoroethoxy)phenyl)methanesulfonamide

Intermediate 49

N-(3-(2-Fluoroethoxy)-4-(4,4,5,5-tetramethyl-1,3,2-dioxaborolan-2-yl)phenyl)methanesulfonamide

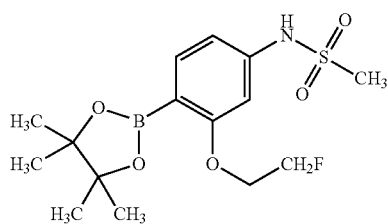

To a solution of N-(4-bromo-3-(2-fluoroethoxy)phenyl)methanesulfonamide (1.06 g, 3.40 mmol) in THF (60 mL) at −78° C. was added methyl lithium (2.335 mL, 3.74 mmol). The reaction mixture was stirred at −78° C. for 5 minutes, followed by dropwise addition of tert-butyllithium (4.39 mL, 7.47 mmol) and stirred for additional 1 hour. To the above mixture, 4,4,5,5-tetramethyl-1,3,2-dioxaborolane (6.79 mL, 6.79 mmol) was added and the resulting mixture was warmed up to −40° C., quenched with a 1:1 solution of brine/NH$_4$Cl and extracted twice with EtOAc. The combined organics were dried over MgSO$_4$, filtered and concentrated. The crude material was purified by flash chromatography on silica gel (eluting with 05 to 20% EtOAc in CH$_2$Cl$_2$) to give Intermediate 49 (631 mg, 1.581 mmol, 46.6% yield) as a dark yellow oil. MS (ES): m/z=360.2 [M+H]$^+$. Intermediate 49 was used in the synthesis of Examples 237 to 239.

Intermediate 50

N-(3-Methyl-4-(4,4,5,5-tetramethyl-1,3,2-dioxaborolan-2-yl)phenyl) methanesulfonamide

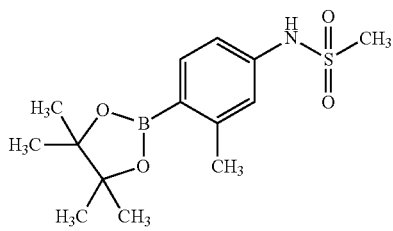

To a solution of Intermediate 26 in THF (10.00 mL) at 0° C. was added pyridine (3.07 mL, 38.0 mmol) followed by the addition of methanesulfonyl chloride (0.3.82 mL, 4.94 mmol). The reaction mixture was stirred overnight, diluted with saturated solution of sodium bicarbonate (50 mL) and extracted with EtOAc (2×50 mL). The combined organics were washed with brine, dried over anhydrous sodium sulfate, and concentrated under reduced pressure to yield Intermediate 50 (1.045 g, 3.36 mmol, 88% yield) as an orange-yellow solid. MS (ES): m/z=344.2 [M+MeOH]$^+$. $^1$H NMR (400 MHz, MeOD) δ ppm 1.14-1.25 (m, 12 H) 2.28 (s, 3 H) 4.78 (s, 2 H) 6.25-6.47 (m, 2 H) 7.24-7.41 (m, 1 H). Intermediate 50 was used in the synthesis of Examples 185 to 195.

Intermediate 51

N-(3-Methoxy-4-(4,4,5,5-tetramethyl-1,3,2-dioxaborolan-2-yl)phenyl)methanesulfonamide

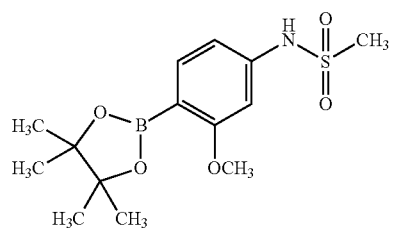

To a solution of Intermediate 45 (5.4 g, 19.28 mmol) in THF (82 mL) at −78° C. was added dropwise methyl lithium (13.25 mL, 21.20 mmol, 1.6M in hexane) followed by the addition of tert-butyllithium (35.3 mL, 42.4 mmol, 1.2 M in pentane), and the resulting mixture was stirred at −78° C. for 30 min. To the above mixture, 4,4,5,5-tetramethyl-1,3,-dioxaborolane (5.59 mL, 38.6 mmol) was added, and the mixture was gradually warmed to room temperature, stirred for 16 hours and then quenched with saturated aqueous ammonium chloride. The mixture was extracted with CH$_2$Cl$_2$ (3×20 mL) and the combined organics were washed with brine, dried over anhydrous sodium sulfate and concentrated under reduced pressure. The crude material was purified by silica gel chromatography (160 g BIOTAGE® column, eluting with CH$_2$Cl$_2$:EtOAc/7:3) to provide Intermediate 51 (1.48 g, 23.5% yield). MS (ES): m/z=328.2 [M+H]$^+$. Intermediate 51 was used in the synthesis of Examples 213, 214, 218 to 227, 247 to 252, 254, and 255.

Intermediate 52

N-(4-(4,4,5,5-Tetramethyl-1,3,2-dioxaborolan-2-yl)-3-(trifluoromethyl)phenyl)methanesulfonamide

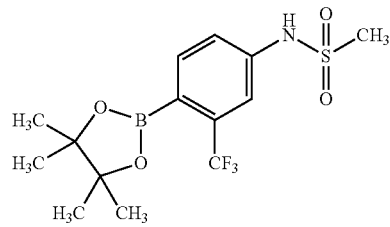

Intermediate 52A: N-(4-Bromo-3-(trifluoromethyl)phenyl)methanesulfonamide

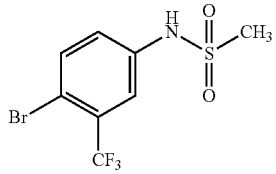 [SMILES: CS(=O)(=O)Nc1ccc(Br)c(C(F)(F)F)c1]

A solution of 4-bromo-3-(trifluoromethyl)aniline (5.0 g, 20.8 mmol) and pyridine (16.9 mL, 208 mmol) in THF (60 mL) was treated slowly with methanesulfonyl chloride (2.10 mL, 27.1 mmol). The resulting yellow solution was stirred at room temperature for 2 hours, concentrated to dryness and then evaporated twice from toluene to afford syrup. The crude material was purified by silica gel chromatography eluting with 0% to 10% acetone in CH$_2$Cl$_2$ to afford Intermediate 52A (6.6 g, 100% yield) as a white solid. HPLC Ret time$^d$: 3.32 min. MS: m/z=318, 320 [M+H]+; $^1$H NMR (500 MHz, CD$_3$OD) δ ppm 7.80-7.75 (1 H, d), 7.63 (1 H, brs), 7.43-7.37 (1 H, d), 3.03 (3 H, s).

Intermediate 52: N-(4-(4,4,5,5-Tetramethyl-1,3,2-dioxaborolan-2-yl)-3-(trifluoromethyl)phenyl)methanesulfonamide Intermediate 52 was prepared by the procedure described for the preparation of Intermediate 51, and obtained as a white solid. HPLC Ret time$^e$: 3.10 min. (MS: m/z=364 [M−H]$^-$; $^1$H NMR (500 MHz, CD$_3$OD) δ ppm 7.73 (1 H, d), 7.55 (1 H, s), 7.46 (1 H, d), 3.03 (3 H, s), 1.37 (s, 12 H). Intermediate 52 was used in the synthesis of Examples 240 to 243.

Intermediate 53

N-(4-(4-Methylpyridin-3-yl)phenyl)-2-oxooxazolidine-3-sulfonamide

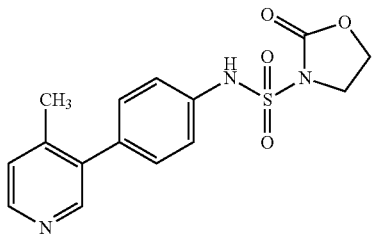 [SMILES: Cc1ccncc1-c1ccc(NS(=O)(=O)N2CCOC2=O)cc1]

To a colorless solution of chlorosulfonylisocyanate (0.026 mL, 0.299 mmol) in $CH_2Cl_2$ (10 mL) was added 2-chloroethanol (0.040 mL, 0.597 mmol). The reaction mixture was stirred at room temperature for 1 hour followed by the addition of a mixture of Intermediate 5 (55 mg, 0.299 mmol) and TEA (0.052 mL, 0.299 mmol). The resulting mixture was stirred at room temperature overnight, concentrated and stripped with $CH_2Cl_2$ twice to give the crude Intermediate 53, which was used in the next step without further purification. Intermediate 53 was used in the synthesis of Examples 205 to 207.

Intermediate 54

N-(3-Methyl-4-(4-methylpyridin-3-yl)phenyl)-2-oxooxazolidine-3-sulfonamide

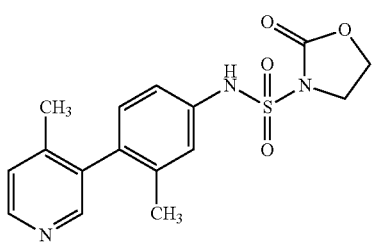 [SMILES: Cc1cc(NS(=O)(=O)N2CCOC2=O)ccc1-c1cnccc1C]

Intermediate 54 was prepared from Intermediate 1 by the procedure described for the preparation of Intermediate 53. MS (ES): m/z=348.2 [M+H]$^+$. Intermediate 54 was used in the synthesis of Examples 208 to 211.

Intermediate 55

5-Iodo-4-(2,2,2-trifluoroethoxy)pyrimidine

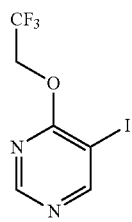

Intermediate 55 was prepared by the procedure described for the preparation of Intermediate 30A substituting 2,2,2-trifluoroethanol for methanol to give the crude Intermediate 55 (180 mg, 71.2% yield), which was used directly in subsequent reaction. MS (ES): m/z=304.8 [M+H]$^+$. $^1$H NMR (400 MHz, DMSO-d$_6$) δ ppm 8.99 (1 H, s), 8.79 (1 H, s), 5.13 (2 H, q, J=8.88 Hz). Intermediate 55 was used in the synthesis of Example 247.

Intermediate 56

5-Iodo-N-(2,2,2-trifluoroethyl)pyrimidin-4-amine

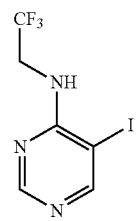 [SMILES: FC(F)(F)CNc1ncncc1I]

Intermediate 56 was prepared by the procedure described for the preparation of Intermediate 30A substituting 2,2,2-trifluoroethyl amine for methanol to give the crude Intermediate 56 (35.7% yield), which was used directly in subsequent reaction. MS (ES): m/z=303.8 [M+H]$^+$. $^1$H NMR (400 MHz, DMSO-d$_6$) δ ppm 8.99 (1 H, s), 8.79 (1 H, s), 5.13 (2 H, q, J=8.88 Hz). Intermediate 56 was used in the synthesis of Example 248.

Intermediate 57

4-Ethoxy-5-iodopyrimidine

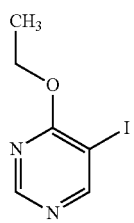

Intermediate 57 was prepared by the procedure described for the preparation of Intermediate 30A substituting ethanol for methanol to give the crude Intermediate 57 (35.7% yield), which was used directly in subsequent reaction. MS (ES): m/z=250.8 [M+H]$^+$. $^1$H NMR (400 MHz, DMSO-d$_6$) δ ppm 8.85 (1 H, s), 8.69 (1 H, s), 4.44 (2 H, q, J=7.04 Hz), 1.35 (3 H, t, J=7.04 Hz). Intermediate 57 was used in the synthesis of Example 249.

Intermediate 58

4-Bromopyrrolo[1,2-c]pyrimidine

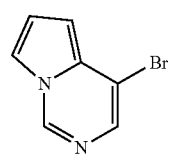

Intermediate 58A: 4-(2-(1,3-Dioxan-2-yl)ethyl)-5-bromopyrimidine

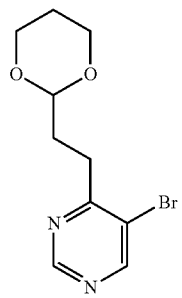 [SMILES: Brc1cncnc1CCC1OCCCO1]

To a solution of 5-bromopyrimidine (2 g, 12.58 mmol) in Et$_2$O (40 mL) at room temperature was slowly added (2-(1,3-dioxan-2-yl)ethylmegnesium bromide (0.5M, 27.7 mL, 13.84 mmol). After 1 hour, water (2 mL) was added followed by the careful addition of a solution of 4,5-dichloro-3,6-dioxocyclohexa-1,4-diene-1,2-dicarbonitrile (3.14 g, 13.84 mmol) in THF (15 mL). The resulting dark brown suspension was stirred at room temperature for an additional 24 hours. The resulting mixture was then diluted with EtOAc and water, the organics were separated and the remaining aqueous layer was extracted further with EtOAc (2×). The combined organic layers were washed with 1N NaOH and brine, dried over sodium sulfate and concentrated to provide the crude Intermediate 58A (2.62 g, 76% yield), which was used without further purification. MS (ES): m/z=274.8 [M+H]$^+$. $^1$H NMR (400 MHz, DMSO-d$_6$) δ ppm 9.05 (1 H, s), 8.89 (1 H, s), 4.62 (1 H, t, J=4.95 Hz), 3.92-4.04 (2 H, m), 3.61-3.75 (2 H, m), 2.83-3.00 (2 H, m), 1.77-1.98 (4 H, m).

Intermediate 58B: 3-(5-Bromopyrimidin-4-yl)propanal

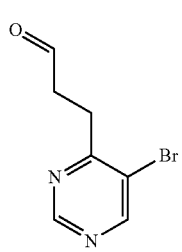 [SMILES: O=CCCc1ncncc1Br]

To a solution of Intermediate 58A (0.920 g, 3.37 mmol) in DCE (6.5 mL) at 0° C. was slowly added formic acid (6.46 mL, 168 mmol). The reaction mixture was heated to 50° C. for 5 hours and allowed to cool to room temperature. The volatile solvents were removed in vacuo. The residue was diluted with CH$_2$Cl$_2$ and washed with saturated aqueous sodium bicarbonate solution, then washed with brine, dried over sodium sulfate and concentrated to provide the crude Intermediate 58B (724 mg, 100% yield), which was used without further purification. MS (ES): m/z=216.8 [M+H]$^+$. $^1$H NMR (400 MHz, DMSO-d$_6$) δ ppm 9.77 (1 H, s), 9.03 (1 H, s), 8.91 (1 H, s), 3.14 (2 H, t, J=6.60 Hz), 2.96 (3 H, t, J=6.60 Hz).

Intermediate 58: 4-Bromopyrrolo[1,2-c]pyrimidine

To a solution of Intermediate 58B (724 mg, 3.37 mmol) in THF (10 mL) at room temperature was added Burgess Reagent (964 mg, 4.04 mmol). The mixture was stirred for 10 minutes and then concentrated under reduced pressure. The crude material was diluted with CH$_2$Cl$_2$ and washed with water, then washed with brine, dried over sodium sulfate and concentrated to provide the crude Intermediate 58 (664 mg, 100% yield), which was used without further purification. MS (ES): m/z=198.8 [M+H]$^+$. $^1$H NMR (400 MHz, DMSO-d$_6$) δ ppm 9.17 (1 H, s), 7.81 (1 H, dd, J=2.86, 1.32 Hz), 7.61 (1 H, s), 6.95-7.03 (1 H, m), 6.55 (1 H, d, J=3.96 Hz). Intermediate 58 was used in the synthesis of Example 250.

Intermediate 59

5-Chloroimidazo[1,2-a]pyrazine

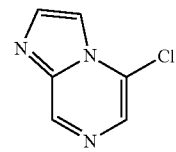

To a solution of 6-chloropyrazin-2-amine (0.5 g, 3.86 mmol) in DME (3 mL) at room temperature was slowly added 2-chloroacetaldehyde (45% aqueous solution, 2.4 mL, 14 mmol). The resulting mixture was heated to 66° C. for 90 minutes, cooled to room temperature, and then basified with 1N NaOH. This basified mixture was extracted with EtOAc (2×). The combined organic layers were washed with brine, dried over sodium sulfate and concentrated. The crude material was purified by silica gel chromatography (eluting with 0-10% MeOH in DCM) to provide Intermediate 59 (430 mg, 73% yield). MS (ES): m/z=153.9 [M+H]$^+$. $^1$H NMR (400 MHz, DMSO-d$_6$) δ ppm 9.12 (1 H, s), 8.27 (1 H, s), 8.15 (1 H, s), 7.85 (1 H, s). Intermediate 59 was used in the synthesis of Example 251.

Intermediate 60

3-Bromo-4-(2,2,2-trifluoroethoxy)pyridine

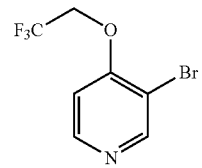 [SMILES: FC(F)(F)COc1ccncc1Br]

To a solution of 2,2,2-trifluoroethanol (0.78 g, 7.79 mmol) in THF (15 mL) at 0° C. was slowly added sodium hydride (0.27 g, 6.76 mmol, 60% suspension in mineral oil). The mixture was stirred at that temperature for 30 minutes, followed by the addition of 3-bromo-4-chloropyridine (1 g, 5.20 mmol). The reaction mixture was then refluxed for 16 hours and then quenched with saturated aqueous ammonium chloride solution. The volatile solvent was removed under reduced pressure, and the residual material was diluted with water and extracted with ethyl acetate (3×15 mL). The combined organics were washed with brine, dried over anhydrous sodium sulfate and concentrated under reduced pressure. The crude material was purified by silica gel chromatography using 90 g BIOTAGE® column eluting with hexanes/EtOAc (1:1) to provide Intermediate 60 as a colorless oil (0.8 g, 60% yield). MS (ES): m/z=256.02 [M+H]+. Intermediate 60 was used in the synthesis of Example 213.

Intermediate 61

5-Bromo-4-cyclopropylpyrimidine

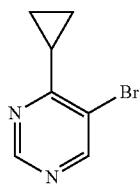

5-Bromopyrimidine (8 g, 50.3 mmol) was taken in anhydrous THF (160 mL) followed by the addition of cyclopropylmagnesium bromide (106 mL, 52.8 mmol, 0.5 M solution in THF) at 0° C. The reaction mixture was stirred at room temperature for 1 hour, and then treated with a solution of 2,3-dichloro-5,6-dicyano-1,4-benzoquinone (11.42 g, 50.3 mmol) in THF (26 mL). The resultant brown mixture was allowed to stir at room temperature for 16 hours and then evaporated under reduced pressure. The brown solid was suspended in water and extracted with dichloromethane (3×50 mL). The combined organics were washed with a 1N aqueous solution of sodium hydroxide (2×15 mL), water, and brine, dried over anhydrous sodium sulfate, and concentrated under reduced pressure. The crude material was purified by silica gel chromatography using 160 g BIOTAGE® column eluting with hexanes/EtOAc (9:1) to provide Intermediate 61 as a pale yellow solid (4.1 g, 41% yield). MS (ES): m/z=199.05 [M+H]+. Intermediate 61 was used in the synthesis of Example 214.

Intermediate 62

N-(4-Bromo-3-chlorophenyl)methanesulfonamide

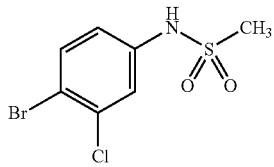

Intermediate 62A: 4-Bromo-3-chloroaniline

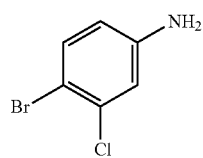

To a solution of 1-bromo-2-chloro-4-nitrobenzene (1.0 g, 4.23 mmol) in THF (7.24 mL) was added EtOH (7.24 mL) followed by ammonium chloride (0.339 g, 6.34 mmol) in water (7.23 mL, 401 mmol) and iron (0.945 g, 16.92 mmol). The reaction mixture was heated at 60° C. in a sealed tube. After 3.5 hours, the reaction mixture was allowed to cool to room temperature and the heterogeneous mixture filtered through a disposable fritted funnel. The filter cake was washed with EtOAc. The solution was concentrated to half-volume, then diluted with EtOAc (10 mL) and 1 N NaOH (10 mL). Layers were separated. Aqueous phase was extracted with EtOAc (3×). The organic phases were combined, dried over $Na_2SO_4$, filtered, and concentrated to afford the title compounds as a tan solid. The crude material was used without further purification.

Intermediate 62:
N-(4-Bromo-3-chlorophenyl)methanesulfonamide

To a solution of Intermediate 62A (0.843 g, 4.08 mmol) in THF (20.41 mL) was added triethylamine (5.69 mL, 40.8 mmol) followed by methanesulfonyl chloride (0.414 mL, 5.31 mmol). The reaction mixture was allowed to stir at room temperature for 3 days, then quenched with a saturated aqueous solution of $NaHCO_3$ and diluted with EtOAc. The layers were separated and the aqueous phase was extracted with EtOAc (2×). The organic phases were combined, dried over $Na_2SO_4$, filtered, and concentrated to afford the title compound (245 mg, 0.861 mmol, 21.09% yield) as a white solid. HPLC Ret time$^j$: 1.32 min. MS (ES): m/z=284.2 [M+H]−. Intermediate 62 was used in the synthesis of Example 212.

Intermediate 63

N-(4-(4-Formylpyridin-3-yl)-3-methoxyphenyl)methanesulfonamide

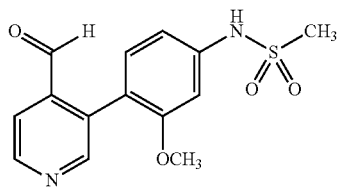 [SMILES: COc1cc(NS(C)(=O)=O)ccc1-c1cnccc1C=O]

To a solution of Intermediate 51 (1.50 g, 4.58 mmol) and 3-bromoisonicotinaldehyde (1.023 g, 5.50 mmol) in a mixture of DME (20 mL), ethanol (10 mL), and water (10 mL) was added $Na_2CO_3$ (1.944 g, 18.34 mmol). This suspension was degassed with a stream of $N_2$ for 10 minutes and then tetrakis(triphenylphosphine) palladium(0) (0.265 g, 0.229 mmol) was added followed by degassing for 10 minutes. The tube was then sealed and heated at 90° C. for 16 hours. The reaction mixture was cooled to room temperature and diluted with MeOH. The resulting suspension was filtered and washed with methanol and the filtrate concentrated to a brown sludge. The crude material used without purification. HPLC Ret. time$^j$: 1.02 min. MS (ES): m/z=307.1 [M+H]+. Intermediate 63 was used in the synthesis of Example 253.

Intermediate 64

N-(4-Iodo-3,5-dimethylphenyl)methanesulfonamide

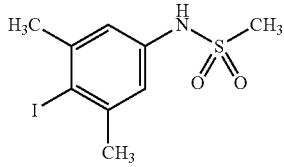

To a solution of 4-iodo-3,5-dimethylaniline (268 mg, 1.085 mmol) in THF (1 mL) were added pyridine (0.877 mL, 10.85 mmol) and methanesulfonyl chloride (0.110 mL, 1.410 mmol). The mixture was stirred at 0° C. for 30 min and then at room temperature overnight. The reaction mixture was diluted with EtOAc and a solution of sodium bicarbonate. The EtOAc layer was washed with brine, dried over anhydrous sodium sulfate, and concentrated in vacuo. The residue was purified by silica gel chromatography using an ISCO machine to give Intermediate 63 (353 mg, 1.085 mmol, 100% yield). Intermediate 63 was used in the synthesis of Example 246.

Intermediate 65

3-Bromo-4-(methoxymethyl)pyridine

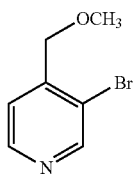

Intermediate 65A: (3-Bromopyridin-4-yl)methanol

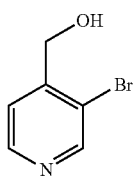

To an ice-cold solution of 3-bromoisonicotinaldehyde (2.5 g, 13.44 mmol) in MeOH (Volume: 100 ml) was added sodium borohydride (1.017 g, 26.9 mmol) and the reaction mixture was stirred at that temperature for 1 hour. The reaction mixture was then quenched with satd. NaHCO$_3$, filtered, and evaporated to remove MeOH. The aqueous layer was extracted with EtOAc (2×). The combined organics were washed with satd. NaHCO$_3$ and brine, dried, and concentrated to give Intermediate 65A as a white solid. MS (ES): m/z=189.9 [M+H]$^+$.

Intermediate 65:
3-Bromo-4-(methoxymethyl)pyridine

To an ice-cold solution of Intermediate 65A (1.0 g, 5.32 mmol) in THF (Volume: 26.6 ml) was added sodium hydride (0.255 g, 6.38 mmol). The ice bath was removed and the reaction mixture was allowed to stir at room temperature for 30 min, then cooled to 0° C. and followed by addition of methyl iodide (0.366 ml, 5.85 mmol). The ice bath was removed and the reaction mixture was allowed to stir at room temperature for 16 hours. The reaction mixture was then quenched with water and concentrated to remove the THF. The resulting aqueous layer was extracted with DCM (3×). The combined organics were washed with water and brine, dried, and concentrated to give an oil. The oil was purified by silica gel chromatography (hexane: ethyl acetate 70:30) to afforded the title compound as a colorless oil. MS (ES): m/z=203.9 [M+H]$^+$. Intermediate 65 was used in the synthesis of Example 254.

Intermediate 66

3-Bromo-4-(cyclopropylmethoxy)pyridine

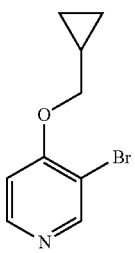 [SMILES: Brc1cnccc1OCC1CC1]

To an ice-cold solution of cyclopropylmethanol (0.562 g, 7.79 mmol) in THF (Volume: 15.06 ml) was added NaH (0.270 g, 6.76 mmol). The reaction was stirred at room temperature for 30 min, and then cooled to 0° C. To this mixture was added 3-bromo-4-chloropyridine (1 g, 5.20 mmol). The resulting mixture was refluxed for 16 hours, cooled to room temperature, and quenched with water. The mixture was evaporated to remove the THF and then extracted with DCM (2×). The combined organic layers were washed with water and brine, dried, and concentrated to give an oil. The oil was purified by silica gel chromatography (hexane: ethyl acetate 50:50) to afforded the title compound as a colorless oil. MS (ES): m/z=229 [M+H]$^+$. Intermediate 66 was used in the synthesis of Example 255.

Example 1

N-(3-Methyl-4-(4-methyl-3-pyridinyl)phenyl)methanesulfonamide

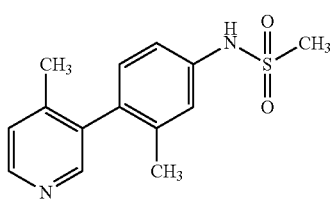

Intermediate 1 (60 mg, 0.303 mmol) was dissolved in THF (1 mL) followed by the addition of pyridine (0.245 mL, 3.03 mmol) and methanesulfonyl chloride (0.031 mL, 0.393 mmol). The resulting solution was stirred at 0° C. for 30 min, diluted with a saturated solution of sodium bicarbonate (50 mL) and then extracted with EtOAc (2×50 mL). The combined organics were washed with brine, dried over anhydrous sodium sulfate, and concentrated under reduced pressure. The crude material was purified by silica gel chromatography (12 g ISCO column, eluting with 0% to 4% MeOH in CH$_2$Cl$_2$) to provide Example 1 (74 mg, 87% yield) as a white powdery material. HPLC Ret time$^a$: 1.333 min. MS (ES): m/z=277.1 [M+H]$^+$. $^1$H NMR (400 MHz, DMSO-d$_6$) δ ppm 1.99 (s, 3 H) 2.05 (s, 3 H) 3.05 (s, 3 H) 7.09 (d, 1 H) 7.12 (dd, 1 H) 7.16 (d, J=2.01 Hz, 1 H) 7.34 (d, J=5.04 Hz, 1 H) 8.24 (s, 1 H) 8.44 (d, J=5.04 Hz, 1 H) 9.83 (s, 1 H).

Examples 2 to 177

The compounds of Examples 2 to 177 in Table 7 were prepared by the procedure described for the preparation of Example 1 using appropriate anilines and sulfonyl halides.

TABLE 7

| Ex. No. | Structure | Name | [M + H]$^+$ | Ret time |
|---|---|---|---|---|
| 2 | 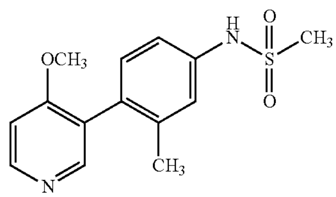 [SMILES: COc1ccncc1-c1ccc(NS(C)(=O)=O)cc1C] | N-(4-(4-methoxypyridin-3-yl)-3-methylphenyl)methanesulfonamide | 293.1 | |
| 3 | 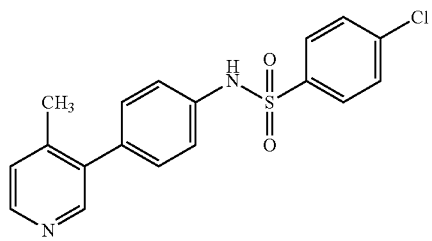 | 4-chloro-N-(4-(4-methyl-3-pyridinyl)phenyl)benzenesulfonamide | 358.9 | 2.733$^a$ |
| 4 | 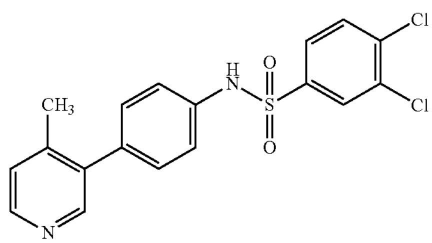 [SMILES: Cc1ccncc1-c1ccc(NS(=O)(=O)c2ccc(Cl)c(Cl)c2)cc1] | 3,4-dichloro-N-(4-(4-methyl-3-pyridinyl)phenyl)benzenesulfonamide | 392.9 | 3.101$^a$ |
| 5 | 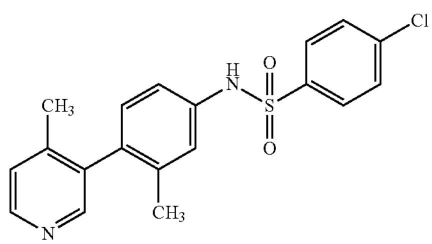 | 4-chloro-N-(3-methyl-4-(4-methyl-3-pyridinyl)phenyl)benzenesulfonamide | 372.9 | 2.758$^a$ |
| 6 | 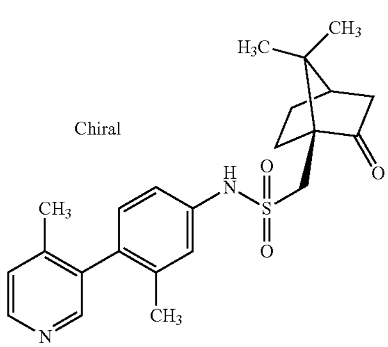 [SMILES: Cc1cc(NS(=O)(=O)C[C@]23CCC(CC2=O)C3(C)C)ccc1-c1cnccc1C] | 1-((1S)-7,7-dimethyl-2-oxobicyclo[2.2.1]hept-1-yl)-N-(3-methyl-4-(4-methyl-3-pyridinyl)phenyl)methanesulfonamide | 413.2 | 2.626$^a$ |

TABLE 7-continued

| Ex. No. | Structure | Name | [M + H]+ | Ret time |
|---|---|---|---|---|
| 7 | 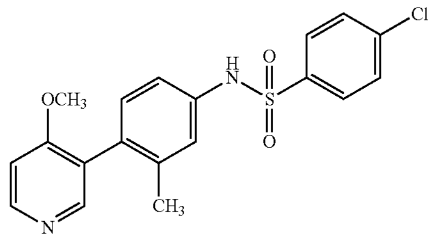 [SMILES: COc1ccncc1-c1ccc(NS(=O)(=O)c2ccc(Cl)cc2)cc1C] | 4-chloro-N-(4-(4-methoxypyridin-3-yl)-3-methylphenyl)benzenesulfonamide | 388.9 | 2.723[a] |
| 8 | 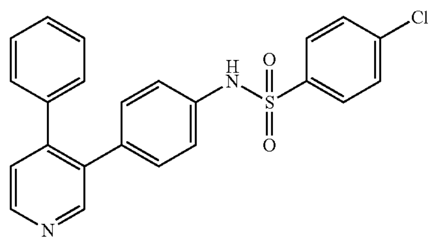 [SMILES: O=S(=O)(Nc1ccc(-c2cnccc2-c2ccccc2)cc1)c1ccc(Cl)cc1] | 4-chloro-N-(4-(4-phenyl-3-pyridinyl)phenyl)benzenesulfonamide | 420.9 | 3.410[a] |
| 9 | 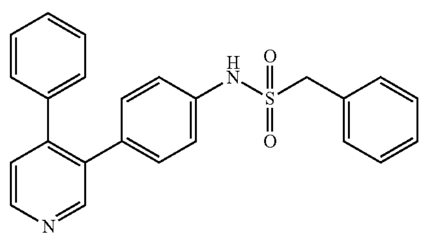 [SMILES: O=S(=O)(Cc1ccccc1)Nc1ccc(-c2cnccc2-c2ccccc2)cc1] | 1-phenyl-N-(4-(4-phenyl-3-pyridinyl)phenyl)methanesulfonamide | 401.0 | 3.110[a] |
| 10 | 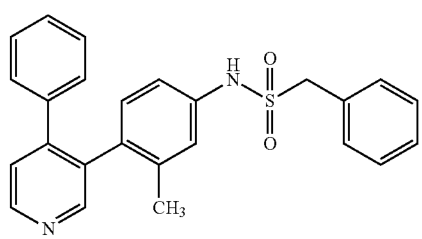 [SMILES: Cc1cc(NS(=O)(=O)Cc2ccccc2)ccc1-c1cnccc1-c1ccccc1] | N-(3-methyl-4-(4-phenyl-3-pyridinyl)phenyl)-1-phenylmethanesulfonamide | 415.0 | 3.190[a] |
| 11 | 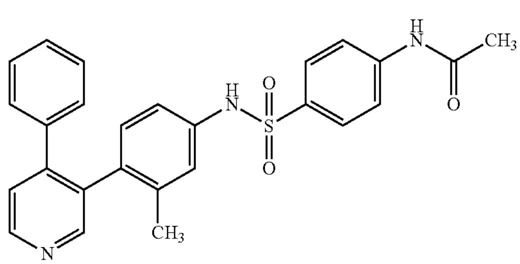 [SMILES: CC(=O)Nc1ccc(S(=O)(=O)Nc2ccc(-c3cnccc3-c3ccccc3)c(C)c2)cc1] | N-(4-((3-methyl-4-(4-phenyl-3-pyridinyl)phenyl)sulfamoyl)phenyl)acetamide | 458.0 | 2.878[a] |
| 12 | 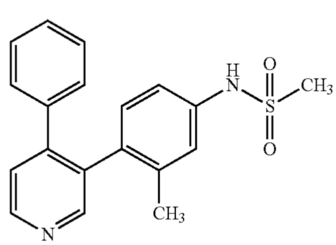 [SMILES: Cc1cc(NS(C)(=O)=O)ccc1-c1cnccc1-c1ccccc1] | N-(3-methyl-4-(4-phenyl-3-pyridinyl)phenyl)methanesulfonamide | 339.1 | 2.440[a] |

TABLE 7-continued

| Ex. No. | Structure | Name | [M + H]+ | Ret time |
|---|---|---|---|---|
| 13 | 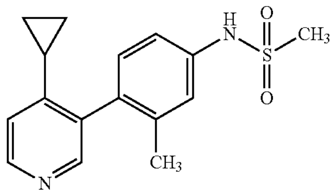 [SMILES: Cc1cc(NS(C)(=O)=O)ccc1-c1cnccc1C1CC1] | N-(4-(4-cyclopropyl-3-pyridinyl)-3-methylphenyl)methanesulfonamide | 303.1 | 1.897[a] |
| 14 | 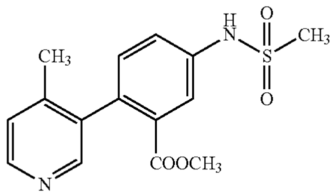 [SMILES: COC(=O)c1cc(NS(C)(=O)=O)ccc1-c1cnccc1C] | methyl2-(4-methyl-3-pyridinyl)-5-((methylsulfonyl)amino)benzoate | 321.1 | 1.722[a] |
| 15 | 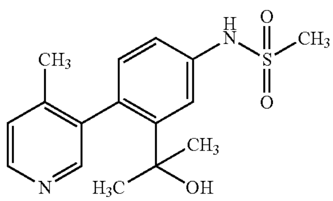 [SMILES: Cc1ccncc1-c1ccc(NS(C)(=O)=O)cc1C(C)(C)O] | N-(3-(2-hydroxypropan-2-yl)-4-(4-methylpyridin-3-yl)phenyl)methanesulfonamide | 321.1 | 1.425[a] |
| 16 | 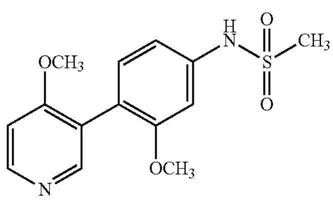 [SMILES: COc1cc(NS(C)(=O)=O)ccc1-c1cnccc1OC] | N-(3-methoxy-4-(4-methoxy-3-pyridinyl)phenyl)methanesulfonamide | 309.2 | 1.595[a] |
| 17 | 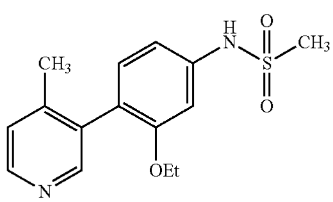 [SMILES: CCOc1cc(NS(C)(=O)=O)ccc1-c1cnccc1C] | N-(3-ethoxy-4-(4-methyl-3-pyridinyl)phenyl)methanesulfonamide | 307.2 | 1.943[a] |
| 18 | 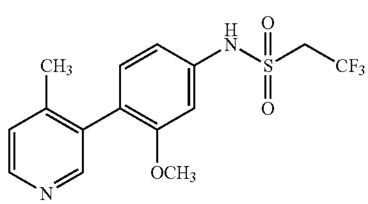 [SMILES: COc1cc(NS(=O)(=O)CC(F)(F)F)ccc1-c1cnccc1C] | 2,2,2-trifluoro-N-(3-methoxy-4-(4-methyl-3-pyridinyl)phenyl)ethanesulfonamide | 361.1 | 2.048[a] |
| 19 | 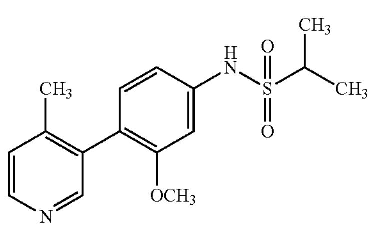 [SMILES: COc1cc(NS(=O)(=O)C(C)C)ccc1-c1cnccc1C] | N-(3-methoxy-4-(4-methyl-3-pyridinyl)phenyl)-2-propanesulfonamide | 321.2 | 2.018[a] |

TABLE 7-continued

| Ex. No. | Structure | Name | [M + H]+ | Ret time |
|---|---|---|---|---|
| 20 | 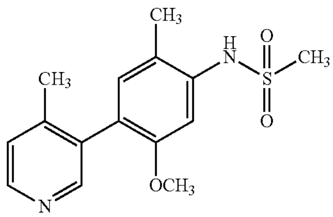 [SMILES: COc1cc(NS(C)(=O)=O)c(C)cc1-c1cnccc1C] | N-(5-methoxy-2-methyl-4-(4-methyl-3-pyridinyl)phenyl)methanesulfonamide | 307.2 | 1.585[a] |
| 21 | 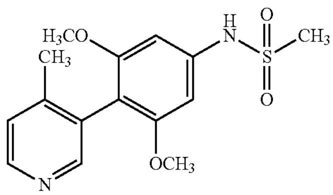 [SMILES: COc1cc(NS(C)(=O)=O)cc(OC)c1-c1cnccc1C] | N-(3,5-dimethoxy-4-(4-methyl-3-pyridinyl)phenyl)methanesulfonamide | 323.1 | 1.767[a] |
| 22 | 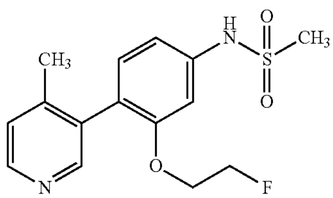 [SMILES: Cc1ccncc1-c1ccc(NS(C)(=O)=O)cc1OCCF] | N-(3-(2-fluoroethoxy)-4-(4-methyl-3-pyridinyl)phenyl)methanesulfonamide | 325.0 | 1.695[a] |
| 23 | 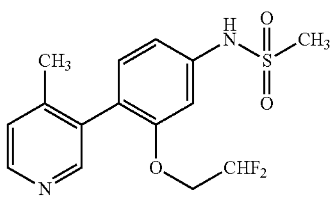 [SMILES: Cc1ccncc1-c1ccc(NS(C)(=O)=O)cc1OCC(F)F] | N-(3-(2,2-difluoroethoxy)-4-(4-methyl-3-pyridinyl)phenyl)methanesulfonamide | 343.0 | 1.778[a] |
| 24 | 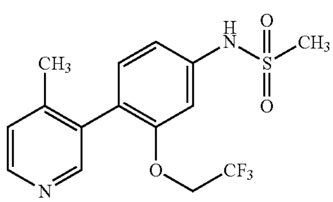 [SMILES: Cc1ccncc1-c1ccc(NS(C)(=O)=O)cc1OCC(F)(F)F] | N-(4-(4-methyl-3-pyridinyl)-3-(2,2,2-trifluoroethoxy)phenyl)methanesulfonamide | 360.9 | 2.058[A] |
| 25 | 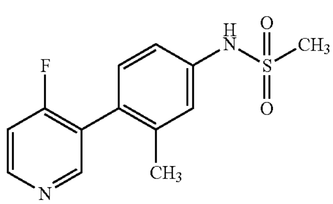 [SMILES: Cc1cc(NS(C)(=O)=O)ccc1-c1cnccc1F] | N-(4-(4-fluoro-3-pyridinyl)-3-methylphenyl)methanesulfonamide | 281.0 | 1.897[a] |
| 26 | 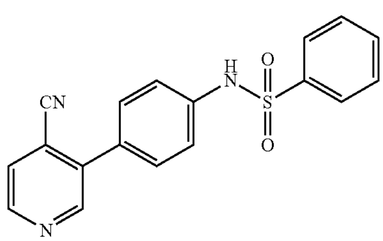 [SMILES: N#Cc1ccncc1-c1ccc(NS(=O)(=O)c2ccccc2)cc1] | N-(4-(4-cyano-3-pyridinyl)phenyl)benzenesulfonamide | 336.2 | 2.372[a] |

TABLE 7-continued

| Ex. No. | Structure | Name | [M + H]+ | Ret time |
|---|---|---|---|---|
| 27 | 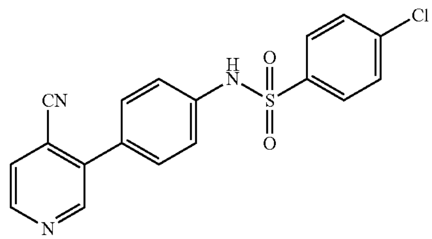 [SMILES: N#Cc1ccncc1-c1ccc(NS(=O)(=O)c2ccc(Cl)cc2)cc1] | 4-chloro-N-(4-(4-cyanopyridin-3-yl)phenyl)benzenesulfonamide | 370.1 | 2.763[a] |
| 28 | 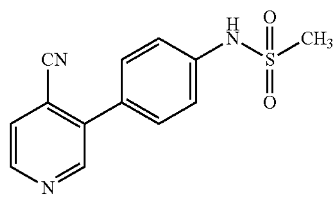 [SMILES: CS(=O)(=O)Nc1ccc(-c2cnccc2C#N)cc1] | N-(4-(4-cyano-3-pyridinyl)phenyl)methanesulfonamide | 291.1 | 1.678[a] |
| 29 | 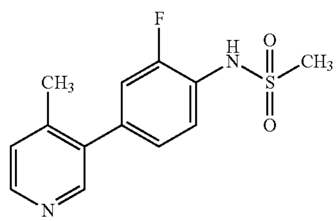 [SMILES: Cc1ccncc1-c1ccc(NS(C)(=O)=O)c(F)c1] | N-(2-fluoro-4-(4-methyl-3-pyridinyl)phenyl)methanesulfonamide | 281.1 | 0.748[a] |
| 30 | 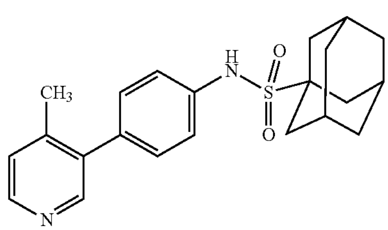 [SMILES: Cc1ccncc1-c1ccc(NS(=O)(=O)C23CC4CC(CC(C4)C2)C3)cc1] | N-(4-(4-methyl-3-pyridinyl)phenyl)-1-adamantanesulfonamide | 383.3 | 2.298[a] |
| 31 | 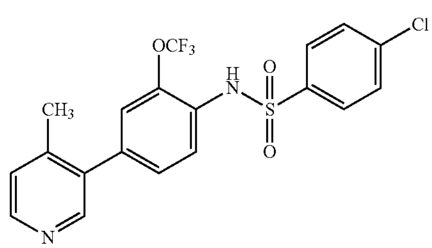 [SMILES: Cc1ccncc1-c1ccc(NS(=O)(=O)c2ccc(Cl)cc2)c(OC(F)(F)F)c1] | 4-chloro-N-(4-(4-methyl-3-pyridinyl)-2-(trifluoromethoxy)phenyl)benzenesulfonamide | 443.3 | 2.230[a] |
| 32 | 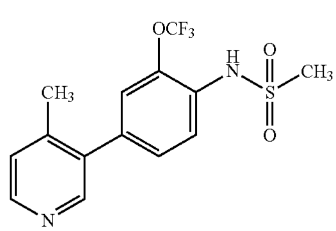 [SMILES: Cc1ccncc1-c1ccc(NS(C)(=O)=O)c(OC(F)(F)F)c1] | N-(4-(4-methyl-3-pyridinyl)-2-(trifluoromethoxy)phenyl)methanesulfonamide | 347.1 | 1.073[a] |

TABLE 7-continued

| Ex. No. | Structure | Name | [M + H]+ | Ret time |
|---|---|---|---|---|
| 33 | 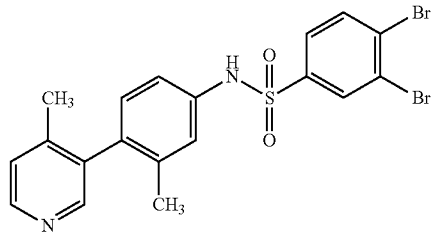 [SMILES: Cc1cc(NS(=O)(=O)c2ccc(Br)c(Br)c2)ccc1-c1cnccc1C] | 3,4-dibromo-N-(3-methyl-4-(4-methylpyridin-3-yl)phenyl)benzenesulfonamide | 496.9 | 2.403[a] |
| 34 | 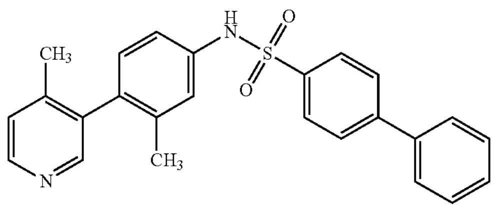 [SMILES: Cc1cc(NS(=O)(=O)c2ccc(-c3ccccc3)cc2)ccc1-c1cnccc1C] | N-(3-methyl-4-(4-methyl-3-pyridinyl)phenyl)-4-biphenylsulfonamide | 415.01 | 2.62[f] |
| 35 | 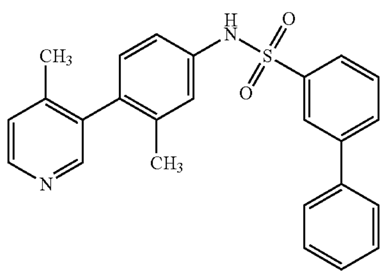 [SMILES: Cc1cc(NS(=O)(=O)c2cccc(-c3ccccc3)c2)ccc1-c1cnccc1C] | N-(3-methyl-4-(4-methyl-3-pyridinyl)phenyl)-3-biphenylsulfonamide | 415.01 | 2.62[f] |
| 36 | 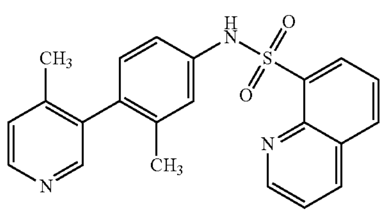 [SMILES: Cc1cc(NS(=O)(=O)c2cccc3cccnc23)ccc1-c1cnccc1C] | N-(3-methyl-4-(4-methyl-3-pyridinyl)phenyl)-8-quinolinesulfonamide | 390.01 | 2.16[f] |
| 37 | 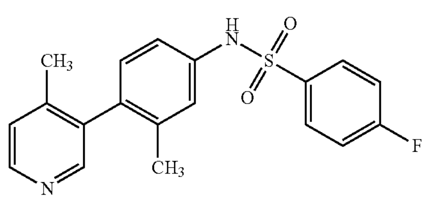 [SMILES: Cc1cc(NS(=O)(=O)c2ccc(F)cc2)ccc1-c1cnccc1C] | 4-fluoro-N-(3-methyl-4-(4-methyl-3-pyridinyl)phenyl)benzenesulfonamide | 357.01 | 2.2[f] |
| 38 | 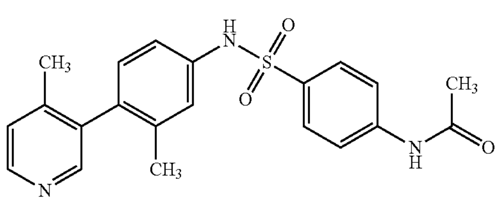 [SMILES: CC(=O)Nc1ccc(S(=O)(=O)Nc2ccc(-c3cnccc3C)c(C)c2)cc1] | N-(4-((3-methyl-4-(4-methyl-3-pyridinyl)phenyl)sulfamoyl)phenyl)acetamide | 396.04 | 1.8[f] |
| 39 | 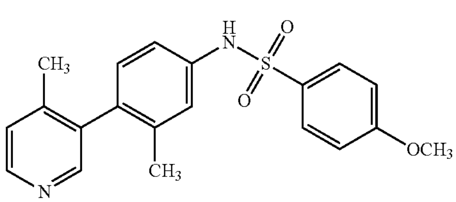 [SMILES: COc1ccc(S(=O)(=O)Nc2ccc(-c3cnccc3C)c(C)c2)cc1] | 4-methoxy-N-(3-methyl-4-(4-methyl-3-pyridinyl)phenyl)benzenesulfonamide | 369.04 | 2.14[f] |

TABLE 7-continued

| Ex. No. | Structure | Name | [M + H]+ | Ret time |
|---|---|---|---|---|
| 40 | 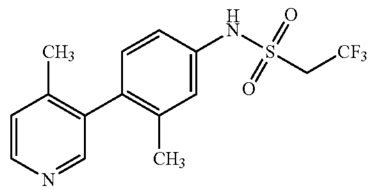 [SMILES: Cc1cc(NS(=O)(=O)CC(F)(F)F)ccc1-c1cnccc1C] | 2,2,2-trifluoro-N-(3-methyl-4-(4-methyl-3-pyridinyl)phenyl)ethanesulfonamide | 344.97 | 2.04$^f$ |
| 41 | 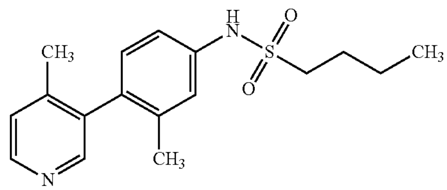 [SMILES: CCCCS(=O)(=O)Nc1ccc(-c2cnccc2C)c(C)c1] | N-(3-methyl-4-(4-methyl-3-pyridinyl)phenyl)-1-butanesulfonamide | 319.04 | 2.03$^f$ |
| 42 | 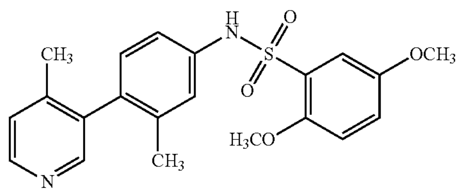 [SMILES: COc1ccc(OC)c(S(=O)(=O)Nc2ccc(-c3cnccc3C)c(C)c2)c1] | 2,5-dimethoxy-N-(3-methyl-4-(4-methyl-3-pyridinyl)phenyl)benzenesulfonamide | 399.04 | 2.14$^f$ |
| 43 | 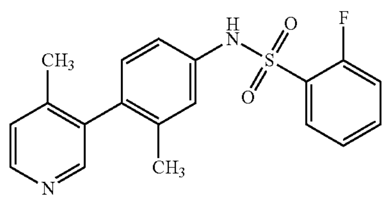 [SMILES: Cc1cc(NS(=O)(=O)c2ccccc2F)ccc1-c1cnccc1C] | 2-fluoro-N-(3-methyl-4-(4-methyl-3-pyridinyl)phenyl)benzenesulfonamide | 357.01 | 2.13$^f$ |
| 44 | 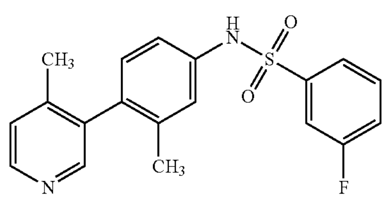 | 3-fluoro-N-(3-methyl-4-(4-methyl-3-pyridinyl)phenyl)benzenesulfonamide | 357.01 | 2.22$^f$ |
| 45 | 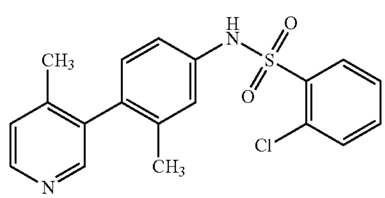 [SMILES: Cc1cc(NS(=O)(=O)c2ccccc2Cl)ccc1-c1cnccc1C] | 2-chloro-N-(3-methyl-4-(4-methyl-3-pyridinyl)phenyl)benzenesulfonamide | 372.97 | 2.23$^f$ |
| 46 | 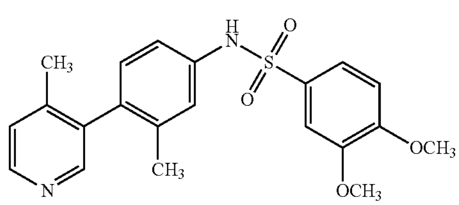 [SMILES: COc1ccc(S(=O)(=O)Nc2ccc(-c3cnccc3C)c(C)c2)cc1OC] | 3,4-dimethoxy-N-(3-methyl-4-(4-methyl-3-pyridinyl)phenyl)benzenesulfonamide | 399.04 | 2.01$^f$ |

| Ex. No. | Structure | Name | [M + H]⁺ | Ret time |
|---|---|---|---|---|
| 47 | 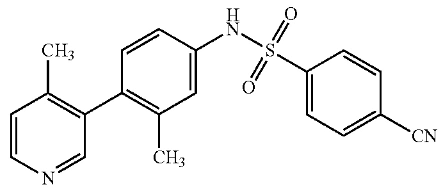 [SMILES: Cc1cc(NS(=O)(=O)c2ccc(C#N)cc2)ccc1-c1cnccc1C] | 4-cyano-N-(3-methyl-4-(4-methyl-3-pyridinyl)phenyl)benzenesulfonamide | 364 | 2.11ᶠ |
| 48 | 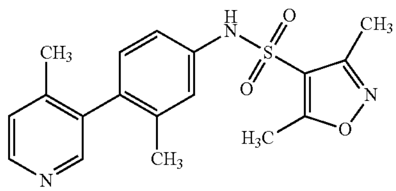 [SMILES: Cc1cc(NS(=O)(=O)c2c(C)noc2C)ccc1-c1cnccc1C] | 3,5-dimethyl-N-(3-methyl-4-(4-methyl-3-pyridinyl)phenyl)-4-isoxazolesulfonamide | 358.01 | 2.07ᶠ |
| 49 | 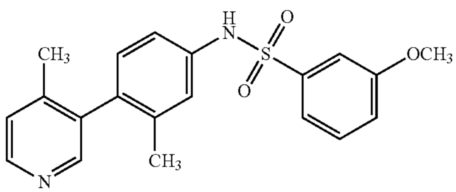 [SMILES: COc1cccc(S(=O)(=O)Nc2ccc(-c3cnccc3C)c(C)c2)c1] | 3-methoxy-N-(3-methyl-4-(4-methyl-3-pyridinyl)phenyl)benzenesulfonamide | 368.46 | 2.18ᶠ |
| 50 | 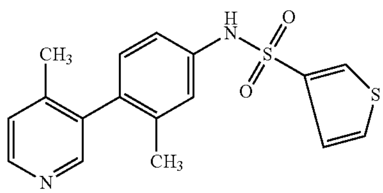 [SMILES: Cc1cc(NS(=O)(=O)c2ccsc2)ccc1-c1cnccc1C] | N-(3-methyl-4-(4-methyl-3-pyridinyl)phenyl)-3-thiophenesulfonamide | 2.03 | 345ᶠ |
| 51 | 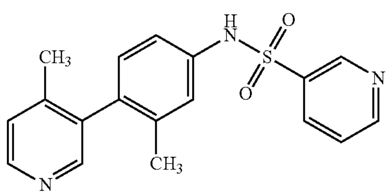 [SMILES: Cc1cc(NS(=O)(=O)c2cccnc2)ccc1-c1cnccc1C] | N-(3-methyl-4-(4-methyl-3-pyridinyl)phenyl)-3-pyridinesulfonamide | 340.02 | 1.76ᶠ |
| 52 | 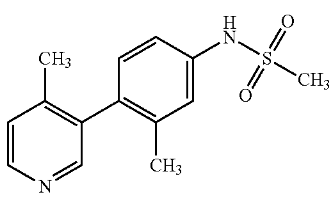 [SMILES: Cc1cc(NS(C)(=O)=O)ccc1-c1cnccc1C] | N-(3-methyl-4-(4-methyl-3-pyridinyl)phenyl)methanesulfonamide | 277.07 | 1.62ᶠ |
| 53 | 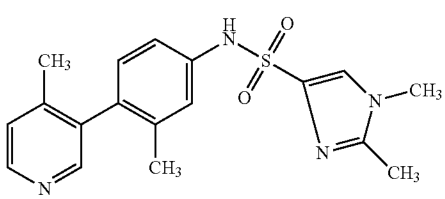 [SMILES: Cc1cc(NS(=O)(=O)c2cn(C)c(C)n2)ccc1-c1cnccc1C] | 1,2-dimethyl-N-(3-methyl-4-(4-methyl-3-pyridinyl)phenyl)-1H-imidazole-4-sulfonamide | 357.01 | 1.58ᶠ |
| 54 | 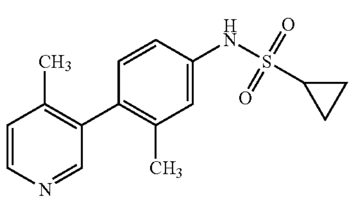 [SMILES: Cc1cc(NS(=O)(=O)C2CC2)ccc1-c1cnccc1C] | N-(3-methyl-4-(4-methyl-3-pyridinyl)phenyl)cyclopropanesulfonamide | 303.07 | 1.81ᶠ |

TABLE 7-continued

| Ex. No. | Structure | Name | [M + H]+ | Ret time |
|---|---|---|---|---|
| 55 | 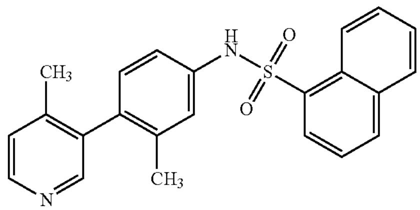 [SMILES: Cc1cc(NS(=O)(=O)c2cccc3ccccc23)ccc1-c1cnccc1C] | N-(3-methyl-4-(4-methyl-3-pyridinyl)phenyl)-1-naphthalenesulfonamide | 389.01 | 2.4[f] |
| 56 | 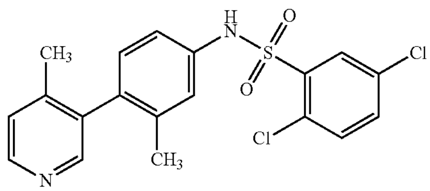 [SMILES: Cc1cc(NS(=O)(=O)c2cc(Cl)ccc2Cl)ccc1-c1cnccc1C] | 2,5-dichloro-N-(3-methyl-4-(4-methyl-3-pyridinyl)phenyl)benzenesulfonamide | 406.91 | 2.47[f] |
| 57 | 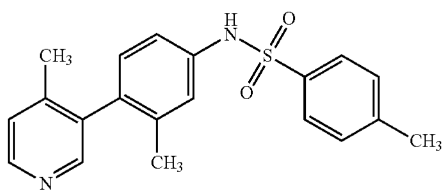 [SMILES: Cc1ccc(S(=O)(=O)Nc2ccc(-c3cnccc3C)c(C)c2)cc1] | 4-methyl-N-(3-methyl-4-(4-methyl-3-pyridinyl)phenyl)benzenesulfonamide | 353.01 | 2.26[d] |
| 58 | 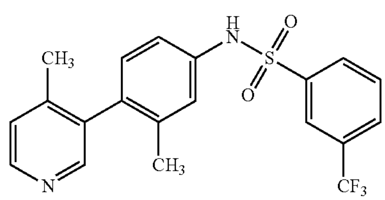 [SMILES: Cc1cc(NS(=O)(=O)c2cccc(C(F)(F)F)c2)ccc1-c1cnccc1C] | N-(3-methyl-4-(4-methyl-3-pyridinyl)phenyl)-3-(trifluoromethyl)benzenesulfonamide | 406.97 | 2.47[f] |
| 59 | 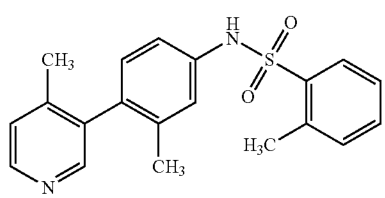 [SMILES: Cc1cc(NS(=O)(=O)c2ccccc2C)ccc1-c1cnccc1C] | 2-methyl-N-(3-methyl-4-(4-methyl-3-pyridinyl)phenyl)benzenesulfonamide | 353.02 | 2.25[f] |
| 60 | 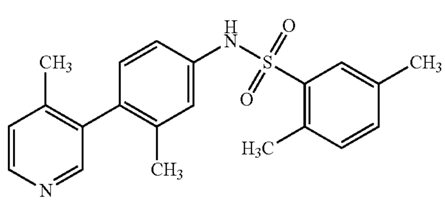 [SMILES: Cc1ccc(C)c(S(=O)(=O)Nc2ccc(-c3cnccc3C)c(C)c2)c1] | 2,5-dimethyl-N-(3-methyl-4-(4-methyl-3-pyridinyl)phenyl)benzenesulfonamide | 367.05 | 2.4[f] |
| 61 | 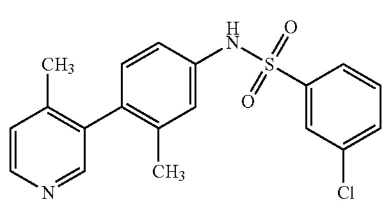 [SMILES: Cc1cc(NS(=O)(=O)c2cccc(Cl)c2)ccc1-c1cnccc1C] | 3-chloro-N-(3-methyl-4-(4-methyl-3-pyridinyl)phenyl)benzenesulfonamide | 372.97 | 2.37[f] |

TABLE 7-continued

| Ex. No. | Structure | Name | [M + H]⁺ | Ret time |
|---|---|---|---|---|
| 62 | 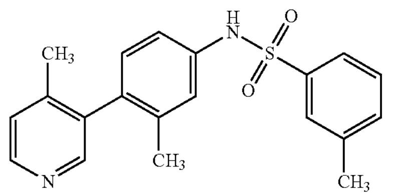 [SMILES: Cc1cccc(S(=O)(=O)Nc2ccc(-c3cnccc3C)c(C)c2)c1] | 3-methyl-N-(3-methyl-4-(4-methyl-3-pyridinyl)phenyl)benzenesulfonamide | 353.02 | 2.27$^f$ |
| 63 | 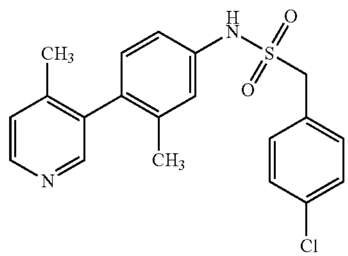 [SMILES: Cc1cc(NS(=O)(=O)Cc2ccc(Cl)cc2)ccc1-c1cnccc1C] | 1-(4-chlorophenyl)-N-(3-methyl-4-(4-methyl-3-pyridinyl)phenyl)methanesulfonamide | 386.98 | 2.38$^f$ |
| 64 | 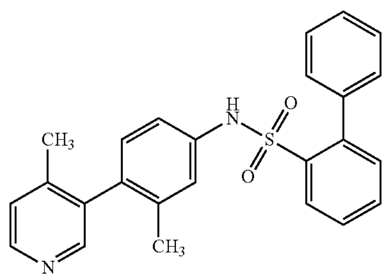 [SMILES: Cc1cc(NS(=O)(=O)c2ccccc2-c2ccccc2)ccc1-c1cnccc1C] | N-(3-methyl-4-(4-methyl-3-pyridinyl)phenyl)-2-biphenylsulfonamide | 415.02 | 2.57$^f$ |
| 65 | 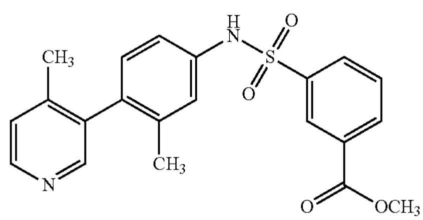 [SMILES: COC(=O)c1cccc(S(=O)(=O)Nc2ccc(-c3cnccc3C)c(C)c2)c1] | methyl3-((3-methyl-4-(4-methyl-3-pyridinyl)phenyl)sulfamoyl)benzoate | 397.00 | 2.17$^f$ |
| 66 | 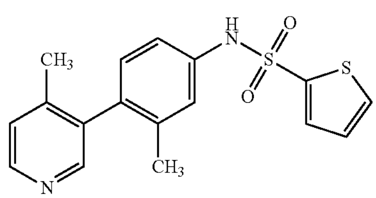 [SMILES: Cc1cc(NS(=O)(=O)c2cccs2)ccc1-c1cnccc1C] | N-(3-methyl-4-(4-methyl-3-pyridinyl)phenyl)-2-thiophenesulfonamide | 344.86 | 2.17$^f$ |
| 67 | 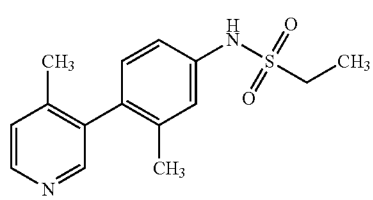 [SMILES: CCS(=O)(=O)Nc1ccc(-c2cnccc2C)c(C)c1] | N-(3-methyl-4-(4-methyl-3-pyridinyl)phenyl)ethanesulfonamide | 290.95 | 1.8$^d$ |
| 68 | 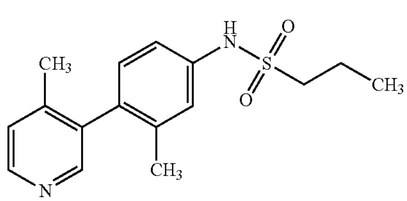 [SMILES: CCCS(=O)(=O)Nc1ccc(-c2cnccc2C)c(C)c1] | N-(3-methyl-4-(4-methyl-3-pyridinyl)phenyl)-1-propanesulfonamide | 305.01 | 2.05$^f$ |

TABLE 7-continued

| Ex. No. | Structure | Name | [M + H]⁺ | Ret time |
|---|---|---|---|---|
| 69 | 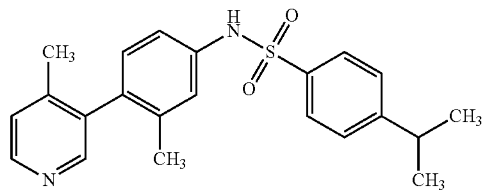 [SMILES: Cc1cc(NS(=O)(=O)c2ccc(C(C)C)cc2)ccc1-c1cnccc1C] | 4-isopropyl-N-(3-methyl-4-(4-methyl-3-pyridinyl)phenyl)benzenesulfonamide | 380.95 | 2.61$^f$ |
| 70 | 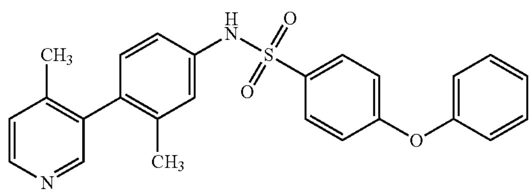 [SMILES: Cc1cc(NS(=O)(=O)c2ccc(Oc3ccccc3)cc2)ccc1-c1cnccc1C] | N-(3-methyl-4-(4-methyl-3-pyridinyl)phenyl)-4-phenoxybenzenesulfonamide | 430.91 | 2.65$^f$ |
| 71 | 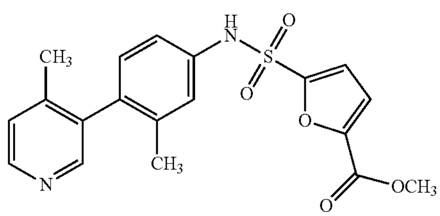 [SMILES: COC(=O)c1ccc(S(=O)(=O)Nc2ccc(-c3cnccc3C)c(C)c2)o1] | methyl5-((3-methyl-4-(4-methyl-3-pyridinyl)phenyl)sulfamoyl)-2-furoate | 386.89 | 2.08$^f$ |
| 72 | 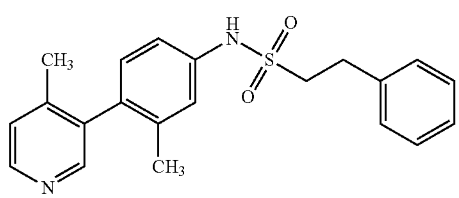 [SMILES: Cc1cc(NS(=O)(=O)CCc2ccccc2)ccc1-c1cnccc1C] | N-(3-methyl-4-(4-methyl-3-pyridinyl)phenyl)-2-phenylethanesulfonamide | 366.95 | 2.34$^f$ |
| 73 | 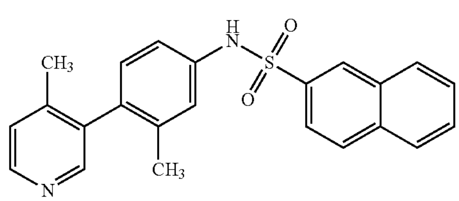 [SMILES: Cc1cc(NS(=O)(=O)c2ccc3ccccc3c2)ccc1-c1cnccc1C] | N-(3-methyl-4-(4-methyl-3-pyridinyl)phenyl)-2-naphthalenesulfonamide | 388.92 | 2.48$^f$ |
| 74 | 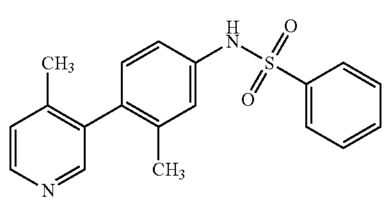 [SMILES: Cc1cc(NS(=O)(=O)c2ccccc2)ccc1-c1cnccc1C] | N-(3-methyl-4-(4-methyl-3-pyridinyl)phenyl)benzenesulfonamide | 339.08 | 2.02$^f$ |
| 75 | 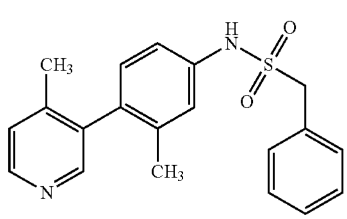 [SMILES: Cc1cc(NS(=O)(=O)Cc2ccccc2)ccc1-c1cnccc1C] | N-(3-methyl-4-(4-methyl-3-pyridinyl)phenyl)-1-phenylmethanesulfonamide | 353.1 | 2.11$^f$ |

TABLE 7-continued

| Ex. No. | Structure | Name | [M + H]+ | Ret time |
|---|---|---|---|---|
| 76 | 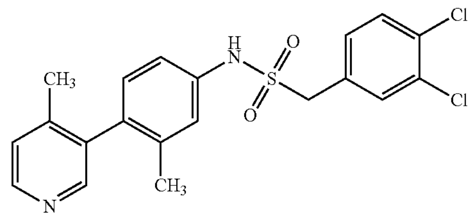 [SMILES: Cc1cc(NS(=O)(=O)Cc2ccc(Cl)c(Cl)c2)ccc1-c1cnccc1C] | 1-(3,4-dichlorophenyl)-N-(3-methyl-4-(4-methyl-3-pyridinyl)phenyl)methanesulfonamide | 420.95 | 2.44<sup>f</sup> |
| 77 | 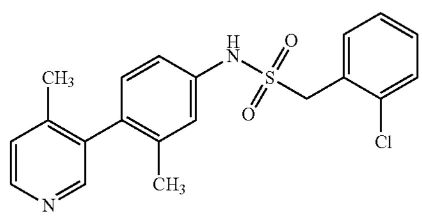 [SMILES: Cc1cc(NS(=O)(=O)Cc2ccccc2Cl)ccc1-c1cnccc1C] | 1-(2-chlorophenyl)-N-(3-methyl-4-(4-methyl-3-pyridinyl)phenyl)methanesulfonamide | 387.01 | 2.25<sup>f</sup> |
| 78 | 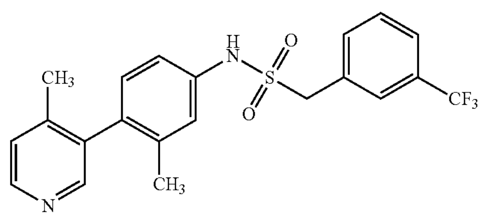 [SMILES: Cc1cc(NS(=O)(=O)Cc2cccc(C(F)(F)F)c2)ccc1-c1cnccc1C] | N-(3-methyl-4-(4-methyl-3-pyridinyl)phenyl)-1-(3-(trifluoromethyl)phenyl)methanesulfonamide | 420.82 | 2.55<sup>f</sup> |
| 79 | 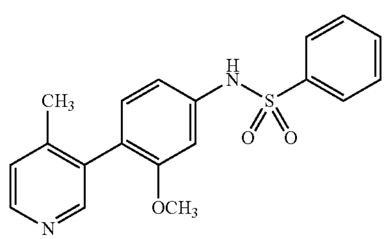 [SMILES: COc1cc(NS(=O)(=O)c2ccccc2)ccc1-c1cnccc1C] | N-(3-methoxy-4-(4-methyl-3-pyridinyl)phenyl)benzenesulfonamide | 354.85 | 2.52<sup>f</sup> |
| 80 | 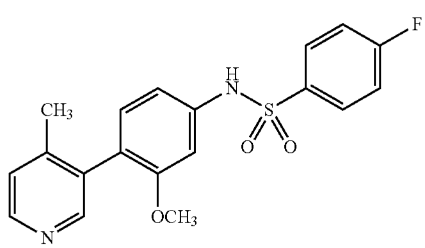 [SMILES: COc1cc(NS(=O)(=O)c2ccc(F)cc2)ccc1-c1cnccc1C] | 4-fluoro-N-(3-methoxy-4-(4-methyl-3-pyridinyl)phenyl)benzenesulfonamide | 372.83 | 2.62<sup>f</sup> |
| 81 | 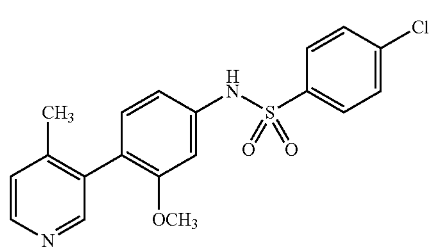 [SMILES: COc1cc(NS(=O)(=O)c2ccc(Cl)cc2)ccc1-c1cnccc1C] | 4-chloro-N-(3-methoxy-4-(4-methyl-3-pyridinyl)phenyl)benzenesulfonamide | 388.77 | 2.84<sup>f</sup> |

TABLE 7-continued

| Ex. No. | Structure | Name | [M + H]+ | Ret time |
|---|---|---|---|---|
| 82 | 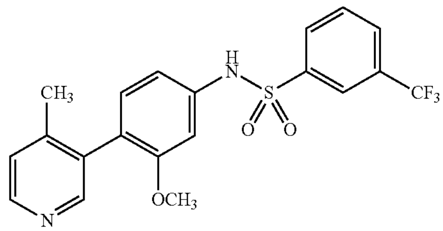 [SMILES: COc1cc(NS(=O)(=O)c2cccc(C(F)(F)F)c2)ccc1-c1cnccc1C] | N-(3-methoxy-4-(4-methyl-3-pyridinyl)phenyl)-3-(trifluoromethyl)benzenesulfonamide | 422.79 | 2.98[f] |
| 83 | 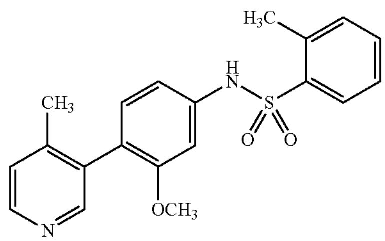 [SMILES: COc1cc(NS(=O)(=O)c2ccccc2C)ccc1-c1cnccc1C] | N-(3-methoxy-4-(4-methyl-3-pyridinyl)phenyl)-2-methylbenzenesulfonamide | 368.86 | 2.7[f] |
| 84 | 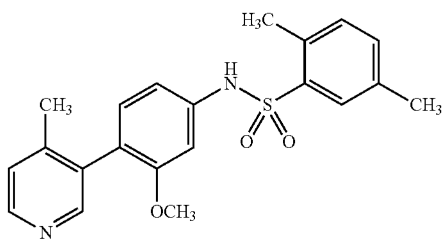 [SMILES: COc1cc(NS(=O)(=O)c2cc(C)ccc2C)ccc1-c1cnccc1C] | N-(3-methoxy-4-(4-methyl-3-pyridinyl)phenyl)-2,5-dimethylbenzenesulfonamide | 382.96 | 2.9[f] |
| 85 | 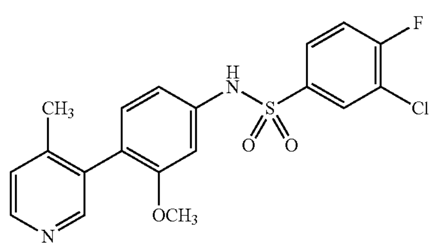 [SMILES: COc1cc(NS(=O)(=O)c2ccc(F)c(Cl)c2)ccc1-c1cnccc1C] | 3-chloro-4-fluoro-N-(3-methoxy-4-(4-methyl-3-pyridinyl)phenyl)benzenesulfonamide | 406.76 | 2.92[f] |
| 86 | 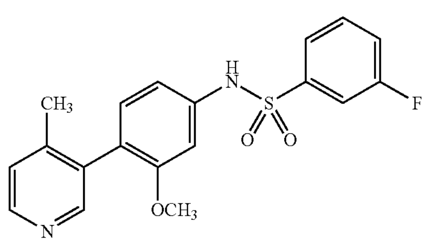 [SMILES: COc1cc(NS(=O)(=O)c2cccc(F)c2)ccc1-c1cnccc1C] | 3-fluoro-N-(3-methoxy-4-(4-methyl-3-pyridinyl)phenyl)benzenesulfonamide | 372.85 | 2.64[f] |
| 87 | 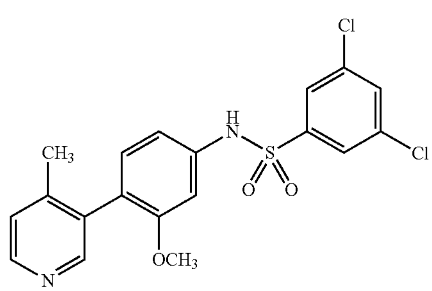 [SMILES: COc1cc(NS(=O)(=O)c2cc(Cl)cc(Cl)c2)ccc1-c1cnccc1C] | 3,5-dichloro-N-(3-methoxy-4-(4-methyl-3-pyridinyl)phenyl)benzenesulfonamide | 422.73 | 3.18 |

TABLE 7-continued

| Ex. No. | Structure | Name | [M + H]+ | Ret time |
|---|---|---|---|---|
| 88 | 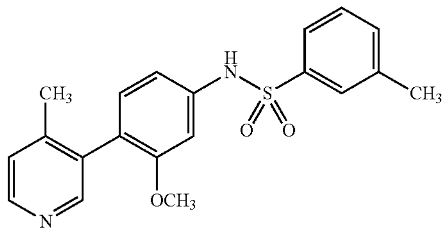 [SMILES: COc1cc(NS(=O)(=O)c2cccc(C)c2)ccc1-c1cnccc1C] | N-(3-methoxy-4-(4-methyl-3-pyridinyl)phenyl)-3-methylbenzenesulfonamide | 368.86 | 2.72[f] |
| 89 | 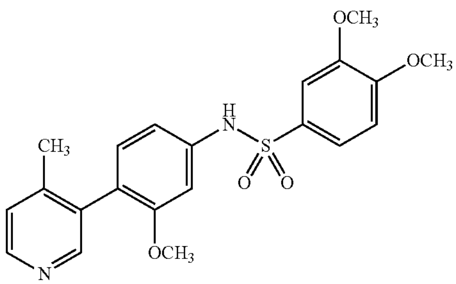 [SMILES: COc1ccc(S(=O)(=O)Nc2ccc(-c3cnccc3C)c(OC)c2)cc1OC] | 3,4-dimethoxy-N-(3-methoxy-4-(4-methyl-3-pyridinyl)phenyl)benzenesulfonamide | 414.85 | 2.42[f] |
| 90 | 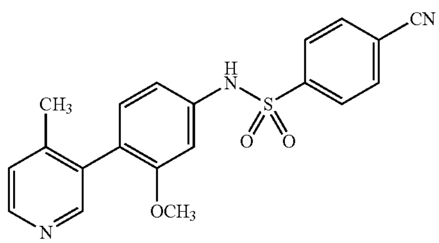 [SMILES: COc1cc(NS(=O)(=O)c2ccc(C#N)cc2)ccc1-c1cnccc1C] | 4-cyano-N-(3-methoxy-4-(4-methyl-3-pyridinyl)phenyl)benzenesulfonamide | 379.83 | 2.49[f] |
| 91 | 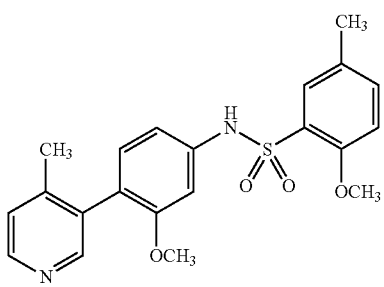 [SMILES: COc1cc(NS(=O)(=O)c2cc(C)ccc2OC)ccc1-c1cnccc1C] | 2-methoxy-N-(3-methoxy-4-(4-methyl-3-pyridinyl)phenyl)-5-methylbenzenesulfonamide | 398.85 | 2.71[f] |
| 92 | 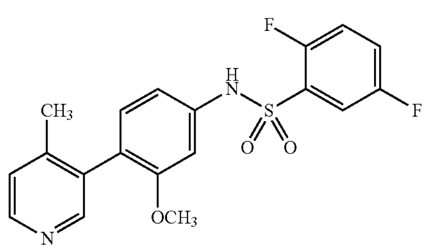 [SMILES: COc1cc(NS(=O)(=O)c2cc(F)ccc2F)ccc1-c1cnccc1C] | 2,5-difluoro-N-(3-methoxy-4-(4-methyl-3-pyridinyl)phenyl)benzenesulfonamide | 390.8 | 2.64[f] |
| 93 | 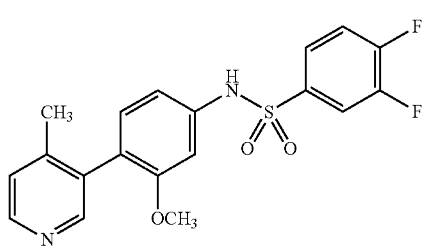 [SMILES: COc1cc(NS(=O)(=O)c2ccc(F)c(F)c2)ccc1-c1cnccc1C] | 3,4-difluoro-N-(3-methoxy-4-(4-methyl-3-pyridinyl)phenyl)benzenesulfonamide | 390.82 | 2.76[f] |

TABLE 7-continued

| Ex. No. | Structure | Name | [M + H]+ | Ret time |
|---|---|---|---|---|
| 94 | 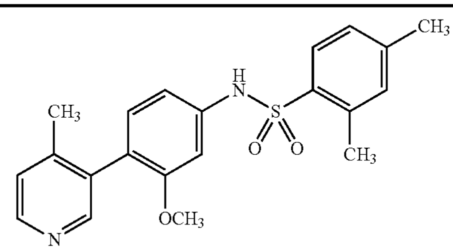 | N-(3-methoxy-4-(4-methyl-3-pyridinyl)phenyl)-2,4-dimethylbenzenesulfonamide | 382.85 | 2.91$^f$ |
| 95 | 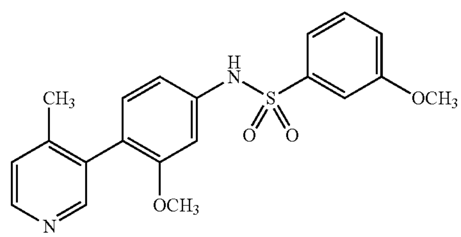 [SMILES: COc1cccc(S(=O)(=O)Nc2ccc(-c3cnccc3C)c(OC)c2)c1] | 3-methoxy-N-(3-methoxy-4-(4-methyl-3-pyridinyl)phenyl)benzenesulfonamide | 384.85 | 2.61$^f$ |
| 96 | 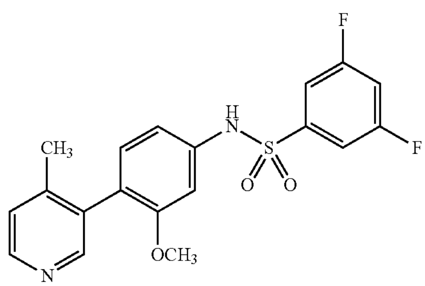 [SMILES: COc1cc(NS(=O)(=O)c2cc(F)cc(F)c2)ccc1-c1cnccc1C] | 3,5-difluoro-N-(3-methoxy-4-(4-methyl-3-pyridinyl)phenyl)benzenesulfonamide | 390.8 | 2.78$^f$ |
| 97 | 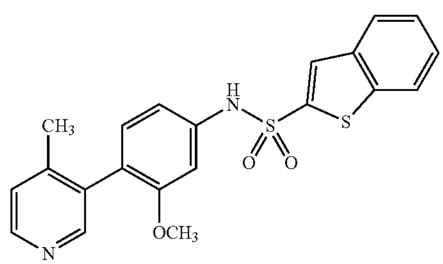 [SMILES: COc1cc(NS(=O)(=O)c2cc3ccccc3s2)ccc1-c1cnccc1C] | N-(3-methoxy-4-(4-methyl-3-pyridinyl)phenyl)-1-benzothiophene-2-sulfonamide | 410.82 | 2.94$^f$ |
| 98 | 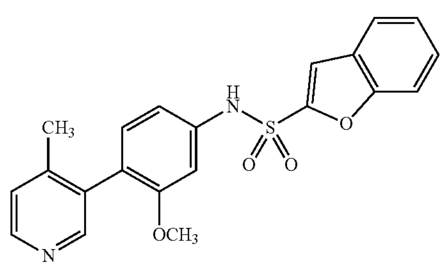 [SMILES: COc1cc(NS(=O)(=O)c2cc3ccccc3o2)ccc1-c1cnccc1C] | N-(3-methoxy-4-(4-methyl-3-pyridinyl)phenyl)-1-benzofuran-2-sulfonamide | 394.85 | 2.78$^f$ |
| 99 | 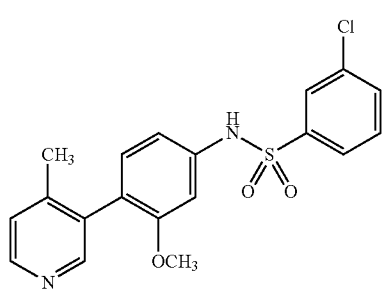 [SMILES: COc1cc(NS(=O)(=O)c2cccc(Cl)c2)ccc1-c1cnccc1C] | 3-chloro-N-(3-methoxy-4-(4-methyl-3-pyridinyl)phenyl)benzenesulfonamide | 388.77 | 2.84$^f$ |

TABLE 7-continued

| Ex. No. | Structure | Name | [M + H]+ | Ret time |
|---|---|---|---|---|
| 100 | 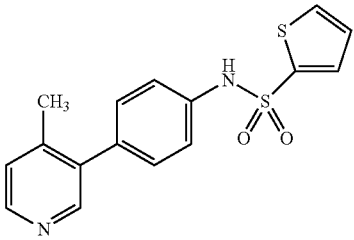 [SMILES: Cc1ccncc1-c1ccc(NS(=O)(=O)c2cccs2)cc1] | N-(4-(4-methyl-3-pyridinyl)phenyl)-2-thiophenesulfonamide | 330.88 | 2.21[f] |
| 101 | 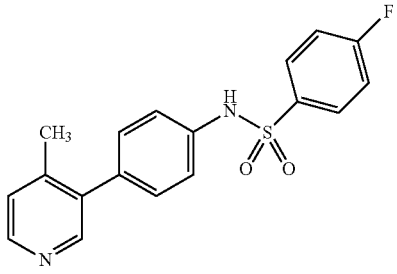 [SMILES: Cc1ccncc1-c1ccc(NS(=O)(=O)c2ccc(F)cc2)cc1] | 4-fluoro-N-(4-(4-methyl-3-pyridinyl)phenyl)benzenesulfonamide | 342.86 | 2.3[f] |
| 102 | 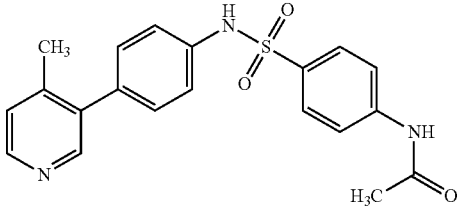 [SMILES: CC(=O)Nc1ccc(S(=O)(=O)Nc2ccc(-c3cnccc3C)cc2)cc1] | N-(4-((4-(4-methyl-3-pyridinyl)phenyl)sulfamoyl)phenyl)acetamide | 381.86 | 1.98[f] |
| 103 | 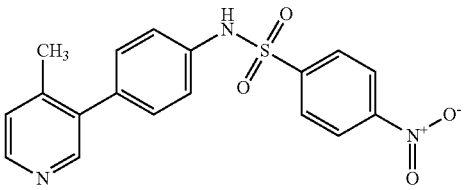 [SMILES: Cc1ccncc1-c1ccc(NS(=O)(=O)c2ccc([N+](=O)[O-])cc2)cc1] | N-(4-(4-methyl-3-pyridinyl)phenyl)-4-nitrobenzenesulfonamide | 369.83 | 2.33[f] |
| 104 | 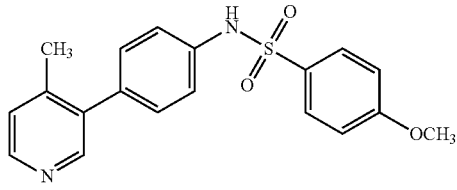 [SMILES: COc1ccc(S(=O)(=O)Nc2ccc(-c3cnccc3C)cc2)cc1] | 4-methoxy-N-(4-(4-methyl-3-pyridinyl)phenyl)benzenesulfonamide | 354.92 | 2.26[f] |
| 105 | 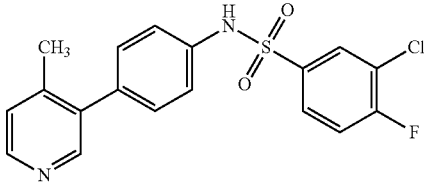 [SMILES: Cc1ccncc1-c1ccc(NS(=O)(=O)c2ccc(F)c(Cl)c2)cc1] | 3-chloro-4-fluoro-N-(4-(4-methyl-3-pyridinyl)phenyl)benzenesulfonamide | 376.82 | 2.66[f] |
| 106 | 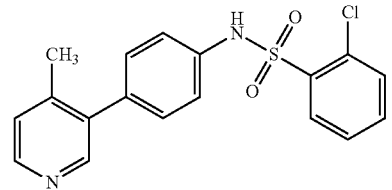 [SMILES: Cc1ccncc1-c1ccc(NS(=O)(=O)c2ccccc2Cl)cc1] | 2-chloro-N-(4-(4-methyl-3-pyridinyl)phenyl)benzenesulfonamide | 358.83 | 2.33[f] |

TABLE 7-continued

| Ex. No. | Structure | Name | [M + H]+ | Ret time |
|---|---|---|---|---|
| 107 | 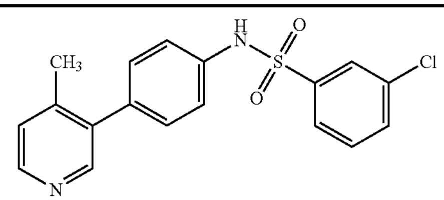 | 3-chloro-N-(4-(4-methyl-3-pyridinyl)phenyl)benzenesulfonamide | 358.82 | 2.45[f] |
| 108 | 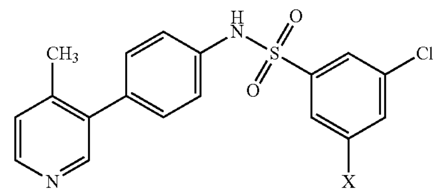 | 3,5-dichloro-N-(4-(4-methyl-3-pyridinyl)phenyl)benzenesulfonamide | 392.76 | 2.66[f] |
| 109 | 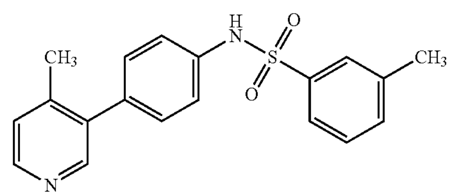 [SMILES: Cc1cccc(S(=O)(=O)Nc2ccc(-c3cnccc3C)cc2)c1] | 3-methyl-N-(4-(4-methyl-3-pyridinyl)phenyl)benzenesulfonamide | 338.94 | 2.37[f] |
| 110 | 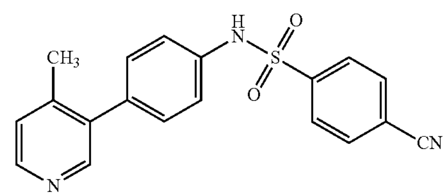 [SMILES: Cc1ccncc1-c1ccc(NS(=O)(=O)c2ccc(C#N)cc2)cc1] | 4-cyano-N-(4-(4-methyl-3-pyridinyl)phenyl)benzenesulfonamide | 349.88 | 2.22[f] |
| 111 | 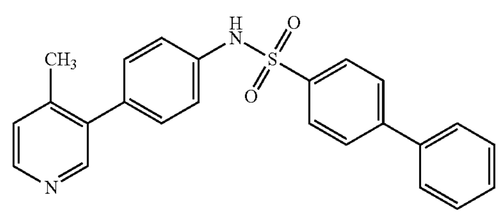 [SMILES: Cc1ccncc1-c1ccc(NS(=O)(=O)c2ccc(-c3ccccc3)cc2)cc1] | N-(4-(4-methyl-3-pyridinyl)phenyl)-4-biphenylsulfonamide | 400.88 | 2.67[f] |
| 112 | 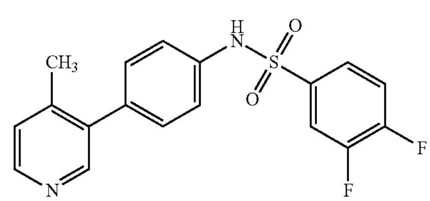 [SMILES: Cc1ccncc1-c1ccc(NS(=O)(=O)c2ccc(F)c(F)c2)cc1] | 3,4-difluoro-N-(4-(4-methyl-3-pyridinyl)phenyl)benzenesulfonamide | 360.38 | 2.39[f] |
| 113 | 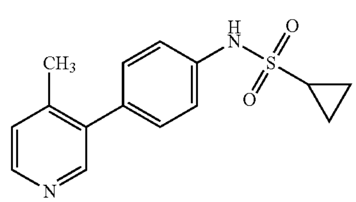 [SMILES: Cc1ccncc1-c1ccc(NS(=O)(=O)C2CC2)cc1] | N-(4-(4-methyl-3-pyridinyl)phenyl)cyclopropanesulfonamide | 288.98 | 1.97[f] |
| 114 | 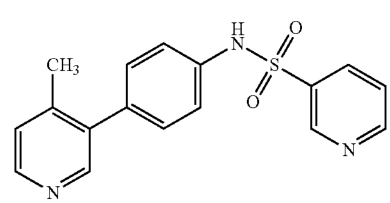 [SMILES: Cc1ccncc1-c1ccc(NS(=O)(=O)c2cccnc2)cc1] | N-(4-(4-methyl-3-pyridinyl)phenyl)-3-pyridinesulfonamide | 325.92 | 1.94[f] |

TABLE 7-continued

| Ex. No. | Structure | Name | [M + H]+ | Ret time |
|---|---|---|---|---|
| 115 | 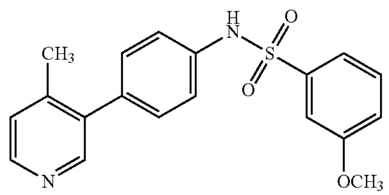 [SMILES: COc1cccc(S(=O)(=O)Nc2ccc(-c3cnccc3C)cc2)c1] | 3-methoxy-N-(4-(4-methyl-3-pyridinyl)phenyl)benzenesulfonamide | 354.91 | 2.29$^f$ |
| 116 | 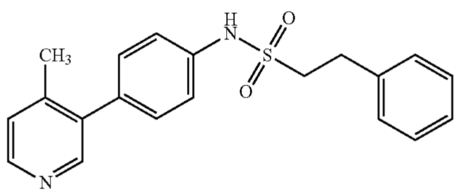 [SMILES: Cc1ccncc1-c1ccc(NS(=O)(=O)CCc2ccccc2)cc1] | N-(4-(4-methyl-3-pyridinyl)phenyl)-2-phenylethanesulfonamide | 352.92 | 2.41$^f$ |
| 117 | 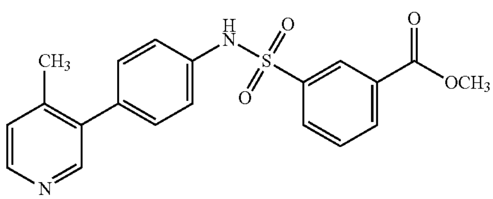 [SMILES: COC(=O)c1cccc(S(=O)(=O)Nc2ccc(-c3cnccc3C)cc2)c1] | methyl 3-((4-(4-methyl-3-pyridinyl)phenyl)sulfamoyl)benzoate | 382.88 | 2.27$^f$ |
| 118 | 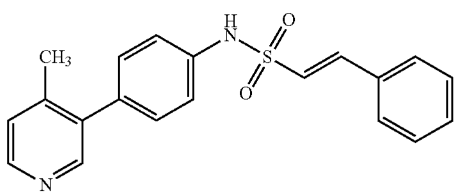 [SMILES: Cc1ccncc1-c1ccc(NS(=O)(=O)/C=C/c2ccccc2)cc1] | (E)-N-(4-(4-methyl-3-pyridinyl)phenyl)-2-phenylethenesulfonamide | 350.92 | 2.4$^f$ |
| 119 | 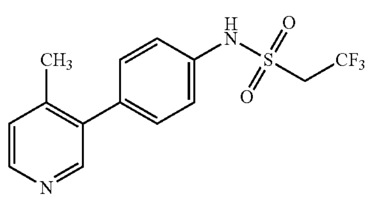 [SMILES: Cc1ccncc1-c1ccc(NS(=O)(=O)CC(F)(F)F)cc1] | 2,2,2-trifluoro-N-(4-(4-methyl-3-pyridinyl)phenyl)ethanesulfonamide | 330.88 | 2.14$^f$ |
| 120 | 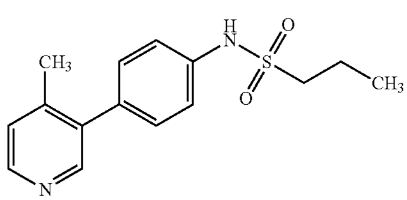 [SMILES: CCCS(=O)(=O)Nc1ccc(-c2cnccc2C)cc1] | N-(4-(4-methyl-3-pyridinyl)phenyl)-1-propanesulfonamide | 291 | 2.05$^f$ |
| 121 | 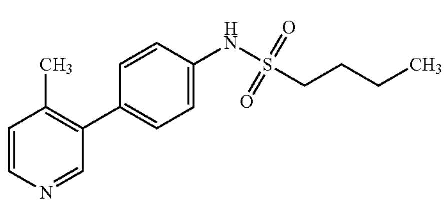 [SMILES: CCCCS(=O)(=O)Nc1ccc(-c2cnccc2C)cc1] | N-(4-(4-methyl-3-pyridinyl)phenyl)-1-butanesulfonamide | 305 | 2.24$^f$ |

TABLE 7-continued

| Ex. No. | Structure | Name | [M + H]⁺ | Ret time |
|---|---|---|---|---|
| 122 | 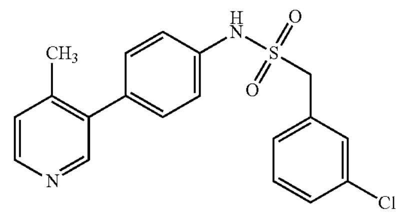 [SMILES: Cc1ccncc1-c1ccc(NS(=O)(=O)Cc2cccc(Cl)c2)cc1] | 1-(3-chlorophenyl)-N-(4-(4-methyl-3-pyridinyl)phenyl)methanesulfonamide | 372.82 | 2.46$^f$ |
| 123 | 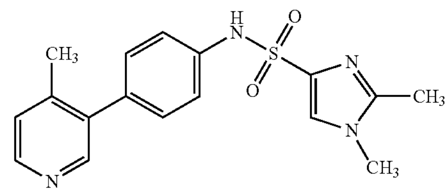 [SMILES: Cc1ccncc1-c1ccc(NS(=O)(=O)c2cn(C)c(C)n2)cc1] | 1,2-dimethyl-N-(4-(4-methyl-3-pyridinyl)phenyl)-1H-imidazole-4-sulfonamide | 342.92 | 1.82$^f$ |
| 124 | 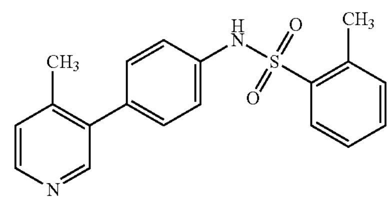 [SMILES: Cc1ccncc1-c1ccc(NS(=O)(=O)c2ccccc2C)cc1] | 2-methyl-N-(4-(4-methyl-3-pyridinyl)phenyl)benzenesulfonamide | 338.94 | 2.44$^f$ |
| 125 | 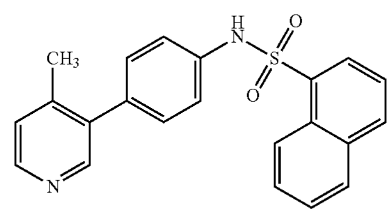 [SMILES: Cc1ccncc1-c1ccc(NS(=O)(=O)c2cccc3ccccc23)cc1] | N-(4-(4-methyl-3-pyridinyl)phenyl)-1-naphthalenesulfonamide | 374.85 | 2.58$^f$ |
| 126 | 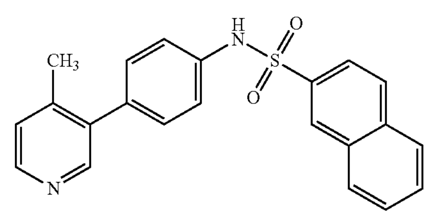 [SMILES: Cc1ccncc1-c1ccc(NS(=O)(=O)c2ccc3ccccc3c2)cc1] | N-(4-(4-methyl-3-pyridinyl)phenyl)-2-naphthalenesulfonamide | 374.85 | 2.52$^f$ |
| 127 | 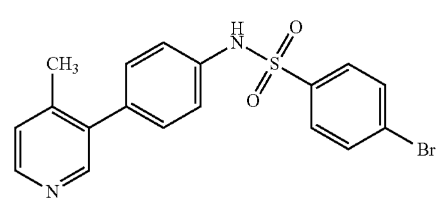 [SMILES: Cc1ccncc1-c1ccc(NS(=O)(=O)c2ccc(Br)cc2)cc1] | 4-bromo-N-(4-(4-methyl-3-pyridinyl)phenyl)benzenesulfonamide | 404.72 | 2.5$^f$ |
| 128 | 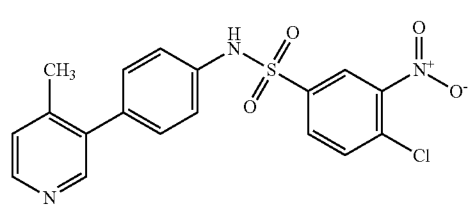 [SMILES: Cc1ccncc1-c1ccc(NS(=O)(=O)c2ccc(Cl)c([N+](=O)[O-])c2)cc1] | 4-chloro-N-(4-(4-methyl-3-pyridinyl)phenyl)-3-nitrobenzenesulfonamide | 403.77 | 2.46$^f$ |

TABLE 7-continued

| Ex. No. | Structure | Name | [M + H]+ | Ret time |
|---|---|---|---|---|
| 129 | 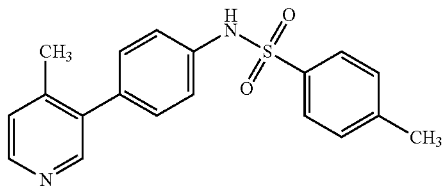 [SMILES: Cc1ccc(S(=O)(=O)Nc2ccc(-c3cnccc3C)cc2)cc1] | 4-methyl-N-(4-(4-methyl-3-pyridinyl)phenyl)benzenesulfonamide | 338.92 | 2.37$^f$ |
| 130 | 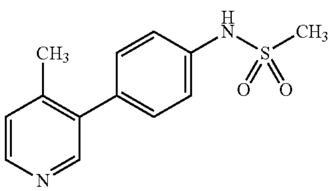 [SMILES: Cc1ccncc1-c1ccc(NS(C)(=O)=O)cc1] | N-(4-(4-methyl-3-pyridinyl)phenyl)methanesulfonamide | 262.02 | 1.87$^f$ |
| 131 | 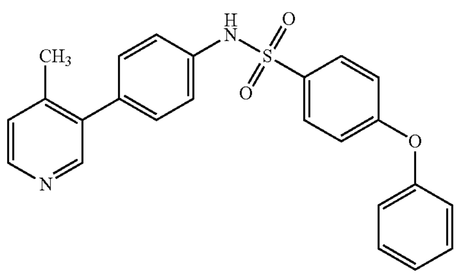 [SMILES: Cc1ccncc1-c1ccc(NS(=O)(=O)c2ccc(Oc3ccccc3)cc2)cc1] | N-(4-(4-methyl-3-pyridinyl)phenyl)-4-phenoxybenzenesulfonamide | 416.85 | 2.69$^f$ |
| 132 | 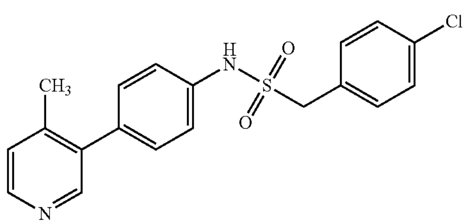 [SMILES: Cc1ccncc1-c1ccc(NS(=O)(=O)Cc2ccc(Cl)cc2)cc1] | 1-(4-chlorophenyl)-N-(4-(4-methyl-3-pyridinyl)phenyl)methanesulfonamide | 372.82 | 2.47$^f$ |
| 133 | 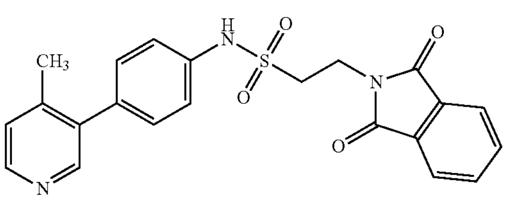 [SMILES: Cc1ccncc1-c1ccc(NS(=O)(=O)CCN2C(=O)c3ccccc3C2=O)cc1] | 2-(1,3-dioxo-1,3-dihydro-2H-isoindol-2-yl)-N-(4-(4-methyl-3-pyridinyl)phenyl)ethanesulfonamide | 421.82 | 2.21$^f$ |
| 134 | 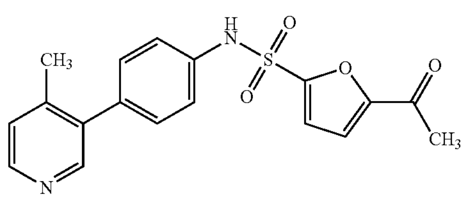 [SMILES: CC(=O)c1ccc(S(=O)(=O)Nc2ccc(-c3cnccc3C)cc2)o1] | methyl5-((4-(4-methyl-3-pyridinyl)phenyl)sulfamoyl)-2-furoate | 372.83 | 2.11$^f$ |
| 135 | 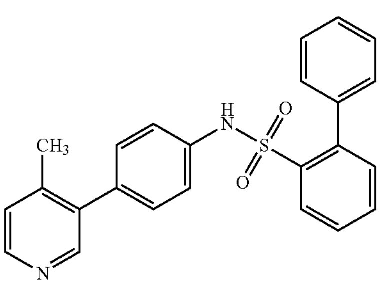 [SMILES: Cc1ccncc1-c1ccc(NS(=O)(=O)c2ccccc2-c2ccccc2)cc1] | N-(4-(4-methyl-3-pyridinyl)phenyl)-2-biphenylsulfonamide | 400.86 | 2.62$^f$ |

TABLE 7-continued

| Ex. No. | Structure | Name | [M + H]+ | Ret time |
|---|---|---|---|---|
| 136 | 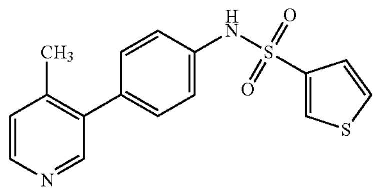 [SMILES: Cc1ccncc1-c1ccc(NS(=O)(=O)c2ccsc2)cc1] | N-(4-(4-methyl-3-pyridinyl)phenyl)-3-thiophenesulfonamide | 330.88 | 2.16$^f$ |
| 137 | 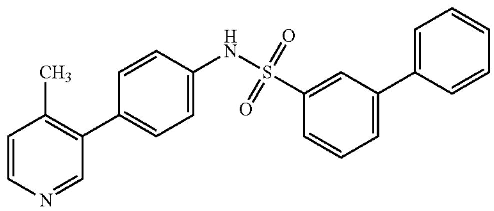 [SMILES: Cc1ccncc1-c1ccc(NS(=O)(=O)c2cccc(-c3ccccc3)c2)cc1] | N-(4-(4-methyl-3-pyridinyl)phenyl)-3-biphenylsulfonamide | 400.85 | 2.66$^f$ |
| 138 | 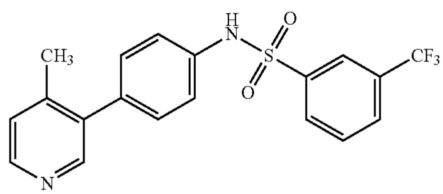 [SMILES: Cc1ccncc1-c1ccc(NS(=O)(=O)c2cccc(C(F)(F)F)c2)cc1] | N-(4-(4-methyl-3-pyridinyl)phenyl)-3-(trifluoromethyl)benzenesulfonamide | 392.82 | 2.6$^f$ |
| 139 | 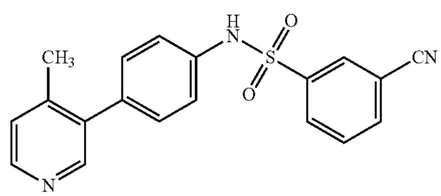 [SMILES: Cc1ccncc1-c1ccc(NS(=O)(=O)c2cccc(C#N)c2)cc1] | 3-cyano-N-(4-(4-methyl-3-pyridinyl)phenyl)benzenesulfonamide | 349.85 | 2.21$^f$ |
| 140 | 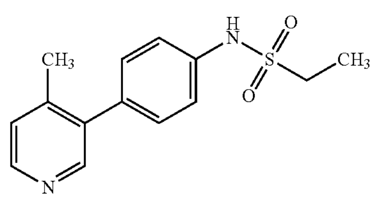 [SMILES: CCS(=O)(=O)Nc1ccc(-c2cnccc2C)cc1] | N-(4-(4-methyl-3-pyridinyl)phenyl)ethanesulfonamide | 277 | 1.98$^f$ |
| 141 | 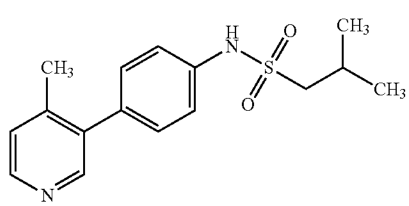 [SMILES: Cc1ccncc1-c1ccc(NS(=O)(=O)CC(C)C)cc1] | 2-methyl-N-(4-(4-methyl-3-pyridinyl)phenyl)-1-propanesulfonamide | 304.98 | 2.24$^f$ |
| 142 | 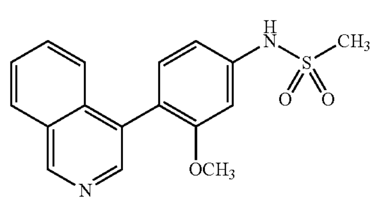 [SMILES: COc1cc(NS(C)(=O)=O)ccc1-c1cncc2ccccc12] | N-(4-isoquinolin-4-yl)-3-methoxyphenyl)methanesulfonamide | 329.12 | 1.760$^f$ |

TABLE 7-continued

| Ex. No. | Structure | Name | [M + H]⁺ | Ret time |
|---|---|---|---|---|
| 143 | 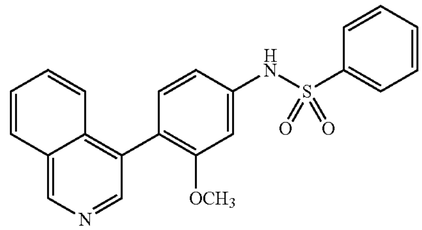 [SMILES: COc1cc(NS(=O)(=O)c2ccccc2)ccc1-c1cncc2ccccc12] | N-(4-isoquinolin-4-yl)-3-methoxyphenyl)benzenesulfonamide | 391.02 | 2.26$^f$ |
| 144 | 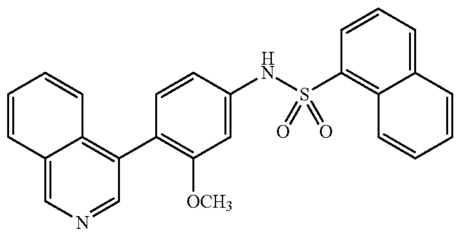 [SMILES: COc1cc(NS(=O)(=O)c2cccc3ccccc23)ccc1-c1cncc2ccccc12] | N-(4-isoquinolin-4-yl)-3-methoxyphenyl)naphthalene-1-sulfonamide | 441.02 | 2.540$^f$ |
| 145 | 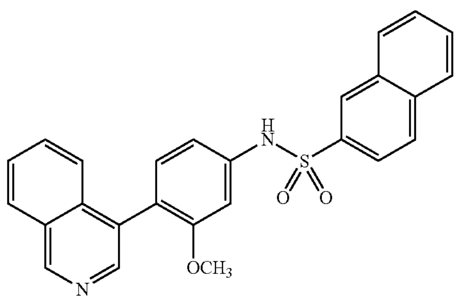 [SMILES: COc1cc(NS(=O)(=O)c2ccc3ccccc3c2)ccc1-c1cncc2ccccc12] | N-(4-isoquinolin-4-yl)-3-methoxyphenyl)naphthalene-2-sulfonamide | 441.02 | 2.570$^f$ |
| 146 | 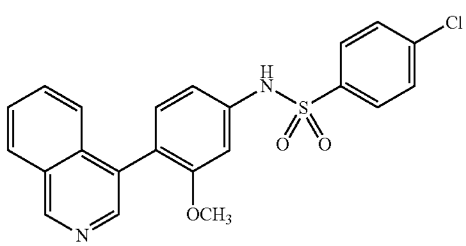 [SMILES: COc1cc(NS(=O)(=O)c2ccc(Cl)cc2)ccc1-c1cncc2ccccc12] | 4-chloro-N-(4-isoquinolin-4-yl)-3-methoxyphenyl)benzenesulfonamide | 424.96 | 2.510$^f$ |
| 147 | 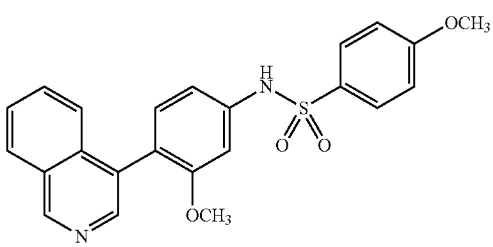 [SMILES: COc1ccc(S(=O)(=O)Nc2ccc(-c3cncc4ccccc34)c(OC)c2)cc1] | N-(4-isoquinolin-4-yl)-3-methoxyphenyl)-4-methoxybenzenesulfonamide | 421.03 | 2.290$^f$ |
| 148 | 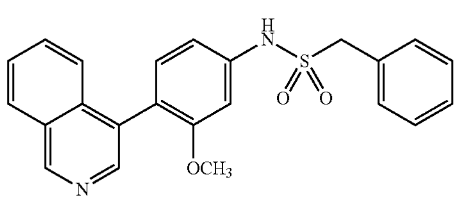 [SMILES: COc1cc(NS(=O)(=O)Cc2ccccc2)ccc1-c1cncc2ccccc12] | N-(4-isoquinolin-4-yl)-3-methoxyphenyl)-1-phenylmethanesulfonamide | 405.04 | 2.340$^f$ |

TABLE 7-continued

| Ex. No. | Structure | Name | [M + H]+ | Ret time |
|---|---|---|---|---|
| 149 | 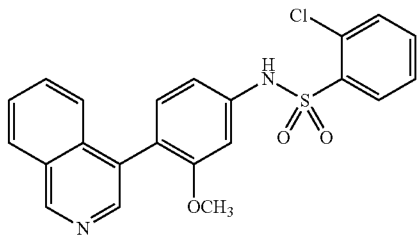 [SMILES: COc1cc(NS(=O)(=O)c2ccccc2Cl)ccc1-c1cncc2ccccc12] | 2-chloro-N-(4-isoquinolin-4-yl)-3-methoxyphenyl)benzenesulfonamide | 424.97 | 2.370$^f$ |
| 150 | 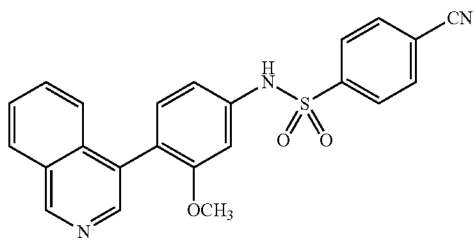 [SMILES: COc1cc(NS(=O)(=O)c2ccc(C#N)cc2)ccc1-c1cncc2ccccc12] | 4-cyano-N-(4-isoquinolin-4-yl)-3-methoxyphenyl)benzenesulfonamide | 416.02 | 2.220$^f$ |
| 151 | 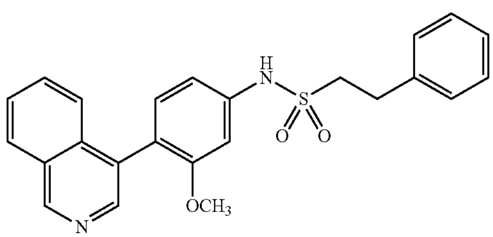 [SMILES: COc1cc(NS(=O)(=O)CCc2ccccc2)ccc1-c1cncc2ccccc12] | N-(4-isoquinolin-4-yl)-3-methoxyphenyl)-2-phenylethanesulfonamide | 419.07 | 2.490$^f$ |
| 152 | 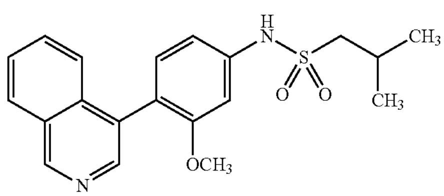 [SMILES: COc1cc(NS(=O)(=O)CC(C)C)ccc1-c1cncc2ccccc12] | N-(4-isoquinolin-4-yl)-3-methoxyphenyl)-2-methylpropane-1-sulfonamide | 371.03 | 2.290$^f$ |
| 153 | 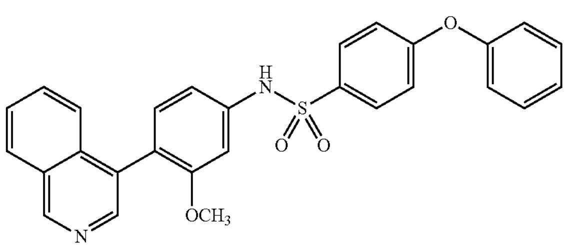 [SMILES: COc1cc(NS(=O)(=O)c2ccc(Oc3ccccc3)cc2)ccc1-c1cncc2ccccc12] | N-(4-isoquinolin-4-yl)-3-methoxyphenyl)-4-phenoxybenzenesulfonamide | 483.04 | 2.810$^f$ |
| 154 | 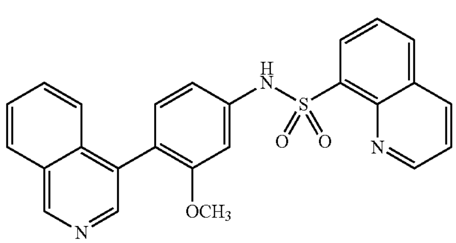 [SMILES: COc1cc(NS(=O)(=O)c2cccc3cccnc23)ccc1-c1cncc2ccccc12] | N-(4-isoquinolin-4-yl)-3-methoxyphenyl)quinoline-8-sulfonamide | 442.04 | 2.310$^f$ |
| 155 | 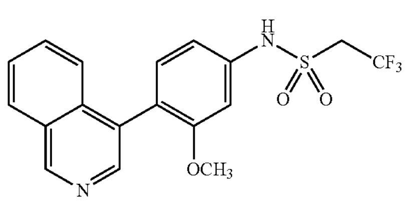 [SMILES: COc1cc(NS(=O)(=O)CC(F)(F)F)ccc1-c1cncc2ccccc12] | 2,2,2-trifluoro-N-(4-isoquinolin-4-yl)-3-methoxyphenyl)ethanesulfonamide | 396.98 | 2.160$^f$ |

TABLE 7-continued

| Ex. No. | Structure | Name | [M + H]⁺ | Ret time |
|---|---|---|---|---|
| 156 | 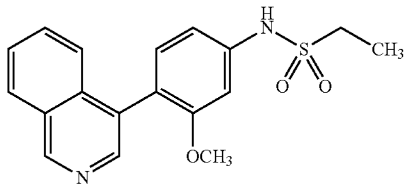 [SMILES: CCS(=O)(=O)Nc1ccc(-c2cncc3ccccc23)c(OC)c1] | N-(4-isoquinolin-4-yl)-3-methoxyphenyl)ethanesulfonamide | 343.02 | 1.930$^f$ |
| 157 | 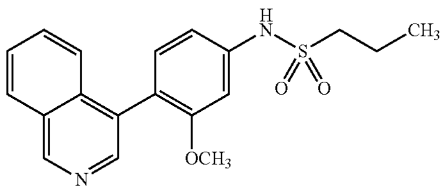 [SMILES: CCCS(=O)(=O)Nc1ccc(-c2cncc3ccccc23)c(OC)c1] | N-(4-isoquinolin-4-yl)-3-methoxyphenyl)propane-1-sulfonamide | 357.03 | 2.110$^f$ |
| 158 | 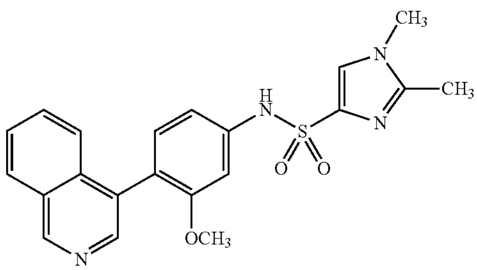 [SMILES: COc1cc(NS(=O)(=O)c2cn(C)c(C)n2)ccc1-c1cncc2ccccc12] | N-(4-isoquinolin-4-yl)-3-methoxyphenyl)-1,2-dimethyl-1H-imidazole-4-sulfonamide | 409.04 | 1.760$^f$ |
| 159 | 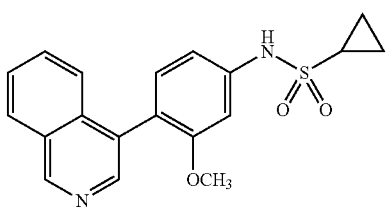 [SMILES: COc1cc(NS(=O)(=O)C2CC2)ccc1-c1cncc2ccccc12] | N-(4-isoquinolin-4-yl)-3-methoxyphenyl)cyclopropanesulfonamide | 355.01 | 1.990$^f$ |
| 160 | 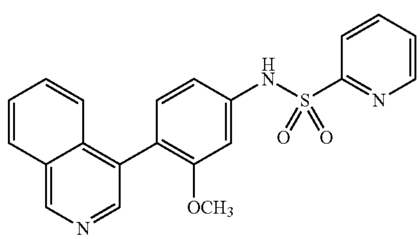 [SMILES: COc1cc(NS(=O)(=O)c2ccccn2)ccc1-c1cncc2ccccc12] | N-(4-isoquinolin-4-yl)-3-methoxyphenyl)pyridine-2-sulfonamide | 392.02 | 1.900$^f$ |
| 161 | 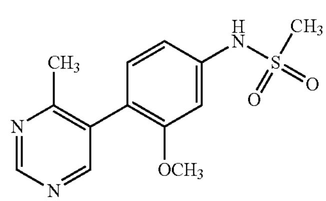 [SMILES: COc1cc(NS(C)(=O)=O)ccc1-c1cncnc1C] | N-(3-methoxy-4-(4-methylpyrimidin-5-yl)phenyl)methanesulfonamide | 294.10 | 1.200$^f$ |
| 162 | 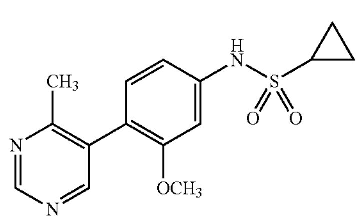 [SMILES: COc1cc(NS(=O)(=O)C2CC2)ccc1-c1cncnc1C] | N-(3-methoxy-4-(4-methylpyrimidin-5-yl)phenyl)cyclopropanesulfonamide | 320.03 | 1.460$^f$ |

TABLE 7-continued

| Ex. No. | Structure | Name | [M + H]⁺ | Ret time |
|---|---|---|---|---|
| 163 | 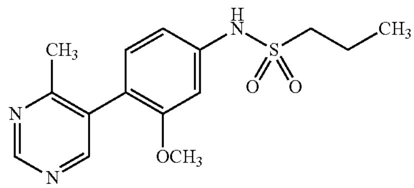 [SMILES: CCCS(=O)(=O)Nc1ccc(-c2cncnc2C)c(OC)c1] | N-(3-methoxy-4-(4-methylpyrimidin-5-yl)phenyl)propane-1-sulfonamide | 322.05 | 1.590ᶠ |
| 164 | 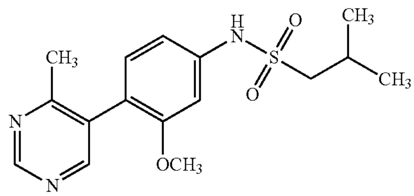 [SMILES: COc1cc(NS(=O)(=O)CC(C)C)ccc1-c1cncnc1C] | N-(3-methoxy-4-(4-methylpyrimidin-5-yl)phenyl)methanesulfonamide | 336.07 | 1.790ᶠ |
| 165 | 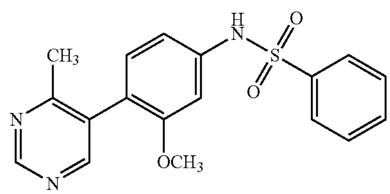 [SMILES: COc1cc(NS(=O)(=O)c2ccccc2)ccc1-c1cncnc1C] | N-(3-methoxy-4-(4-methylpyrimidin-5-yl)phenyl)benzenesulfonamide | 356.03 | 1.790ᶠ |
| 166 | 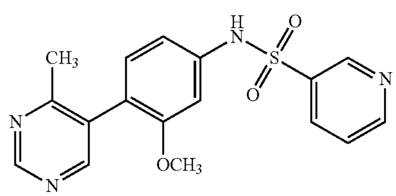 [SMILES: COc1cc(NS(=O)(=O)c2cccnc2)ccc1-c1cncnc1C] | N-(3-methoxy-4-(4-methylpyrimidin-5-yl)phenyl)pyridine-3-sulfonamide | 357.01 | 1.420ᶠ |
| 167 | 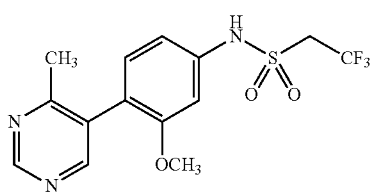 [SMILES: COc1cc(NS(=O)(=O)CC(F)(F)F)ccc1-c1cncnc1C] | 2,2,2-trifluoro-N-(3-methoxy-4-(4-methylpyrimidin-5-yl)phenyl)ethanesulfonamide | 361.98 | 1.610ᶠ |
| 168 | 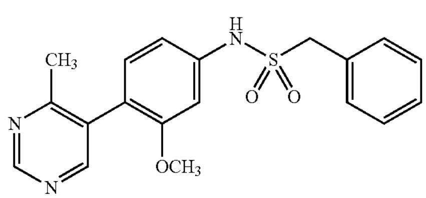 [SMILES: COc1cc(NS(=O)(=O)Cc2ccccc2)ccc1-c1cncnc1C] | N-(3-methoxy-4-(4-methylpyrimidin-5-yl)phenyl)-1-phenylmethanesulfonamide | 370.02 | 1.860ᶠ |
| 169 | 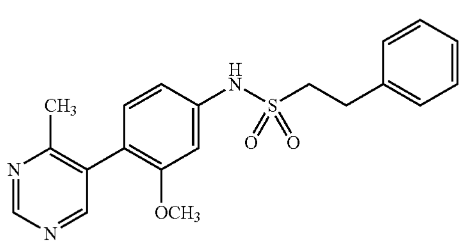 [SMILES: COc1cc(NS(=O)(=O)CCc2ccccc2)ccc1-c1cncnc1C] | N-(3-methoxy-4-(4-methylpyrimidin-5-yl)phenyl)-2-phenylethanesulfonamide | 384.17 | 2.000ᶠ |

TABLE 7-continued

| Ex. No. | Structure | Name | [M + H]+ | Ret time |
|---|---|---|---|---|
| 170 | 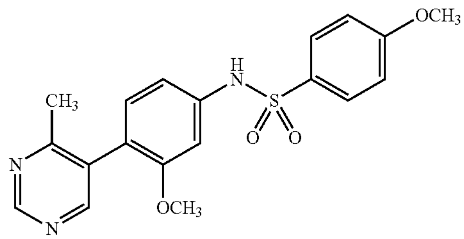 [SMILES: COc1ccc(S(=O)(=O)Nc2ccc(-c3cncnc3C)c(OC)c2)cc1] | 4-methoxy-N-(3-methoxy-4-(4-methylpyrimidin-5-yl)phenyl)benzenesulfonamide | 386.00 | 1.840$^f$ |
| 171 | 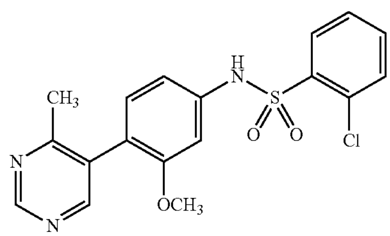 [SMILES: COc1cc(NS(=O)(=O)c2ccccc2Cl)ccc1-c1cncnc1C] | 2-chloro-N-(3-methoxy-4-(4-methylpyrimidin-5-yl)phenyl)benzenesulfonamide | 389.98 | 1.890$^f$ |
| 172 | 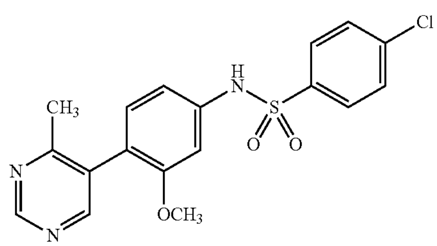 [SMILES: COc1cc(NS(=O)(=O)c2ccc(Cl)cc2)ccc1-c1cncnc1C] | 4-chloro-N-(3-methoxy-4-(4-methylpyrimidin-5-yl)phenyl)benzenesulfonamide | 390.11 | 2.010$^f$ |
| 173 | 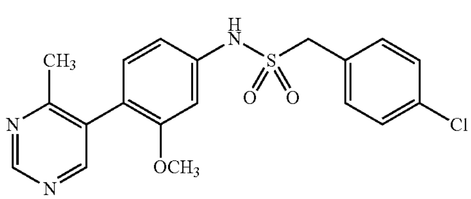 [SMILES: COc1cc(NS(=O)(=O)Cc2ccc(Cl)cc2)ccc1-c1cncnc1C] | 1-(4-chlorophenyl)-N-(3-methoxy-4-(4-methylpyrimidin-5-yl)phenyl)methanesulfonamide | 404.15 | 2.040$^f$ |
| 174 | 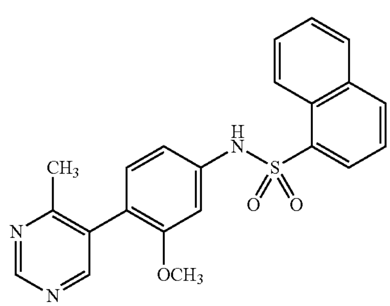 [SMILES: COc1cc(NS(=O)(=O)c2cccc3ccccc23)ccc1-c1cncnc1C] | N-(3-methoxy-4-(4-methylpyrimidin-5-yl)phenyl)naphthalene-1-sulfonamide | 406.21 | 2.080$^f$ |

TABLE 7-continued

| Ex. No. | Structure | Name | [M + H]+ | Ret time |
|---|---|---|---|---|
| 175 | 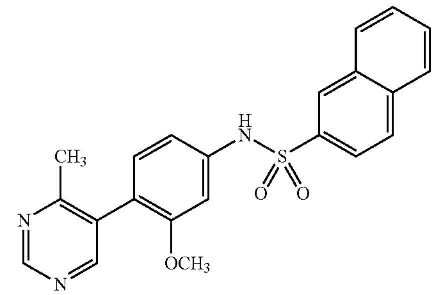 [SMILES: COc1cc(NS(=O)(=O)c2ccc3ccccc3c2)ccc1-c1cncnc1C] | N-(3-methoxy-4-(4-methylpyrimidin-5-yl)phenyl)naphthalene-2-sulfonamide | 406.21 | 2.150f |
| 176 | 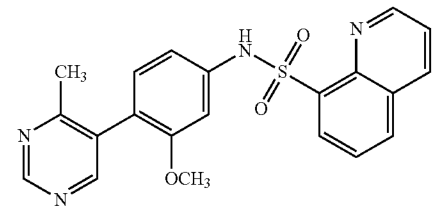 [SMILES: COc1cc(NS(=O)(=O)c2cccc3cccnc23)ccc1-c1cncnc1C] | N-(3-methoxy-4-(4-methylpyrimidin-5-yl)phenyl)quinoline-8-sulfonamide | 407.01 | 1.840f |
| 177 | 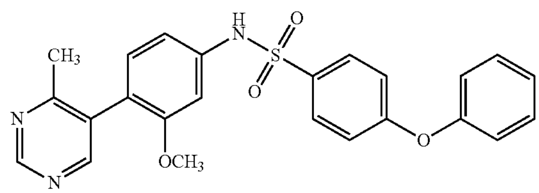 [SMILES: COc1cc(NS(=O)(=O)c2ccc(Oc3ccccc3)cc2)ccc1-c1cncnc1C] | N-(3-methoxy-4-(4-methylpyrimidin-5-yl)phenyl)naphthalene-2-sulfonamide | 448.03 | 2.410f |

Example 178

N-(3-Chloro-4-(4-methylpyridin-3-yl)phenyl)methanesulfonamide

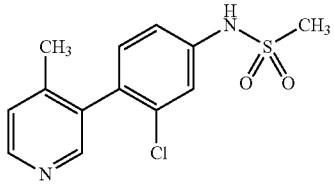 [SMILES: Cc1ccncc1-c1ccc(NS(C)(=O)=O)cc1Cl]

To a solution of Intermediate 27 (0.102 g, 0.466 mmol) and methanesulfonyl chloride (0.043 mL, 0.560 mmol) in DMF (3.26 mL) was added sodium hydride (0.037 g, 0.933 mmol) at room temperature. The reaction mixture was allowed to stir at room temperature for 3 days, then quenched with saturated aqueous NH$_4$Cl solution and diluted with EtOAc. The layers were separated and the aqueous phase was extracted with EtOAc (5×). The organic phases were combined, dried over Na$_2$SO$_4$, filtered, and concentrated to afford a yellow residue, which was further dried under high vacuum. The crude material was dissolved in CH$_2$Cl$_2$ and purified by silica gel chromatography using an ISCO machine (12 g column, 30 mL/min, 0-10% MeOH in CH$_2$Cl$_2$ over 25 min, t$_r$=14 min) to afford the title compound (5.1 mg, 0.016 mmol, 3.54% yield) as a white solid.

Example 179

4-Chloro-N-(4-(4-isoquinolinyl)phenyl)benzenesulfonamide

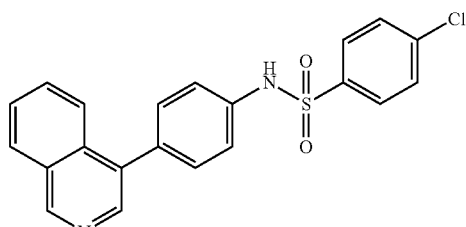

To a solution of Intermediate 10 in CH$_2$Cl$_2$ (3 mL) at 0° C. was add DIEA (0.204 mL, 1.170 mmol) and 4-chlorobenzene-1-sulfonyl chloride (0.054 g, 0.258 mmol). The mixture was slowly warmed to room temperature and stirred overnight. The reaction mixture was then diluted with CH$_2$Cl$_2$ (10 mL), washed with saturated solution of sodium bicarbonate (10 mL) and dried with sodium sulfate. The organics were filtered, concentrated and purified by preparative reverse-phase HPLC. The obtained mixture was washed with sodium bicarbonate, dried and concentrated. The residue was purified by silica gel chromatography (12 g ISCO column, eluting with 0% to 20% acetone in CH$_2$Cl$_2$) to provide Example 179 as a white crystalline solid (0.014 g, 0.035 mmol, 14.99% yield). HPLC Ret time$^a$: 2.357 min. MS (ES): m/z=395.1 [M+H]+. $^1$H NMR (400 MHz, DMSO-d$_6$) δ ppm 7.31-7.40 (m, 2 H) 7.46-7.57 (m, 2 H) 7.71-7.81 (m, 3 H) 7.81-7.87 (m, 2 H) 7.89-7.95 (m, 2 H) 8.27 (d, J=8.03 Hz, 1 H) 8.43 (s, 1 H) 9.38 (s, 1 H) 10.73 (s, 1 H).

Examples 180 to 182

The compounds of Examples 180 to 182 in Table 8 were prepared by the general procedure described for Example 179 using appropriate anilines and sulfonyl halides.

TABLE 8

| Ex. No. | Structure | Name | [M + H]+ | Ret time |
|---|---|---|---|---|
| 180 | 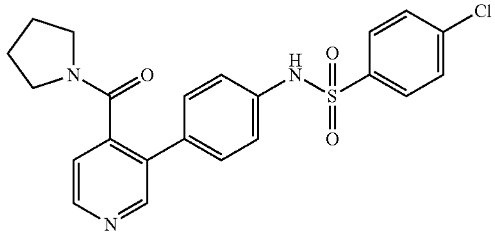 [SMILES: O=C(c1ccncc1-c1ccc(NS(=O)(=O)c2ccc(Cl)cc2)cc1)N1CCCC1] | 4-chloro-N-(4-(4-(1-pyrrolidinylcarbonyl)-3-pyridinyl)phenyl)benzenesulfonamide | 442.0 | 2.317[a] |
| 181 | 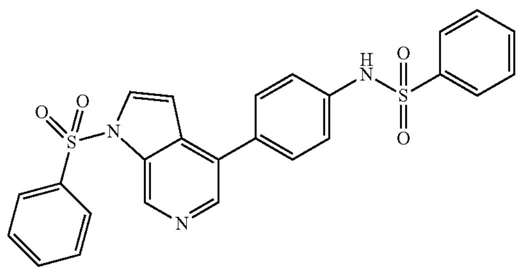 [SMILES: O=S(=O)(Nc1ccc(-c2cncc3c2ccn3S(=O)(=O)c2ccccc2)cc1)c1ccccc1] | N-(4-(1-(phenylsulfonyl)-1H-pyrrolo[2,3-c]pyridin-4-yl)phenyl)benzenesulfonamide | 490.0 | 2.407[a] |
| 182 | 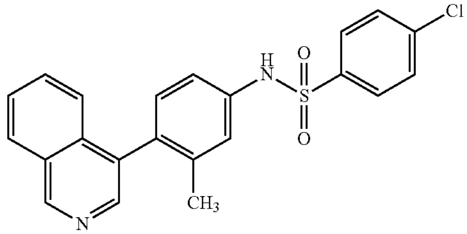 [SMILES: Cc1cc(NS(=O)(=O)c2ccc(Cl)cc2)ccc1-c1cncc2ccccc12] | 4-chloro-N-(4-(4-isoquinolinyl)-3-methylphenyl)benzenesulfonamide | 409.2 | 2.407[a] |

Example 183

N-(4-(4-Methylpyridin-3-yl)-3-(2,2,2-trifluoroethoxy)phenylbenzenesulfonamide

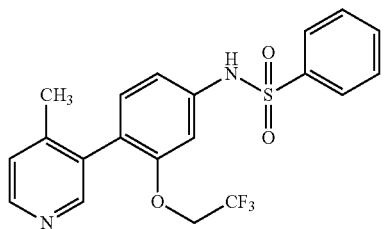 [SMILES: Cc1ccncc1-c1ccc(NS(=O)(=O)c2ccccc2)cc1OCC(F)(F)F]

To a stirred solution of Intermediate 29 (58 mg, 0.205 mmol) in THF (0.87 mL) at 0° C. was added pyridine (0.17 mL, 2.055 mmol) and followed by the addition of benzenesulfonyl chloride (0.031 mL, 0.247 mmol). The reaction mixture was stirred at room temperature overnight and concentrated under reduced pressure. The crude material was purified by Preparative HPLC (PHENOMENEX® Luna 30×100 mm S5 column, eluting with aqueous MeOH containing 0.1% TFA) to provide the TFA salt of Example 183. The salt was dissolved in MeOH and then applied on a 1 g MCX cartridge, which was washed with methanol and eluted with 2M solution of ammonia in methanol (30 mL). The collected eluent was evaporated to provide Example 183 (56 mg, 64.2% yield) as a free base. HPLC Ret time[e]: 3.463 min.

MS (ES): m/z=423.2 [M+H]+. 1H NMR (400 MHz, MeOD) δ ppm 8.65 (d, J=6.04 Hz, 1 H), 8.58 (s, 1 H), 7.97 (d, J=6.04 Hz, 1 H), 7.90-7.83 (m, 2 H), 7.63-7.48 (m, 3 H), 7.18 (d, J=8.31 Hz, 1 H), 7.0-6.93 (m, 2 H), 4.51 (q, J=8.39 Hz, 2 H), 2.39 (s, 3 H).

Example 184

N-(4-(4-Methylpyridin-3-yl)-3-(2,2,2-trifluoroethoxy)phenylcyclopropylsulfonamide

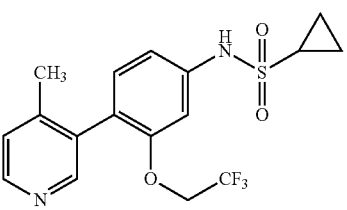 [SMILES: Cc1ccncc1-c1ccc(NS(=O)(=O)C2CC2)cc1OCC(F)(F)F]

The compound of Example 184 was prepared by the procedure described for the preparation of Example 183 using Intermediate 29 and cyclopropylsulfonyl chloride, and was obtained as a pale brown solid (68% yield). HPLC Ret times: 1.933 min. MS (ES): m/z=387.19 [M+H]+. 1H NMR (400 MHz, MeOH) δ ppm 8.68 (d, J=6.04 Hz, 1 H), 8.65 (s, 1 H), 8.01 (d, J=6.04 Hz, 1 H), 7.30 (d, J=8.06 Hz, 1 H), 7.16-7.09

(m, 2 H), 4.59 (q, J=8.48 Hz, 1 H), 2.70 (tt, J=7.93 Hz, 4.78 Hz, 1 H), 2.48 (s, 3 H), 1.15-1.08 (m, 2 H), 1.04-0.97 (m, 2 H).

Example 185

N-(4-(5-Bromo-4-methoxypyridin-3-yl)-3-methylphenyl)methane sulfonamide

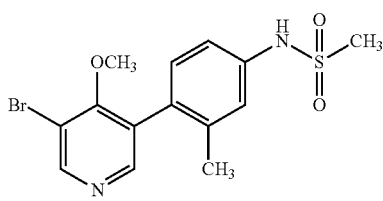 [SMILES: COc1c(Br)cncc1-c1ccc(NS(C)(=O)=O)cc1C]

A pressure vessel charged with a mixture of tetrakis(triphenylphosphine) palladium(0) (21.65 mg, 0.019 mmol), Intermediate 50 (128 mg, 0.412 mmol), sodium carbonate (199 mg, 1.873 mmol), and Intermediate 31 (100 mg, 0.375 mmol) was stirred at room temperature for 10 min under a nitrogen atmosphere. To the above mixture, ethanol (0.5 mL), DME (1 mL), and water (0.5 mL) were sequentially added. The resulting mixture was stirred at room temperature for 30 min, heated at 90° C. for 1 hour, cooled and filtered. The filtrate was concentrated and purified by silica gel chromatography (12 g ISCO column, eluting with 0% to 50% EtOAc in $CH_2Cl_2$) to provide Example 185 (80 mg, 0.213 mmol, 56.9% yield) as a pale yellow solid. HPLC Ret time[a]: 2.943 min. MS (ES): m/z=373.0 [M+H]+. $^1$H NMR (500 MHz, DMSO-$d_6$) δ ppm 2.07 (s, 3 H) 3.04 (s, 3 H) 3.43 (s, 3 H) 7.11-7.14 (m, 1 H) 7.15 (s, 1 H) 7.23 (d, J=8.25 Hz, 1 H) 8.27 (s, 1 H) 8.70 (s, 1 H) 9.88 (s, 1 H).

Examples 186 to 195

The compounds of Examples 186 to 195 in Table 9 were prepared by the procedure described for the preparation of Example 185 using Intermediate 50 and appropriate bromides.

TABLE 9

| Ex. No. | Structure | Name | [M + H]+ | Ret time |
|---|---|---|---|---|
| 186 | 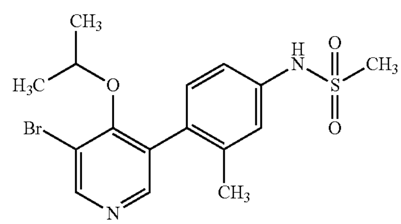 [SMILES: Cc1cc(NS(C)(=O)=O)ccc1-c1cncc(Br)c1OC(C)C] | N-(4-(5-bromo-4-isopropoxy-3-pyridinyl)-3-methylphenyl)methanesulfonamide | 401.0 | 3.560[a] |
| 187 | 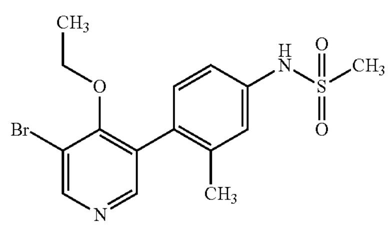 | N-(4-(5-bromo-4-ethoxy-3-pyridinyl)-3-methylphenyl)methanesulfonamide | 387.0 | 3.296[a] |
| 188 | 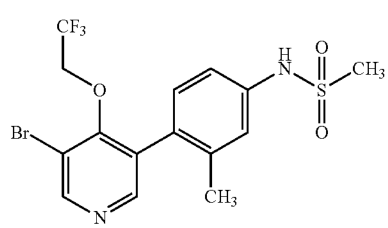 [SMILES: Cc1cc(NS(C)(=O)=O)ccc1-c1cncc(Br)c1OCC(F)(F)F] | N-(4-(5-bromo-4-(2,2,2-trifluoroethoxy)-3-pyridinyl)-3-methylphenyl)methanesulfonamide | 441.0 | 3.610[a] |
| 189 | 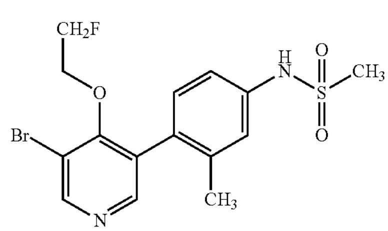 | N-(4-(5-bromo-4-(2-fluoroethoxy)-3-pyridinyl)-3-methylphenyl)methanesulfonamide | 404.9 | 3.026[a] |

TABLE 9-continued

| Ex. No. | Structure | Name | [M + H]+ | Ret time |
|---|---|---|---|---|
| 190 | 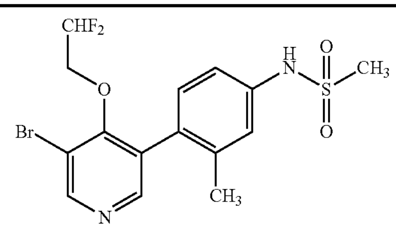 | N-(4-(5-bromo-4-(2,2-difluoroethoxy)-3-pyridinyl)-3-methylphenyl)methanesulfonamide | 422.9 | 3.375[a] |
| 191 | 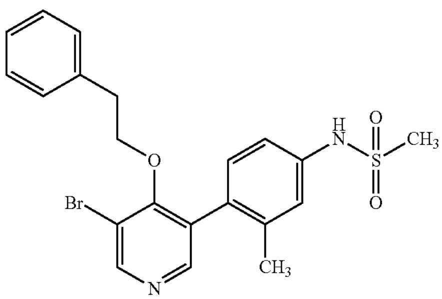 [SMILES: Cc1cc(NS(C)(=O)=O)ccc1-c1cncc(Br)c1OCCc1ccccc1] | N-(4-(5-bromo-4-(2-phenylethoxy)-3-pyridinyl)-3-methylphenyl)methanesulfonamide | 462.9 | 4.021[a] |
| 192 | 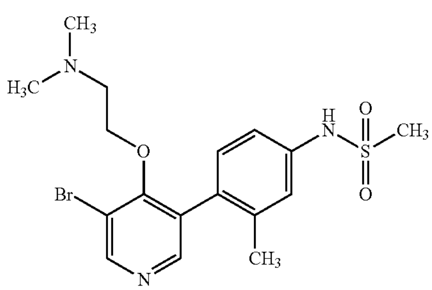 | N-(4-(5-bromo-4-(2-(dimethylamino)ethoxy)-3-pyridinyl)-3-methylphenyl)methanesulfonamide | 429.9 | 1.88[a] |
| 193 | 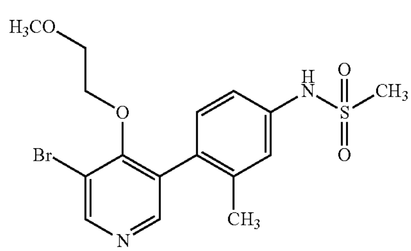 [SMILES: COCCOc1c(Br)cncc1-c1ccc(NS(C)(=O)=O)cc1C] | N-(4-(5-bromo-4-(2-methoxyethoxy)-3-pyridinyl)-3-methylphenyl)methanesulfonamide | 416.9 | 3.075[a] |
| 194 | 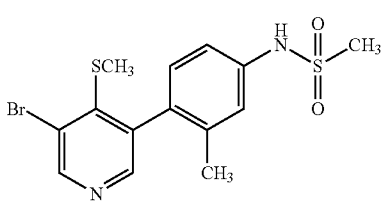 | N-(4-(5-bromo-4-(methylsulfanyl)-3-pyridinyl)-3-methylphenyl)methanesulfonamide | 388.9 | 3.533[a] |
| 195 | 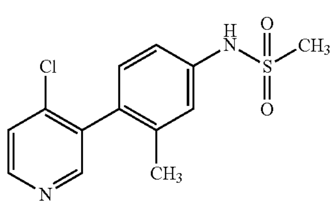 | N-(4-(4-chloro-3-pyridinyl)-3-methylphenyl)methanesulfonamide | 297.0 | 2.492[a] |

Example 196

N-(4-(4-Isopropoxy-3-pyridinyl)-3-methylphenyl)methanesulfonamide

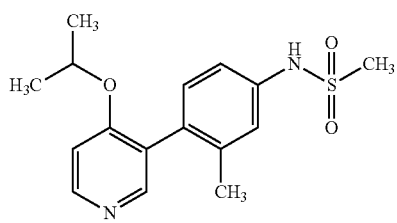 [SMILES: Cc1cc(NS(C)(=O)=O)ccc1-c1cnccc1OC(C)C]

Example 186 (30 mg, 0.075 mmol) was dissolved in MeOH (2 mL), followed by the addition of Pd/C (8.00 mg, 0.075 mmol). The reaction mixture was kept under a hydrogen atmosphere for 6 hours and filtered through a pad of CELITE®. The filtrate was concentrated and purified by silica gel chromatography (12 g ISCO column, eluting with 0% to 100% EtOAc in $CH_2Cl_2$) to provide Example 196 (14 mg, 0.043 mmol, 57.6% yield) as a white solid. HPLC Ret time$^a$: 1.963 min. MS (ES): m/z=321.2 [M+H]$^+$. $^1$H NMR (400 MHz, MeOD) δ ppm 1.30 (s, 6 H) 2.14 (s, 3 H) 3.02 (s, 3 H) 4.66-4.86 (m, 1 H) 6.94-7.34 (m, 4 H) 8.13 (s, 1 H) 8.40 (s, 1 H).

Examples 197 to 204

The compounds of Examples 197 to 204 in Table 10 were prepared by the procedure described for the preparation of Example 196 using the compounds of Examples 187 to 194, respectively.

TABLE 10

| Ex. No. | Structure | Name | [M + H]$^+$ | Ret time |
|---|---|---|---|---|
| 197 | 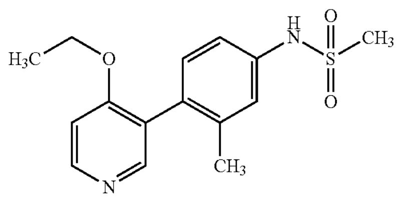 [SMILES: CCOc1ccncc1-c1ccc(NS(C)(=O)=O)cc1C] | N-(4-(4-ethoxy-3-pyridinyl)-3-methylphenyl)methanesulfonamide | 307.2 | 1.740$^a$ |
| 198 | 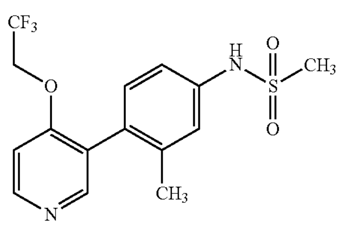 [SMILES: Cc1cc(NS(C)(=O)=O)ccc1-c1cnccc1OCC(F)(F)F] | N-(3-methyl-4-(4-(2,2,2-trifluoroethoxy)-3-pyridinyl)phenyl)methanesulfonamide | 361.1 | 1.943$^a$ |
| 199 | 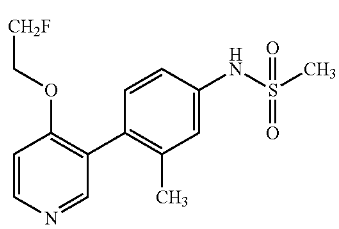 | N-(4-(4-(2-fluoroethoxy)-3-pyridinyl)-3-methylphenyl)methanesulfonamide | 325.0 | 1.513$^a$ |
| 200 | 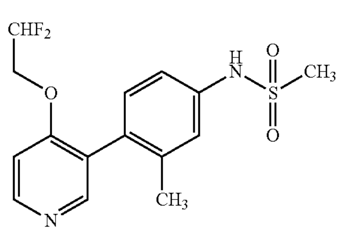 [SMILES: Cc1cc(NS(C)(=O)=O)ccc1-c1cnccc1OCC(F)F] | N-(4-(4-2,2-difluoroethoxy)-3-pyridinyl)-3-methylphenyl)methanesulfonamide | 343.0 | 1.623$^a$ |

TABLE 10-continued

| Ex. No. | Structure | Name | [M + H]+ | Ret time |
|---|---|---|---|---|
| 201 | 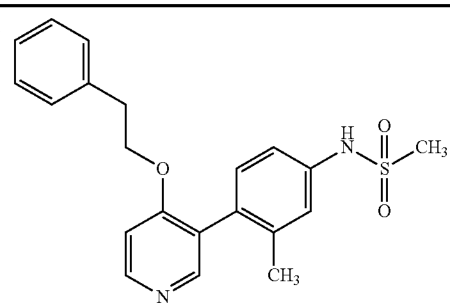 | N-(3-methyl-4-(4-(2-phenylethoxy)-3-pyridinyl)phenyl)methanesulfonamide | 383.0 | 3.587[a] |
| 202 | 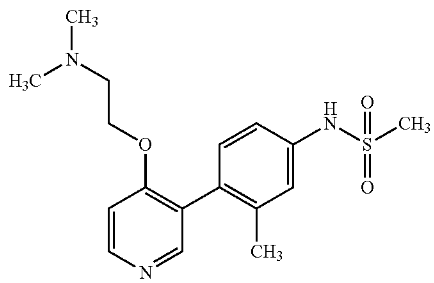 | N-(4-(4-(2-(dimethylamino)ethoxy)-3-pyridinyl)-3-methylphenyl)methanesulfonamide | 350.0 | 0.195[a] |
| 203 | 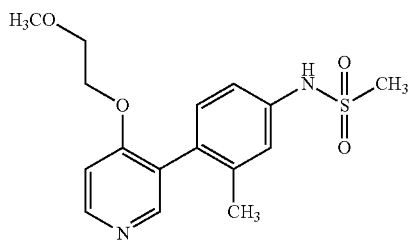 [SMILES: COCCOc1ccncc1-c1ccc(NS(C)(=O)=O)cc1C] | N-(4-(4-(2-methoxyethoxy)-3-pyridinyl)-3-methylphenyl)methanesulfonamide | 337.1 | 1.545[a] |
| 204 | 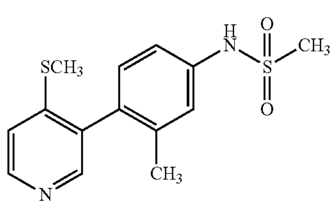 [SMILES: CSc1ccncc1-c1ccc(NS(C)(=O)=O)cc1C] | N-(3-methyl-4-(4-(methylsulfanyl)-3-pyridinyl)phenyl)methanesulfonamide | 309.0 | 1.730[a] |

Example 205

N-(4-(4-Methyl-3-pyridinyl)phenyl)-N'-phenylsulfamide

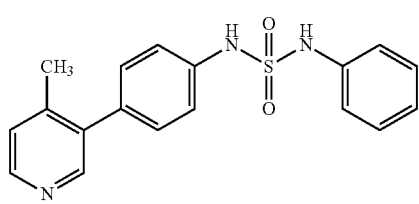 [SMILES: Cc1ccncc1-c1ccc(NS(=O)(=O)Nc2ccccc2)cc1]

To a solution of Intermediate 53 (17 mg, 0.051 mmol) in DCE (2 mL) was added aniline (4.75 mg, 0.051 mmol) and TEA (8.91 μL, 0.051 mmol). The resulting mixture was heated at 80° C. for 1 hour, cooled to room temperature and concentrated. The residue was purified by Prep HPLC to provide Example 205 (9 mg, 0.025 mmol, 49.4% yield) as a white solid. HPLC Ret time[a]: 1.370 min. MS (ES): m/z=340.2 [M+H]+. $^1$H NMR (400 MHz, MeOD) δ ppm 2.52-2.55 (m, 3 H) 7.04 (t, J=7.28 Hz, 1 H) 7.11-7.16 (m, 2 H) 7.22-7.27 (m, 2 H) 7.28-7.33 (m, 2 H) 7.33-7.39 (m, 2 H) 7.91 (d, J=6.02 Hz, 1 H) 8.58-8.66 (m, 2 H).

Examples 206 to 211

The compounds of Examples 206 to 211 in Table 11 were prepared from Intermediate 53 or Intermediate 54 by the procedure described for the preparation of Example 205.

TABLE 11

| Ex. No. | Structure | Name | [M + H]+ | Ret time |
|---|---|---|---|---|
| 206 | 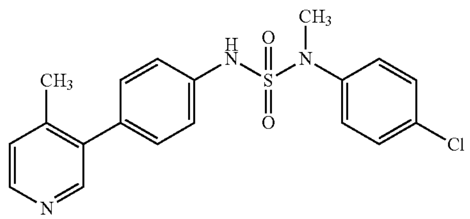 [SMILES: Cc1ccncc1-c1ccc(NS(=O)(=O)N(C)c2ccc(Cl)cc2)cc1] | N-(4-chlorophenyl)-N-methyl-N'-(4-(4-methyl-3-pyridinyl)phenyl)sulfamide | 388.2 | 1.937[a] |
| 207 | 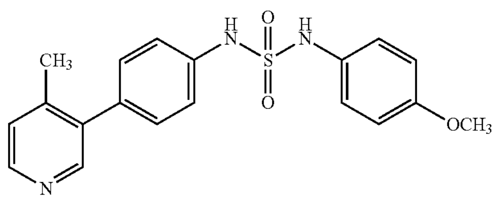 [SMILES: COc1ccc(NS(=O)(=O)Nc2ccc(-c3cnccc3C)cc2)cc1] | N-(4-methoxyphenyl)-N'-(4-(4-methyl-3-pyridinyl)phenyl)sulfamide | 370.1 | 1.383[a] |
| 208 | 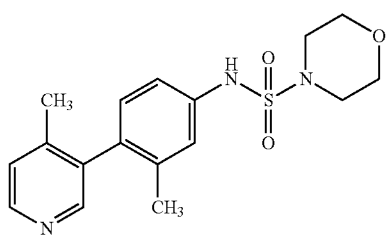 [SMILES: Cc1cc(NS(=O)(=O)N2CCOCC2)ccc1-c1cnccc1C] | N-(3-methyl-4-(4-methyl-3-pyridinyl)phenyl)-4-morpholinesulfonamide | 348.2 | 1.162[a] |
| 209 | 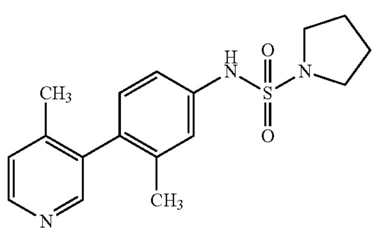 [SMILES: Cc1cc(NS(=O)(=O)N2CCCC2)ccc1-c1cnccc1C] | N-(3-methyl-4-(4-methyl-3-pyridinyl)phenyl)-1-pyrrolidinesulfonamide | 332.2 | 1.363[a] |
| 210 | 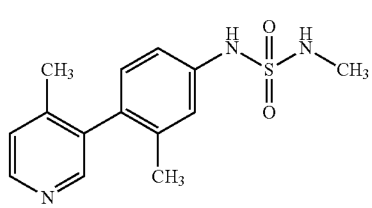 [SMILES: CNS(=O)(=O)Nc1ccc(-c2cnccc2C)c(C)c1] | N-methyl-N'-(3-methyl-4-(4-methyl-3-pyridinyl)phenyl)sulfamide | 292.2 | 0.790[a] |
| 211 | 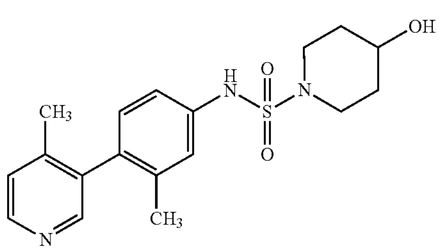 [SMILES: Cc1cc(NS(=O)(=O)N2CCC(O)CC2)ccc1-c1cnccc1C] | 4-hydroxy-N-(3-methyl-4-(4-methylpyridin-3-yl)phenyl)piperidine-1-sulfonamide | 362.3 | 1.087[a] |

Example 212

N-(3-Chloro-4-(4-methoxypyridin-3-yl)phenyl)methanesulfonamide

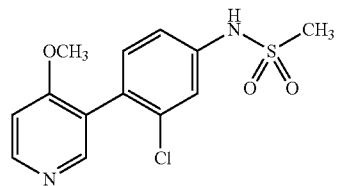 [SMILES: COc1ccncc1-c1ccc(NS(C)(=O)=O)cc1Cl]

The compound of Example 212 was prepared by the procedure described for the preparation of Intermediate 1C using 4-methoxypyridin-3-ylboronic acid, HCl and Intermediate 62. The collected fractions were evaporated to yield the title compound (3.6 mg, 12%). MS (ES): m/z=313.1 [M+H]$^+$.

Example 213

N-(3-Methoxy-4-(4-(2,2,2-trifluoroethoxy)pyridine-3-yl)phenyl)methanesulfonamide

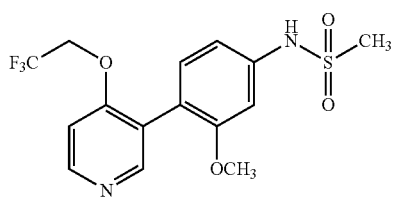 [SMILES: COc1cc(NS(C)(=O)=O)ccc1-c1cnccc1OCC(F)(F)F]

A pressure vessel charged with a mixture of [1,1'-Bis(diphenylphosphino)ferrocine]dichloropalladium(II) complex with dichloromethane (0.011 g, 0.014 mmol), Intermediate 60 (0.035 g, 0.137 mmol), potassium phosphate tribasic (0.087 g, 0.41 mmol) and Intermediate 51 (0.077 g, 0.164 mmol) was stirred at room temperature for 5 min under a nitrogen atmosphere. Then 1,4-dioxane (2.3 mL) and water (0.205 mL) were added and the mixture was degassed for 2 min, and then heated at 85° C. in a microwave oven for 90 min. The resulting mixture was cooled and filtered, and the filtrate was concentrated under reduced pressure. The crude material was taken up in MeOH and purified by preparative HPLC using Waters-Sunfire 30×100 mm S5 column eluting with aqueous acetonitrile containing 0.1% TFA, gradient 5 to 70%, gradient time 12 min. Concentration of the appropriate fractions provided the TFA salt of Example 213. The salt was adsorbed on a 1 g MCX cartridge, followed by elution with 2M solution of ammonia in methanol (30 mL). The evaporation of the solvent under reduced pressure provided Example 213 as a free base (30 mg, 58% yield). MS (ES): m/z=377.0 [M+H]+. $^1$H NMR (400 MHz, MeOD) δ ppm 8.79 (1 H, dd, J=6.78, 1.26 Hz), 8.68 (1 H, d, J=1.25 Hz), 7.79 (1 H, d, J=6.78 Hz), 7.32 (1 H, d, J=8.28 Hz), 6.99-7.07 (2 H, m), 5.03 (2 H, q, J=8.03 Hz), 3.81 (3 H, s), 3.07 (3 H, s).

Example 214

N-(4-(4-Cyclopropylpyrimidin-5-yl-)3-methoxyphenyl)methanesulfonamide

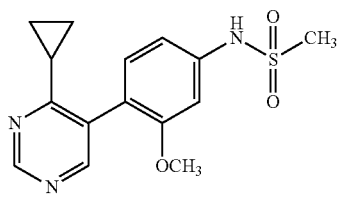 [SMILES: COc1cc(NS(C)(=O)=O)ccc1-c1cncnc1C1CC1]

Example 214 was prepared from Intermediates 51 and 61 by the procedure described for the preparation of Example 213. The collected fractions were evaporated to yield the title compound (15 mg, 37%). MS (ES): m/z=319.99 [M+H]+. $^1$H NMR (400 MHz, MeOD) δ ppm 8.88 (1 H, s), 8.38 (1 H, s), 7.26 (1 H, d, J=7.93 Hz), 7.06 (1 H, d, J=2.14 Hz), 7.00 (1 H, dd, J=8.24, 2.14 Hz), 3.83 (3 H, s), 3.06 (3 H, s), 1.90 (1 H, d, J=4.88 Hz), 1.35 (2 H, br. s.), 1.31 (1 H, br. s.), 1.21 (2 H, br. s.), 1.04 (2 H, br. s.).

Example 215

N-(3-Hydroxy-4-(4-methyl-3-pyridinyl)phenyl)methanesulfonamide

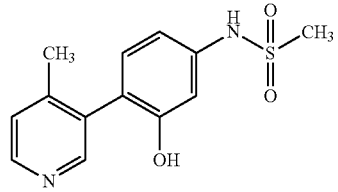

To a solution of Example 17 (20 mg, 0.065 mmol) in CH$_2$Cl$_2$ (1 mL) at −78° C. was added tribromoborane (0.196 mL, 0.196 mmol). After stirring at 78° C. for 1 hour, the reaction mixture was warmed up to 0° C., and additional tribromoborane (0.196 mL, 0.196 mmol) was added. The mixture was stirred at room temperature overnight and concentrated under reduced pressure. The crude product was purified by Prep HPLC (YMC ODS C-18 5u 30×250 mm column; Solvent A 10% MeOH-90% H$_2$O-0.1% TFA; Solvent B 90% MeOH-10% H$_2$O-0.1% TFA; Run time 40 min; Gradient time 30 min) to provide Example 215 (22 mg, TFA salt, 85% yield) as a sticky/white solid. HPLC Ret time[a]: 1.197 min. MS (ES): m/z=279.1 [M+H]$^+$. $^1$H NMR (400 MHz, MeOD) δ ppm 2.47-2.66 (m, 3 H) 2.99-3.10 (m, 3 H) 6.73-6.92 (m, 1 H) 6.97-7.07 (m, 1 H) 7.13-7.26 (m, 1 H) 8.00 (t, J=5.41 Hz, 1 H) 8.55-8.72 (m, 2 H).

Example 216

N-(4-(5-Cyano-4-methoxy-3-pyridinyl)-3-methylphenyl)methane sulfonamide

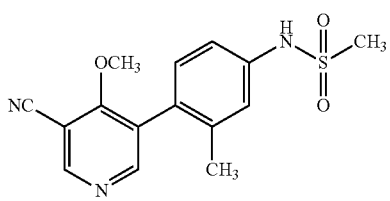 [SMILES: COc1c(C#N)cncc1-c1ccc(NS(C)(=O)=O)cc1C]

To a stirring solution of Example 185 (30 mg, 0.081 mmol) in DMF (1 mL) at room temperature was added copper(I) cyanide (14.47 mg, 0.162 mmol). The reaction mixture was subjected to microwave irradiation at 185° C. for 10 min. The reaction mixture was cooled to room temperature, diluted with water (5 mL) and then extracted with EtOAc (2×10 mL). The combined organics were washed with brine, dried over anhydrous sodium sulfate, and concentrated under reduced pressure. The crude material was purified by Prep HPLC (:YMC ODS C-18 5u 30×250 mm column; Solvent A 10% MeOH-90% $H_2O$-0.1% TFA; Solvent B 90% MeOH-10% $H_2O$-0.1% TFA; Run time 50 min; Gradient time 40 min) to provide Example 216 (5 mg, 0.011 mmol, 14.20% yield) as a white solid. HPLC Ret time[a]: 1.735 min. MS (ES): m/z=318.0 [M+H]+. 1H NMR (400 MHz, MeOD) δ ppm 2.08 (s, 3 H) 2.87 (s, 3 H) 3.74 (s, 3 H) 6.95-7.10 (m, 3 H) 7.63-7.72 (m, 1 H) 8.29-8.36 (m, 1 H).

Example 217

N-(3-Methoxy-4-(4-methyl-3-pyridinyl)phenyl)methanesulfonamide

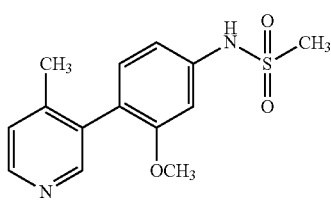 [SMILES: COc1cc(NS(C)(=O)=O)ccc1-c1cnccc1C]

The compound of Example 217 was prepared by the procedure described for the preparation of Intermediate 1C using Intermediate 1A (782 mg, 5.71 mmol) and Intermediate 45 (1 g, 3.57 mmol), and was obtained as a dark brown oil (660 mg, 2.235 mmol, 62.6% yield). HPLC Ret time[a]: 1.585 min. MS (ES): m/z=293.0 [M+H]+. 1H NMR (400 MHz, DMSO-$d_6$) δ ppm 2.10 (s, 3 H) 3.10 (s, 3 H) 3.72 (s, 3 H) 6.91 (dd, J=8.03, 2.01 Hz, 1 H) 6.97 (d, J=2.01 Hz, 1 H) 7.13 (d, J=8.28 Hz, 1 H) 7.29 (d, J=5.02 Hz, 1 H) 8.25 (s, 1 H) 8.40 (d, J=4.77 Hz, 1 H) 9.93 (s, 1 H).

Examples 218 to 222

The compounds of Examples 218 to 222 in Table 12 were prepared by the procedure described for the preparation of Intermediate 1C using Intermediate 51 and corresponding bromides.

TABLE 12

| Ex. No. | Structure | Name | [M + H]+ | Ret time |
|---|---|---|---|---|
| 218 | 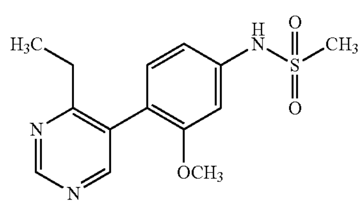 [SMILES: CCc1ncncc1-c1ccc(NS(C)(=O)=O)cc1OC] | N-(4-(4-ethylpyrimidin-5-yl)-3-methoxyphenyl)methanesulfonamide | 308.14 | 1.403[i] |
| 219 | 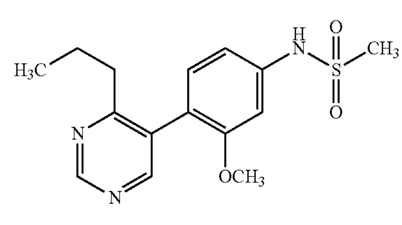 [SMILES: CCCc1ncncc1-c1ccc(NS(C)(=O)=O)cc1OC] | N-(3-methoxy-4-(4-propylpyrimidin-5-yl)phenyl)methanesulfonamide | 322.14 | 1.598[i] |
| 220 | 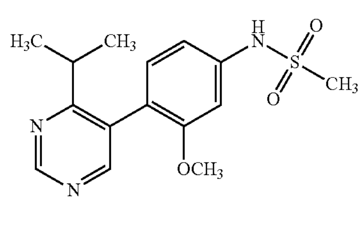 [SMILES: COc1cc(NS(C)(=O)=O)ccc1-c1cncnc1C(C)C] | N-(4-(4-isopropylpyrimidin-5-yl)-3-methoxyphenyl)methanesulfonamide | 322.14 | 1.643[i] |

TABLE 12-continued

| Ex. No. | Structure | Name | [M + H]+ | Ret time |
|---|---|---|---|---|
| 221 | ![structure] | N-(4-(4-cyclohexylpyrimidin-5-yl)-3-methoxyphenyl)methanesulfonamide | 362.17 | 2.058[i] |
| 222 | ![structure] | N-(3-methoxy-4-(1,7-naphthyridin-5-yl)phenyl)methanesulfonamide | 330.08 | 1.368[i] |

Example 223

N-(3-Methoxy-4-(4-(pyrrolidin-1-yl)pyrimidin-5-yl)phenyl)methanesulfonamide

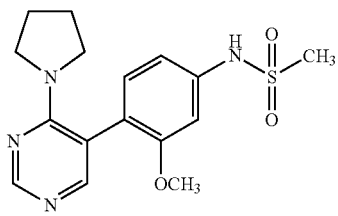 [SMILES: COc1cc(NS(C)(=O)=O)ccc1-c1cncnc1N1CCCC1]

To a stirred solution of 4-chloro-5-iodopyrimidine (30.6 mg, 0.127 mmol) in DME (1 mL) was added cesium carbonate (83 mg, 0.254 mmol) and pyrrolidine (9.04 mg, 0.127 mmol). The reaction mixture was purged with $N_2$ and heated to 90° C. for 12 hours. To this mixture at room temperature was added palladium tetrakis (5.65 mg, 4.89 µmol), Intermediate 51 (32 mg, 0.098 mmol), sodium carbonate (10.37 mg, 0.098 mmol), and additional DME (1.0 mL), EtOH (1.0 mL) and water (1.0 mL). The resulting mixture was purged with $N_2$ and reheated to 90° C. The crude material was purified by preparative HPLC (Column Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient 10-100% B over 25 minutes, then a 5-minute hold at 100% B; Flow rate 20 mL/min) The collected fractions were combined and dried by centrifugal evaporation. The material was further purified by preparative LC/MS Waters XBridge C18, 19×250 mm, 5-µm particles column; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 10-minute hold at 70% B; Flow: 20 mL/min. The collected fractions were evaporated to yield the title compound (3.0 mg, 8.8%). MS (ES): m/z=349.0 [M+H]+. 1H NMR (400 MHz, MeOD) δ ppm 8.35 (1 H, s), 7.79 (1 H, s), 7.16 (1 H, d, J=7.92 Hz), 6.93 (1 H, d, J=1.98 Hz), 6.89 (1 H, dd, J=8.03, 2.09 Hz), 3.77 (3 H, s), 3.19 (4 H, br. s.), 3.02 (3 H, s).

Example 224

N-(3-Methoxy-4-(4-morpholinopyrimidin-5-yl)phenyl)methanesulfonamide

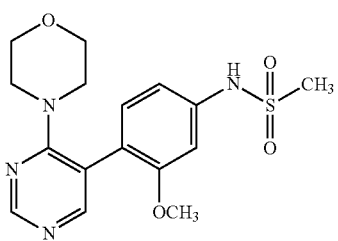 [SMILES: COc1cc(NS(C)(=O)=O)ccc1-c1cncnc1N1CCOCC1]

A pressure vessel charged with a mixture of Pd(Ph₃P)₄ (5.76 mg, 4.98 µmol), Intermediate 51 (32.6 mg, 0.100 mmol), $Na_2CO_3$ (52.8 mg, 0.498 mmol) and Intermediate 44 (29 mg, 0.100 mmol) was stirred at room temperature for 10 min under $N_2$, followed by the addition of ethanol (0.500 mL), DME (1 mL) and water (0.500 mL). The resulting mixture was stirred under $N_2$ for 30 min and then heated at 90° C. for 12 hours. The reaction mixture was cooled to room temperature, diluted with MeOH, filtered and concentrated. The crude material was purified as described for the preparation of Example 223 to provide the title compound (16.4 mg, 45.2%). MS (ES): m/z=364.99 [M+H]+. 1H NMR (400 MHz, MeOD) δ ppm 8.65 (1 H, d, J=1.32 Hz), 8.04 (1 H, d, J=1.32 Hz), 7.28-7.35 (1 H, m), 7.00 (2 H, dq, J=4.32, 2.15 Hz), 3.85 (3 H, s), 3.58-3.79 (6 H, m), 3.05 (2 H, s).

Example 225

N-(4-(4-Cyclopropylpyridin-3-yl)-3-methoxyphenyl)methanesulfonamide

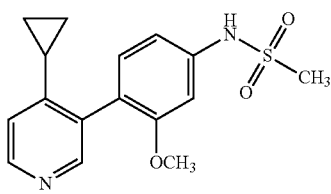 [SMILES: COc1cc(NS(C)(=O)=O)ccc1-c1cnccc1C1CC1]

A pressure vessel charged with a mixture of tetrakis(triphenylphosphine) palladium (0) (0.058 g, 0.050 mmol), Intermediate 43 (0.1 g, 0.505 mmol), potassium phosphate tribasic (0.321 g, 1.515 mmol) and Intermediate 51 (0.215 g, 0.656 mmol) was stirred at room temperature for 5 min under a nitrogen atmosphere followed by the addition of 1,4-dioxane (1.9 mL) and water (0.76 mL). The resulting mixture was degassed for 2 min, then heated at 85° C. in a microwave oven for 4 hours, cooled and filtered. The filtrate was concentrated and purified by preparative HPLC (PHENOMENEX® Luna column eluting with aqueous MeOH containing 0.1% TFA, gradient 10% to 55%, gradient time 12 min) The collected fractions were concentrated to provide the TFA salt of Example 225. The salt was applied on a 1 g MCX cartridge, which was washed with methanol followed by elution with 2M solution of ammonia in methanol (30 mL). The evaporation of the collected eluent under reduced pressure provided Example 225 (26 mg, 16% yield) as a buff powder (free base). HPLC Ret time$^h$ (monitored at 254 nm): 1.18 min. MS (ES): m/z=319.1 [M+H]+. $^1$H NMR (400 MHz, DMSO-D-6) δ ppm 9.90 (s, 1 H), 8.34 (s, 1 H), 8.18 (s, 1 H), 7.17 (s, 1 H), 7.04-6.76 (m, 3 H), 3.70 (s, 3 H), 3.08 (s, 3 H), 1.68-1.51 (m, 1 H), 0.92 (br. s 2 H), 0.75 (br. s, 2 H).

Examples 226 and 227

The compounds of Examples 226 and 227 in Table 13 were prepared by the procedure described for the preparation of Example 225 using Intermediate 51 and corresponding bromides.

TABLE 13

| Ex. No. | Structure | Name | [M + H]+ | Ret time |
|---|---|---|---|---|
| 226 | 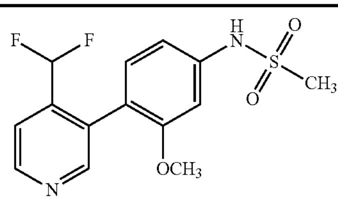 | N-(4-(4-(difluoromethyl)pyridin-3-yl)-3-methoxyphenyl)methanesulfonamide | 329.17 | 1.87$^g$ |
| 227 | 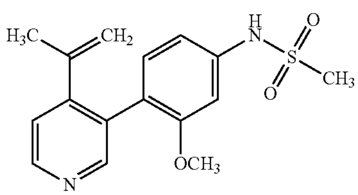 [SMILES: C=C(C)c1ccncc1-c1ccc(NS(C)(=O)=O)cc1OC] | N-(3-methoxy-4-(4-(prop-1-en-2-yl)pyridin-3-yl)phenyl)methanesulfonamide | 319.17 | 1.24$^h$ |

Examples 228 to 231

The compounds of Examples 228 to 231 in Table 14 were prepared by the procedure described for the preparation of Example 225 using Intermediate 46 and corresponding boronic acids.

TABLE 14

| Ex. No. | Structure | Name | [M + H]+ | Ret time |
|---|---|---|---|---|
| 228 | 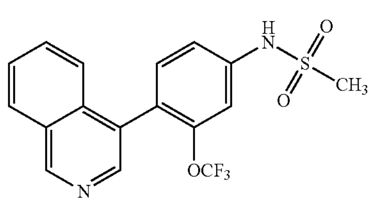 [SMILES: CS(=O)(=O)Nc1ccc(-c2cncc3ccccc23)c(OC(F)(F)F)c1] | N-(4-isoquinolin-4-yl)-3-(trifluoromethoxy)phenyl)methanesulfonamide | 383.19 | 2.17$^g$ |

TABLE 14-continued

| Ex. No. | Structure | Name | [M + H]⁺ | Ret time |
|---|---|---|---|---|
| 229 | 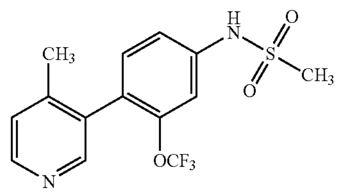 [SMILES: Cc1ccncc1-c1ccc(NS(C)(=O)=O)cc1OC(F)(F)F] | N-(4-(4-methylpyridin-3-yl)-3-(trifluoromethoxy)phenyl)methanesulfonamide | 347.2 | 1.80$^g$ |
| 230 | 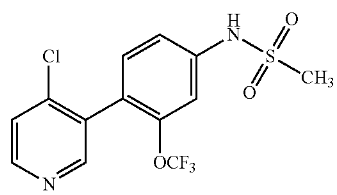 [SMILES: CS(=O)(=O)Nc1ccc(-c2cnccc2Cl)c(OC(F)(F)F)c1] | N-(4-(4-chloropyridin-3-yl)-3-(trifluoromethoxy)phenyl)methanesulfonamide | 367.09 | 2.52$^g$ |
| 231 | 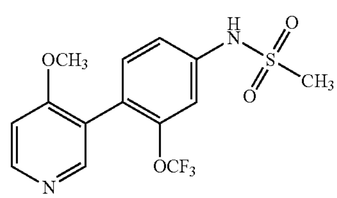 [SMILES: COc1ccncc1-c1ccc(NS(C)(=O)=O)cc1OC(F)(F)F] | N-(4-(4-methoxypyridin-3-yl)-3-(trifluoromethoxy)phenyl)methanesulfonamide | 363.16 | 1.75$^g$ |

Examples 232 and 233

The compounds of Examples 232 and 233 in Table 15 were prepared by the procedure described for the preparation of Example 225 using Intermediate 47 and corresponding boronic acids.

Examples 234 to 236

The compounds of Examples 234 to 236 in Table 16 were prepared by the procedure described for the preparation of Intermediate 1C using Intermediate 48 and corresponding boronic acids.

TABLE 15

| Ex. No. | Structure | Name | [M + H]⁺ | Ret time |
|---|---|---|---|---|
| 232 | 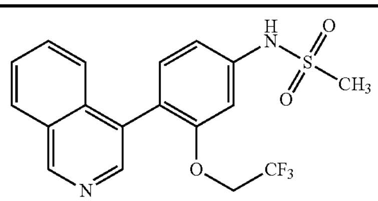 | N-(4-(isoquinolin-4-yl)-3-(2,2,2-trifluoroethoxy)phenyl)methanesulfonamide | 397.21 | 2.047$^g$ |
| 233 | 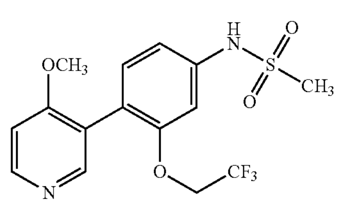 [SMILES: COc1ccncc1-c1ccc(NS(C)(=O)=O)cc1OCC(F)(F)F] | N-(4-(4-methoxypyridin-3-yl)-3-(2,2,2-trifluoroethoxy)phenyl)methanesulfonamide | 377.18 | 1.642$^g$ |

TABLE 16

| Ex. No. | Structure | Name | [M + H]+ | Ret time |
|---|---|---|---|---|
| 234 | 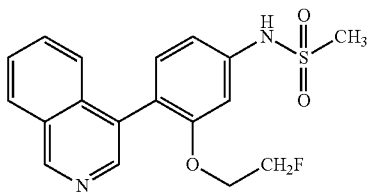 | N-(3-(2-fluoroethoxy)-4-(isoquinolin-4-yl)phenyl)methanesulfonamide | 360.90 | 1.810$^i$ |
| 235 | 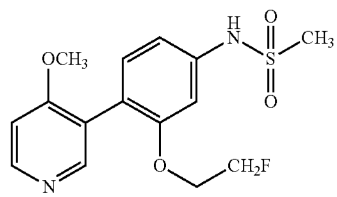 | N-(3-(2-fluoroethoxy)-4-(4-methoxypyridin-3-yl)phenyl)methanesulfonamide | 341.00 | 1.402$^i$ |
| 236 | 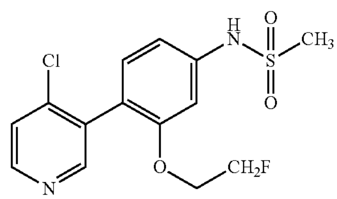 | N-(4-(4-chloropyridin-3-yl)-3-(2-fluoroethoxy)phenyl)methanesulfonamide | 345.00 | 1.680$^i$ |

Examples 237 to 239

The compounds of Examples 237 to 239 in Table 17 were prepared by the procedure described for Intermediate 1C using Intermediate 49 and corresponding bromides.

TABLE 17

| Ex. No. | Structure | Name | [M + H]+ | Ret time |
|---|---|---|---|---|
| 237 | 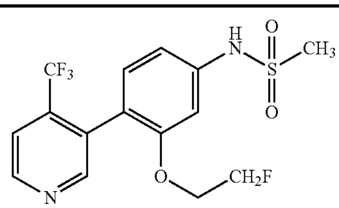 | N-(3-(2-fluoroethoxy)-4-(4-(trifluoromethyl)pyridin-3-yl)phenyl)methanesulfonamide | 379.00 | 1.865$^i$ |
| 238 | 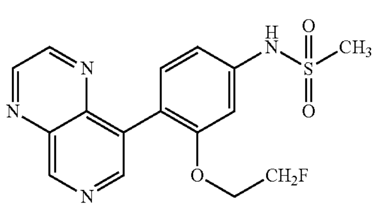 | N-(3-(2-fluoroethoxy)-4-(pyrido[4,3-b]pyrazin-8-yl)phenyl)methanesulfonamide | 363.06 | 1.287$^i$ |
| 239 | 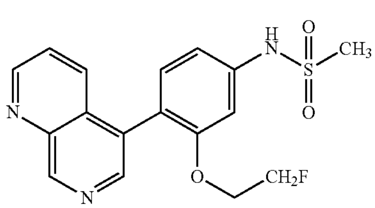 | N-(3-(2-fluoroethoxy)-4-(1,7-naphthyridin-5-yl)phenyl)methanesulfonamide | 362.12 | 1.398$^i$ |

Example 240

N-(4-(4-Methylpyridin-3-yl)-3-(trifluoromethyl)phenyl)methanesulfonamide

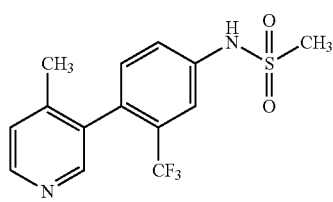 [SMILES: Cc1ccncc1-c1ccc(NS(C)(=O)=O)cc1C(F)(F)F]

The compound of Example 240 was prepared by the procedure described for the preparation of Intermediate 1C using Intermediate 52 and 3-bromo-4-methylpyridine. The crude material was purified by reverse phase preparative HPLC using a PHENOMENEX® Luna 30×100 mm column with a linear gradient of Solvent A (10% methanol/90% water with 0.1% TFA) and Solvent B (90% methanol/10% water with 0.1% TFA) over 12 min with peak detection at 254 nM. Collected fractions were applied to a 1 g Waters OASIS® MCX cation exchange cartridge, which was washed with methanol and 2 M ammonia in methanol, to provide the title compound (43 mg, 58%) as a solid: HPLC Ret time[d]: 1.21 min. MS: m/z=331 [M+H]+; $^1$H NMR (400 MHz, CD$_3$OD) δ ppm 8.42 (1 H, d, J=5.0 Hz), 8.24 (1 H, s), 7.70 (1 H, s), 7.60 (1 H, d, J=8.3 Hz), 7.24-7.49 (2 H, m), 3.09 (3 H, s), 2.12 (3 H, s); $^{19}$F NMR (CD$_3$OD) δ ppm 60.8.

Examples 241 to 243

The compounds of Examples 241 to 243 in Table 18 were prepared by the procedure described for the preparation of Example 240 using Intermediate 52 and corresponding bromides.

TABLE 18

| Ex. No. | Structure | Name | [M + H]+ | Ret time |
|---|---|---|---|---|
| 241 | 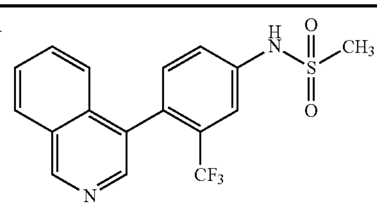 | N-(4-(isoquinolin-4-yl)-3-(trifluoromethyl)phenyl)methanesulfonamide | 367 | 1.50[d] |
| 242 | 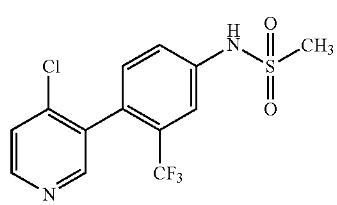 [SMILES: CS(=O)(=O)Nc1ccc(-c2cnccc2Cl)c(C(F)(F)F)c1] | N-(4-(4-chloropyridin-3-yl)-3-(trifluoromethyl)phenyl)methanesulfonamide | 351 | 1.83[d] |
| 243 | 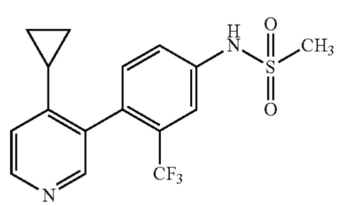 [SMILES: CS(=O)(=O)Nc1ccc(-c2cnccc2C2CC2)c(C(F)(F)F)c1] | N-(4-(4-cyclopropylpyridin-3-yl)-3-(trifluoromethyl)phenyl)methanesulfonamide | 357 | 1.43[d] |

Example 244

N-(4-(4-Isopropylpyridin-3-yl)-3-)methoxyphenyl)methanesulfonamide

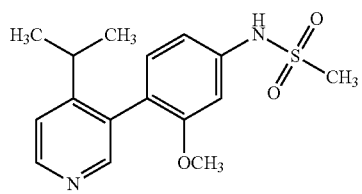 [SMILES: COc1cc(NS(C)(=O)=O)ccc1-c1cnccc1C(C)C]

To a mixture of Example 227 (63 mg, 0.198 mmol) and trifluoroacetic acid (0.015 mL, 0.198 mmol) in MeOH (1.5 mL) was added Pd/C (21 mg, 0.02 mmol). The resulting mixture was kept under a hydrogen atmosphere for 16 hours and then filtered through a pad of CELITE®. The filtrate was concentrated, basified with a saturated aqueous sodium bicarbonate solution and extracted with $CH_2Cl_2$ (2×4 mL). The combined organics were washed with brine, dried over anhydrous sodium sulfate and concentrated under reduced pressure to provide Example 244 (63 mg, 97% yield) as a colorless film. MS (ES): m/z=321.19 [M+H]$^+$. $^1$H NMR (400 MHz, MeOD) δ ppm 8.43 (d, J=5.49, 1 H), 8.17 (s, 1 H), 7.44 (d, J=5.49, 1 H), 7.11 (d, J=7.93, 1 H), 7.02 (d, J=1.83 Hz, 1 H), 6.96 (dd, J=8.09, 1.98 Hz, 1 H), 3.76 (s, 3 H), 3.06 (s, 3 H), 2.83 (dt, J=13.73 Hz, 6.87 Hz, 1 H), 1.23 (d, J=6.71 Hz, 3 H), 1.09 (d, J=6.71 Hz, 3 H).

Example 245

N-(3-Methoxy-4-(4-methoxypyrimidin-5-yl)methanesulfonamide

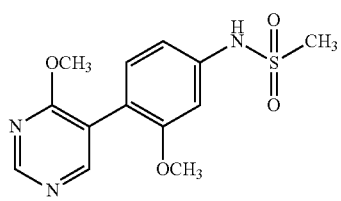 [SMILES: COc1cc(NS(C)(=O)=O)ccc1-c1cncnc1OC]

A solution of Intermediate 30 (20 mg, 0.086 mmol) and DIEA (0.023 mL, 0.13 mmol) in $CH_2Cl_2$ (1.0 mL) was treated with methanesulfonyl chloride (0.0087 mL, 0.112 mmol), and the resulting mixture was stirred at room temperature for 4 hours. The mixture was then evaporated, and the residue was suspended in DMF (1 mL) and treated with 3 M aqueous sodium hydroxide (0.2 mL). After stirring at room temperature for 30 min, the reaction mixture was acidified with TFA (0.3 mL) and purified by reverse phase preparative HPLC using a PHENOMENEX® Luna 30×100 mm column with a linear gradient of Solvent A (10% methanol/90% water with 0.1% TFA) and Solvent B (90% methanol/10% water with 0.1% TFA) over 12 min with peak detection at 254 nM. The collected fractions were then applied to a 1 g Waters OASIS® MCX cation exchange cartridge, which was washed with methanol and 2 M ammonia in methanol, to give the title compound (15 mg, 53%) as a solid. HPLC Ret time$^a$: 0.88 min. MS: m/z=310 [M+H]$^+$; $^1$H NMR (500 MHz, DMSO-$d_6$) δ ppm 9.83 (brs, 1 H), 8.44 (1 H, s), 7.87 (1 H, s), 7.21 (1 H, d, J=8.24 Hz), 6.91 (1 H, d, J=2.14 Hz), 6.84 (1 H, dd, J=8.24, 2.14 Hz), 3.70 (3 H, s), 3.45 (3 H, s), 3.05 (3 H, s).

Example 246

N-(3,5-Dimethyl-4-(4-methyl-3-pyridinyl)phenyl)methanesulfonamide

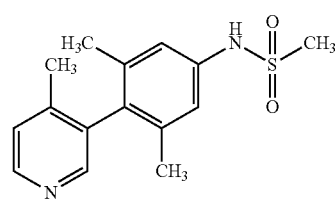 [SMILES: Cc1ccncc1-c1c(C)cc(NS(C)(=O)=O)cc1C]

The compound of Example 246 was prepared from Intermediate 1A and Intermediate 64, and was obtained as a white solid (6% yield). HPLC Ret time$^a$: 1.422 min. MS (ES): m/z=291.1 [M+H]$^+$. $^1$H NMR (500 MHz, Solvent) δ ppm 1.92 (s, 6 H) 2.05 (s, 3 H) 3.00 (s, 3 H) 7.07 (s, 2 H) 7.41 (d, J=5.22 Hz, 1 H) 8.12 (s, 1 H) 8.41 (d, J=5.22 Hz, 1 H).

Example 247

N-(3-Methoxy-4-(4-(2,2,2-trifluoroethoxy)-5-pyrimidinyl)phenyl)methanesulfonamide

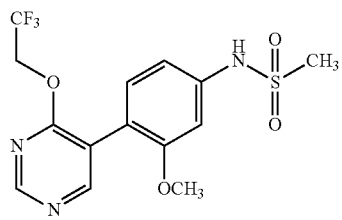 [SMILES: COc1cc(NS(C)(=O)=O)ccc1-c1cncnc1OCC(F)(F)F]

Prepared and purified according to the procedure described for Example 224 using Intermediates 51 and 55. The collected fractions were evaporated to yield the title compound (23.5 mg, 65.7%). MS (ES): m/z=378.02 [M+H]$^+$. $^1$H NMR (500 MHz, MeOD) δ ppm 8.70 (1 H, s), 8.43 (1 H, s), 7.19 (1 H, d, J=8.05 Hz), 6.95 (1 H, d, J=1.94 Hz), 6.89 (1 H, dd, J=8.18, 2.08 Hz), 4.88 (1 H, q, J=8.32 Hz), 4.18 (2 H, d, J=10.54 Hz), 3.76 (2 H, s), 3.03 (3 H, s).

Example 248

N-(3-Methoxy-4-(4-(2,2,2-trifluoroethylamino)pyrimidin-5-yl)phenyl)methanesulfonamide

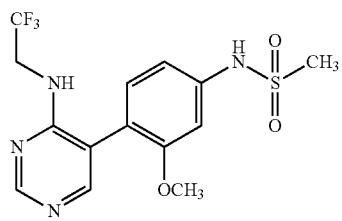 [SMILES: COc1cc(NS(C)(=O)=O)ccc1-c1cncnc1NCC(F)(F)F]

The compound of Example 248 was prepared by the procedure described for the preparation of Example 224 using Intermediates 51 and 56. The collected fractions were evaporated to yield the title compound (4.6 mg, 12.0%). MS (ES): m/z=377.09 [M+H]$^+$. $^1$H NMR (400 MHz, MeOD) δ ppm 8.63 (1 H, s), 7.99 (1 H, s), 7.57 (1 H, s), 7.18 (1 H, d, J=8.36 Hz), 7.00 (1 H, d, J=1.98 Hz), 6.94 (1 H, dd, J=8.14, 1.98 Hz), 3.79 (2 H, s), 3.05 (2 H, s), 2.80-3.01 (1 H, m).

Example 249

N-(4-(4-Ethoxy-5-pyrimidinyl)-3-methoxyphenyl)methanesulfonamide

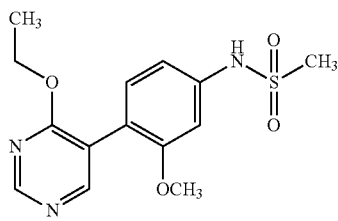 [SMILES: CCOc1ncncc1-c1ccc(NS(C)(=O)=O)cc1OC]

The compound of Example 249 was prepared by the procedure described for the preparation of Example 224 using Intermediates 51 and 57. The collected fractions were evaporated to yield the title compound (4.6 mg, 12.0%). MS (ES): m/z=324.02 [M+H]$^+$. $^1$H NMR (400 MHz, MeOD) δ ppm 8.62 (1 H, s), 8.29 (1 H, s), 7.56 (1 H, s), 7.18 (1 H, d, J=8.28 Hz), 6.94 (1 H, d, J=1.76 Hz), 6.87 (1 H, dd, J=8.16, 1.88 Hz), 4.45 (2 H, q, J=7.19 Hz), 3.77 (3 H, s), 3.02 (3 H, s), 1.26-1.40 (3 H, m).

Example 250

N-(3-Methoxy-4-(pyrrolo[1,2-c]pyrimidin-4-yl)phenyl)methanesulfonamide

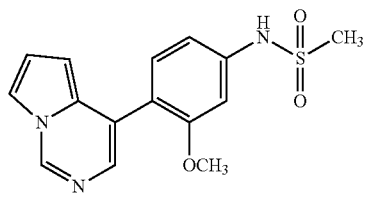 [SMILES: COc1cc(NS(C)(=O)=O)ccc1-c1cncn2cccc12]

The compound of Example 250 was prepared by the procedure described for the preparation of Example 224 using Intermediates 51 and 58. The collected fractions were evaporated to yield the title compound (5.9 mg, 19.0%). MS (ES): m/z=318.07 [M+H]$^+$. $^1$H NMR (500 MHz, MeOD) δ ppm 8.84 (1 H, s), 7.56 (2 H, s), 7.51 (1 H, dd, J=2.77, 1.11 Hz), 7.36 (1 H, d, J=8.05 Hz), 7.00 (1 H, d, J=2.22 Hz), 6.90 (1 H, dd, J=8.18, 2.08 Hz), 6.82-6.88 (1 H, m), 6.27 (1 H, d, J=3.88 Hz), 3.77 (3 H, s), 3.04 (3 H, s).

Example 251

N-(4-(Imidazo[1,2-a]pyrazin-5-yl)-3-methoxyphenyl)methanesulfonamide

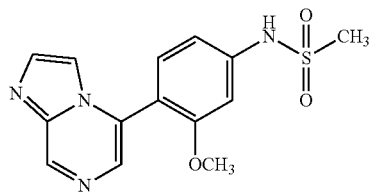 [SMILES: COc1cc(NS(C)(=O)=O)ccc1-c1cncc2nccn12]

The compound of Example 251 was prepared by the procedure described for the preparation of Example 224 using Intermediates 51 and 59. The collected fractions were evaporated to yield the title compound (4.5 mg, 14.2%). MS (ES): m/z=319.03 [M+H]$^+$. $^1$H NMR (500 MHz, MeOD) δ ppm 8.98 (1 H, s), 7.73-7.81 (2 H, m), 7.48 (1 H, s), 7.37 (1 H, d, J=8.05 Hz), 7.07 (1 H, d, J=1.94 Hz), 6.99 (1 H, dd, J=8.32, 1.94 Hz), 3.78 (3 H, s), 3.08 (3 H, s).

Example 252

N-(4-(4-Cyanopyridin-3-yl)-3-methoxyphenyl)methanesulfonamide

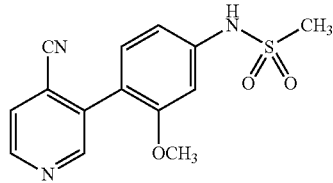 [SMILES: COc1cc(NS(C)(=O)=O)ccc1-c1cnccc1C#N]

The compound of Example 252 was prepared by the procedure described for the preparation of Example 224 using Intermediate 51 and 3-bromoisonicotinonitrile. The collected fractions were evaporated to yield the title compound (11.5 mg, 56%). MS (ES): m/z=304.0 (M+H)$^+$.

Example 253

N-(4-(4-(Hydroxymethyl)pyridin-3-yl)-3-methoxyphenyl)methanesulfonamide

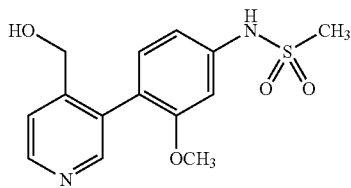 [SMILES: COc1cc(NS(C)(=O)=O)ccc1-c1cnccc1CO]

Intermediate 63 (1.532 g, 5.0 mmol) was dissolved in MeOH (10.0 mL) and THF (50 mL) followed by addition of NaBH$_4$ (0.378 g, 10.00 mmol) at room temperature. After 20 minutes, the reaction was quenched carefully with 1N HCl until pH=1. MeOH and THF were removed. The crude material was diluted with water (10 mL) and extracted with EtOAc (2×). The aqueous layer was neutralized with solid NaHCO₃ and extracted with 10% iPrOH in DCM (3×). The organics were combined, dried over Na₂SO₄, and filtered. Concentration gave the crude product as a yellow solid. The crude material was purified by flash chromatography on silica using an ISCO machine (40 g column, 0 to 15% methanol in CH₂Cl₂ over 25 minutes) to give the title compound (1.06 g, 3.30 mmol, 66.0% yield) as a white solid. HPLC Ret time$^a$: 0.607 min, MS (ES): m/z=309.2 [M+H]⁺.

Example 254

N-(3-Methoxy-4-(4-(methoxymethyl)pyridin-3-yl)phenyl)methanesulfonamide

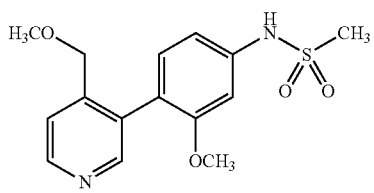 [SMILES: COCc1ccncc1-c1ccc(NS(C)(=O)=O)cc1OC]

Example 254 was prepared from Intermediates 51 and 65 by the procedure described for the preparation of Example 213. HPLC Ret. time$^e$: 1.83 min. MS (ES): m/z=323.09 [M+H]⁺. ¹H NMR (400 MHz, MeOD) δ ppm 8.81 (1 H, d, J=6.78 Hz), 8.67 (1 H, s), 8.24 (1 H, d, J=6.02 Hz), 7.27 (1 H, d, J=8.28 Hz), 6.98-7.12 (2 H, m), 4.53 (2 H, s), 3.83 (3 H, s), 3.45 (3 H, s), 3.10 (3 H, s).

Example 255

N-(4-(4-(Cyclopropylmethoxy)pyridin-3-yl)-3-methoxyphenyl)methanesulfonamide

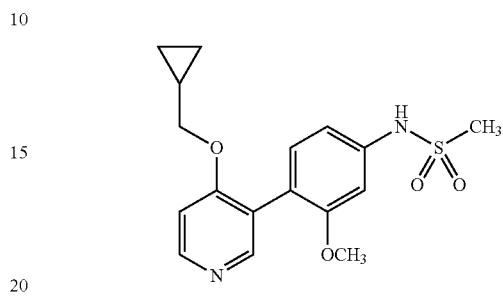

Example 255 was prepared from Intermediates 51 and 66 by the procedure described for the preparation of Example 213. HPLC Ret. time$^e$: 2.42 min. MS (ES): m/z=349.16 [M+H]⁺. ¹H NMR (400 MHz, MeOD) δ ppm 8.65 (1 H, dd, J=6.90, 1.38 Hz), 8.54 (1 H, d, J=1.25 Hz), 7.64 (1 H, d, J=7.03 Hz), 7.32 (1 H, d, J=8.03 Hz), 7.05 (1 H, d, J=2.01 Hz), 6.98 (1 H, dd, J=8.16, 2.13 Hz), 4.25 (2 H, d, J=7.03 Hz), 3.84 (3 H, s), 3.07 (3 H, s), 1.27 (1 H, d, J=6.78 Hz), 0.56-0.74 (2 H, m), 0.31-0.49 (2 H, m).

TABLE 19

Additional NMR Data for Intermediates

| Intermediate No. | NMR Data |
|---|---|
| 4 | ¹H NMR (400 MHz, MeOD) δ ppm 2.18 (s, 3 H) 3.61-3.75 (m, 3 H) 6.34-6.45 (m, 1 H) 6.48 (s, 1 H) 6.75-6.90 (m, 1 H) 7.27 (d, J = 4.78 Hz, 1 H) 8.18 (s, 1 H) 8.27 (d, J = 5.04 Hz, 1 H) |
| 5 | ¹H NMR (400 MHz, DMSO-d₆) δ ppm 2.27 (s, 3 H) 5.26 (s, 2 H) 6.65 (d, 2 H) 7.05 (d, J = 8.31 Hz, 2 H) 7.25 (d, J = 5.04 Hz, 1 H) 8.30 (s, 1 H) 8.32 (d, J = 5.04 Hz, 1 H) |
| 18 | ¹H NMR (400 MHz, DMSO-d₆) δ ppm 2.12 (s, 3 H) 4.58 (q, J = 9.03 Hz, 2 H) 5.36 (s, 2 H) 6.35 (dd, J = 8.03, 2.01 Hz, 1 H) 6.38 (d, J = 2.01 Hz, 1 H) 6.85 (d, J = 8.03 Hz, 1 H) 7.25 (d, J = 5.02 Hz, 1 H) 8.21 (s, 1 H) 8.34 (d, J = 5.02 Hz, 1 H) |
| 32 | ¹H NMR (400 MHz, DMSO-d₆) δ ppm 1.35 (d, J = 6.30 Hz, 6 H) 4.78-4.91 (m, 1 H) 8.71 (s, 2 H) |
| 33 | ¹H NMR (400 MHz, DMSO-d₆) δ ppm 1.41 (t, J = 6.92 Hz, 3 H) 4.19 (q, J = 7.05 Hz, 2 H) 8.72 (s, 2 H) |
| 34 | ¹H NMR (400 MHz, DMSO-d₆) δ ppm 4.90 (q, J = 8.65 Hz, 2 H) 8.78 (s, 2 H) |

TABLE 20

Additional NMR Data for Examples

| Ex. No. | NMR Data |
|---|---|
| 2 | ¹H NMR (400 MHz, MeOD) δ ppm 1.99 (s, 3 H) 2.90 (s, 3 H) 3.78 (s, 3 H) 7.00 (d, 1 H) 7.03-7.06 (m, 1 H) 7.07 (s, 2 H) 8.03 (s, 1 H) 8.34 (d, J = 5.79 Hz, 1 H) |
| 3 | ¹H NMR (400 MHz, MeOD) δ ppm 2.27 (s, 3 H) 7.24 (s, 4 H) 7.34 (d, J = 4.78 Hz, 1 H) 7.50-7.57 (m, 2 H) 7.76-7.85 (m, 2 H) 8.31 (d, J = 34.50 Hz, 2 H) |
| 4 | ¹H NMR (400 MHz, DMSO-d₆) δ ppm 2.21 (s, 3 H) 7.18 (s, 1 H) 7.20 (s, 1 H) 7.28-7.32 (m, 2 H) 7.33 (s, 1 H) 7.74 (dd, J = 8.44, 2.14 Hz, 1 H) 7.88 (d, J = 8.56 Hz, 1 H) 7.95 (d, J = 2.27 Hz, 1 H) 8.30 (s, 1 H) 8.40 (d, J = 4.78 Hz, 1 H) |
| 5 | ¹H NMR (400 MHz, DMSO-d₆) δ ppm 1.91 (s, 3 H) 1.97 (s, 3 H) 7.00 (s, 2 H) 7.05 (s, 1 H) 7.31 (d, J = 5.04 Hz, 1 H) 7.63-7.69 (m, 2 H) 7.77-7.85 (m, 2 H) 8.18 (s, 1 H) 8.41 (d, J = 5.04 Hz, 1 H) 10.48 (s, 1 H) |

TABLE 20-continued

Additional NMR Data for Examples

| Ex. No. | NMR Data |
|---|---|
| 6 | $^1$H NMR (500 MHz, Solvent) δ ppm 0.86 (s, 3 H) 1.08 (s, 3 H) 1.40-1.53 (m, 1 H) 1.67-1.78 (m, 1 H) 1.94 (d, J = 18.70 Hz, 1 H) 2.05 (s, 3 H) 2.06-2.12 (m, 2 H) 2.13 (s, 3 H) 2.34-2.50 (m, 2 H) 3.08 (d, J = 15.12 Hz, 1 H) 3.56 (d, J = 14.85 Hz, 1 H) 7.08 (d, J = 8.25 Hz, 1 H) 7.22 (d, J = 7.97 Hz, 1 H) 7.27 (s, 1 H) 7.38 (d, J = 5.22 Hz, 1 H) 8.21 (s, 1 H) 8.38 (d, J = 4.95 Hz, 1 H) |
| 7 | $^1$H NMR (400 MHz, DMSO-d$_6$) δ ppm 1.97 (s, 3 H) 3.79 (s, 3 H) 6.95-7.05 (m, 3 H) 7.16 (d, J = 5.54 Hz, 1 H) 7.67 (s, 1 H) 7.70 (s, 1 H) 7.83 (s, 1 H) 7.85 (s, 1 H) 8.14 (s, 1 H) 8.48 (d, J = 5.29 Hz, 1 H) 10.51 (s, 1 H) |
| 8 | $^1$H NMR (400 MHz, DMSO-d$_6$) δ ppm 6.96-7.13 (m, 6 H) 7.24-7.39 (m, 3 H) 7.52 (d, J = 5.29 Hz, 1 H) 7.62-7.68 (m, 2 H) 7.69-7.75 (m, 2 H) 8.59 (s, 1 H) 8.65 (d, J = 5.29 Hz, 1 H) 10.45 (s, 1 H) |
| 9 | $^1$H NMR (400 MHz, DMSO-d$_6$) δ ppm 4.47 (s, 2 H) 7.10 (d, J = 2.01 Hz, 4 H) 7.18-7.25 (m, 4 H) 7.32-7.37 (m, 6 H) 7.43 (d, 1 H) 8.60 (s, 1 H) 8.62 (d, J = 5.04 Hz, 1 H) 9.91 (s, 1 H) |
| 10 | $^1$H NMR (400 MHz, DMSO-d$_6$) δ ppm 1.79 (s, 3 H) 4.47 (s, 2 H) 6.91 (d, J = 1.76 Hz, 1 H) 7.02 (dd, J = 8.31, 2.27 Hz, 1 H) 7.13 (d, J = 8.31 Hz, 1 H) 7.18-7.25 (m, 4 H) 7.29-7.34 (m, 6 H) 7.70 (d, J = 5.29 Hz, 1 H) 8.61 (s, 1 H) 8.76 (d, J = 5.29 Hz, 1 H) 9.88 (s, 1 H) |
| 11 | $^1$H NMR (400 MHz, DMSO-d$_6$) δ ppm 1.70 (s, 3 H) 2.10 (s, 3 H) 6.85 (d, J = 2.01 Hz, 1 H) 6.94 (d, J = 2.27 Hz, 1 H) 7.01-7.11 (m, 3 H) 7.22 (t, J = 7.55 Hz, 2 H) 7.62-7.68 (m, 3 H) 7.72 (s, 1 H) 7.74 (s, 1 H) 7.77-7.85 (m, 1 H) 8.73 (d, J = 5.29 Hz, 1 H) 8.80 (d, J = 4.53 Hz, 1 H) 10.20 (s, 1 H) 10.38 (s, 1 H) |
| 12 | $^1$H NMR (400 MHz, DMSO-d$_6$) δ ppm 1.79 (s, 3 H) 3.34 (s, 2 H) 6.96 (d, J = 2.01 Hz, 1 H) 7.05 (d, J = 2.01 Hz, 1 H) 7.12 (d, J = 8.31 Hz, 1 H) 7.14-7.19 (m, 2 H) 7.26-7.33 (m, 2 H) 7.49 (d, J = 5.04 Hz, 1 H) 8.45 (s, 1 H) 8.65 (d, J = 5.04 Hz, 1 H) 9.75 (s, 1 H) |
| 13 | $^1$H NMR (400 MHz, MeOD) δ ppm 0.69-0.82 (m, 2 H) 0.84-1.00 (m, 2 H) 1.44-1.58 (m, 1 H) 2.02 (s, 3 H) 2.91 (s, 3 H) 6.82 (d, J = 5.54 Hz, 1 H) 7.00-7.17 (m, 3 H) 8.06 (s, 1 H) 8.26 (s, 1 H) |
| 14 | $^1$H NMR (400 MHz, MeOD) δ ppm 2.26 (s, 3 H) 2.99 (s, 3 H) 3.63 (s, 3 H) 7.26 (d, J = 8.31 Hz, 1 H) 7.54 (dd, J = 8.31, 2.52 Hz, 1 H) 7.88 (d, J = 6.04 Hz, 1 H) 7.95 (d, J = 2.27 Hz, 1 H) 8.47 (s, 1 H) 8.59 (d, J = 5.79 Hz, 1 H) |
| 15 | $^1$H NMR (400 MHz, MeOD) δ ppm 1.47 (s, 3 H) 1.50 (s, 3 H) 2.37 (s, 3 H) 3.06 (s, 3 H) 7.05 (d, J = 8.31 Hz, 1 H) 7.30 (dd, J = 8.31, 2.27 Hz, 1 H) 7.47 (d, J = 2.27 Hz, 1 H) 7.84 (d, J = 5.79 Hz, 1 H) 8.51 (s, 1 H) 8.58 (d, J = 5.79 Hz, 1 H) |
| 16 | $^1$H NMR (400 MHz, DMF) δ ppm 3.49 (s, 3 H) 4.11 (s, 3 H) 4.21 (s, 3 H) 7.28 (dd, J = 8.18, 1.89 Hz, 1 H) 7.34 (d, J = 2.01 Hz, 1 H) 7.51-7.60 (m, 2 H) 8.60 (s, 1 H) 8.84 (d, J = 5.79 Hz, 1 H) 10.27 (s, 1 H) |
| 17 | $^1$H NMR (400 MHz, DMSO-d$_6$) δ ppm 1.20 (t, J = 6.92 Hz, 3 H) 2.12 (s, 3 H) 3.07 (s, 3 H) 3.99 (q, J = 6.97 Hz, 2 H) 6.88 (dd, J = 8.06, 2.01 Hz, 1 H) 6.95 (d, J = 1.76 Hz, 1 H) 7.12 (d, J = 8.06 Hz, 1 H) 7.28 (d, J = 5.04 Hz, 1 H) 8.25 (s, 1 H) 8.38 (d, J = 5.04 Hz, 1 H) 9.88 (s, 1 H) |
| 18 | $^1$H NMR (400 MHz, DMSO-d$_6$) δ ppm 2.10 (s, 3 H) 3.72 (s, 3 H) 4.64 (q, J = 9.82 Hz, 2 H) 6.90 (dd, J = 8.18, 1.89 Hz, 1 H) 6.96 (d, J = 2.01 Hz, 1 H) 7.14 (d, J = 8.06 Hz, 1 H) 7.29 (d, J = 5.04 Hz, 1 H) 8.24 (s, 1 H) 8.39 (d, J = 5.04 Hz, 1 H) 10.61 (s, 1 H) |
| 19 | $^1$H NMR (400 MHz, MeOD) δ ppm 1.40 (d, J = 7.05 Hz, 6 H) 2.19 (s, 3 H) 3.34-3.45 (m, 1 H) 3.78 (s, 3 H) 6.96 (dd, J = 8.18, 2.14 Hz, 1 H) 7.05 (d, J = 2.01 Hz, 1 H) 7.10 (d, J = 8.06 Hz, 1 H) 7.33 (d, J = 5.04 Hz, 1 H) 8.21 (s, 1 H) 8.35 (d, J = 5.04 Hz, 1 H) |
| 20 | $^1$H NMR (400 MHz, MeOD) δ ppm 2.08 (s, 3 H) 2.23 (s, 3 H) 2.94 (s, 3 H) 3.65 (s, 3 H) 6.93 (s, 1 H) 7.03 (s, 1 H) 7.22 (d, J = 5.04 Hz, 1 H) 8.10 (s, 1 H) 8.23 (d, J = 5.04 Hz, 1 H) |
| 21 | $^1$H NMR (400 MHz, MeOD) δ ppm 2.11 (s, 3 H) 3.08 (s, 3 H) 3.72 (s, 6 H) 6.69 (s, 2 H) 7.32 (d, J = 5.29 Hz, 1 H) 8.11 (s, 1 H) 8.30 (d, J = 5.29 Hz, 1 H) |
| 22 | $^1$H NMR (400 MHz, DMSO-d$_6$) δ ppm 2.14 (s, 3 H) 3.10 (s, 3 H) 4.12-4.19 (m, 1 H) 4.21-4.29 (m, 1 H) 4.56 (dd, J = 4.64, 2.89 Hz, 1 H) 4.68 (dd, J = 4.52, 3.26 Hz, 1 H) 6.92 (dd, J = 8.03, 2.01 Hz, 1 H) 6.97 (d, J = 2.01 Hz, 1 H) 7.16 (d, J = 8.28 Hz, 1 H) 7.30 (d, J = 5.02 Hz, 1 H) 8.27 (s, 1 H) 8.40 (d, J = 5.02 Hz, 1 H) 9.94 (s, 1 H) |
| 23 | $^1$H NMR (400 MHz, MeOD) δ ppm 2.10 (s, 3 H) 2.95 (s, 3 H) 4.05-4.17 (m, 2 H) 5.69-6.08 (m, 1 H) 6.87-6.96 (m, 2 H) 7.04-7.09 (m, 1 H) 7.23 (d, J = 5.02 Hz, 1 H) 8.13 (s, 1 H) 8.25 (d, J = 5.27 Hz, 1 H) |
| 24 | $^1$H NMR (400 MHz, DMSO-d$_6$) δ ppm 2.13 (s, 3 H) 3.13 (s, 3 H) 4.72 (q, J = 8.78 Hz, 2 H) 6.98 (dd, J = 8.03, 2.01 Hz, 1 H) 7.02 (d, J = 1.76 Hz, 1 H) 7.21 (d, J = 8.03 Hz, 1 H) 7.31 (d, J = 5.02 Hz, 1 H) 8.27 (s, 1 H) 8.42 (d, J = 4.77 Hz, 1 H) 10.02 (s, 1 H) |
| 25 | $^1$H NMR (400 MHz, DMSO-d$_6$) δ ppm 2.14 (s, 3 H) 3.08 (s, 3 H) 7.14-7.19 (m, 1 H) 7.20 (d, J = 2.26 Hz, 1 H) 7.23-7.30 (m, 1 H) 7.52 (dd, J = 9.91, 5.65 Hz, 1 H) 8.58 (d, J = 10.29 Hz, 1 H) 8.69 (d, J = 7.78, 5.52 Hz, 1 H) 9.93 (s, 1 H) |
| 26 | $^1$H NMR (500 MHz, Solvent) δ ppm 7.20 (d, J = 8.80 Hz, 2 H) 7.41 (t, J = 8.52 Hz, 4 H) 7.48 (d, J = 7.15 Hz, 1 H) 7.69 (d, J = 4.40 Hz, 1 H) 7.74 (d, J = 7.15 Hz, 2 H) 8.60 (d, J = 4.95 Hz, 1 H) 8.68 (s, 1 H) |
| 27 | $^1$H NMR (400 MHz, Solvent) δ ppm 7.32 (d, J = 8.53 Hz, 2 H) 7.48-7.64 (m, 4 H) 7.74-7.90 (m, 3 H) 8.72 (d, J = 5.02 Hz, 1 H) 8.80 (s, 1 H) |

TABLE 20-continued

Additional NMR Data for Examples

| Ex. No. | NMR Data |
|---|---|
| 28 | $^1$H NMR (400 MHz, MeOD) δ ppm 3.06 (s, 3 H) 7.45 (d, J = 8.53 Hz, 2 H) 7.66 (d, J = 8.53 Hz, 2 H) 7.83 (d, J = 5.02 Hz, 1 H) 8.74 (d, J = 5.27 Hz, 1 H) 8.86 (s, 1 H) |
| 29 | $^1$H NMR (400 MHz, MeOD) δ ppm 2.25 (s, 3 H) 2.96 (s, 3 H) 7.10 (d, J = 8.28 Hz, 1 H) 7.17 (dd, J = 11.29, 1.76 Hz, 1 H) 7.28 (d, J = 5.02 Hz, 1 H) 7.53 (t, J = 8.16 Hz, 1 H) 8.24 (s, 1 H) 8.29 (d, J = 5.02 Hz, 1 H) |
| 30 | $^1$H NMR (400 MHz, MeOD) δ ppm 1.53-1.63 (m, 3 H) 1.66 (s, 3 H) 1.97 (s, 6 H) 2.01 (s, 4 H) 2.49 (s, 3 H) 7.26-7.33 (m, 2 H) 7.36-7.43 (m, 2 H) 7.86 (d, J = 6.02 Hz, 1 H) 8.54 (d, J = 6.02 Hz, 1 H) 8.56 (s, 1 H) |
| 31 | $^1$H NMR (400 MHz, MeOD) δ ppm 2.19 (s, 3 H) 7.11-7.17 (m, 1 H) 7.21 (dd, J = 8.41, 1.88 Hz, 1 H) 7.27 (d, J = 5.02 Hz, 1 H) 7.40-7.49 (m, 2 H) 7.60 (d, J = 8.53 Hz, 1 H) 7.69-7.77 (m, 2 H) 8.21 (s, 1 H) 8.29 (d, J = 5.02 Hz, 1 H) |
| 32 | $^1$H NMR (400 MHz, MeOD) δ ppm 2.59-2.66 (m, 3 H) 3.14 (s, 3 H) 7.50 (dd, J = 8.41, 2.13 Hz, 1 H) 7.59 (d, J = 1.51 Hz, 1 H) 7.89 (d, J = 8.53 Hz, 1 H) 8.05 (d, J = 6.02 Hz, 1 H) 8.69-8.82 (m, 2 H) |
| 33 | $^1$H NMR (400 MHz, MeOD) δ ppm 1.88 (s, 3 H) 1.98 (s, 3 H) 6.87-7.00 (m, 3 H) 7.27 (d, J = 5.02 Hz, 1 H) 7.55 (dd, J = 8.41, 2.13 Hz, 1 H) 7.75 (d, J = 8.28 Hz, 1 H) 7.87 (d, J = 2.01 Hz, 1 H) 8.07 (s, 1 H) 8.28 (d, J = 5.27 Hz, 1 H) |
| 179 | $^1$H NMR (400 MHz, acetone) δ ppm 2.10 (s, 3 H) 6.99-7.16 (m, 3 H) 7.42-7.52 (m, 2 H) 7.73-7.81 (m, 2 H) 7.93 (s, 1 H) 8.66 (d, J = 1.76 Hz, 1 H) 8.77 (d, J = 1.26 Hz, 1 H) |
| 181 | $^1$H NMR (400 MHz, CCl$_3$D) δ ppm 6.78 (d, J = 3.51 Hz, 1 H) 7.10 (s, 1 H) 7.21 (d, J = 8.53 Hz, 2 H) 7.39-7.53 (m, 6 H) 7.53-7.63 (m, 2 H) 7.75 (d, J = 3.76 Hz, 1 H) 7.80-7.87 (m, 2 H) 7.91-8.02 (m, 2 H) 8.41 (s, 1 H) 9.30 (s, 1 H) |
| 182 | $^1$H NMR (400 MHz, DMSO-d$_6$) δ ppm 1.88 (s, 3 H) 7.02-7.08 (m, 1 H) 7.10-7.17 (m, 2 H) 7.23-7.32 (m, 1 H) 7.34-7.41 (m, 1 H) 7.65-7.73 (m, 2 H) 7.82-7.90 (m, 2 H) 8.09-8.23 (m, 1 H) 8.27 (s, 1 H) 8.57 (dd, J = 5.90, 1.63 Hz, 1 H) 9.33 (s, 1 H) 10.56 (s, 1 H) |
| 186 | $^1$H NMR (400 MHz, DMSO-d$_6$) δ ppm 0.97 (s, 6 H) 2.11 (s, 3 H) 3.04 (s, 3 H) 3.86-3.96 (m, 1 H) 7.13-7.19 (m, 2 H) 7.26 (d, J = 8.06 Hz, 1 H) 8.29 (s, 1 H) 8.72 (s, 1 H) 9.89 (s, 1 H) |
| 187 | $^1$H NMR (400 MHz, DMSO-d$_6$) δ ppm 1.01 (t, J = 7.05 Hz, 3 H) 2.10 (s, 3 H) 3.05 (s, 3 H) 3.62 (t, 2 H) 7.09-7.19 (m, 2 H) 7.24 (d, J = 8.06 Hz, 1 H) 8.30 (s, 1 H) 8.72 (s, 1 H) 9.90 (s, 1 H) |
| 188 | $^1$H NMR (500 MHz, Solvent) δ ppm 2.15 (s, 3 H) 3.00 (s, 3 H) 4.10 (d, J = 85.23 Hz, 2 H) 7.17-7.31 (m, 3 H) 8.32 (s, 1 H) 8.71 (s, 1 H) |
| 189 | $^1$H NMR (400 MHz, DMSO-d$_6$) δ ppm 2.10 (s, 3 H) 3.04 (s, 3 H) 3.75 (s, 2 H) 4.34 (t, 1 H) 4.46 (t, 1 H) 7.11-7.19 (m, 2 H) 7.25 (d, J = 8.31 Hz, 1 H) 8.31 (s, 1 H) 8.73 (s, 1 H) 9.91 (s, 1 H) |
| 190 | $^1$H NMR (400 MHz, DMSO-d$_6$) δ ppm 2.07-2.15 (m, 3 H) 3.05 (s, 3 H) 3.79 (s, 2 H) 5.76-6.31 (m, 1 H) 7.12-7.22 (m, 2 H) 7.26 (d, J = 8.06 Hz, 1 H) 8.34 (s, 1 H) 8.76 (s, 1 H) 9.93 (s, 1 H) |
| 191 | $^1$H NMR (400 MHz, DMSO-d$_6$) δ ppm 2.07-2.15 (m, 3 H) 3.05 (s, 3 H) 3.79 (s, 2 H) 5.76-6.31 (m, 1 H) 7.12-7.22 (m, 2 H) 7.26 (d, J = 8.06 Hz, 1 H) 8.34 (s, 1 H) 8.76 (s, 1 H) 9.93 (s, 1 H) |
| 192 | $^1$H NMR (400 MHz, MeOD) δ ppm 2.14 (s, 6 H) 2.18 (s, 3 H) 2.50 (t, J = 5.79 Hz, 2 H) 3.04 (s, 3 H) 3.79 (d, J = 17.12 Hz, 2 H) 7.15-7.37 (m, 3 H) 8.28 (s, 1 H) 8.68 (s, 1 H) |
| 193 | $^1$H NMR (400 MHz, MeOD) δ ppm 2.18 (s, 3 H) 3.03 (s, 3 H) 3.20 (s, 3 H) 3.43 (t, J = 4.28 Hz, 2 H) 3.80 (s, 2 H) 7.18-7.33 (m, 3 H) 8.25 (s, 1 H) 8.66 (s, 1 H) |
| 194 | $^1$H NMR (400 MHz, MeOD) δ ppm 2.07 (s, 3 H) 2.16 (s, 3 H) 3.03 (s, 3 H) 7.11-7.31 (m, 3 H) 8.21 (s, 1 H) 8.66 (s, 1 H) |
| 195 | $^1$H NMR (400 MHz, DMSO-d$_6$) δ ppm 2.04 (s, 3 H) 3.07 (s, 3 H) 7.11-7.21 (m, 3 H) 7.68 (d, J = 5.29 Hz, 1 H) 8.47 (s, 1 H) 8.56 (d, J = 5.29 Hz, 1 H) 9.91 (s, 1 H) |
| 197 | $^1$H NMR (400 MHz, DMSO-d$_6$) δ ppm 1.24 (t, J = 7.05 Hz, 3 H) 2.06 (s, 3 H) 3.04 (s, 3 H) 4.14 (q, J = 6.97 Hz, 2 H) 7.06-7.11 (m, 3 H) 7.12 (d, J = 5.79 Hz, 1 H) 8.15 (s, 1 H) 8.44 (d, J = 5.79 Hz, 1 H) 9.80 (s, 1 H) |
| 198 | $^1$H NMR (500 MHz, Solvent) δ ppm 2.15 (s, 3 H) 3.01 (s, 3 H) 4.99 (d, J = 7.97 Hz, 2 H) 7.15-7.26 (m, 3 H) 7.74 (d, J = 6.87 Hz, 1 H) 8.60 (s, 1 H) 8.80 (d, J = 6.87 Hz, 1 H) |
| 199 | $^1$H NMR (400 MHz, MeOD) δ ppm 2.15 (s, 3 H) 3.02 (s, 3 H) 4.37 (d, J = 28.71 Hz, 2 H) 4.54-4.63 (m, 1 H) 4.67-4.76 (m, 1 H) 7.10-7.27 (m, 4 H) 8.19 (s, 1 H) 8.45 (d, J = 5.79 Hz, 1 H) |
| 200 | $^1$H NMR (500 MHz, Solvent) δ ppm 2.02 (s, 3 H) 2.90 (s, 3 H) 4.19-4.38 (m, 2 H) 5.83-6.17 (m, 1 H) 7.00-7.04 (m, 1 H) 7.04-7.08 (m, 2 H) 7.10 (d, J = 5.77 Hz, 1 H) 8.10 (s, 1 H) 8.36 (d, J = 5.77 Hz, 1 H) |
| 201 | $^1$H NMR (400 MHz, MeOD) δ ppm 1.86 (s, 3 H) 2.95 (t, J = 6.04 Hz, 2 H) 3.03 (s, 3 H) 4.28 (t, J = 6.17 Hz, 2 H) 6.97-7.06 (m, 3 H) 7.12 (d, J = 6.04 Hz, 1 H) 7.14-7.26 (m, 5 H) 8.12 (s, 1 H) 8.40 (d, J = 5.79 Hz, 1 H) |
| 202 | $^1$H NMR (400 MHz, MeOD) δ ppm 2.02 (s, 3 H) 2.06 (s, 6 H) 2.59 (t, J = 5.41 Hz, 2 H) 2.87 (s, 3 H) 4.12 (t, J = 5.41 Hz, 2 H) 6.90-7.15 (m, 4 H) 8.06 (s, 1 H) 8.33 (d, J = 6.04 Hz, 1 H) |

TABLE 20-continued

Additional NMR Data for Examples

| Ex. No. | NMR Data |
|---|---|
| 203 | $^1$H NMR (400 MHz, MeOD) δ ppm 2.02 (s, 3 H) 2.88 (s, 3 H) 3.14 (s, 3 H) 3.46-3.66 (m, 2 H) 4.21 (d, J = 3.78 Hz, 2 H) 6.91-7.13 (m, 3 H) 7.26 (d, J = 6.04 Hz, 1 H) 8.15 (s, 1 H) 8.41 (d, J = 6.04 Hz, 1 H) |
| 204 | $^1$H NMR (400 MHz, MeOD) δ ppm 1.98 (s, 3 H) 2.36 (s, 3 H) 2.91 (s, 3 H) 6.96-7.01 (m, 1 H) 7.04-7.12 (m, 2 H) 7.26 (d, J = 5.79 Hz, 1 H) 7.95 (s, 1 H) 8.30 (d, J = 5.54 Hz, 1 H) |
| 206 | $^1$H NMR (400 MHz, MeOD) δ ppm 2.59 (s, 3 H) 3.30 (s, 3 H) 7.23-7.35 (m, 6 H) 7.35-7.41 (m, 2 H) 7.98 (d, J = 5.77 Hz, 1 H) 8.62-8.69 (m, 2 H) |
| 207 | $^1$H NMR (400 MHz, MeOD) δ ppm 2.33 (s, 3 H) 3.75 (s, 3 H) 6.77-6.83 (m, 2 H) 7.02-7.06 (m, 2 H) 7.23-7.30 (m, 4 H) 7.36 (d, J = 5.27 Hz, 1 H) 8.31 (s, 1 H) 8.35 (d, J = 5.27 Hz, 1 H) |
| 208 | $^1$H NMR (400 MHz, MeOD) δ ppm 1.99 (s, 3 H) 2.30 (s, 3 H) 3.07-3.16 (m, 4 H) 3.50-3.58 (m, 4 H) 7.01-7.08 (m, 1 H) 7.13-7.19 (m, 2 H) 7.93 (d, J = 6.02 Hz, 1 H) 8.53 (s, 1 H) 8.61 (d, J = 6.02 Hz, 1 H) |
| 210 | $^1$H NMR (400 MHz, MeOD) δ ppm 2.10 (s, 3 H) 2.43 (s, 3 H) 2.64 (s, 3 H) 7.13-7.17 (m, 1 H) 7.18-7.23 (m, 1 H) 7.25 (d, J = 2.26 Hz, 1 H) 8.05 (d, J = 6.02 Hz, 1 H) 8.63 (s, 1 H) 8.73 (d, J = 6.02 Hz, 1 H) |
| 211 | $^1$H NMR (400 MHz, MeOD) δ ppm 1.33-1.49 (m, 2 H) 1.72 (d, J = 12.80 Hz, 2 H) 1.93 (s, 3 H) 2.03 (s, 3 H) 2.88-3.03 (m, 2 H) 3.42-3.53 (m, 2 H) 3.53-3.70 (m, 1 H) 6.94 (d, J = 8.28 Hz, 1 H) 7.02-7.12 (m, 2 H) 7.28 (d, J = 5.02 Hz, 1 H) 8.10 (s, 1 H) 8.28 (d, J = 5.27 Hz, 1 H) |
| 226 | $^1$H NMR (400 MHz, MeOD) δ ppm 8.80 (s, J = 5.54 Hz, 1 H), 8.65 (s, 1 H), 7.97 (s, 1 H), 7.23 (s, J = 8.06 Hz, 1 H), 7.04 (s, 1 H), 6.98 (d, J = 8.06, 1 H), 6.69 (s, 1 H), 3.78 (s, 3 H), 3.05 (s, 3 H) |
| 227 | $^1$H NMR (400 MHz, MeOD) δ ppm 8.70 (d, J = 6.04 Hz, 1 H), 8.68 (s, 1 H), 7.97 (d, J = 6.04 Hz, 1 H), 7.25 (d, J = 6.04 Hz, 1 H), 7.02-6.95 (m, 2 H), 5.29 (s, 1 H), 5.08 (s, 1 H), 3.76 (s, 3 H), 3.03 (s, 3 H), 1.90 (s, 3 H) |
| 228 | $^1$H NMR (400 MHz, DMSO-$d_6$) δ ppm 10.39 (s, 1 H), 9.49 (s, 1 H), 8.30 (d, J = 8.31 Hz, 1 H), 7.90-7.70 (s, 2 H), 7.57 (d, J = 8.31 Hz, 2 H), 7.44-7.38 (m, 2 H), 3.18 (s, 3 H) |
| 229 | $^1$H NMR (400 MHz, MeOD) δ ppm 8.74-8.68 (m, 2 H), 8.0 (d, J = 6.04 Hz, 1 H), 7.48-7.38 (m, 3 H), 3.08 (3, 3 H), 2.45 (s, 3 H) |
| 230 | $^1$H NMR (400 MHz, MeOD) δ ppm 8.56 (d, J = 5.54 Hz, 1 H), 8.53 (s, 1 H), 7.74 (d, J = 5.54 Hz, 1 H), 7.45-7.32 (m, 3 H), 3.07 (s, 3 H) |
| 231 | $^1$H NMR (400 MHz, MeOD) δ ppm 8.78 (dd, J = 7.05 Hz, 1.26 Hz, 1 H), 8.63 (d, J = 1.26 Hz, 1 H), 7.74 (d, J = 7.05 Hz, 1 H), 7.46 (d, J = 8.31 Hz, 1 H), 7.39-7.32 (m, 2 H), 4.13 (s, 3 H), 3.06 (s, 3 H) |
| 232 | $^1$H NMR (400 MHz, MeOD) δ ppm 9.72-9.67 (m, 1 H), 8.50 (d, J = 8.31 Hz, 1 H), 8.48 (s, 1 H), 8.15-8.06 (m, 1 H), 8.00 (t, J = 7.68 Hz, 1 H), 7.90 (d, J = 8.81 Hz, 1 H), 7.42 (d, J = 7.81 Hz, 1 H), 7.19-7.10 (m, 2 H), 4.54 (dd, J = 8.31 Hz, 2.52 Hz, 2 H), 3.10 (s, 3 H) |
| 233 | $^1$H NMR (400 MHz, MeOD) δ ppm 8.71 (dd, J = 6.92 Hz, 1.39 Hz, 1 H), 8.55 (d, J = 1.26 Hz, 1 H), 7.68 (d, J = 7.05 Hz, 1 H), 7.33 (d, J = 8.06 Hz, 1 H), 7.06-7.0 (m, 2 H), 4.57 (q, J = 8.48 Hz, 2 H), 4.10 (s, 3 H), 3.05 (s, 3 H) |
| 241 | $^1$H NMR (400 MHz, CD$_3$OD) δ ppm 9.30 (1 H, s), 8.30 (1 H, s), 8.09-8.25 (1 H, m), 7.69-7.86 (3 H, m), 7.65 (1 H, dd, J = 8.3, 2.0 Hz), 7.32-7.50 (2 H, m), 3.13 (3 H, s); $^{19}$F NMR (CD$_3$OD) δ ppm −60.2 |
| 242 | $^1$H NMR (400 MHz, CD$_3$OD) δ ppm 8.54 (d, J = 5.3 Hz, 1 H), 8.43 (s, 1 H), 7.70 (d, J = 2.3 Hz, 1 H), 7.55-7.67 (m, 2 H), 7.37 (d, J = 8.5 Hz, 1 H), 3.09 (3 H, s); 19F NMR (CD$_3$OD) δ ppm −60.8 |
| 243 | $^1$H NMR (500 MHz, CDCl$_3$) δ ppm 8.64 (s, 1H), 8.36 (d, 1 H, J = 5.4 Hz), 6.81 (d, 1H, J = 5.4 Hz), 2.39-2.19 (1 H, m), 1.31-1.13 (2 H, m), 0.87-0.74 (2 H, m) |

Biological Assays

The pharmacological properties of the compounds of this invention may be confirmed by a number of biological assays. The exemplified biological assays, which follow, have been carried out with the compounds of the present invention.

CYP17 Total SPA Assay

The assays were performed in U-bottom 384-well opti-plates. The final assay volume was 15 µl prepared from 7.5 µl additions of microsomes (prepared as a high-speed pellet from homogenized HEK2 cells stably transfected with CYP17), substrates (3H-Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 µl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a TOPCOUNT® (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

Table 22 below lists the $IC_{50}$ values for the following Examples of this invention measured in the Total CYP17 SPA Assay hereinabove. The compounds of the present invention, as exemplified by the following Examples, showed Human CYP17 SPA $IC_{50}$ values of less than 1 μM.

TABLE 22

Human CYP17 Inhibition

| Example No. | Human CYP17 SPA IC50 (nM) |
| --- | --- |
| 12 | 104 |
| 23 | 32 |
| 24 | 42 |
| 142 | 6.6 |
| 143 | 2.9 |
| 144 | 11 |
| 147 | 2.7 |
| 154 | 27 |
| 156 | 8.1 |
| 158 | 118 |
| 159 | 6.2 |
| 160 | 6 |
| 161 | 112 |
| 162 | 169 |
| 163 | 134 |
| 164 | 100 |
| 165 | 5.4 |
| 166 | 131 |
| 167 | 158 |
| 168 | 9.6 |
| 169 | 119 |
| 170 | 56 |
| 172 | 117 |
| 173 | 3.4 |
| 175 | 59 |
| 176 | 118 |
| 184 | 7.7 |
| 195 | 52 |
| 198 | 1.4 |
| 217 | 2.5 |
| 218 | 49 |
| 220 | 103 |
| 221 | 100 |
| 225 | 2.1 |
| 228 | 3.2 |
| 232 | 59 |
| 233 | 56 |
| 234 | 40 |
| 236 | 174 |
| 239 | 51 |
| 240 | 26 |
| 241 | 48 |
| 243 | 39 |
| 245 | 57 |
| 250 | 120 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (Cal-Biochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and $IC_{50}$ values.

Cyp17 Hydroxylase Assay

*E. coli* was transformed to express active human CYP17 and membranes prepared from the transformed *E. coli* were used as the source of enzyme. The reaction was carried out in a 50 μL, final volume containing 200 nM hCYP17 membranes, 25 μM Pregnenolone (Sigma), 7 mM NADPH (Cal-Biochem), 1 μM cytochrome P450 reductase (Invitrogen), and 50 mM sodium phosphate buffer, pH 7.3. The $IC_{50}$ determination of compounds dissolved in 100% DMSO was done by serial dilution into the assay buffer to a final concentration of 0.2% DMSO. The reaction was incubated at 37° C. for 120 minutes and stopped by the addition of 200 μL of 0.02N HCl in acetonitrile. Samples were then spun at 750000 g and 200 μL of the supernatant was transferred to a clean tube for analysis. The product of the reaction, 17 alpha pregnenolone, was measured via LC/MS.

Cyp17 HEK293 Cell Based Assay

HEK293 cells were stably transfected with human Cyp17 and individual clones analyzed for Cyp17 enzymatic activity via LC/MS. A single clone showing robust activity was selected and scaled up. Cells were seeded in 96 well plates and a serial dilution of compounds dissolved in DMSO was added to the cells. Following an incubation of 4 hours, reactions were neutralized by the addition of 200 ul of acetonitrile containing 0.5 uM pregnenolone as tracer. Plates were spun down at 2K for 15 minutes and supernatants transferred to siliconized 96 well plates. The end product of the reaction DHEA was analyzed via LC/MS.

1-Day Cyno PK/PD Study Protocol

Animals: All procedures involving animals and their care were conducted in conformity with the guidelines that are in compliance with the Bristol-Myers Squibb Institutional Animal Care and Use Committee. Fully mature male cynomolgus monkeys (>4 yrs of age; 5-6 kg) were from an in-house colony. All the monkeys used had chronically implanted femoral vein access ports. For oral studies, all animals were fasted overnight prior to dosing and were fed 4 hr after dosing. All animals had free access to water and were conscious throughout the study.

Drug: For all oral pharmacokinetic studies in cynomolgus monkeys, the tested compound was formulated in polyethylene glycol (PEG 400): water (80:20, v:v) at concentrations of 1-5 mg/mL.

Drug Treatment: The tested compound was administered by oral gavage to cynomolgus monkeys.

Sampling: Blood samples were collected from the femoral port, at 15, 30, and 45 min, and 1, 2, 4, 6, 8, 12, 24, 30, and 48 hr after oral administration. All blood samples were collected into syringes containing sodium heparin. The plasma fraction was immediately separated by centrifugation (14,000 rpm, 10 min, 4° C.), frozen on dry ice, and stored at −20° C. until the samples were analyzed.

Analysis of Tested Compound: Plasma samples were thawed and treated with two volumes of acetonitrile containing internal standard. After centrifugation to remove precipitated proteins, an aliquot of supernatant was analyzed by LC/MS/MS.

Analysis of Steroids: Plasma samples were thawed, and assayed in accordance with package insert instructions for the following kits: Coat-A-Count total testosterone solid phase RIA kit, Coat-A-Count total progesterone solid phase RIA kit, and Coat-A-Count total cortisol solid phase RIA kit (Diagnostic Product Corp, Siemens Healthcare Diagnostics, Deerfield, Ill.).

FIG. 1 shows the results of a 1-day PK/PD study in NHP cynomolgus monkeys with Example 217. Example 217 was formulated in 80% PEG-400/water at a volume of 1 mL/Kg of monkey and a dose of 5 mg/Kg. The formulation was then administered orally at time=0 and blood samples were taken over a 24 hour period to monitor for drug exposure and testosterone levels. FIG. 1 shows that testosterone levels are reduced after single oral dose of Example 217, consistent with an inhibitor of CYP17 lyase.

What is claimed is:

1. A compound of Formula (I):

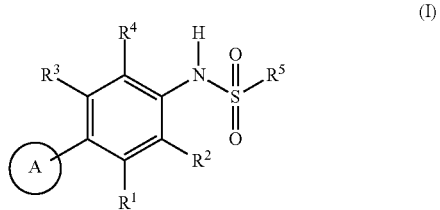

or a stereoisomer, or a pharmaceutically acceptable salt thereof,
wherein:
ring A is:

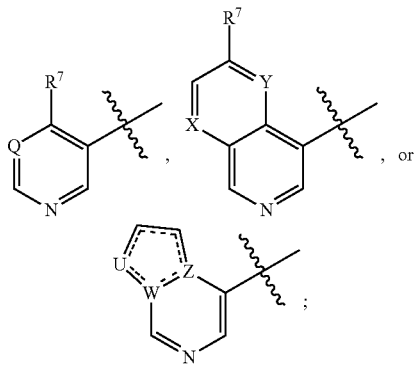

X, Y, and Q are independently N and/or $CR^6$;
U is independently N, $NR^8$, and/or CH;
W and Z are independently N and/or C;
provided that:
  (i) if U is $NR^8$, then W and Z are each C;
  (ii) if U is N or CH, then one of W and Z is N, and the other of W and Z is C;
the ≡≡≡ bond represents a single or double bond;
$R^1$ is H, halo, —OH, $C_{1-4}$alkyl, $C_{1-4}$haloalkyl, $C_{1-4}$alkoxy, $C_{1-4}$haloalkoxy, $C_{1-4}$hydroxyalkyl, or —C(O)O($C_{1-4}$alkyl);
$R^2$ is H, halo, or $C_{1-3}$alkyl;
$R^3$ is H, halo, $C_{1-3}$alkyl, or $C_{1-3}$alkoxy;
$R^4$ is H, halo, $C_{1-3}$alkyl, $C_{1-3}$alkoxy, or $C_{1-3}$haloalkoxy;
$R^5$ is:
  (i) $C_{1-6}$alkyl substituted with zero to 3 substituents independently selected from halo, phenyl, isoindoline-1,3-dione, and/or camphor, wherein said phenyl may be substituted with zero to 3 $R^a$;
  (ii) $C_{2-6}$alkenyl substituted with zero to 3 substituents independently selected from halo and/or phenyl;
  (iii) $C_{3-6}$cycloalkyl substituted with zero to 2 substituents independently selected from halo, $C_{1-3}$alkyl, and/or $C_{1-3}$haloalkyl;
  (iv) adamantanyl;
  (v) —$NR^cR^d$;
  (vi) phenyl substituted with zero to 3 substituents independently selected from halo, —CN, —$NO_2$, $C_{1-6}$alkyl, $C_{1-4}$haloalkyl, $C_{1-4}$alkoxy, $C_{1-4}$haloalkoxy, —C(O)O($C_{1-4}$alkyl), —$NR^bC(O)(C_{1-4}$alkyl), phenyl, and/or phenoxy;
  (vii) naphthalenyl substituted with zero to 3 substituents independently selected from halo, $C_{1-3}$alkyl, $C_{1-3}$haloalkyl, $C_{1-3}$alkoxy, and/or $C_{1-3}$haloalkoxy;
  (viii) 5- to 10-membered heteroaryl substituted with zero to 2 substituents independently selected from halo, —C(O)($C_{1-3}$alkyl), —C(O)O($C_{1-3}$alkyl), $C_{1-3}$alkyl, and/or $C_{1-3}$haloalkyl; or
  (ix) 5- to 6-membered heterocyclyl substituted with zero to 2 substituents independently selected from halo, —OH, $C_{1-3}$alkyl, and/or $C_{1-3}$haloalkyl;
  wherein each of said heteroaryl or heterocyclyl groups comprises 1 to 2 heteroatoms;
$R^6$ is H, halo, —CN, $C_{1-3}$alkyl, $C_{1-3}$haloalkyl, $C_{1-3}$alkoxy, or $C_{1-3}$haloalkoxy;
$R^7$ is:
  (i) halo;
  (ii) —CN;
  (iii) $C_{1-3}$alkyl with zero to 1 $C_{1-3}$alkoxy group;
  (iv) $C_{1-4}$haloalkyl or $C_{1-4}$hydroxyalkyl;
  (v) $C_{2-4}$alkenyl;
  (vi) $C_{1-4}$alkoxy substituted with zero to 2 substituents independently selected from halo, —$NR^bR^c$, phenyl, $C_{3-6}$cycloalkyl, and/or $C_{1-3}$alkoxy;
  (vii) $C_{3-6}$cycloalkyl substituted with zero to 2 substituents independently selected from halo, $C_{1-3}$alkyl, and/or $C_{1-3}$haloalkyl;
  (viii) —S($C_{1-3}$alkyl);
  (ix) —$NR^bR^c$;
  (x) —C(O)M, wherein M is 5- to 6-membered heterocyclyl;
  (xi) phenyl substituted with zero to 4 substituents independently selected from halo, —CN, $C_{1-3}$alkyl, $C_{1-3}$haloalkyl, and/or $C_{1-3}$alkoxy; or 3- to 6-membered heterocyclyl substituted with zero to 4 substituents independently selected from halo, $C_{1-3}$alkyl, and/or $C_{1-3}$haloalkyl;
  wherein each of said heterocyclyl groups comprises 1 to 3 heteroatoms;
$R^8$ is H, $C_{1-3}$alkyl, or —$S(O)_2$(phenyl);
each $R^a$ is independently halo, $C_{1-3}$alkyl, $C_{1-3}$haloalkyl, $C_{1-3}$alkoxy, and/or $C_{1-3}$haloalkoxy;
each $R^b$ is independently H and/or $C_{1-3}$alkyl;
each $R^c$ is independently H, $C_{1-3}$alkyl, and/or $C_{1-3}$haloalkyl; and
each $R^d$ is independently H, $C_{1-3}$alkyl, $C_{1-3}$haloalkyl, and/or phenyl substituted with zero to 2 substituents independently selected from halo, $C_{1-3}$alkyl, $C_{1-3}$haloalkyl, $C_{1-3}$alkoxy, and/or $C_{1-3}$haloalkoxy; or
$R^c$ and $R^d$ together with the nitrogen atom to which they are attached form a 5- to 6-membered heterocyclyl having zero to 1 additional heteroatom independently selected from N and/or O, wherein said heterocyclyl may be substituted with zero to 2 substituents independently selected from halo, $C_{1-3}$alkyl, and/or —OH.

2. The compound according to claim 1, wherein:
ring A is:

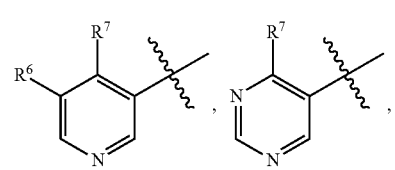

-continued

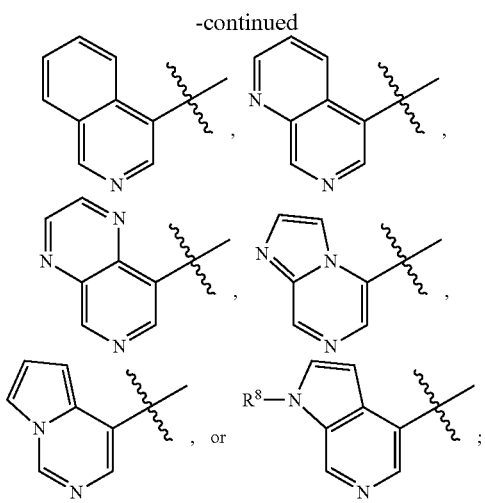

R¹ is H, halo, —OH, C$_{1-3}$alkyl, C$_{1-3}$fluoroalkyl, C$_{1-3}$alkoxy, C$_{1-3}$fluoroalkoxy, C$_{1-4}$hydroxyalkyl, or —C(O)O(C$_{1-3}$alkyl);
R² is H;
R³ is H, C$_{1-3}$alkyl, or C$_{1-3}$alkoxy;
R⁴ is H, halo, or C$_{1-3}$fluoroalkoxy;
R⁵ is:
(i) C$_{1-6}$alkyl substituted with zero to 3 substituents independently selected from halo, phenyl, isoindoline-1,3-dione, and/or camphor, wherein said phenyl may be substituted with zero to 3 R$^a$;
(ii) C$_{2-6}$alkenyl substituted with phenyl;
(iii) C$_{3-6}$cycloalkyl;
(iv) adamantanyl;
(v) —NR$^c$R$^d$;
(vi) phenyl substituted with zero to 3 substituents independently selected from halo, —CN, —NO$_2$, C$_{1-4}$alkyl, C$_{1-4}$fluoroalkyl, C$_{1-4}$alkoxy, —C(O)O (C$_{1-4}$alkyl), —NHC(O)(C$_{1-4}$alkyl), phenyl, and/or phenoxy;
(vii) naphthalenyl; or
(viii) 5- to 10-membered heteroaryl substituted with zero to 2 substituents independently selected from —C(O)(C$_{1-3}$alkyl), —C(O)O(C$_{1-3}$alkyl) and/or C$_{1-3}$alkyl, wherein said heteroaryl comprises 1 to 2 heteroatoms;
R⁶ is H, halo, or —CN;
R⁷ is:
(i) halo;
(ii) —CN;
(iii) C$_{1-4}$alkyl substituted with zero to 1 C$_{1-3}$alkoxy group;
(iv) C$_{1-4}$fluoroalkyl or C$_{1-4}$hydroxyalkyl;
(v) C$_{2-4}$alkenyl;
(vi) C$_{1-4}$alkoxy substituted with zero to 2 substituents independently selected from halo, —NR$^b$R$^c$, phenyl, C$_{3-6}$cycloalkyl, and/or C$_{1-3}$alkoxy;
(vii) C$_{3-6}$ cycloalkyl;
(viii) —S(C$_{1-3}$alkyl);
(ix) —NH(C$_{1-3}$fluoroalkyl);
(x) —C(O)(pyrrolidinyl);
(xi) phenyl; or
(xii) 3- to 6-membered heterocyclyl substituted with zero to 2 substituents independently selected from halo and/or C$_{1-3}$alkyl, wherein said heterocyclyl group comprises 1 to 3 heteroatoms;
R⁸ is —S(O)$_2$(phenyl);
each R$^a$ is independently halo and/or C$_{1-3}$fluoroalkyl;
each R$^c$ is independently H and/or C$_{1-3}$alkyl; and
each R$^d$ is independently H, C$_{1-3}$alkyl, and/or phenyl substituted with zero to 2 substituents independently selected from halo and/or C$_{1-3}$alkoxy; or
R$^{c\ and\ Rd}$ together with the nitrogen atom to which they are attached form a 5- to 6-membered heterocyclyl having zero to 1 additional heteroatom independently selected from N and/or O, wherein said heterocyclyl may be substituted with zero to 1 hydroxyl group.

3. The compound according to claim 2 having Formula (Ia):

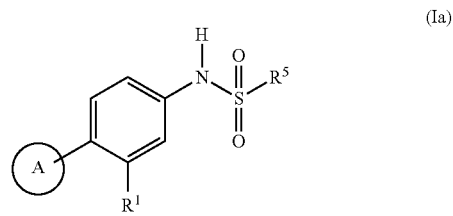

or a stereoisomer, or a pharmaceutically acceptable salt thereof.

4. The compound according to claim 3, wherein:
R¹ is H, Cl, —CH$_3$, —CF$_3$, —OH, —OCH$_3$, —OCH$_2$CH$_3$, —OCF$_3$, —OCH$_2$CH$_2$F, —OCH$_2$CHF$_2$, —OCH$_2$CF$_3$, or —C(CH$_3$)$_2$OH;
R⁵ is:
(i) —CH$_3$, —CH$_2$CH$_3$, —(CH$_2$)$_2$CH$_3$, —CH(CH$_3$)$_2$, —(CH$_2$)$_3$ CH$_3$, —CH$_2$ CH(CH$_3$)$_2$, —CH$_2$CF$_3$, —CH$_2$(phenyl), —(CH$_2$)$_2$(phenyl), —CH$_2$(camphor), —CH$_2$(chlorophenyl), —CH$_2$(di-chlorophenyl), or —CH$_2$(trifluoromethylphenyl);
(ii) —CH═CH$_2$(phenyl);
(iii) cyclopropyl;
(iv) adamantanyl;
(v) —NH(CH$_3$), —NH(phenyl), —N(CH$_3$)(chlorophenyl), —NH(methoxyphenyl),

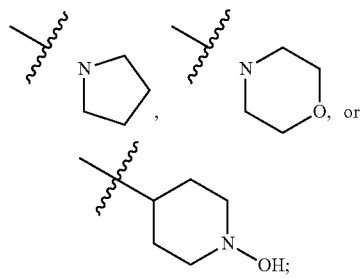

(vi) phenyl substituted with zero to 3 substituents independently selected from F, Cl, Br, —CH$_3$, —CF$_3$, —OCH$_3$, —CN, —NO$_2$, —CH(CH$_3$)$_2$, —C(O) OCH$_3$, —NHC(O)CH$_3$, phenyl, and/or phenoxy;
(vii) naphthalenyl; or

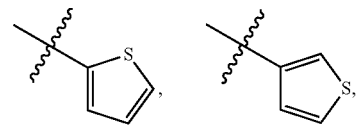

-continued

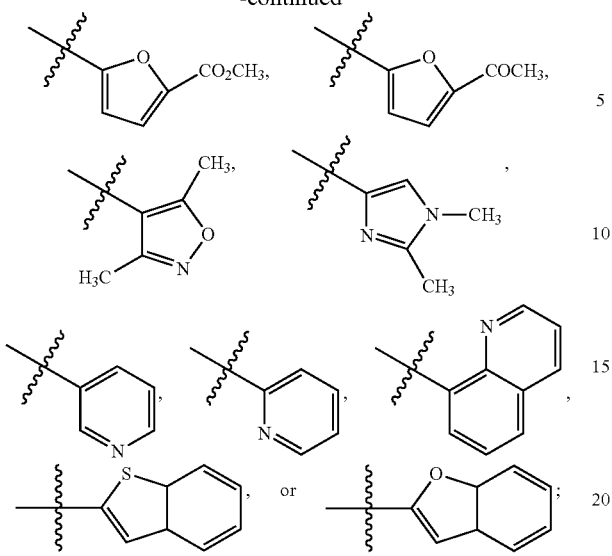

R⁶ is H; and
R⁷ is F, Cl, —CN, —CH₃, —CH₂CH₃, —CH(CH₃)₂, —(CH₂)₂CH₃, —CF₃, —CHF₂, —CH₂OH, —CH₂OCH₃, —CH(CH₃)=CH₂, —SCH₃, —NHCH₂CF₃, —OCH₃, —OCH₂CH₃, —OCH(CH₃)₂, —OCH₂CF₃, —OCH₂CH₂F, —OCH₂CHF₂, —O(CH₂)₂N(CH₃)₂, —O(CH₂)₂OCH₃, —O(CH₂)₂(phenyl), —O(CH₂)cyclopropyl, cyclopropyl, cyclohexyl, phenyl,

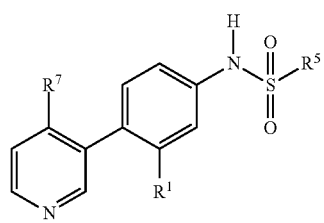

5. The compound according to claim 4 having Formula (Ib):

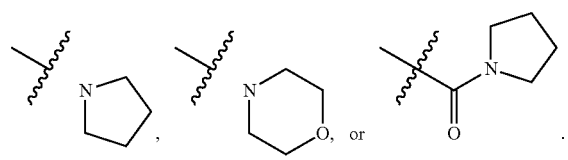

or a stereoisomer, or a pharmaceutically acceptable salt thereof.

6. The compound according to claim 5, wherein:
R¹ is H, Cl, —CH₃, —OH, —OCH₃, —OCH₂CH₃, —OCF₃, —OCH₂CH₂F, —OCH₂CHF₂, or —OCH₂CF₃; and
R⁷ is F, Cl, —CH₃, —CH₂CH₃, —(CH₂)₂CH₃, —CF₃, —CHF₂, —CH₂OH, —CH₂OCH₃, —NHCH₂CF₃, —OCH₃, —OCH₂CH₃, —OCH₂CF₃, —OCH₂CH₂F, —OCH₂CHF₂, —O(CH₂)(cyclopropyl), or cyclopropyl.

7. The compound according to claim 4 having Formula (Ic):

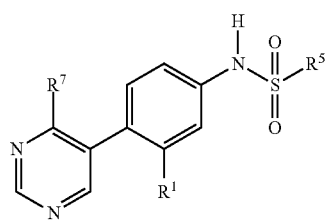

or a stereoisomer, or a pharmaceutically acceptable salt thereof.

8. The compound according to claim 7, wherein:
R¹ is —OCH₃; and
R⁷ is —CH₃, —CH₂CH₃, —CH(CH₃)₂, —(CH₂)₂CH₃, —NHCH₂CF₃, —OCH₃, —OCH₂CH₃, —OCH₂CF₃, cyclopropyl, cyclohexyl

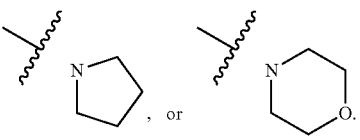

9. The compound according to claim 4 having Formula (Id):

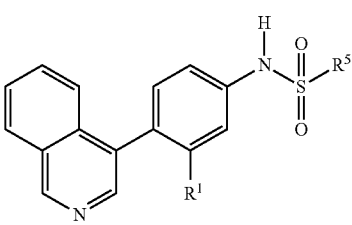

or a stereoisomer, or a pharmaceutically acceptable salt thereof.

10. The compound according claim 9, wherein:
R¹ is H, —CH₃, —CF₃, —OCH₃, —OCF₃, —OCH₂CH₂F, or —OCH₂CF₃.

11. The compound according to claim 1, or a stereoisomer, or a pharmaceutically acceptable salt thereof, wherein said compound is selected from: N-(3-methyl-4-(4-methyl-3-pyridinyl)phenyl)methanesulfonamide (1); N-(4-(4-methoxypyridin-3-yl)-3-methylphenyl)methanesulfonamide (2); 4-chloro-N-(4-(4-methyl-3-pyridinyl) phenyl) benzenesulfonamide (3); 3,4-dichloro-N-(4-(4-methyl-3-pyridinyl) phenyl) benzenesulfonamide (4); 4-chloro-N-(3-methyl-4-(4-methyl-3-pyridinyl)phenyl)benzene sulfonamide (5); 1-((1S)-7,7-dimethyl-2-oxobicyclo[2.2.1]hept-1-yl)-N-(3-methyl-4-(4-methyl-3-pyridinyl)phenyl)methanesulfonamide (6); 4-chloro-N-(4-(4-methoxypyridin-3-yl)-3-methylphenyl)benzenesulfonamide (7); 4-chloro-N-(4-(4-phenyl-3-pyridinyl) phenyl)benzenesulfonamide (8); 1-phenyl-N-(4-(4-phenyl-3-pyridinyl)phenyl) methanesulfonamide (9); N-(3-methyl-4-(4-phenyl-3-pyridinyl)phenyl)-1-phenyl-methane sulfonamide (10); N-(4-43-methyl-4-(4-phenyl-3-pyridinyl)phenyl)sulfamoyl)phenyl) acetamide (11); N-(3- methyl-4-(4-phenyl-3-pyridinyl)phenyl) methanesulfonamide (12); N-(4-(4-cyclopropyl-3-pyridinyl)-3-methylphenyl)methanesulfonamide (13); methyl 2-(4-methyl-3-pyridinyl)-5-((methylsulfonyl)amino) benzoate (14); N-(3-(2-hydroxypropan-2-yl)-4-(4-methylpyridin-3-yl)phenyl)methanesulfonamide (15); N -(3-methoxy-4-(4-methoxy-3-pyridinyl)phenyl)methanesulfonamide (16); N-(3-ethoxy-4-(4-methyl-3-pyridinyl)phenyl)methanesulfonamide (17); 2,2,2-trifluoro-N-(3-methoxy-4-(4-methyl-3-pyridinyl)phenyl)ethane sulfonamide (18); N-(3-methoxy-4-(4-methyl-3-pyridinyl) phenyl)-2-propanesulfonamide (19); N-(5-methoxy-2-methyl-4-(4-methyl-3-pyridinyl)phenyl)methane sulfonamide (20); N-(3,5-dimethoxy-4-(4-methyl -3-pyridinyl)phenyl) methanesulfonamide (21); N-(3-(2-fluoroethoxy)-4-(4-methyl-3-pyridinyl)phenyl)methane sulfonamide (22); N-(3-(2,2-difluoroethoxy)-4-(4-methyl-3-pyridinyl)phenyl) methane sulfonamide (23); N-(4-(4-methyl-3-pyridinyl))-3-(2,2,2-trifluoroethoxy)phenyl)methane sulfonamide (24); N-(4-(4-fluoro-3-pyridinyl)-3-methylphenyl)methanesulfonamide (25); N-(4-(4-cyano-3-pyridinyl)phenyl) benzenesulfonamide (26); 4-chloro-N-(4-(4-cyanopyridin-3-yl) phenyl) benzenesulfonamide (27); N-(4-(4-cyano-3-pyridinyl)phenyl)methanesulfonamide (28); N-(2-fluoro-4-(4-methyl-3-pyridinyl)phenyl)methanesulfonamide (29); N-(4-(4-methyl -3-pyridinyl)phenyl)-1-adamantanesulfonamide (30); 4-chloro-N-(4-(4-methyl-3-pyridinyl)-2-(trifluoromethoxy)phenyl)benzenesulfonamide (31); N-(4-(4-methyl-3-pyridinyl)-2-(trifluoromethoxy)phenyl) methanesulfonamide (32); 3,4-dibromo-N-(3-methyl-4-(4-methylpyridin-3-yl)phenyl)benzenesulfonamide (33); N-(3-methyl-4-(4-methyl-3-pyridinyl)phenyl)-4-biphenylsulfonamide (34); N-(3-methyl-4-(4-methyl-3-pyridinyl)phenyl)-3-biphenylsulfonamide (35); N-(3-methyl-4-(4-methyl-3-pyridinyl) phenyl)-8-quinolinesulfonamide (36); 4-fluoro-N-(3-methyl-4-(4-methyl-3-pyridinyl) phenyl)benzenesulfonamide (37); N-(4-43-methyl-4-(4-methyl-3-pyridinyl) phenyl)sulfamoyl) phenyl)acetamide (38); 4-methoxy-N-(3-methyl-4-(4-methyl-3-pyridinyl)phenyl)benzenesulfonamide (39); 2,2,2-trifluoro-N-(3-methyl-4-(4-methyl-3-pyridinyl)phenyl) ethanesulfonamide (40); N-(3-methyl-4-(4-methyl-3-pyridinyl)phenyl) -1-butanesulfonamide (41); 2,5-dimethoxy-N-(3-methyl-4-(4-methyl-3-pyridinyl)phenyl) benzenesulfonamide (42); 2-fluoro-N-(3-methyl-4-(4-methyl-3-pyridinyl)phenyl) benzenesulfonamide (43); 3-fluoro-N-(3-methyl-4-(4-methyl-3-pyridinyl)phenyl) benzenesulfonamide (44); 2-chloro-N-(3-methyl-4-(4-methyl-3-pyridinyl)phenyl) benzenesulfonamide (45); 3,4-dimethoxy-N-(3-methyl-4-(4-methyl3-pyridinyl)phenyl) benzenesulfonamide (46); 4-cyano-N-(3-methyl-4-(4-methyl-3-pyridinyl)phenyl) benzenesulfonamide (47); 3,5-dimethyl-N-(3-methyl-4-(4-methyl-3-pyridinyl)phenyl)-4-isoxazolesulfonamide (48); 3-methoxy-N-(3-methyl-4-(4-methyl-3-pyridinyl)phenyl) benzenesulfonamide (49); N-(3-methyl-4-(4-methyl-3-pyridinyl)phenyl)-3-thiophenesulfonamide (50); N-(3-methyl-4-(4-methyl-3-pyridinyl)phenyl)-3-pyridinesulfonamide (51); N-(3-methyl-4-(4-methyl-3-pyridinyl)phenyl) methanesulfonamide (52); 1,2-dimethyl-N-(3-methyl-4-(4-methyl-3-pyridinyl)phenyl)-1H-imidazole-4-sulfonamide (53); N-(3-methyl-4-(4-methyl-3-pyridinyl)phenyl) cyclopropanesulfonamide (54); N-(3-methyl-4-(4-methyl-3-pyridinyl) phenyl)-1-naphthalene sulfonamide (55); 2,5-dichloro-N-(3-methyl-4-(4-methyl-3-pyridinyl) phenyl) benzenesulfonamide (56); 4-methyl-N-(3-methyl-4-(4-methyl-3-pyridinyl) phenyl) benzenesulfonamide (57); N-(3-methyl-4-(4-methyl-3-pyridinyl)phenyl)-3-(trifluoromethyl) benzenesulfonamide (58); 2-methyl-N-(3-methyl-4-(4-methyl-3-pyridinyl)phenyl)benzenesulfonamide (59); 2,5-dimethyl-N-(3-methyl-4-(4-methyl-3-pyridinyl)phenyl) benzenesulfonamide (60); 3-chloro-N-(3-methyl-4-(4-methyl-3-pyridinyl)phenyl)benzenesulfonamide (61); 3-methyl-N-(3-methyl-4-(4-methyl-3-pyridinyl)phenyl)benzenesulfonamide (62); 1-(4-chlorophenyl)-N-(3-methyl-4-(4-methyl-3-pyridinyl)phenyl)methanesulfonamide (63); N-(3-methyl-4-(4-methyl-3-pyridinyl)phenyl)-2-biphenylsulfonamide (64); methyl 3-43-methyl-4-(4-methyl-3-pyridinyl)phenyl)sulfamoyl)benzoate (65); N-(3-methyl-4-(4-methyl-3-pyridinyl) phenyl)-2-thiophenesulfonamide (66); N-(3-methyl-4-(4-methyl-3-pyridinyl)phenyl) ethanesulfonamide (67); N-(3-methyl-4-(4-methyl-3-pyridinyl) phenyl)-1-propanesulfonamide (68); 4-isopropyl-N-(3-methyl-4-(4-methyl-3-pyridinyl)phenyl) benzenesulfonamide (69); N-(3-methyl-4-(4-methyl-3-pyridinyl)phenyl)-4-phenoxybenzenesulfonamide (70); methyl 5-43-methyl-4-(4-methyl3-pyridinyl)phenyl) sulfamoyl)-2-furoate (71); N-(3-methyl-4-(4-methyl-3-pyridinyl)phenyl)-2-phenylethanesulfonamide (72); N-(3-methyl-4-(4-methyl-3-pyridinyl)phenyl)-2-naphthalenesulfonamide (73); N-(3-methyl-4-(4-methyl-3-pyridinyl)phenyl) benzenesulfonamide (74); N-(3-methyl-4-(4-methyl-3-pyridinyl)phenyl)-1-phenylmethanesulfonamide (75); 1-(3,4-dichlorophenyl)-N-(3-methyl-4-(4-methyl-3-pyridinyl)phenyl)methanesulfonamide (76); 1-(2-chlorophenyl)-N-(3-methyl-4-(4-methyl-3-pyridinyl)phenyl) methanesulfonamide (77); N-(3-methyl-4-(4-methyl-3-pyridinyl)phenyl)-1-(3-(trifluoromethyl)phenyl) methanesulfonamide (78); N(3-methoxy-4-(4-methyl-3-pyridinyl)phenyl)benzenesulfonamide (79); 4-fluoro-N-(3-methoxy-4-(4-methyl-3-pyridinyl)phenyl) benzenesulfonamide (80); 4-chloro-N-(3-methoxy-4-(4-methyl-3-pyridinyl)phenyl)benzenesulfonamide (81); N-(3-methoxy-4-(4-methyl-3-pyridinyl)phenyl)-3-(trifluoromethyl)benzenesulfonamide (82); N-(3-methoxy-4-(4-methyl-3-pyridinyl)phenyl)-2-methylbenzenesulfonamide (83); N-(3-methoxy-4-(4-methyl-3-pyridinyl)phenyl)-2,5-dimethylbenzenesulfonamide (84); 3-chloro-4-fluoro-N-(3-methoxy-4-(4-methyl-3-pyridinyl)phenyl) benzenesulfonamide (85); 3-fluoro-N-(3-methoxy-4-(4-methyl-3-pyridinyl)phenyl)benzenesulfonamide (86); 3,5-dichloro-N-(3-methoxy-4-(4-methyl-3-pyridinyl)phenyl) benzenesulfonamide (87); N-(3-methoxy-4-(4-methyl-3-pyridinyl)phenyl)-3-methylbenzenesulfonamide (88); 3,4-dimethoxy-N-(3-methoxy-4-(4-methyl-3-pyridinyl)phenyl) benzenesulfonamide (89); 4-cyano-N-(3-methoxy-4-(4-methyl-3-pyridinyl)phenyl)benzenesulfonamide (90); 2-methoxy-N-(3-methoxy-4-(4-methyl-3-pyridinyl)phenyl)-5-methylbenzenesulfonamide (91); 2,5-difluoro-N-(3-methoxy-4-(4-methyl-3-pyridinyl)phenyl) benzenesulfonamide (92); 3,4-difluoro-N-(3-methoxy-4-(4-methyl-3-pyridinyl)phenyl)benzenesulfonamide (93); N-(3-methoxy-4-(4-methyl-3-pyridinyl)phenyl)-2,4-dimethylbenzenesulfonamide (94); 3-methoxy-N-(3-methoxy-4-(4-methyl-3-pyridinyl)phenyl) benzenesulfonamide (95); 3,5-difluoro-N-(3-methoxy-4-(4-methyl-3-pyridinyl)phenyl)benzenesulfonamide (96); N-(3-methoxy-4-(4-methyl-3-pyridinyl)phenyl)-1-benzothiophene-2-sulfonamide (97); N-(3-methoxy-4-(4-methyl-3-pyridinyl)phenyl)-1-benzofuran-2-sulfonamide (98); 3-chloro-N-(3-methoxy-4-(4-methyl-3-pyridinyl)phenyl)benzenesulfonamide (99); N-(4-(4-methyl-3-pyridinyl) phenyl)-2-thiophenesulfonamide (100); 4-fluoro-N-(4-(4-methyl-3-pyridinyl) phenyl)benzenesulfonamide (101);

N-(4-44-(4-methyl-3-pyridinyl)phenyl)sulfamoyl) phenyl) acetamide (102); N-(4-(4-methyl-3-pyridinyl)phenyl)-4-nitrobenzenesulfonamide (103); 4-methoxy-N-(4-(4-methyl-3-pyridinyl)phenyl)benzenesulfonamide (104); 3-chloro-4-fluoro-N-(4-(4-methyl-3-pyridinyl)phenyl) benzenesulfonamide (105); 2-chloro-N-(4-(4-methyl-3-pyridinyl)phenyl)benzenesulfonamide (106); 3-chloro-N-(4-(4-methyl-3-pyridinyl)phenyl)benzenesulfonamide (107); 3,5-dichloro-N-(4-(4-methyl-3-pyridinyl)phenyl)benzenesulfonamide (108); 3-methyl-N-(4-(4-methyl-3-pyridinyl) phenyl)benzenesulfonamide (109); 4-cyano-N-(4-(4-methyl-3-pyridinyl)phenyl) benzenesulfonamide (110); N-(4-(4-methyl-3-pyridinyl)phenyl)-4-biphenylsulfonamide (111); 3,4-difluoro-N-(4-(4-methyl-3-pyridinyl)phenyl) benzenesulfonamide (112); N-(4-(4-methyl-3-pyridinyl) phenyl)cyclopropanesulfonamide (113); N-(4-(4-methyl-3-pyridinyl)phenyl)-3-pyridinesulfonamide (114); 3-methoxy-N-(4-(4-methyl-3-pyridinyl)phenyl)benzenesulfonamide (115); N-(4-(4-methyl-3-pyridinyl)phenyl)-2-phenylethanesulfonamide (116); methyl 344-(4-methyl-3-pyridinyl)phenyl)sulfamoyl) benzoate (117); (E)-N-(4-(4-methyl-3-pyridinyl)phenyl)-2-phenylethenesulfonamide (118); 2,2,2-trifluoro-N-(4-(4-methyl-3-pyridinyl)phenyl) ethanesulfonamide (119); N-(4-(4-methyl-3-pyridinyl) phenyl)-1-propanesulfonamide (120); N-(4-(4-methyl-3-pyridinyl) phenyl)-1-butanesulfonamide (121); 1-(3-chlorophenyl)-N-(4-(4-methyl-3-pyridinyl) phenyl) methanesulfonamide (122); 1,2-dimethyl-N-(4-(4-methyl-3-pyridinyl)phenyl) -1H-imidazole-4-sulfonamide (123); 2-methyl-N-(4-(4-methyl-3-pyridinyl)phenyl) benzenesulfonamide (124); N-(4-(4-methyl-3-pyridinyl)phenyl)-1-naphthalenesulfonamide (125); N-(4-(4-methyl-3-pyridinyl) phenyl)-2-naphthalenesulfonamide (126); 4-bromo-N-(4-(4-methyl-3-pyridinyl)phenyl) benzenesulfonamide (127); 4-chloro-N-(4-(4-methyl-3-pyridinyl)phenyl)-3-nitrobenzenesulfonamide (128); 4-methyl-N-(4-(4-methyl-3-pyridinyl) phenyl) benzenesulfonamide (129); N-(4-(4-methyl-3-pyridinyl)phenyl)methanesulfonamide (130); N-(4-(4-methyl-3-pyridinyl)phenyl)-4-phenoxybenzenesulfonamide (131); 1-(4-chlorophenyl)-N-(4-(4-methyl-3-pyridinyl)phenyl) methanesulfonamide (132); 2-(1,3-dioxo-1,3-dihydro-2H-isoindol-2-yl)-N-(4-(4-methyl-3-pyridinyl)phenyl) ethanesulfonamide (133); methyl 5-44-(4-methyl-3-pyridinyl) phenyl)sulfamoyl)-2-furoate (134); N-(4-(4-methyl-3-pyridinyl)phenyl)-2-biphenylsulfonamide (135); N-(4-(4-methyl-3-pyridinyl)phenyl)-3-thiophenesulfonamide (136); N-(4-(4-methyl-3-pyridinyl)phenyl)-3-biphenylsulfonamide (137); N-(4-(4-methyl-3-pyridinyl)phenyl)-3-(trifluoromethyl)benzenesulfonamide (138); 3-cyano-N-(4-(4-methyl-3-pyridinyl)phenyl) benzenesulfonamide (139); N-(4-(4-methyl-3-pyridinyl)phenyl)ethanesulfonamide (140); 2-methyl-N-(4-(4-methyl-3-pyridinyl)phenyl)-1-propanesulfonamide (141); N-(4-(isoquinolin-4-yl)-3-methoxyphenyl)methanesulfonamide (142); N-(4-(isoquinolin-4-yl)-3-methoxyphenyl)benzenesulfonamide (143); N-(4-(isoquinolin-4-yl)-3-methoxyphenyl) naphthalene-1-sulfonamide (144); N-(4-(isoquinolin-4-yl)-3-methoxyphenyl) naphthalene-2-sulfonamide (145); 4-chloro-N-(4-(isoquinolin-4-yl) -3-methoxyphenyl) benzenesulfonamide (146); N-(4-(isoquinolin-4-yl)-3-methoxyphenyl)-4-methoxybenzenesulfonamide (147); N-(4-(isoquinolin-4-yl)-3-methoxyphenyl)-1-phenylmethanesulfonamide (148); 2-chloro-N-(4-(isoquinolin-4-yl)-3-methoxyphenyl) benzenesulfonamide (149); 4-cyano-N-(4-(isoquinolin-4-yl)-3-methoxyphenyl) benzenesulfonamide (150); N-(4-(isoquinolin-4-yl)-3-methoxyphenyl)-2-phenylethanesulfonamide (151); N-(4-(isoquinolin-4-yl)-3-methoxyphenyl)-2-methylpropane-1-sulfonamide (152); N-(4-(isoquinolin-4-yl)-3-methoxyphenyl)-4-phenoxybenzenesulfonamide (153); N-(4-(isoquinolin-4-yl)-3-methoxyphenyl)quinoline -8-sulfonamide (154); 2,2,2-trifluoro-N-(4-(isoquinolin-4-yl)-3-methoxyphenyl) ethanesulfonamide (155); N-(4-(isoquinolin-4-yl)-3-methoxyphenyl)ethanesulfonamide (156); N-(4-(isoquinolin-4-yl)-3-methoxyphenyl)propane-1-sulfonamide (157); N-(4-(isoquinolin-4-yl)-3-methoxyphenyl)-1,2-dimethyl-1H-imidazole-4-sulfonamide (158); N-(4-(isoquinolin-4-yl)-3-methoxyphenyl)cyclopropanesulfonamide (159); N -(4-(isoquinolin-4-yl)-3-methoxyphenyl)pyridine-2-sulfonamide (160); N-(3-methoxy-4-(4-methylpyrimidin-5-yl)phenyl)methanesulfonamide (161); N-(3-methoxy-4-(4-methylpyrimidin-5-yl)phenyl)cyclopropanesulfonamide (162); N-(3-methoxy-4-(4-methylpyrimidin-5-yl)phenyl) propane-1-sulfonamide (163); N-(3-methoxy-4-(4-methylpyrimidin-5-yl)phenyl)methanesulfonamide (164); N-(3-methoxy-4-(4-methylpyrimidin-5-yl)phenyl) benzenesulfonamide (165); N-(3-methoxy-4-(4-methylpyrimidin-5-yl)phenyl)pyridine-3-sulfonamide (166); 2,2,2-trifluoro-N-(3-methoxy-4-(4-methylpyrimidin-5-yl)phenyl)ethanesulfonamide (167); N-(3-methoxy-4-(4-methylpyrimidin-5-yl)phenyl)-1-phenylmethanesulfonamide (168); N-(3-methoxy-4-(4-methylpyrimidin-5-yl) phenyl)-2-phenylethanesulfonamide (169); 4-methoxy-N-(3-methoxy-4-(4-methylpyrimidin-5-yl)phenyl) benzenesulfonamide (170); 2-chloro-N-(3-methoxy-4-(4-methylpyrimidin-5-yl)phenyl)benzenesulfonamide (171); 4-chloro-N-(3-methoxy-4-(4-methylpyrimidin-5-yl)phenyl) benzenesulfonamide (172); 1-(4-chlorophenyl)-N-(3-methoxy-4-(4-methylpyrimidin-5-yl)phenyl)methanesulfonamide (173); N-(3-methoxy-4-(4-methylpyrimidin-5-yl) phenyl)naphthalene-1-sulfonamide (174); N-(3-methoxy-4-(4-methylpyrimidin-5-yl)phenyl)naphthalene-2-sulfonamide (175); N-(3-methoxy-4-(4-methylpyrimidin-5-yl)phenyl)quinoline-8-sulfonamide (176); N-(3-methoxy-4-(4-methylpyrimidin-5-yl)phenyl)naphthalene-2-sulfonamide (177); N-(3-chloro-4-(4-methylpyridin-3-yl) phenyl)methanesulfonamide (178); 4-chloro-N-(4-(4-isoquinolinyl)phenyl)benzenesulfonamide (179); 4-chloro-N-(4-(4-(1-pyrrolidinylcarbonyl)-3-pyridinyl)phenyl) benzene sulfonamide (180); N-(4-(1-(phenylsulfonyl)-1H-pyrrolo[2,3-c]pyridin-4-yl)phenyl) benzenesulfonamide (181); 4-chloro-N-(4-(4-isoquinolinyl)-3-methylphenyl) benzenesulfonamide (182); N-(4-(4-methylpyridin-3-yl)-3-(2,2,2-trifluoroethoxy)phenylbenzenesulfonamide (183); N-(4-(4-methylpyridin-3-yl)-3-(2,2,2-trifluoroethoxy)phenylcyclopropylsulfonamide (184); N-(4-(5-bromo-4-methoxypyridin-3-yl)-3-methylphenyl)methane sulfonamide (185); N-(4-(5-bromo-4-isopropoxy-3-pyridinyl)-3-methylphenyl) methanesulfonamide (186); N-(4-(5-bromo-4-ethoxy-3-pyridinyl)-3-methylphenyl)methane sulfonamide (187); N-(4-(5-bromo-4-(2,2,2-trifluoroethoxy)-3-pyridinyl)-3-methylphenyl] methanesulfonamide (188); N-(4-(5-bromo-4-(2-fluoroethoxy)-3-pyridinyl)-3-methylphenyl) methanesulfonamide (189); N-(4-(5-bromo-4-(2,2-difluoroethoxy)-3-pyridinyl)-3-methylphenyl) methanesulfonamide (190); N-(4-(5-bromo-4-(2-phenylethoxy)-3-pyridinyl)-3-methylphenyl) methanesulfonamide (191); N-(4-(5-bromo-4-(2-(dimethylamino)ethoxy)-3-pyridinyl)-3-methylphenyl) methanesulfonamide (192); N-(4-(5-bromo-4-(2-methoxyethoxy)-3-pyridinyl)-3-methylphenyl) methanesulfonamide (193); N-(4-(5-bromo-4-(methylsulfanyl)-3-pyridinyl)-3-methylphenyl) methanesulfonamide (194); N-(4-(4-chloro-3-pyridinyl)-3-methylphenyl) methanesulfonamide (195); N-(4-(4-isopropoxy-3-pyridinyl)-3-methylphenyl) methanesulfonamide (196); N-(4-(4-ethoxy- 3-pyridinyl)-3-methylphenyl) methanesulfonamide (197); N-(3-methyl-4-(4-(2,2,2-trifluoroethoxy) -3-pyridinyl)phenyl) methane sulfonamide (198); N-(4-(4-(2-fluoroethoxy)-3-pyridinyl)-3-methylphenyl) methane sulfonamide (199); N-(4-(4-(2,2-difluoroethoxy)-3-pyridinyl)-3-methylphenyl) methane sulfonamide (200); N-(3-methyl-4-(4-(2-phenylethoxy)-3-pyridinyl)phenyl) methanesulfonamide (201); N-(4-(4-(2-(dimethylamino)ethoxy)-3-pyridinyl)-3-methylphenyl) methanesulfonamide (202); N-(4-(4-(2-methoxyethoxy)-3-pyridinyl)-3-methylphenyl)methanesulfonamide (203);N-(3-methyl-4-(4-(methylsulfanyl) -3-pyridinyl)phenyl)methanesulfonamide (204); N-(4-(4-methyl-3-pyridinyl) phenyl)-N'-phenylsulfamide (205); N-(4-chlorophenyl)-N-methyl-N'-(4-(4-methyl-3-pyridinyl)phenyl)sulfamide (206); N-(4-methoxyphenyl)-N'-(4-(4-methyl-3-pyridinyl) phenyl)sulfamide (207); N-(3-methyl-4-(4-methyl-3-pyridinyl)phenyl)-4-morpholine sulfonamide (208); N-(3-methyl-4-(4-methyl-3-pyridinyl)phenyl)-1-pyrrolidinesulfonamide (209); N-methyl-N'-(3-methyl-4-(4-methyl-3-pyridinyl)phenyl) sulfamide (210); 4-hydroxy-N-(3-methyl-4-(4-methylpyridin-3-yl)phenyl)piperidine-1-sulfonamide (211); N-(3-chloro-4-(4-methoxypyridin-3-yl)phenyl)methanesulfonamide (212); N-(3-methoxy-4-(4-(2,2,2-trifluoroethoxy)pyridine-3-yl)phenyl) methanesulfonamide (213); N-(4-(4-cyclopropylpyrimidin-5-yl-)3-methoxyphenyl) methanesulfonamide (214); N-(3-hydroxy-4-(4-methyl-3-pyridinyl)phenyl) methanesulfonamide (215); N-(4-(5-cyano-4-methoxy-3-pyridinyl)-3-methylphenyl) methane sulfonamide (216); N-(3-methoxy-4-(4-methyl-3-pyridinyl) phenyl) methanesulfonamide (217); N-(4-(4-ethylpyrimidin-5-yl)-3-methoxyphenyl) methanesulfonamide (218); N-(3-methoxy-4-(4-propylpyrimidin-5-yl)phenyl) methanesulfonamide (219); N-(4-(4-isopropylpyrimidin-5-yl)-3-methoxyphenyl) methanesulfonamide (220); N-(4-(4-cyclohexylpyrimidin-5-yl)-3-methoxyphenyl) methanesulfonamide (221); N-(3-methoxy-4-(1,7-naphthyridin-5-yl) phenyl) methanesulfonamide (222); N-(3-methoxy-4-(4-(pyrrolidin-1-yl)pyrimidin-5-yl)phenyl) methanesulfonamide (223); N-(3-methoxy-4-(4-morpholinopyrimidin-5-yl)phenyl)methanesulfonamide (224); N-(4-(4-cyclopropylpyridin-3-yl)-3-methoxyphenyl) methanesulfonamide (225); N-(4-(4-(difluoromethyl)pyridin-3-yl)-3-methoxyphenyl)methanesulfonamide (226); N-(3-methoxy-4-(4-(prop-1-en-2-yl)pyridin-3-yl)phenyl) methanesulfonamide (227); N-(4-(isoquinolin-4-yl)-3-(trifluoromethoxy) phenyl)methanesulfonamide (228); N-(4-(4-methylpyridin-3-yl)-3-(trifluoromethoxy) phenyl) methanesulfonamide (229); N-(4-(4-chloropyridin-3-yl)-3-(trifluoromethoxy) phenyl)methanesulfonamide (230); N-(4-(4-methoxypyridin-3-yl)-3-(trifluoromethoxy) phenyl) methanesulfonamide (231); N-(4-(isoquinolin-4-yl)-3-(2,2,2-trifluoroethoxy) phenyl)methanesulfonamide (232); N-(4-(4-methoxypyridin-3-yl)-3-(2,2,2-trifluoroethoxy)phenyl) methanesulfonamide (233); N-(3-(2-fluoroethoxy)-4-(isoquinolin -4-yl)phenyl)methanesulfonamide (234); N-(3-(2-fluoroethoxy)-4-(4-methoxypyridin-3-yl)phenyl) methanesulfonamide (235); N-(4-(4-chloropyridin-3-yl)-3-(2-fluoroethoxy) phenyl)methanesulfonamide (236); N-(3-(2-fluoroethoxy)-4-(4-(trifluoromethyl) pyridin-3-yl)phenyl) methanesulfonamide (237); N-(3-(2-fluoroethoxy)-4-(pyrido[4,3-b]pyrazin-8-yl)phenyl) methanesulfonamide (238); N-(3-(2-fluoroethoxy)-4-(1,7-naphthyridin-5-yl)phenyl) methanesulfonamide (239); N-(4-(4-methylpyridin-3-yl)-3-(trifluoromethyl) phenyl)methanesulfonamide (240); N-(4-(isoquinolin-4-yl)-3-(trifluoromethyl)phenyl) methanesulfonamide (241); N-(4-(4-chloropyridin-3-yl)-3-(trifluoromethyl)phenyl) methanesulfonamide (242); N-(4-(4-cyclopropylpyridin-3-yl)-3-(trifluoromethyl)phenyl) methanesulfonamide (243); N-(4-(4-isopropylpyridin-3-yl)-3-)methoxyphenyl) methanesulfonamide (244); N-(3-methoxy-4-(4-methoxypyrimidin-5-yl) methanesulfonamide (245); N-(3,5-dimethyl-4-(4-methyl-3-pyridinyl)phenyl) methanesulfonamide (246); N-(3-methoxy-4-(4-(2,2,2-trifluoroethoxy)-5-pyrimidinyl) phenyl)methanesulfonamide (247); N-(3-methoxy-4-(4-(2,2,2-trifluoroethylamino) pyrimidin-5-yl)phenyl)methanesulfonamide (248); N-(4-(4-ethoxy-5-pyrimidinyl)-3-methoxyphenyl)methanesulfonamide (249); N-(3-methoxy-4-(pyrrolo[1,2-c]pyrimidin-4-yl) phenyl)methanesulfonamide (250); N-(4-(imidazo[1,2-a]pyrazin-5-yl)-3-methoxyphenyl)methanesulfonamide (251); N-(4-(4-cyanopyridin-3-yl)-3-methoxyphenyl)methanesulfonamide (252); N-(4-(4-(hydroxymethyl)pyridin-3-yl)-3-methoxyphenyl)methanesulfonamide (253); N-(3-methoxy-4-(4-(methoxymethyl) pyridin-3-yl)phenyl) methanesulfonamide (254); and N-(4-(4-(cyclopropylmethoxy) pyridin-3-yl)-3-methoxyphenyl) methanesulfonamide (255).

12. A pharmaceutical composition comprising a compound according to claim 1, or a stereoisomer, or a pharmaceutically acceptable salt thereof, and a pharmaceutical acceptable carrier.

13. A method for treating a cancer comprising administering a compound according to claim 1, a stereoisomer, or a pharmaceutically acceptable salt thereof, wherein said cancer is breast cancer, ovarian cancer, or prostate cancer.

14. A method of treating a disease associated with the activity of the CYP17 enzyme, the method comprising administering to a mammalian patient a compound according to claim 1, or stereoisomers, N-oxides, or pharmaceutically acceptable salts thereof, wherein said disease is breast cancer, ovarian cancer, or prostate cancer.

\* \* \* \* \*

UNITED STATES PATENT AND TRADEMARK OFFICE
CERTIFICATE OF CORRECTION

Page 1 of 2

PATENT NO. : 8,916,553 B2
APPLICATION NO. : 13/812056
DATED : December 23, 2014
INVENTOR(S) : Joel Austin et al.

It is certified that error appears in the above-identified patent and that said Letters Patent is hereby corrected as shown below:

In the Claims:

Claim 1, col. 190, line 19, delete "$C_{1-3}$alkyl" and insert -- $C_{1-4}$alkyl --, therefor.

Claim 6, col. 193, line 64, delete "-CHF," and insert -- -$CHF_2$, --, therefor.

Claim 10, col. 194, line 48, delete "$R^{1'}$" and insert -- $R^1$ --, therefor.

Claim 11, col. 195, line 6, delete "N -(3-" and insert -- N-(3- --, therefor.

Claim 11, col. 195, line 14, delete "methyl -3-" and insert -- methyl-3- --, therefor.

Claim 11, col. 195, line 26, delete "methyl -3-" and insert -- methyl-3- --, therefor.

Claim 11, col. 195, line 43, delete "phenyl) -1-" and insert -- phenyl)-1- --, therefor.

Claim 11, col. 195, line 50, delete "-methyl3-" and insert -- -methyl-3- --, therefor.

Claim 11, col. 196, line 20, delete "methyl3-" and insert -- methyl-3- --, therefor.

Claim 11, col. 196, line 32, delete "N(3-" and insert -- N-(3- --, therefor.

Claim 11, col. 197, line 29, delete "phenyl) -1H-" and insert -- phenyl)-1H- --, therefor.

Claim 11, col. 197, lines 58-59, delete "yl) -3-" and insert -- yl)-3- --, therefor.

Claim 11, col. 198, line 3, delete "quinoline -8-" and insert -- quinoline-8- --, therefor.

Claim 11, col. 198, line 10, delete "N -(4-" and insert -- N-(4- --, therefor.

Signed and Sealed this
Eighth Day of March, 2016

Michelle K. Lee
*Director of the United States Patent and Trademark Office*

CERTIFICATE OF CORRECTION (continued)
U.S. Pat. No. 8,916,553 B2

In the Claims:

Claim 11, col. 199, line 2, delete "trifluoroethoxy) -3-" and insert -- trifluoroethoxy)-3- --, therefor.

Claim 11, col. 199, line 11, delete "(methylsulfanyl) -3-" and insert -- (methylsulfanyl)-3- --, therefor.

Claim 11, col. 200, line 4, delete "quinolin -4-" and insert -- quinolin-4- --, therefor.